United States Patent
Wang et al.

(10) Patent No.: US 12,145,944 B2
(45) Date of Patent: Nov. 19, 2024

(54) IMIDAZOPYRIMIDINES AS EED INHIBITORS AND THE USE THEREOF

(71) Applicant: THE REGENTS OF THE UNIVERSITY OF MICHIGAN, Ann Arbor, MI (US)

(72) Inventors: Shaomeng Wang, Superior Township, MI (US); Rohan Rej, Ann Arbor, MI (US); Changwei Wang, Ann Arbor, MI (US); Mi Wang, Ann Arbor, MI (US); Jianfeng Lu, Ann Arbor, MI (US); Chao-Yie Yang, Ann Arbor, MI (US); Ester Fernandez-Salas, Ann Arbor, MI (US); Jeanne Stuckey, Fenton, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 161 days.

(21) Appl. No.: 16/971,472

(22) PCT Filed: Jul. 16, 2020

(86) PCT No.: PCT/US2020/042219
§ 371 (c)(1),
(2) Date: Aug. 20, 2020

(87) PCT Pub. No.: WO2021/011713
PCT Pub. Date: Jan. 21, 2021

(65) Prior Publication Data
US 2022/0227778 A1   Jul. 21, 2022

Related U.S. Application Data

(60) Provisional application No. 62/874,606, filed on Jul. 16, 2019, provisional application No. 62/944,608, filed on Dec. 6, 2019.

(51) Int. Cl.

| | |
|---|---|
| A61K 31/277 | (2006.01) |
| A61K 45/06 | (2006.01) |
| A61P 35/00 | (2006.01) |
| C07D 471/22 | (2006.01) |
| C07D 487/04 | (2006.01) |
| C07D 487/14 | (2006.01) |
| C07D 491/22 | (2006.01) |
| C07D 495/14 | (2006.01) |
| C07D 495/22 | (2006.01) |
| C07D 498/22 | (2006.01) |
| C07D 513/22 | (2006.01) |
| C07F 9/6561 | (2006.01) |

(52) U.S. Cl.
CPC ............ *C07D 491/22* (2013.01); *A61K 45/06* (2013.01); *A61P 35/00* (2018.01); *C07D 471/22* (2013.01); *C07D 487/04* (2013.01); *C07D 487/14* (2013.01); *C07D 495/14* (2013.01); *C07D 495/22* (2013.01); *C07D 498/22* (2013.01); *C07D 513/22* (2013.01); *C07F 9/6561* (2013.01)

(58) Field of Classification Search
None
See application file for complete search history.

(56) References Cited

U.S. PATENT DOCUMENTS

| | | |
|---|---|---|
| 6,207,156 B1 | 3/2001 | Kuchroo et al. |
| 6,808,710 B1 | 10/2004 | Wood et al. |
| 6,984,720 B1 | 1/2006 | Korman et al. |
| 7,595,048 B2 | 9/2009 | Honjo et al. |
| 8,008,449 B2 | 8/2011 | Korman et al. |
| 8,114,845 B2 | 2/2012 | Langermann et al. |
| 8,217,149 B2 | 7/2012 | Irving et al. |
| 8,522,156 B2 | 8/2013 | Kumagai et al. |
| 8,728,474 B2 | 5/2014 | Honjo et al. |
| 8,779,105 B2 | 7/2014 | Korman et al. |

(Continued)

FOREIGN PATENT DOCUMENTS

| | | |
|---|---|---|
| CL | 202100989 | 10/2021 |
| CL | 202103191 | 5/2022 |

(Continued)

OTHER PUBLICATIONS

Rej et al., EEDi-5285: An exceptionally potent, efficacious, and orally active small-molecule hibitor embryonic ectoderm development, J. Med. Chem., 63(13):7252-67 (Jun. 24, 2020).

(Continued)

*Primary Examiner* — Layla Soroush
(74) *Attorney, Agent, or Firm* — MARSHALL, GERSTEIN & BORUN LLP

(57) ABSTRACT

The present disclosure provides compounds represented by Formula I:

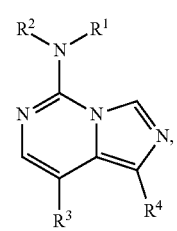

wherein $R^1$, $R^2$, $R^3$, and $R^4$ are as defined in the specification, and the salts and solvates thereof. Compounds of Formula I are EED inhibitors. EED inhibitors are useful for the treatment of cancer and other diseases.

14 Claims, 2 Drawing Sheets

(56) References Cited

U.S. PATENT DOCUMENTS

| | | | |
|---|---|---|---|
| 8,900,587 | B2 | 12/2014 | Carven et al. |
| 8,907,053 | B2 | 12/2014 | Sasikumar et al. |
| 8,952,136 | B2 | 2/2015 | Carven et al. |
| 9,073,994 | B2 | 7/2015 | Honjo et al. |
| 9,084,776 | B2 | 7/2015 | Korman et al. |
| 2011/0150892 | A1 | 6/2011 | Thudium et al. |
| 2013/0022623 | A1 | 1/2013 | Karsunky et al. |
| 2013/0071403 | A1 | 3/2013 | Rolland et al. |
| 2013/0309250 | A1 | 11/2013 | Cogswell et al. |
| 2014/0093511 | A1 | 4/2014 | Lonberg et al. |
| 2014/0286935 | A1 | 9/2014 | Hamblin et al. |
| 2014/0341917 | A1 | 11/2014 | Nastri et al. |
| 2015/0225457 | A1 | 8/2015 | Blumberg et al. |
| 2015/0250853 | A1 | 9/2015 | Mak |
| 2015/0259420 | A1 | 9/2015 | Triebel et al. |

FOREIGN PATENT DOCUMENTS

| | | |
|---|---|---|
| CL | 202103190 | 9/2022 |
| CL | 202201489 | 3/2023 |
| WO | WO-2015/036499 A1 | 3/2015 |
| WO | WO-2016103155 A1 | 6/2016 |
| WO | WO-2017/221092 A1 | 12/2017 |
| WO | WO-2017/221100 A1 | 12/2017 |
| WO | WO-2020/086616 A1 | 4/2020 |
| WO | WO-2020/243415 A2 | 12/2020 |
| WO | WO-2020/243423 A1 | 12/2020 |
| WO | WO-2021/113627 A1 | 6/2021 |

OTHER PUBLICATIONS

International Application No. PCT/US2020/042219, Invitation to Pay Additional Fees, mailed Oct. 19, 2020.
International Application No. PCT/US2020/042219, International Search Report and Written Opinion, mailed Dec. 10, 2020.
Anderson, Tim-3: an emerging target in the cancer immunotherapy landscape, Cancer Immunol. Res., 2(5):393-8 (2014).
Dalle et al., The role of enasidenib in the treatment of mutant IDH2 acute myeloid leukemia, Ther. Adv. Hematol., 9(7):163-173 (2018).
Fiskus et al., Histone deacetylase inhibitors deplete enhancer of zeste 2 and associated polycomb repressive complex 2 proteins in human acute leukemia cells, Mol. Cancer Ther., 5(12):3096-104 (2006).
Huang et al., Role of LAG-3 in regulatory T cells, Immunity, 21(4):503-13 (2004).
Löb et al., IDO1 and IDO2 are expressed in human tumors: levo- but not dextro-1-methyl tryptophan inhibits tryptophan catabolismcancer Immunol. Immunother., 58(1):153-7 (2009).
Moritz et al., Structure, mechanism, and regulation of polycomb-repressive complex 2, J. Biol. Chem., 293(36):13805-13814 (2018).
Naidoo et al., Immune modulation for cancer therapy, Br. J. Cancer, 111(12):2214-9 (2014).
Nassereddine et al., Evaluating ivosidenib for the treatment of relapsed/refractory AML: design, development, and place in therapy, Onco Targets Ther., 12:303-308 (2018).
Ngiow et al., Anti-TIM3 antibody promotes T cell IFN-?-mediated antitumor immunity and suppresses established tumors, Cancer Res., 71(10):3540-51 (2011).
Ngiow et al., Prospects for TIM3-Targeted Antitumor Immunotherapy, Cancer Res., 71(21):6567-71 (2011).
Pardoll, The blockade of immune checkpoints in cancer immunotherapy, Nat. Rev. Cancer, 12(4):252-64 (2012).
Qian et al., Efficacy of levo-1-methyl tryptophan and dextro-1-methyl tryptophan in reversing indoleamine-2,3-dioxygenase-mediated arrest of T-cell proliferation in human epithelial ovarian cancer, Cancer Res., 69(13):5498-504 (2009).
Stein et al., Enasidenib in mutant IDH2 relapsed or refractory acute myeloid leukemia, Blood, 130(6):722-31 (2017).
Unanue, Perspectives on anti-CD47 antibody treatment for experimental cancer, Proc. Natl. Acad. Sci. USA, 110(27):10886-7 (2013).
Wouters, Hitting the target in IDH2 mutant AML, Blood, 130(6):693-694 (2017).
Yue et al., Targeting STAT3 in cancer: how successful are we?, Expert Opin. Investig. Drugs, 18(1):45-56 (2009).

IMIDAZOPYRIMIDINES AS EED INHIBITORS AND THE USE THEREOF

CROSS-REFERENCE TO RELATED APPLICATIONS

This is the U.S. national phase of International Application No. PCT/US20/42219, filed Jul. 16, 2020, which claims the benefit of U.S. Provisional Patent Application No. 62/874,606, filed on Jul. 16, 2019, and U.S. Provisional Patent Application No. 62/944,608, filed Dec. 6, 2019, each incorporated herein by reference in its entirety.

BACKGROUND OF THE INVENTION

Field of the Invention

The present disclosure provides embryonic ectoderm development (EED) inhibitors, synthetic intermediates used to prepare EED inhibitors, and therapeutic methods of treating conditions and diseases, e.g., cancer, wherein the inhibition EED protein provides a benefit.

Background

Polycomb group (PcG) proteins are chromatin modifying enzymes that are dysregulated in many human cancers. The Polycomb Repressive Complex 2 (PRC2), which includes SUZ12 (suppressor of zeste 12), EED, and the catalytic subunit, EZH2 (enhancer of zeste homolog 2), represses genes by methylating the core histone H3 lysine 27 (H3K27me3) at and around the promoter regions of target genes. PRC2 is the critical component of cellular machinery involved in the epigenetic regulation of gene transcription and plays a critical function in development, tissue differentiation, and regeneration. See, e.g., Moritz and Trievel, J. Biol. Chem. 293(36):13805-13814 (2018); Fiskus et al., Mol Cancer Ther 5(12):3096-3014 (2006).

PRC2 requires at least EED and SUZ12 for its methyltransferase activity. EED, SUZ12 and EZH2 are overexpressed in many cancers including, but not limited to, breast cancer, prostate cancer, and hepatocellular carcinoma. There exists for a need in the art for small molecules that inhibit the activity of EED for the treatment of cancer and other diseases.

BRIEF SUMMARY OF THE INVENTION

In one aspect, the present disclosure provides compounds represented by any one of Formulae I-XI, XI-A, XI-B, XII, XII-A, XII-B, XIII, XIII-A, XIII-B, XIV, XIV-A, XIV-B, XV, XV-A, XV-B, or XVI, below, and the pharmaceutically acceptable salts and solvates, e.g., hydrates, thereof, collectively referred to as "Compounds of the Disclosure." Compounds of the Disclosure are EED inhibitors and/or synthetic intermediates that can be used to prepare EED inhibitors. Certain Compounds of the Disclosure are thus useful in treating or preventing diseases or conditions such as cancer wherein the inhibition of EED protein provides a benefit.

In another aspect, the present disclosure provides methods of treating or preventing a condition or disease by administering a therapeutically effective amount of a Compound of the Disclosure to a subject, e.g., a human patient, in need thereof. The disease or condition of interest that is treatable or preventable by inhibition or of EED is, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a Compound of the Disclosure to a subject at risk of developing a condition characterized by unwanted proliferating cells. In some embodiments, Compounds of the Disclosure may reduce the proliferation of unwanted cells by inducing apoptosis in those cells. In some embodiments, Compounds of the Disclosure are administered in combination with an optional therapeutic agent.

In another aspect, the present disclosure provides a method of inhibiting EED in a subject, comprising administering to the subject a therapeutically effective amount of a Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating or preventing diseases or conditions wherein inhibition of EED provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in the treatment or prevention of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising an optional therapeutic agent useful in the treatment of a disease or condition of interest, and a package insert containing directions for use in the treatment of a disease or condition, e.g., cancer.

In another aspect, the present disclosure provides methods of preparing Compounds of the Disclosure and Intermediates of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

I. Compounds of the Disclosure

Figure 1:
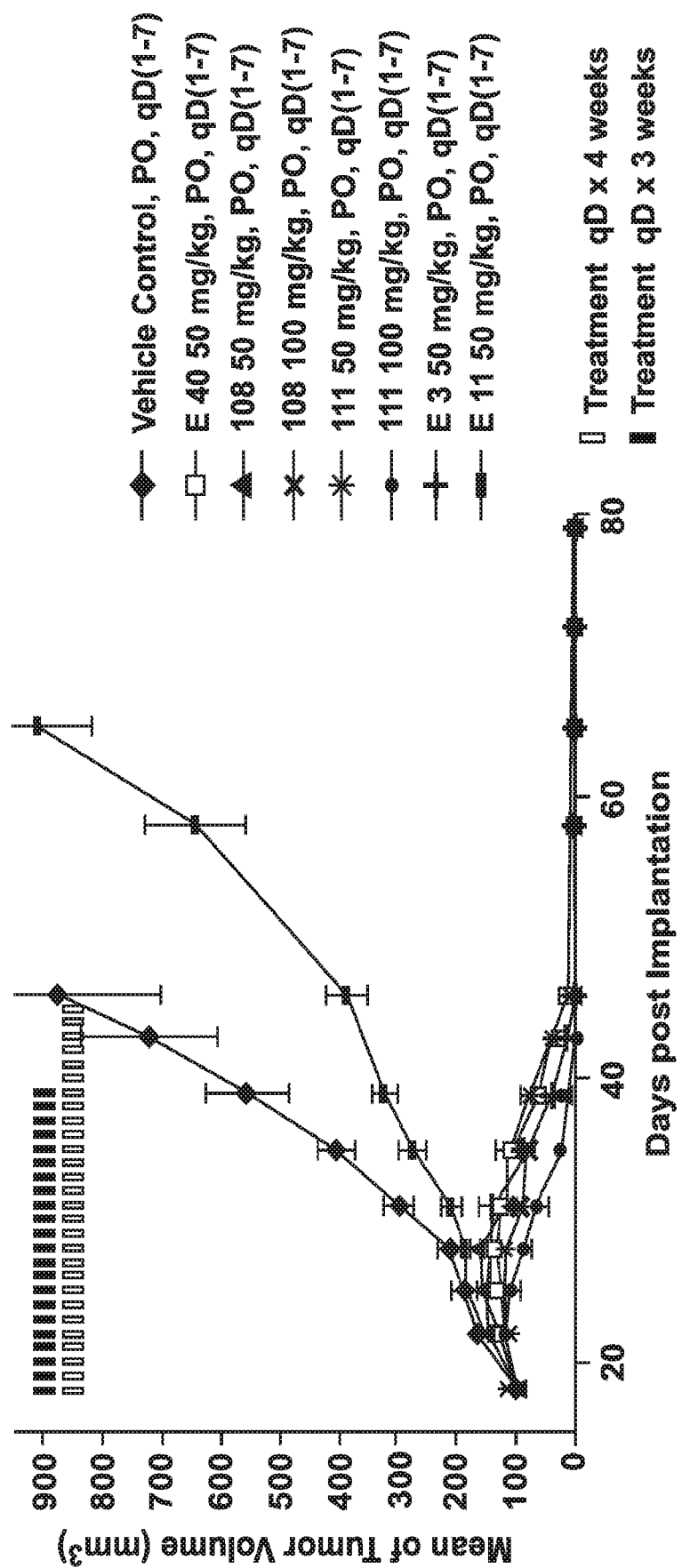
FIG. 1 is a line graph showing the anti-tumor efficacy of representative Compounds of the Disclosure in the KARPAS422 tumor model in mice.

Compounds of the Disclosure are EED inhibitors and/or synthetic intermediates that can be used to prepare EED inhibitors.

In one embodiment, Compounds of the Disclosure are compounds of Formula I:

I wherein:
$R^1$ is aralkyl;
$R^2$ is selected from the group consisting of hydrogen and $C_1$-$C_4$ alkyl;
$R^3$ and $R^4$ taken together with the carbon atoms to which they are attached form a radical of Formula I-A, I-B, or I-C:

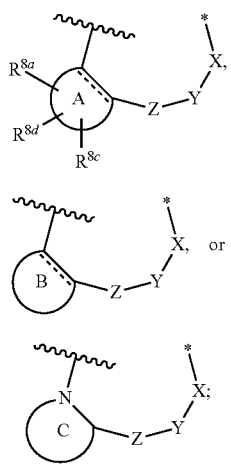

I-A

I-B

I-C

X is selected from the group consisting of —C($R^{5a}$)($R^{5b}$)—, —C(=O)—, and —S(=O)$_2$—;
$R^{5a}$ and $R^{5b}$ are independently selected from the group consisting of hydrogen and $C_1$-$C_4$ alkyl;
Y is selected from the group consisting of —C($R^{6a}$)($R^{6b}$)—, —S—, —O—, and —N($R^7$)—; or
X and Y taken together form a 5-membered heteroarylenyl;
Z is —C($R^{6c}$)($R^{6d}$)$_m$—;
$R^{6a}$ and $R^{6b}$ are independently selected from the group consisting of hydrogen and $C_1$-$C_4$ alkyl;
each $R^{6c}$ and $R^{6d}$ is independently selected from the group consisting of hydrogen and $C_1$-$C_4$ alkyl;
m is 0, 1, or 2;
$R^7$ is selected from the group consisting of hydrogen, $C_1$-$C_6$ alkyl, $C_1$-$C_6$ haloalkyl, optionally substituted $C_3$-$C_8$ cycloalkyl, optionally substituted $C_4$-$C_8$ heterocyclo, hydroxyalkyl, (alkoxy)alkyl, (cycloalkyl)alkyl, and (heterocyclo)alkyl;
$R^{8a}$, $R^{8b}$, and $R^{8c}$ are independently selected from the group consisting of hydrogen, halo, $C_1$-$C_4$ alkyl, $C_1$-$C_4$ haloalkyl, $C_1$-$C_4$ alkoxy, carboxamido, optionally substituted $C_3$-$C_8$ cycloalkyl, optionally substituted 4- to 8-membered heterocyclo, (heterocyclo)$C_1$-$C_4$ alkyl, and alkylsulfonyl;

is a fused phenyl, fused 5-membered heteroaryl, or fused 6-membered heteroaryl;

is an optionally substituted fused 3- to 8-membered cycloalkyl or optionally substituted fused 4- to 8-membered heterocyclo;

is an optionally substituted fused 4- to 8-membered heterocyclo; and
the bond designated with a "⁀" is attached at the $R^3$ position of Formula I and the bond designated with an "*" is attached at the $R^4$ position of Formula I; or
$R^3$ is $R^{3a}$;
$R^4$ is $R^{4a}$;
$R^{3a}$ is selected from group consisting of optionally substituted aryl, optionally substituted 5- to 10-membered heteroaryl, and optionally substituted 4- to 8-membered heterocyclo; and
$R^{4a}$ is selected from the group consisting of hydrogen, halo, $C_1$-$C_4$ haloalkyl, —S(=O)$_2$$R^9$, —P(=O)($R^{10a}$)($R^{10b}$), —C(=O)O$R^{11a}$, —C(=O)N$R^{11b}$$R^{11c}$, and —S(=O)(=N$R^{13a}$)$R^{13b}$;
$R^9$ is selected from the group consisting of $C_1$-$C_4$ alkyl and $C_3$-$C_6$ cycloalkyl;
$R^{10a}$ and $R^{10b}$ are independently $C_1$-$C_4$ alkyl;
$R^{11a}$ is selected from the group consisting of hydrogen and $C_1$-$C_4$ alkyl;
$R^{11b}$ and $R^{11c}$ are independently selected from the group consisting of hydrogen and $C_1$-$C_4$ alkyl; or
$R^{11b}$ and $R^{11c}$ taken together with the nitrogen atom to which they are attached form a 4- to 6-membered optionally substituted heterocyclo;
$R^{13a}$ is selected from the group consisting of hydrogen, $C_1$-$C_6$ alkyl, $C_3$-$C_6$ cycloalkyl, and hydroxyalkyl;
$R^{13b}$ is selected from the group consisting of $C_1$-$C_6$ alkyl and $C_3$-$C_6$ cycloalkyl; or
$R^{13a}$ and $R^{13b}$ taken together form a 5- to 7-membered heterocyclo; and
═══ is a single or double bond, or a pharmaceutically acceptable salt or solvate thereof.

In another embodiment, Compounds of the Disclosure are compounds of Formula I, wherein:

X is selected from the group consisting of —C(R$^{5a}$)(R$^{5b}$)—, —C(=O)—, and —S(=O)$_2$—;

Y is selected from the group consisting of —C(R$^{6a}$)(R$^{6b}$)—, —S—, —O—, and —N(R$^7$)—; and R$^{8a}$, R$^{8b}$, and R$^{8c}$ are independently selected from the group consisting of hydrogen, halo, C$_1$-C$_4$ alkyl, C$_1$-C$_4$ haloalkyl, C$_1$-C$_4$ alkoxy, and alkylsulfonyl, or a pharmaceutically acceptable salt or solvate thereof.

In another embodiment, Compounds of the Disclosure are compounds of Formula I, wherein R$^3$ and R$^4$ taken together with the carbon atoms to which they are attached form a radical of Formula I-A, I-B, or I-C, or a pharmaceutically acceptable salt or solvate thereof.

In another embodiment, Compounds of the Disclosure are compounds of Formula II:

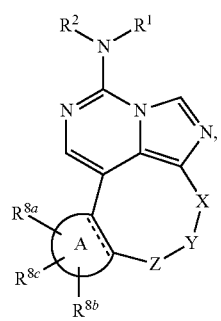

II wherein R$^1$, R$^2$, R$^{8a}$, R$^{8b}$, R$^{8c}$, X, Y, Z,

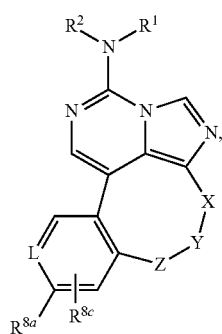

and ═══ are as defined in connection with Formula I, or a pharmaceutically acceptable salt or solvate thereof.

In another embodiment, Compounds of the Disclosure are compounds of Formula III:

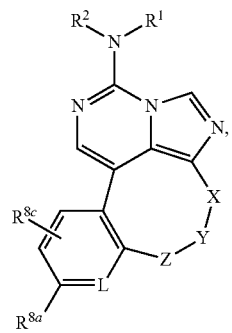

III wherein L is selected from the group consisting of —C(R$^{8b}$)═ and —N═; and R$^1$, R$^2$, R$^{8a}$, R$^{8b}$, R$^{8c}$, X, Y, and Z are as defined in connection with Formula I, or a pharmaceutically acceptable salt or solvate thereof.

In another embodiment, Compounds of the Disclosure are compounds of Formula IV:

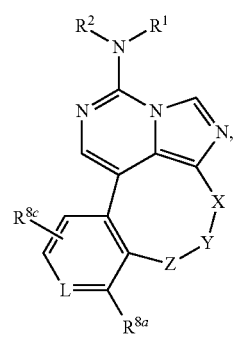

IV wherein L is selected from the group consisting of —C(R$^{8b}$)═ and —N═; and R$^1$, R$^2$, R$^{8a}$, R$^{8b}$, R$^{8c}$, X, Y, and Z are as defined in connection with Formula I, or a pharmaceutically acceptable salt or solvate thereof.

In another embodiment, Compounds of the Disclosure are compounds of Formula V:

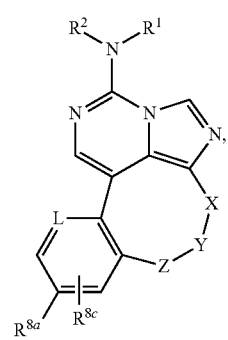

V wherein L is selected from the group consisting of —C(R$^{8b}$)═ and —N═; and R$^1$, R$^2$, R$^{8a}$, R$^{8b}$, R$^{8c}$, X, Y, and Z are as defined in connection with Formula I, or a pharmaceutically acceptable salt or solvate thereof.

In another embodiment, Compounds of the Disclosure are compounds of Formula VI:

VI wherein L is selected from the group consisting of —C(R$^{8b}$)═ and —N═; and R$^1$, R$^2$, R$^{8a}$, R$^{8b}$, R$^{8c}$, X, Y, and Z are as defined in connection with Formula I, or a pharmaceutically acceptable salt or solvate thereof.

In another embodiment, Compounds of the Disclosure are compounds of any one of Formulae III-VI, wherein L is —C(R$^{8b}$)=, or a pharmaceutically acceptable salt or solvate thereof.

In another embodiment, Compounds of the Disclosure are compounds of any one of Formulae III-VI, wherein L is —N=, or a pharmaceutically acceptable salt or solvate thereof.

In another embodiment, Compounds of the Disclosure are compounds of any one of Formulae I-VI, wherein R$^{8a}$, R$^{8b}$, and R$^{8c}$ are independently selected from the group consisting of hydrogen, C$_1$-C$_4$ alkyl, C$_1$-C$_4$ haloalkyl, and C$_3$-C$_6$ cycloalkyl, or a pharmaceutically acceptable salt or solvate thereof. In another embodiment, R$^{8a}$ is selected from the group consisting of —CHF$_2$, —CF$_3$, —CH$_3$, —CD$_3$, and cyclopropyl; and R$^{8b}$ and R$^{8c}$ are hydrogen. In another embodiment, R$^{8a}$ is selected from the group consisting of —CF$_3$ or —CH$_3$; and R$^{8b}$ and R$^{8c}$ are hydrogen.

In another embodiment Compounds of the Disclosure are compounds of any one of Formulae I-VI, wherein, R$^{8a}$ is selected from the group consisting of C$_1$-C$_4$ alkyl, 4- to 8-membered heterocyclo, and (heterocyclo)C$_1$-C$_4$ alkyl; and R$^{8b}$ and R$^{8c}$ are hydrogen, or a pharmaceutically acceptable salt or solvate thereof. In another embodiment, R$^{8a}$ is C$_1$-C$_4$ alkyl. In another embodiment, R$^{8a}$ is 4- to 8-membered heterocyclo. In another embodiment, R$^{8a}$ is (heterocyclo)C$_1$-C$_4$ alkyl. In another embodiment, R$^{8a}$ is selected from the group consisting of:

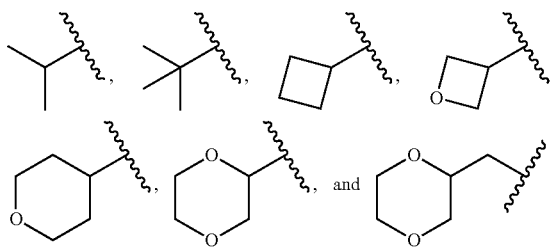

In another embodiment, Compounds of the Disclosure are compounds of Formula VII:

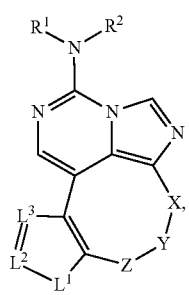

VII wherein:
L$^1$ is selected from the group consisting of —S—, —O—, and —N(R$^{8a}$)—;
L$^2$ is selected from the group consisting of —C(R$^{8b}$)= and —N=;
L$^3$ is selected from the group consisting of —C(R$^{8c}$)= and —N=;
R$^{8a}$ is selected from the group consisting of hydrogen and C$_1$-C$_4$ alkyl;
R$^{8b}$ is selected from the group consisting of hydrogen, C$_1$-C$_4$ alkyl, and C$_1$-C$_4$ haloalkyl;
R$^{8c}$ is selected from the group consisting of hydrogen, C$_1$-C$_4$ alkyl, and C$_1$-C$_4$ haloalkyl; and
R$^1$, R$^2$, X, Y, and Z are as defined in connection with Formula I, or a pharmaceutically acceptable salt or solvate thereof.

In another embodiment, Compounds of the Disclosure are compounds of Formula VIII:

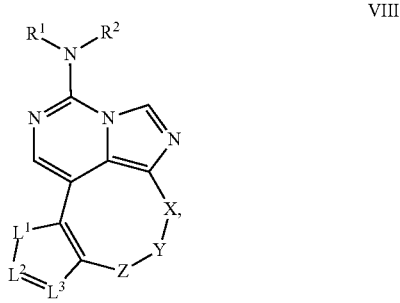

VIII wherein:
L$^1$ is selected from the group consisting of —S—, —O—, and —N(R$^{8a}$)—;
L$^2$ is selected from the group consisting of —C(R$^{8b}$)= and —N=;
L$^3$ is selected from the group consisting of —C(R$^{8c}$)= and —N=;
R$^{8a}$ is selected from the group consisting of hydrogen and C$_1$-C$_4$ alkyl;
R$^{8b}$ is selected from the group consisting of hydrogen, C$_1$-C$_4$ alkyl, and C$_1$-C$_4$ haloalkyl;
R$^{8c}$ is selected from the group consisting of hydrogen, C$_1$-C$_4$ alkyl, and C$_1$-C$_4$ haloalkyl; and
R$^1$, R$^2$, X, Y, and Z are as defined in connection with Formula I, or a pharmaceutically acceptable salt or solvate thereof.

In another embodiment, Compounds of the Disclosure are compounds of Formula IX:

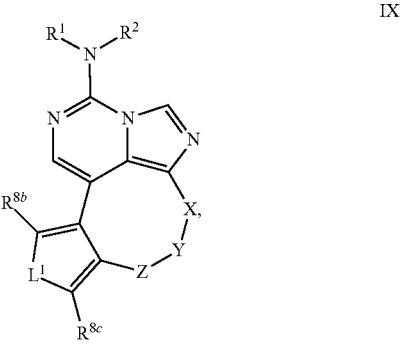

IX wherein:
L$^1$ is selected from the group consisting of —S—, —O—, and —N(R$^{8a}$)—;
R$^{8a}$ is selected from the group consisting of hydrogen and C$_1$-C$_4$ alkyl;
R$^{8b}$ is selected from the group consisting of hydrogen, C$_1$-C$_4$ alkyl, and C$_1$-C$_4$ haloalkyl;

$R^{8c}$ is selected from the group consisting of hydrogen, $C_1$-$C_4$ alkyl, and $C_1$-$C_4$ haloalkyl; and $R^1$, $R^2$, X, Y, and Z are as defined in connection with Formula I, or a pharmaceutically acceptable salt or solvate thereof.

In another embodiment, Compounds of the Disclosure are compounds of Formula X:

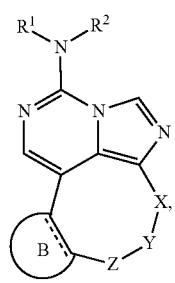

X wherein $R^1$, $R^2$, X, Y, Z,

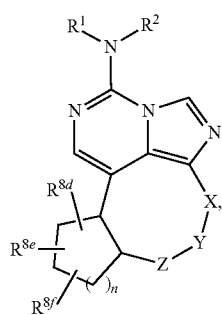

and $=\!=\!=$ are as defined in connection with Formula I, or a pharmaceutically acceptable salt or solvate thereof.

In another embodiment, Compounds of the Disclosure are compounds of Formula XI:

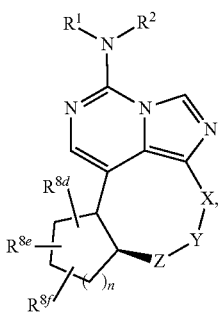

XI wherein:

$R^{8d}$, $R^{8e}$, and $R^{8f}$ are independently selected from the group consisting of hydrogen, halo, and $C_1$-$C_4$ alkyl;

n is 1, 2, or 3; and $R^1$, $R^2$, X, Y, and Z are as defined in connection with Formula I, or a pharmaceutically acceptable salt or solvate thereof.

In another embodiment, Compounds of the Disclosure are compounds of Formula XI-A:

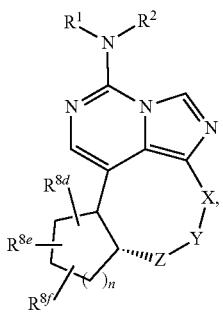

XI-A wherein $R^1$, $R^2$, $R^{8d}$, $R^{8e}$, $R^{8f}$, n, X, Y, and Z are as defined in connection with Formula XI, or a pharmaceutically acceptable salt or solvate thereof.

In another embodiment, Compounds of the Disclosure are compounds of Formula XI-B:

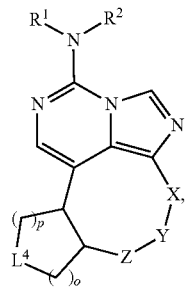

XI-B wherein $R^1$, $R^2$, $R^{8d}$, $R^{8e}$, $R^{8f}$, n, X, Y, and Z are as defined in connection with Formula XI, or a pharmaceutically acceptable salt or solvate thereof.

In another embodiment, Compounds of the Disclosure are compounds of Formula XII:

XII wherein:

$L^4$ is selected from the group consisting of —S—, —O—, and —N($R^{8g}$)—;

$R^{8g}$ is selected from the group consisting of hydrogen, $C_1$-$C_4$ alkyl, optionally substituted $C_3$-$C_6$ cycloalkyl, and optionally substituted 4- to 8-membered heterocyclo;

is 0, 1, 2, or 3;

p is 0, 1, 2, or 3;

wherein the sum of o and p is 1, 2, 3, 4, or 5; and
$R^1$, $R^2$, X, Y, and Z are as defined in connection with Formula I, or a pharmaceutically acceptable salt or solvate thereof.

In another embodiment, Compounds of the Disclosure are compounds of Formula XII-A:

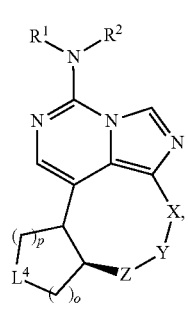

XII-A wherein $R^1$, $R^2$, $L^4$, o, p, X, Y, and Z are as defined in connection with Formula XII, or a pharmaceutically acceptable salt or solvate thereof.

In another embodiment, Compounds of the Disclosure are compounds of Formula XII-B:

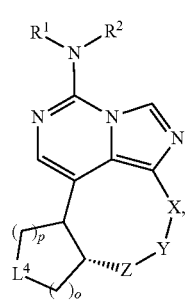

XII-B wherein $R^1$, $R^2$, $L^4$, o, p, X, Y, and Z are as defined in connection with Formula XII, or a pharmaceutically acceptable salt or solvate thereof.

In another embodiment, Compounds of the Disclosure are compounds of Formula XIII:

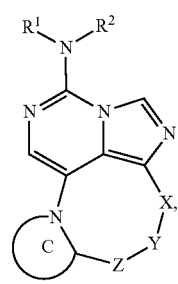

XIII wherein $R^1$, $R^2$, X, Y, Z, and

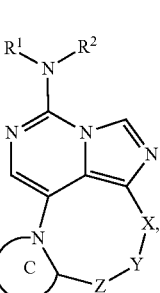

are as defined in connection with Formula I, or a pharmaceutically acceptable salt or solvate thereof.

In another embodiment, Compounds of the Disclosure are compounds of Formula XIII-A:

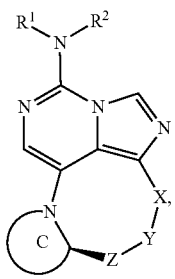

XIII-A wherein $R^1$, $R^2$, X, Y, Z, and

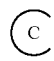

are as defined in connection with Formula I, or a pharmaceutically acceptable salt or solvate thereof.

In another embodiment, Compounds of the Disclosure are compounds of Formula XIII-B:

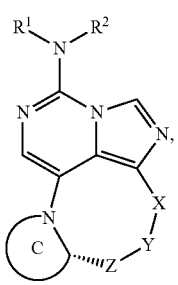

XIII-B wherein $R^1$, $R^2$, X, Y, Z, and

are as defined in connection with Formula I, or a pharmaceutically acceptable salt or solvate thereof.

In another embodiment, Compounds of the Disclosure are compounds of Formula XIV:

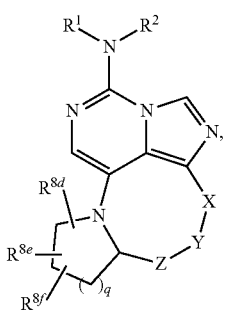

XIV wherein:
$R^{8d}$, $R^{8e}$, and $R^{8f}$ are independently selected from the group consisting of hydrogen and $C_1$-$C_4$ alkyl;
q is 1, 2, or 3; and
$R^1$, $R^2$, X, Y, and Z are as defined in connection with Formula I, or a pharmaceutically acceptable salt or solvate thereof.

In another embodiment, Compounds of the Disclosure are compounds of Formula XIV-A:

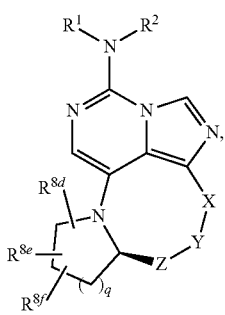

XIV-A wherein $R^1$, $R^2$, $R^{8d}$, $R^{8e}$, $R^{8f}$, q, X, Y, and Z are as defined in connection with Formula XIV, or a pharmaceutically acceptable salt or solvate thereof.

In another embodiment, Compounds of the Disclosure are compounds of Formula XIV-B:

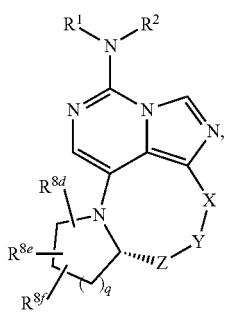

XIV-B wherein $R^1$, $R^2$, $R^{8d}$, $R^{8e}$, $R^{8f}$, q, X, Y, and Z are as defined in connection with Formula XIV, or a pharmaceutically acceptable salt or solvate thereof.

In another embodiment, Compounds of the Disclosure are compounds of Formula XV:

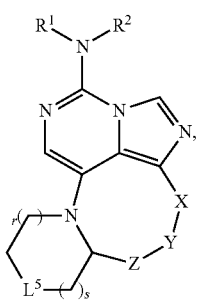

XV wherein:
$L^5$ is selected from the group consisting of —S—, —O—, and —N($R^{8h}$)—;
$R^{8h}$ is selected from the group consisting of hydrogen, $C_1$-$C_4$ alkyl, optionally substituted $C_3$-$C_6$ cycloalkyl, optionally substituted 4- to 8-membered heterocyclo, —C(=O)$R^{14a}$, and —S(=O)$_2$$R^{14b}$;
$R^{14a}$ and $R^{14b}$ are independently selected from the group consisting of $C_1$-$C_6$ alkyl and optionally substituted $C_3$-$C_8$ cycloalkyl;
r is 1, 2, or 3;
s is 1, 2, or 3; and
$R^1$, $R^2$, X, Y, and Z are as defined in connection with Formula I, or a pharmaceutically acceptable salt or solvate thereof.

In another embodiment, Compounds of the Disclosure are compounds of Formula XV-A:

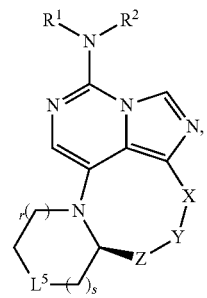

XV-A wherein $R^1$, $R^2$, $L^5$, r, s, X, Y, and Z are as defined in connection with Formula XV, or a pharmaceutically acceptable salt or solvate thereof.

In another embodiment, Compounds of the Disclosure are compounds of Formula XV-B:

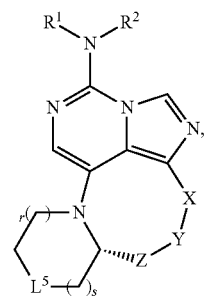

XV-B wherein R¹, R², L⁵, r, s, X, Y, and Z are as defined in connection with Formula XV, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, or XV-B, wherein Z is —CH₂—, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, or XV-B, wherein X is —CH₂—, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, or XV-B, wherein X is —C(=O)—, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, or XV-B, wherein X is —S(=O)₂—, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, or XV-B, wherein Y is —O—, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, or XV-B, wherein Y is —N(R⁷)—, or a pharmaceutically acceptable salt or solvate thereof. In another embodiment, R⁷ is selected from the group consisting of C₁-C₆ alkyl, C₁-C₆ haloalkyl, and optionally substituted C₃-C₈ cycloalkyl, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, or XV-B, wherein Z is —CH₂—, X is —C(=O)—, and Y is —N(R⁷)—, or a pharmaceutically acceptable salt or solvate thereof. In another embodiment, R⁷ is selected from the group consisting of C₁-C₆ alkyl, C₁-C₆ haloalkyl, and optionally substituted C₃-C₈ cycloalkyl. In another embodiment, R⁷ is C₁-C₄ alkyl. In another embodiment, R⁷ is selected from the group consisting of methyl, ethyl, propyl, or isopropyl.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, or XV-B, wherein X-Y taken together form an optionally substituted fused 5- or 6-membered heteroaryl, or a pharmaceutically acceptable salt or solvate thereof. In another embodiment, X and Y taken together form a 5-membered heteroarylenyl.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, or XV-B, wherein X and Y taken together form a 5-membered heteroarylenyl of Formula I-D:

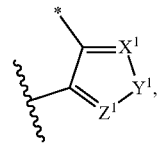

wherein:
 X¹ is selected from the group consisting of =CR¹⁵ᵃ— and =N—;
 Y¹ is selected from the group consisting of —O—, —S—, and —NR¹⁵ᶜ—;
 Z¹ is selected from the group consisting of =CR¹⁵ᵇ— and =N—;
 R¹⁵ᵃ and R¹⁵ᵇ are independently selected from the group consisting of hydrogen, C₁-C₄ alkyl, C₁-C₄ haloalkyl, and C₃-C₆ cycloalkyl;
 R¹⁵ᶜ is selected from the group consisting of hydrogen, C₁-C₄ alkyl, and C₃-C₆ cycloalkyl; and
 the bond designated with a " ⌇ " is attached to Z, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, or XV-B, wherein X and Y taken together form a 5-membered heteroarylenyl of Formula I-E:

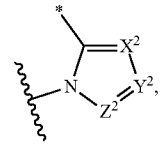

wherein:
 X² is selected from the group consisting of =CR¹⁶ᵃ— and =N—;
 Y² is selected from the group consisting of =CR¹⁶ᵇ— and =N—;
 Z² is selected from the group consisting of =CR¹⁶ᵇ— and =N—; and
 R¹⁶ᵃ, R¹⁶ᵇ, and R¹⁶ᶜ are independently selected from the group consisting of hydrogen, C₁-C₄ alkyl, and C₃-C₆ cycloalkyl; and
 the bond designated with a " ⌇ " is attached to Z, or a pharmaceutically acceptable salt or solvate thereof In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, or XV-B, wherein X and Y taken together form a 5-membered heteroarylenyl selected from the group consisting of:

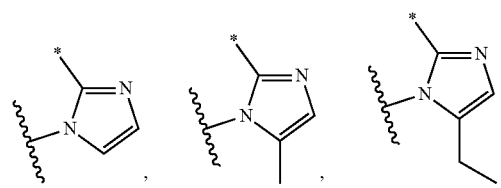

-continued

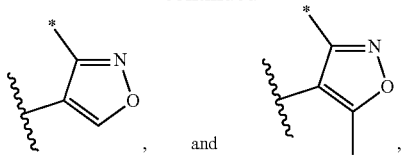, and , wherein the bond designated with a " ⁓ " is attached to Z, or a pharmaceutically acceptable salt or solvate thereof.

In another embodiment, Compounds of the Disclosure are compounds of Formula XVI:

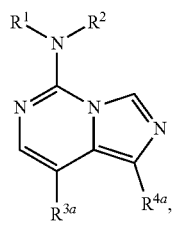

XVI wherein $R^1$, $R^2$, $R^{3a}$, and $R^{4a}$ are as defined in connection with Formula I, or a pharmaceutically acceptable salt or solvate thereof.

In another embodiment, Compounds of the Disclosure are compounds of Formula XVI, wherein $R^{3a}$ is optionally substituted phenyl, or a pharmaceutically acceptable salt or solvate thereof.

In another embodiment, Compounds of the Disclosure are compounds of Formula XVI, wherein $R^{3a}$ is optionally substituted 5-membered heteroaryl, or a pharmaceutically acceptable salt or solvate thereof.

In another embodiment, Compounds of the Disclosure are compounds of Formula XVI, wherein $R^{3a}$ is optionally substituted 6-membered heteroaryl, or a pharmaceutically acceptable salt or solvate thereof. In another embodiment, $R^{3a}$ is selected from the group consisting of:

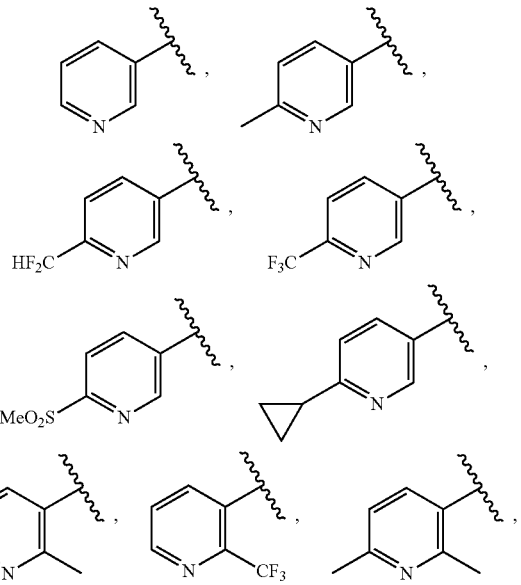

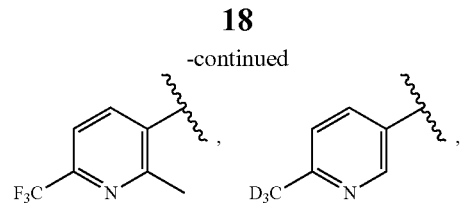

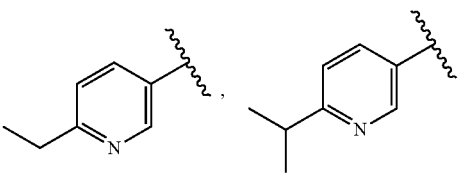

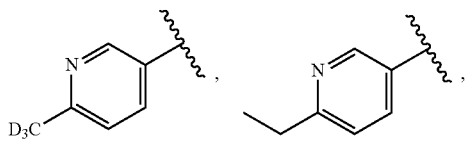

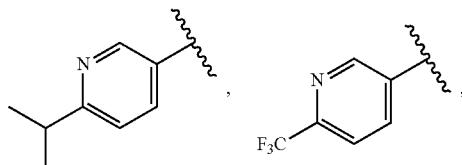

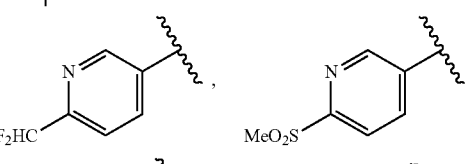

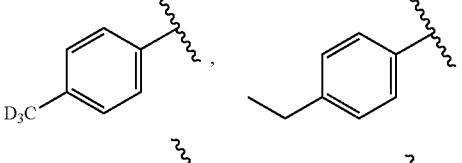

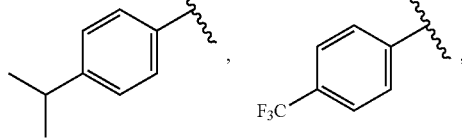

and .

In another embodiment, Compounds of the Disclosure are compounds of Formula XVI, wherein $R^{3a}$ is selected from the group consisting of:

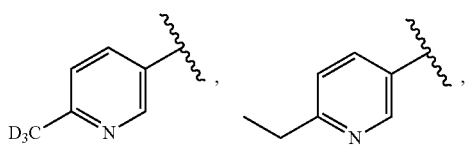

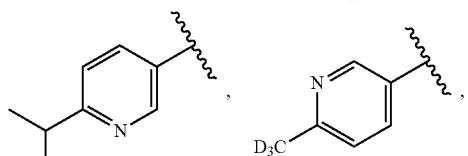

-continued

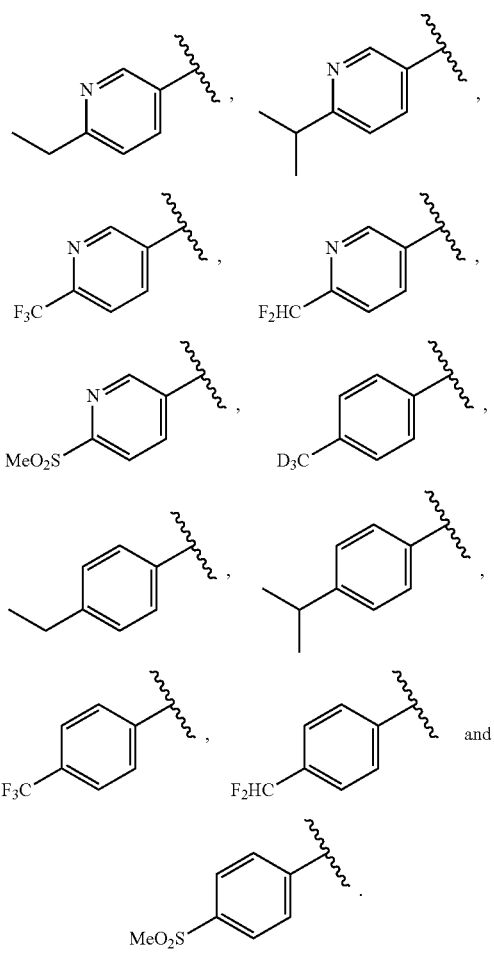

In another embodiment, Compounds of the Disclosure are compounds of Formula XVI, wherein $R^{3a}$ is selected from the group consisting of:

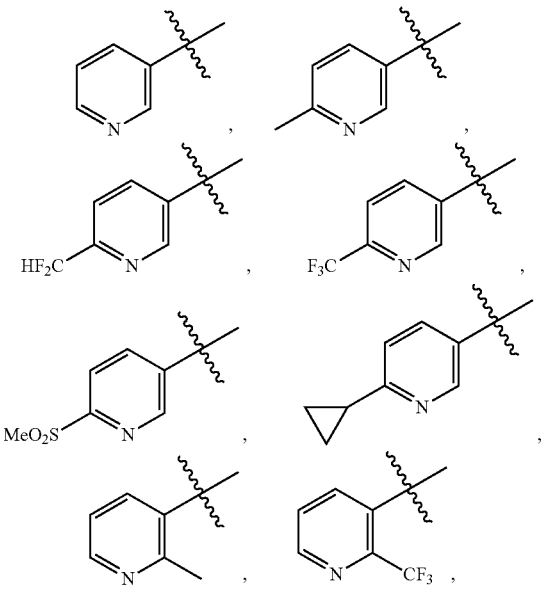

-continued

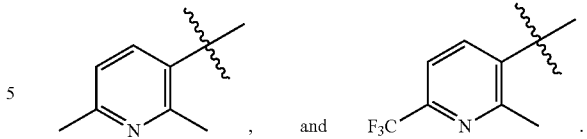

In another embodiment, Compounds of the Disclosure are compounds of Formula XVI, wherein $R^{3a}$ is optionally substituted 4- to 6-membered heterocyclo, or a pharmaceutically acceptable salt or solvate thereof.

In another embodiment, Compounds of the Disclosure are compounds of Formula XVI, wherein $R^{4a}$ is $C_1$-$C_4$ haloalkyl, or a pharmaceutically acceptable salt or solvate thereof.

In another embodiment, Compounds of the Disclosure are compounds of Formula XVI, wherein $R^{4a}$ is —S(=O)$_2$R$^9$, or a pharmaceutically acceptable salt or solvate thereof.

In another embodiment, Compounds of the Disclosure are compounds of Formula XVI, wherein $R^{4a}$ is —P(=O)(R$^{10a}$)(R$^{10b}$), or a pharmaceutically acceptable salt or solvate thereof.

In another embodiment, Compounds of the Disclosure are compounds of Formula XVI, wherein $R^{4a}$ is —C(=O)OR$^{11a}$, or a pharmaceutically acceptable salt or solvate thereof. In another embodiment, $R^{11a}$ is hydrogen.

In another embodiment, Compounds of the Disclosure are compounds of Formula XVI, wherein $R^{4a}$ is —C(=O)NR$^{11b}$R$^{11c}$, or a pharmaceutically acceptable salt or solvate thereof.

In another embodiment, Compounds of the Disclosure are compounds of Formula XVI, wherein $R^{4a}$ is —S(=O)(=NR$^{13a}$)R$^{13b}$, or a pharmaceutically acceptable salt or solvate thereof. In another embodiment, $R^{13a}$ is selected from the group consisting of hydrogen and $C_1$-$C_4$ alkyl and $R^{13b}$ is $C_1$-$C_4$ alkyl. In another embodiment, $R^{13a}$ and $R^{13b}$ taken together form a 6-membered heterocyclo, e.g.,

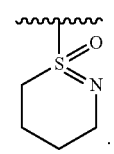

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, XV-B, or XVI, wherein $R^2$ is hydrogen, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, XV-B, or XVI, wherein:

$R^1$ is $R^1$-1:

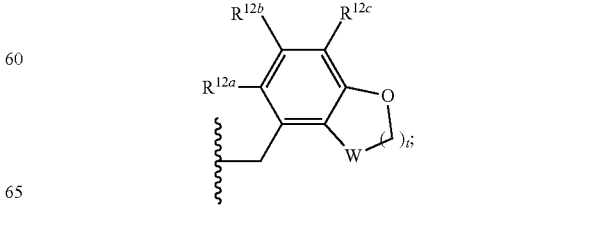

$R^{12a}$, $R^{12b}$, and $R^{12c}$ are each independently selected from the group consisting of hydrogen, halo, $C_1$-$C_4$ alkyl, $C_1$-$C_4$ haloalkyl, and $C_1$-$C_4$ alkoxy;

W is selected from the group consisting of —$CH_2$— and —C(=O)—; and t is 1 or 2, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, XV-B, or XVI, wherein $R^1$ is $R^1$-1, $R^{12a}$ is fluoro; and $R^{12b}$ and $R^{12c}$ are independently selected from the group consisting of hydrogen and fluoro. In another embodiment, $R^{12a}$ is fluoro; and $R^{12b}$ and $R^{12c}$ are hydrogen.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, XV-B, or XVI, wherein:

$R^1$ is $R^1$-2:

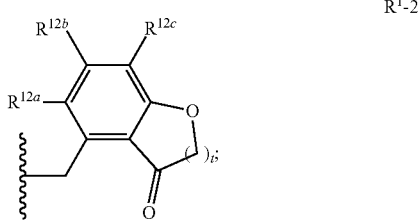

$R^{12a}$, $R^{12b}$, and $R^{12c}$ are each independently selected from the group consisting of hydrogen, halo, $C_1$-$C_4$ alkyl, $C_1$-$C_4$ haloalkyl, and $C_1$-$C_4$ alkoxy; and t is 1 or 2, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, XV-B, or XVI, wherein $R^1$ is $R^1$-2, $R^{12a}$ is fluoro; and $R^{12b}$ and $R^{12c}$ are independently selected from the group consisting of hydrogen and fluoro. In another embodiment, $R^{12a}$ is fluoro; and $R^{12b}$ and $R^{12c}$ are hydrogen.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, XV-B, or XVI, wherein:

$R^1$ is $R^1$-3:

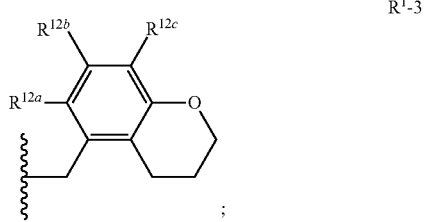

and $R^{12a}$, $R^{12b}$, and $R^{12c}$ are each independently selected from the group consisting of hydrogen, halo, $C_1$-$C_4$ alkyl, $C_1$-$C_4$ haloalkyl, and $C_1$-$C_4$ alkoxy, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, XV-B, or XVI, wherein $R^1$ is $R^1$-3, $R^{12a}$ is fluoro; and $R^{12b}$ and $R^{12c}$ are independently selected from the group consisting of hydrogen and fluoro. In another embodiment, $R^{12a}$ is fluoro; and $R^{12b}$ and $R^{12c}$ are hydrogen.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, XV-B, or XVI, wherein:

$R^1$ is $R^1$-4:

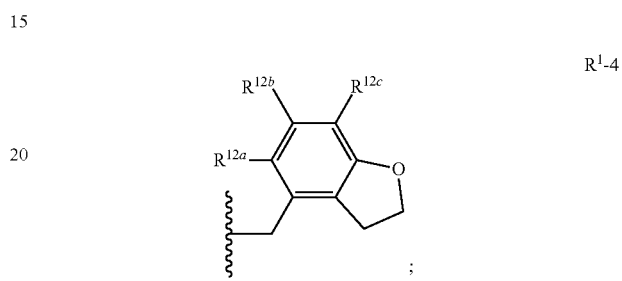

and $R^{12a}$, $R^{12b}$, and $R^{12c}$ are each independently selected from the group consisting of hydrogen, halo, $C_1$-$C_4$ alkyl, $C_1$-$C_4$ haloalkyl, and $C_1$-$C_4$ alkoxy, or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, XV-B, or XVI, wherein $R^1$ is $R^1$-4, $R^{12a}$ is fluoro; and $R^{12b}$ and $R^{12c}$ are independently selected from the group consisting of hydrogen and fluoro. In another embodiment, $R^{12a}$ is fluoro; and $R^{12b}$ and $R^{12c}$ are hydrogen.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, XV-B, or XVI, wherein $R^1$ is selected from the group consisting of:

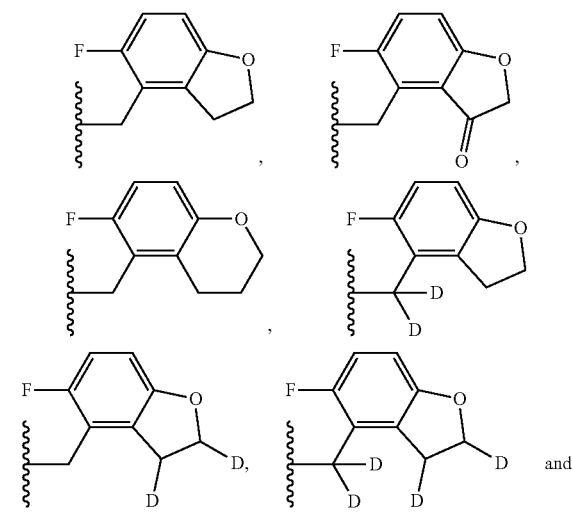

-continued

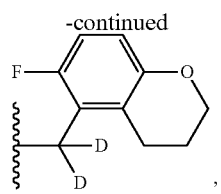

or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, XV-B, or XVI, wherein $R^1$ is selected from the group consisting of:

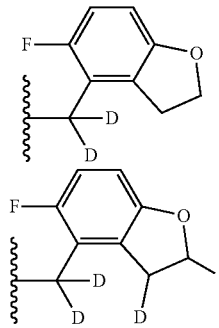
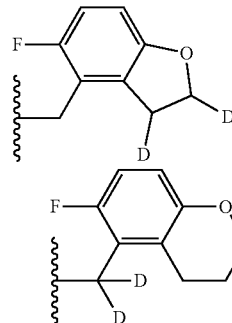
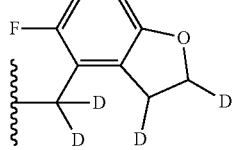
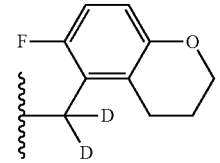

or a pharmaceutically acceptable salt or solvate thereof.

In another embodiment, Compounds of the Disclosure are compounds of any one of Formulae I-XI, XI-A, XI-B, XII, XII-A, XII-B, XIII, XIII-A, XIII-B, XIV, XIV-A, XIV-B, XV, XV-A, XV-B, or XVI, wherein $R^1$ is selected from the group consisting of:

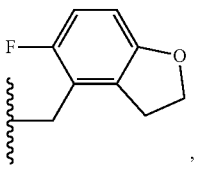
, 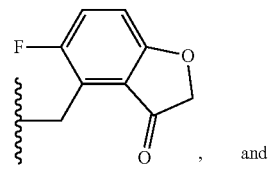
, and

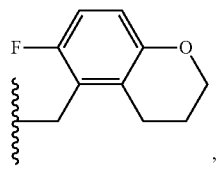

, or a pharmaceutically acceptable salt or solvate thereof.

In another embodiment, Compounds of the Disclosure are any one or more of the compounds listed in Table 1, or a pharmaceutically acceptable salt or solvate thereof.

TABLE 1

| Cpd. No. | Structure | Name |
|---|---|---|
| 1 | 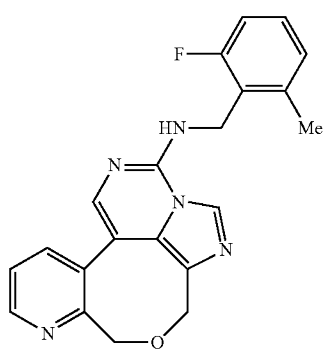 [SMILES: Cc1cccc(F)c1CNc1ncc2c3c(ncn13)COCc1ncccc1-2] | N-(2-fluoro-6-methylbenzyl)-3H,5H-4-oxa-2,6,11,12a-tetraazabenzo[4,5]cycloocta[1,2,3-cd]inden-12-amine |
| 2 | 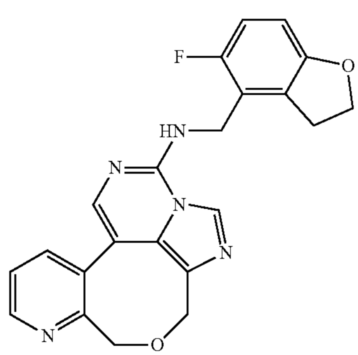 [SMILES: Fc1ccc2c(c1CNc1ncc3c4c(ncn14)COCc1ncccc1-3)CCO2] | N-((5-fluoro-2,3-dihydrobenzofuran-4-yl)methyl)-3H,5H-4-oxa-2,6,11,12a-tetraazabenzo[4,5]cycloocta[1,2,3-cd]inden-12-amine |

TABLE 1-continued

| Cpd. No. | Structure | Name |
| --- | --- | --- |
| 3 | 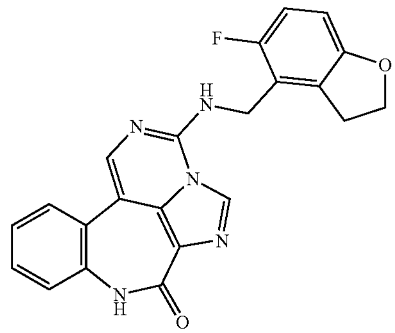 [SMILES: O=C1Nc2ccccc2-c2cnc(NCc3c(F)ccc4c3CCO4)n3cnc1c23] | 11-(((5-fluoro-2,3-dihydrobenzofuran-4-yl)methyl)amino)-2,4,10,11a-tetraazadibenzo[cd,f]azulen-3(4H)-one |
| 4 | 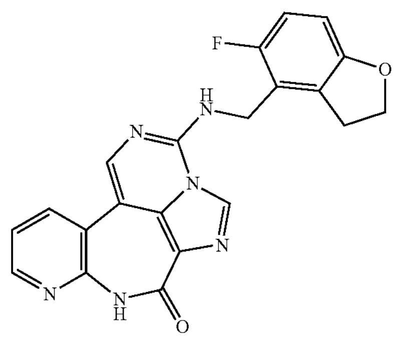 [SMILES: O=C1Nc2ncccc2-c2cnc(NCc3c(F)ccc4c3CCO4)n3cnc1c23] | 11-(((5-fluoro-2,3-dihydrobenzofuran-4-yl)methyl)amino)-2,4,5,10,11a-pentaazadibenzo[cd,f]azulen-3(4H)-one |
| 5 | 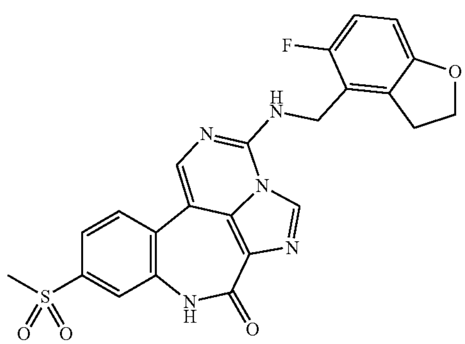 [SMILES: CS(=O)(=O)c1ccc2c(c1)NC(=O)c1ncn3c(NCc4c(F)ccc5c4CCO5)ncc-2c13] | 11-(((5-fluoro-2,3-dihydrobenzofuran-4-yl)methyl)amino)-6-(methylsulfonyl)-2,4,10,11a-tetraazadibenzo[cd,f]azulen-3(4H)-one |
| 6 | 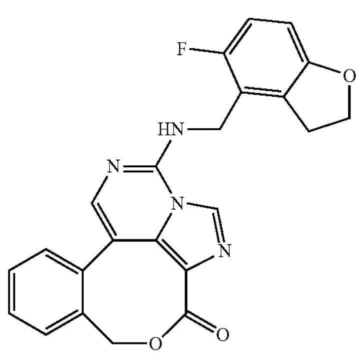 [SMILES: O=C1OCc2ccccc2-c2cnc(NCc3c(F)ccc4c3CCO4)n3cnc1c23] | 12-(((5-fluoro-2,3-dihydrobenzofuran-4-yl)methyl)amino)-3H,5H-4-oxa-2,11,12a-triazabenzo[4,5]cycloocta[1,2,3-cd]inden-3-one |

TABLE 1-continued

| Cpd. No. | Structure | Name |
|---|---|---|
| 7 | 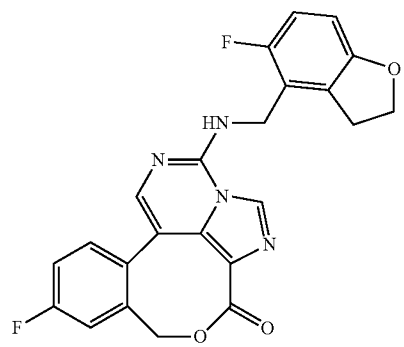 [SMILES: O=C1OCc2cc(F)ccc2-c2cnc(NCc3c(F)ccc4c3CCO4)n3cnc1c23] | 7-fluoro-12-(((5-fluoro-2,3-dihydrobenzofuran-4-yl)methyl)amino)-3H,5H-4-oxa-2,11,12a-triazabenzo[4,5]cycloocta[1,2,3-cd]inden-3-one |
| 8 | 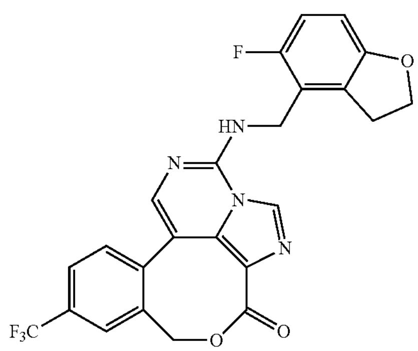 [SMILES: O=C1OCc2cc(C(F)(F)F)ccc2-c2cnc(NCc3c(F)ccc4c3CCO4)n3cnc1c23] | 12-(((5-fluoro-2,3-dihydrobenzofuran-4-yl)methyl)amino)-7-(trifluoromethyl)-3H,5H-4-oxa-2,11,12a-triazabenzo[4,5]cycloocta[1,2,3-cd]inden-3-one |
| 9 | 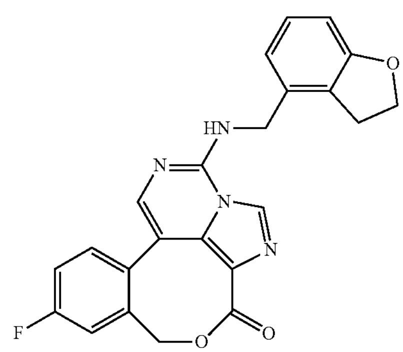 [SMILES: O=C1OCc2cc(F)ccc2-c2cnc(NCc3cccc4c3CCO4)n3cnc1c23] | 12-(((2,3-dihydrobenzofuran-4-yl)methyl)amino)-7-fluoro-3H,5H-4-oxa-2,11,12a-triazabenzo[4,5]cycloocta[1,2,3-cd]inden-3-one |
| 10 | 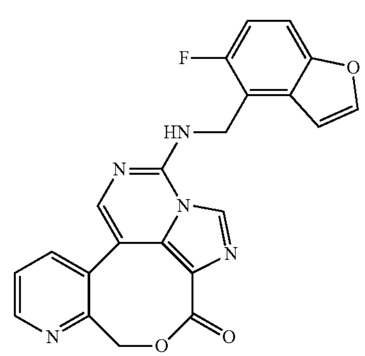 [SMILES: O=C1OCc2ncccc2-c2cnc(NCc3c(F)ccc4occc34)n3cnc1c23] | 12-(((5-fluorobenzofuran-4-yl)methyl)amino)-3H,5H-4-oxa-2,6,11,12a-tetraazabenzo[4,5]cycloocta[1,2,3-cd]inden-3-one |

TABLE 1-continued

| Cpd. No. | Structure | Name |
|---|---|---|
| 11 | 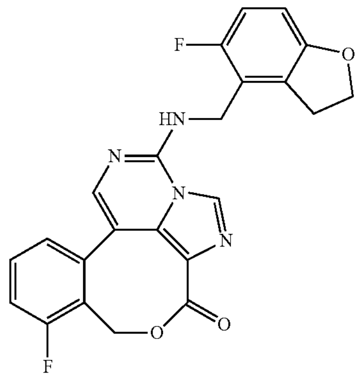 [SMILES: O=C1OCc2c(F)cccc2-c2cnc(NCc3c(F)ccc4c3CCO4)n3cnc1c23] | 6-fluoro-12-(((5-fluoro-2,3-dihydrobenzofuran-4-yl)methyl)amino)-3H,5H-4-oxa-2,11,12a-triazabenzo[4,5]cycloocta[1,2,3-cd]inden-3-one |
| 12 | 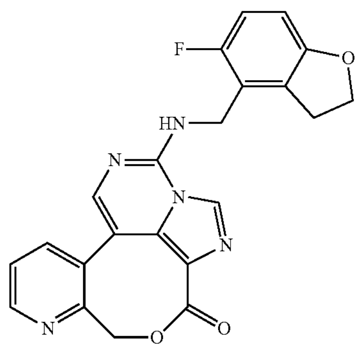 [SMILES: O=C1OCc2ncccc2-c2cnc(NCc3c(F)ccc4c3CCO4)n3cnc1c23] | 12-(((5-fluoro-2,3-dihydrobenzofuran-4-yl)methyl)amino)-3H,5H-4-oxa-2,6,11,12a-tetraazabenzo[4,5]cycloocta[1,2,3-cd]inden-3-one |
| 13 | 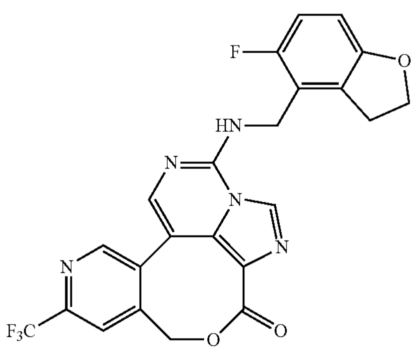 [SMILES: O=C1OCc2cc(C(F)(F)F)ncc2-c2cnc(NCc3c(F)ccc4c3CCO4)n3cnc1c23] | 12-(((5-fluoro-2,3-dihydrobenzofuran-4-yl)methyl)amino)-7-(trifluoromethyl)-3H,5H-4-oxa-2,8,11,12a-tetraazabenzo[4,5]cycloocta[1,2,3-cd]inden-3-one |
| 14 | 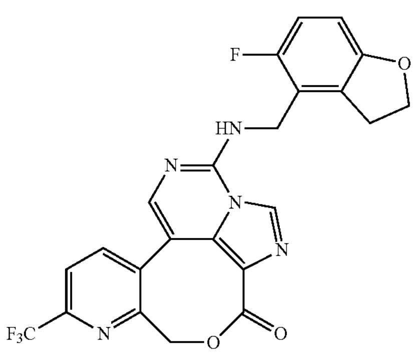 | 12-(((5-fluoro-2,3-dihydrobenzofuran-4-yl)methyl)amino)-7-(trifluoromethyl)-3H,5H-4-oxa-2,6,11,12a-tetraazabenzo[4,5]cycloocta[1,2,3-cd]inden-3-one |

TABLE 1-continued

| Cpd. No. | Structure | Name |
|---|---|---|
| 15 | 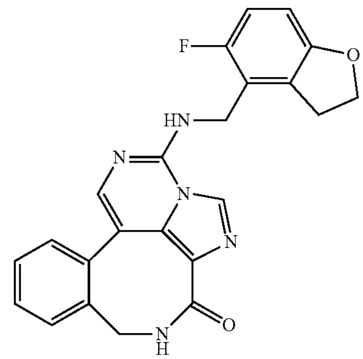 [SMILES: O=C1NCc2ccccc2-c2cnc(NCc3c(F)ccc4c3CCO4)n3cnc1c23] | 12-(((5-fluoro-2,3-dihydrobenzofuran-4-yl)methyl)amino)-4,5-dihydro-3H-2,4,11,12a-tetraazabenzo[4,5]cycloocta[1,2,3-cd]inden-3-one |
| 16 | 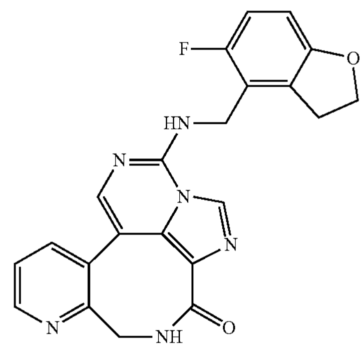 [SMILES: O=C1NCc2ncccc2-c2cnc(NCc3c(F)ccc4c3CCO4)n3cnc1c23] | 12-(((5-fluoro-2,3-dihydrobenzofuran-4-yl)methyl)amino)-4,5-dihydro-3H-2,4,6,11,12a-pentaazabenzo[4,5]cycloocta[1,2,3-cd]inden-3-one |
| 17 | 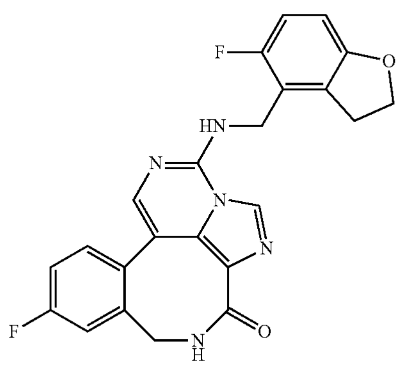 [SMILES: O=C1NCc2cc(F)ccc2-c2cnc(NCc3c(F)ccc4c3CCO4)n3cnc1c23] | 7-fluoro-12-(((5-fluoro-2,3-dihydrobenzofuran-4-yl)methyl)amino)-4,5-dihydro-3H-2,4,11,12a-tetraazabenzo[4,5]cycloocta[1,2,3-cd]inden-3-one |
| 18 | 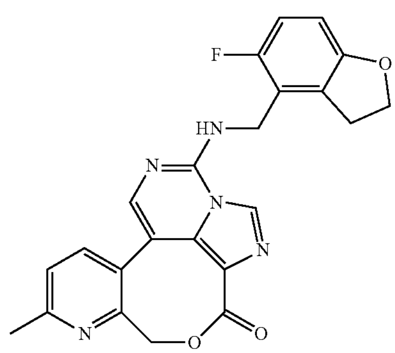 [SMILES: Cc1ccc2c(n1)COC(=O)c1ncn3c(NCc4c(F)ccc5c4CCO5)ncc-2c13] | 12-(((5-fluoro-2,3-dihydrobenzofuran-4-yl)methyl)amino)-7-methyl-3H,5H-4-oxa-2,6,11,12a-tetraazabenzo[4,5]cycloocta[1,2,3-cd]inden-3-one |

TABLE 1-continued

| Cpd. No. | Structure | Name |
| --- | --- | --- |
| 19 | 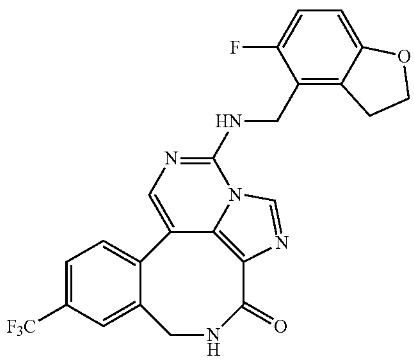 [SMILES: O=C1NCc2cc(C(F)(F)F)ccc2-c2cnc(NCc3c(F)ccc4c3CCO4)n3cnc1c23] | 12-(((5-fluoro-2,3-dihydrobenzofuran-4-yl)methyl)amino)-7-(trifluoromethyl)-4,5-dihydro-3H-2,4,11,12a-tetraazabenzo[4,5]cycloocta[1,2,3-cd]inden-3-one |
| 20 | 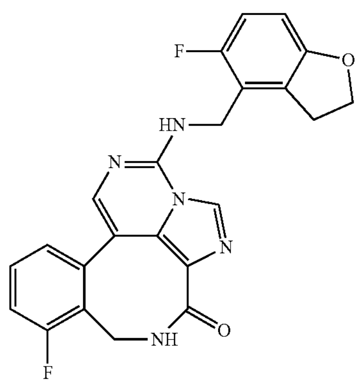 [SMILES: O=C1NCc2c(F)cccc2-c2cnc(NCc3c(F)ccc4c3CCO4)n3cnc1c23] | 6-fluoro-12-(((5-fluoro-2,3-dihydrobenzofuran-4-yl)methyl)amino)-4,5-dihydro-3H-2,4,11,12a-tetraazabenzo[4,5]cycloocta[1,2,3-cd]inden-3-one |
| 21 | 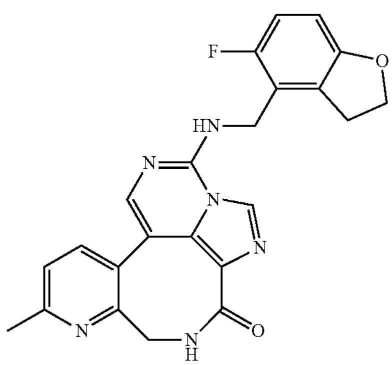 [SMILES: Cc1ccc2c(n1)CNC(=O)c1ncn3c(NCc4c(F)ccc5c4CCO5)ncc-2c13] | 12-(((5-fluoro-2,3-dihydrobenzofuran-4-yl)methyl)amino)-7-methyl-4,5-dihydro-3H-2,4,6,11,12a-pentaazabenzo[4,5]cycloocta[1,2,3-cd]inden-3-one |
| 22 | 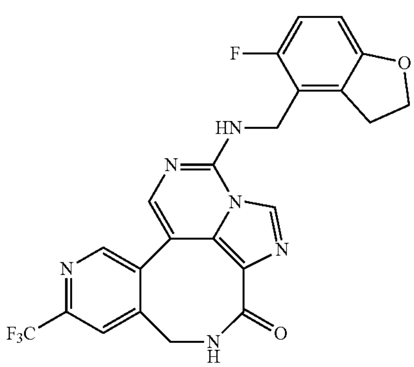 [SMILES: O=C1NCc2cc(C(F)(F)F)ncc2-c2cnc(NCc3c(F)ccc4c3CCO4)n3cnc1c23] | 12-(((5-fluoro-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one |

TABLE 1-continued

| Cpd. No. | Structure | Name |
|---|---|---|
| 23 | 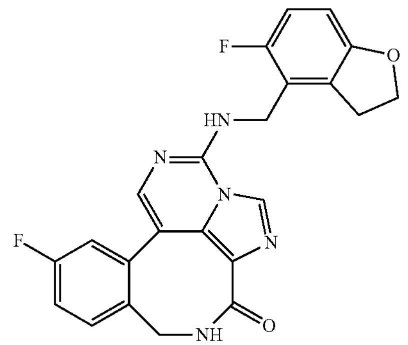 [SMILES: O=C1NCc2ccc(F)cc2-c2cnc(NCc3c(F)ccc4c3CCO4)n3cnc1c23] | 8-fluoro-12-(((5-fluoro-2,3-dihydrobenzofuran-4-yl)methyl)amino)-4,5-dihydro-3H-2,4,11,12a-tetraazabenzo[4,5]cycloocta[1,2,3-cd]inden-3-one |
| 24 | 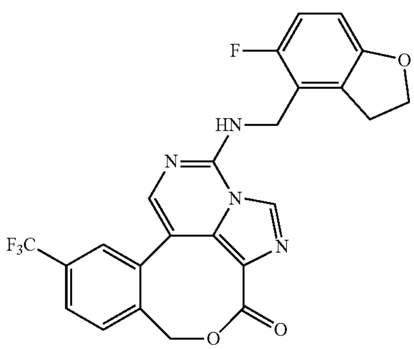 [SMILES: O=C1OCc2ccc(C(F)(F)F)cc2-c2cnc(NCc3c(F)ccc4c3CCO4)n3cnc1c23] | 12-(((5-fluoro-2,3-dihydrobenzofuran-4-yl)methyl)amino)-8-(trifluoromethyl)-3H,5H-4-oxa-2,11,12a-triazabenzo[4,5]cycloocta[1,2,3-cd]inden-3-one |
| 25 | 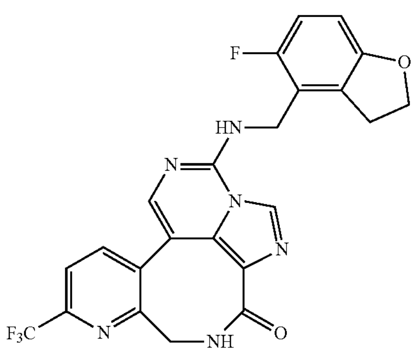 [SMILES: O=C1NCc2nc(C(F)(F)F)ccc2-c2cnc(NCc3c(F)ccc4c3CCO4)n3cnc1c23] | 12-(((5-fluoro-2,3-dihydrobenzofuran-4-yl)methyl)amino)-7-(trifluoromethyl)-4,5-dihydro-3H-2,4,6,11,12a-pentaazabenzo[4,5]cycloocta[1,2,3-cd]inden-3-one |
| 26 | 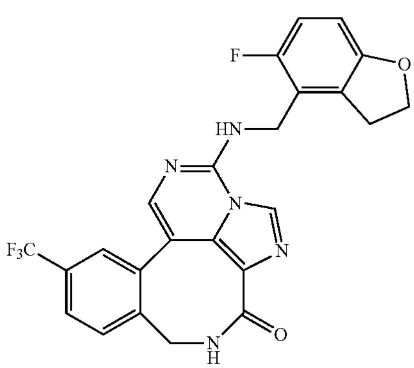 [SMILES: O=C1NCc2ccc(C(F)(F)F)cc2-c2cnc(NCc3c(F)ccc4c3CCO4)n3cnc1c23] | 12-(((5-fluoro-2,3-dihydrobenzofuran-4-yl)methyl)amino)-8-(trifluoromethyl)-4,5-dihydro-3H-2,4,11,12a-tetraazabenzo[4,5]cycloocta[1,2,3-cd]inden-3-one |

TABLE 1-continued

| Cpd. No. | Structure | Name |
|---|---|---|
| 27 | 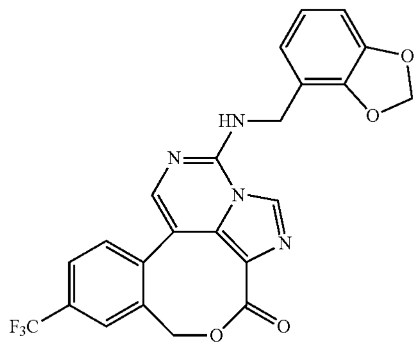 [SMILES: O=C1OCc2cc(C(F)(F)F)ccc2-c2cnc(NCc3cccc4c3OCO4)n3cnc1c23] | 12-((benzo[d][1,3]dioxol-4-ylmethyl)amino)-7-(trifluoromethyl)-3H,5H-4-oxa-2,11,12a-triazabenzo[4,5]cycloocta[1,2,3-cd]inden-3-one |
| 28 | 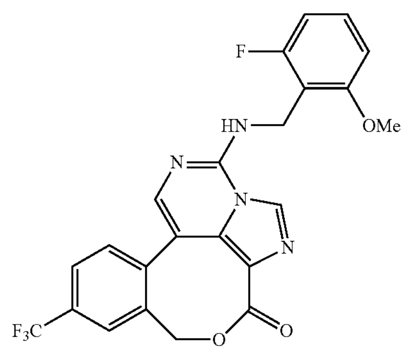 [SMILES: COc1cccc(F)c1CNc1ncc2c3c(ncn13)C(=O)OCc1cc(C(F)(F)F)ccc1-2] | 12-((2-fluoro-6-methoxybenzyl)amino)-7-(trifluoromethyl)-3H,5H-4-oxa-2,11,12a-triazabenzo[4,5]cycloocta[1,2,3-cd]inden-3-one |
| 29 | 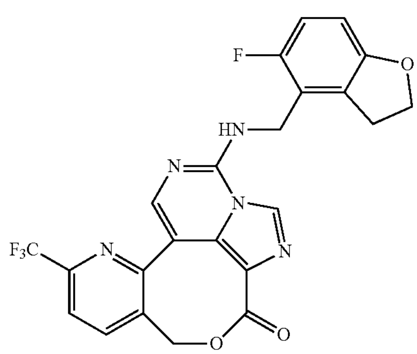 [SMILES: O=C1OCc2ccc(C(F)(F)F)nc2-c2cnc(NCc3c(F)ccc4c3CCO4)n3cnc1c23] | 12-(((5-fluoro-2,3-dihydrobenzofuran-4-yl)methyl)amino)-8-(trifluoromethyl)-3H,5H-4-oxa-2,9,11,12a-tetraazabenzo[4,5]cycloocta[1,2,3-cd]inden-3-one |
| 30 | 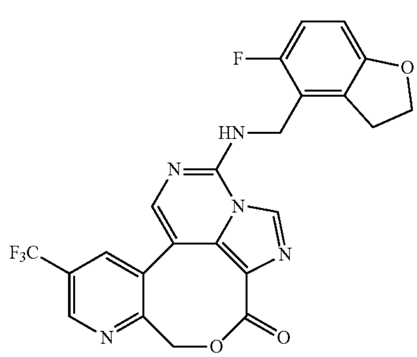 [SMILES: O=C1OCc2ncc(C(F)(F)F)cc2-c2cnc(NCc3c(F)ccc4c3CCO4)n3cnc1c23] | 12-(((5-fluoro-2,3-dihydrobenzofuran-4-yl)methyl)amino)-8-(trifluoromethyl)-3H,5H-4-oxa-2,6,11,12a-tetraazabenzo[4,5]cycloocta[1,2,3-cd]inden-3-one |

TABLE 1-continued

| Cpd. No. | Structure | Name |
|---|---|---|
| 31 | 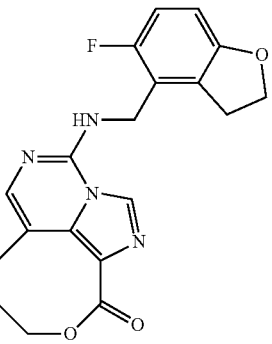 | 12-(((5-fluoro-2,3-dihydrobenzofuran-4-yl)methyl)amino)-7-(trifluoromethoxy)-3H,5H-4-oxa-2,11,12a-triazabenzo[4,5]cycloocta[1,2,3-cd]inden-3-one |
| 32 | 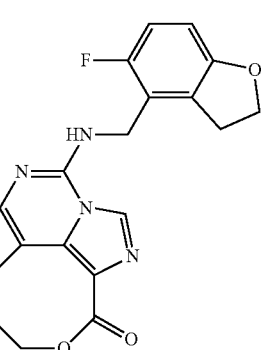 | 12-(((5-fluoro-2,3-dihydrobenzofuran-4-yl)methyl)amino)-8-(trifluoromethyl)-3H,5H-4-oxa-2,7,11,12a-tetraazabenzo[4,5]cycloocta[1,2,3-cd]inden-3-one |
| 33 | 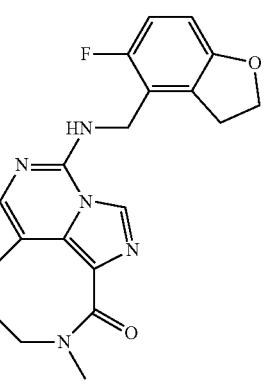 | 12-(((5-fluoro-2,3-dihydrobenzofuran-4-yl)methyl)amino)-4-methyl-7-(trifluoromethyl)-4,5-dihydro-3H-2,4,6,11,12a-pentaazabenzo[4,5]cycloocta[1,2,3-cd]inden-3-one |
| 34 | 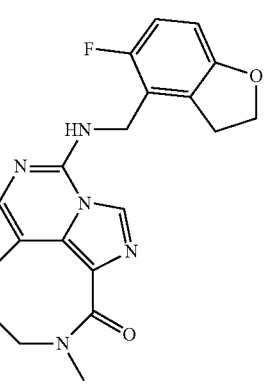 | 12-(((5-fluoro-2,3-dihydrobenzofuran-4-yl)methyl)amino)-4-methyl-7-(trifluoromethyl)-4,5-dihydro-3H-2,4,8,11,12a-pentaazabenzo[4,5]cycloocta[1,2,3-cd]inden-3-one |

TABLE 1-continued

| Cpd. No. | Structure | Name |
|---|---|---|
| 35 | 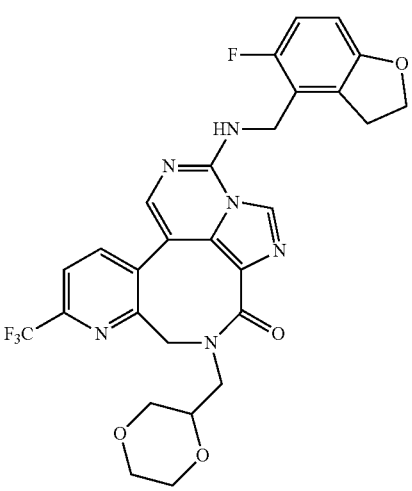 [SMILES: O=C1c2ncn3c(NCc4c(F)ccc5c4CCO5)ncc(c23)-c2ccc(C(F)(F)F)nc2CN1CC1COCCO1] | 4-((1,4-dioxan-2-yl)methyl)-12-(((5-fluoro-2,3-dihydrobenzofuran-4-yl)methyl)amino)-7-(trifluoromethyl)-4,5-dihydro-3H-2,4,6,11,12a-pentaazabenzo[4,5]cycloocta[1,2,3-cd]inden-3-one |
| 36 | 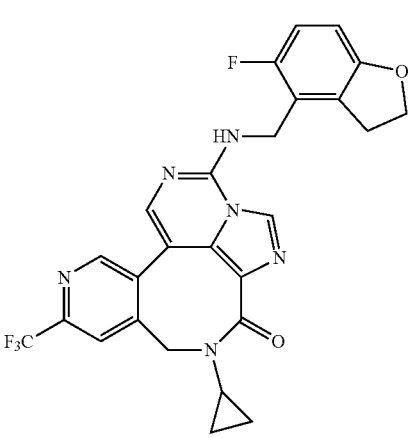 | 4-cyclopropyl-12-(((5-fluoro-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one |
| 37 | 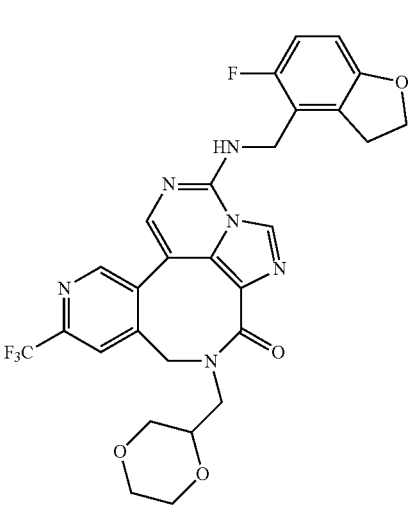 [SMILES: O=C1c2ncn3c(NCc4c(F)ccc5c4CCO5)ncc(c23)-c2cnc(C(F)(F)F)cc2CN1CC1COCCO1] | 4-((1,4-dioxan-2-yl)methyl)-12-(((5-fluoro-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one |

TABLE 1-continued

| Cpd. No. | Structure | Name |
|---|---|---|
| 38 | 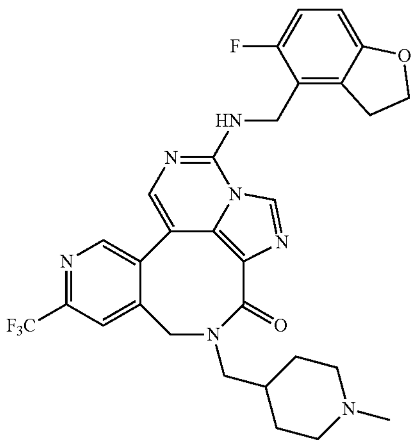 [SMILES: CN1CCC(CN2Cc3cc(C(F)(F)F)ncc3-c3cnc(NCc4c(F)ccc5c4CCO5)n4cnc(c34)C2=O)CC1] | 12-(((5-fluoro-2,3-dihydrobenzofuran-4-yl)methyl)amino)-4-((1-methylpiperidin-4-yl)methyl)-7-(trifluoromethyl)-4,5-dihydro-3H-2,4,8,11,12a-pentaazabenzo[4,5]cycloocta[1,2,3-cd]inden-3-one |
| 39 | 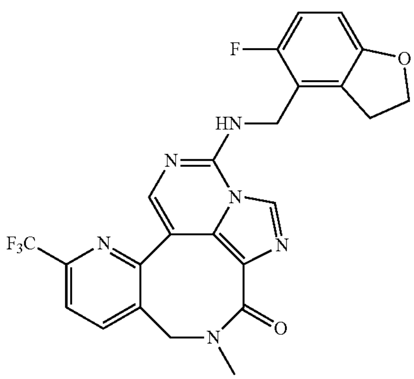 [SMILES: CN1Cc2ccc(C(F)(F)F)nc2-c2cnc(NCc3c(F)ccc4c3CCO4)n3cnc(c23)C1=O] | 12-(((5-fluoro-2,3-dihydrobenzofuran-4-yl)methyl)amino)-4-methyl-8-(trifluoromethyl)-4,5-dihydro-3H-2,4,9,11,12a-pentaazabenzo[4,5]cycloocta[1,2,3-cd]inden-3-one |
| 40 | 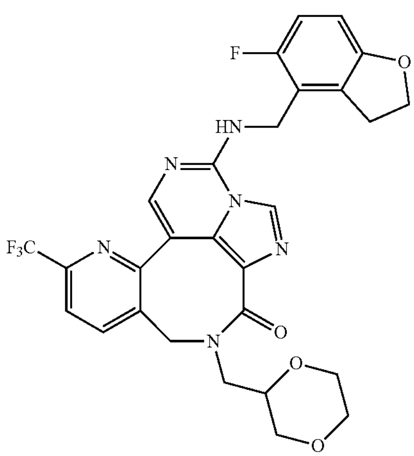 [SMILES: O=C1c2ncn3c(NCc4c(F)ccc5c4CCO5)ncc(c23)-c2nc(C(F)(F)F)ccc2CN1CC1COCCO1] | 4-((1,4-dioxan-2-yl)methyl)-12-(((5-fluoro-2,3-dihydrobenzofuran-4-yl)methyl)amino)-8-(trifluoromethyl)-4,5-dihydro-3H-2,4,9,11,12a-pentaazabenzo[4,5]cycloocta[1,2,3-cd]inden-3-one |

TABLE 1-continued

| Cpd. No. | Structure | Name |
|---|---|---|
| 41 | 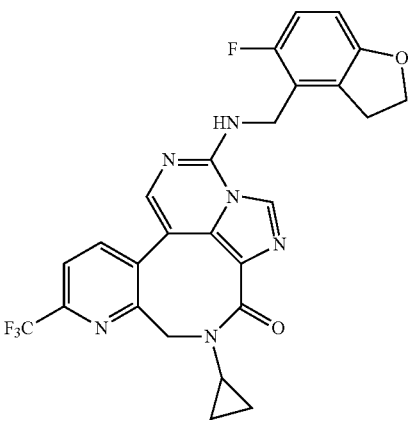 [SMILES: O=C1c2ncn3c(NCc4c(F)ccc5c4CCO5)ncc(c23)-c2ccc(C(F)(F)F)nc2CN1C1CC1] | 4-cyclopropyl-12-(((5-fluoro-2,3-dihydrobenzofuran-4-yl)methyl)amino)-7-(trifluoromethyl)-4,5-dihydro-3H-2,4,6,11,12a-pentaazabenzo[4,5]cycloocta[1,2,3-cd]inden-3-one |
| 42 | 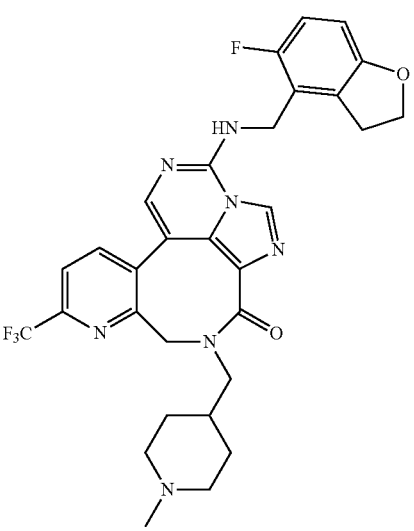 [SMILES: CN1CCC(CN2Cc3nc(C(F)(F)F)ccc3-c3cnc(NCc4c(F)ccc5c4CCO5)n4cnc(c34)C2=O)CC1] | 12-(((5-fluoro-2,3-dihydrobenzofuran-4-yl)methyl)amino)-4-((1-methylpiperidin-4-yl)methyl)-7-(trifluoromethyl)-4,5-dihydro-3H-2,4,6,11,12a-pentaazabenzo[4,5]cycloocta[1,2,3-cd]inden-3-one |
| 43 | 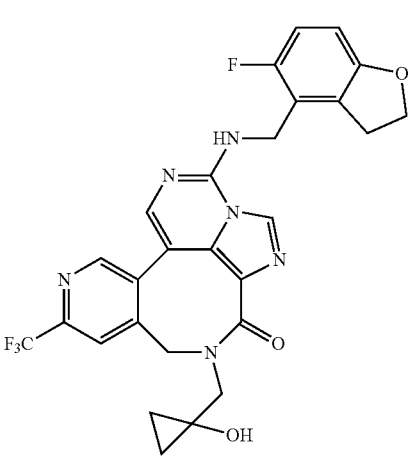 [SMILES: O=C1c2ncn3c(NCc4c(F)ccc5c4CCO5)ncc(c23)-c2cnc(C(F)(F)F)cc2CN1CC1(O)CC1] | 12-(((5-fluoro-2,3-dihydrobenzofuran-4-yl)methyl)amino)-4-((1-hydroxycyclopropyl)methyl)-7-(trifluoromethyl)-4,5-dihydro-3H-2,4,8,11,12a-pentaazabenzo[4,5]cycloocta[1,2,3-cd]inden-3-one |

TABLE 1-continued

| Cpd. No. | Structure | Name |
|---|---|---|
| 44 | 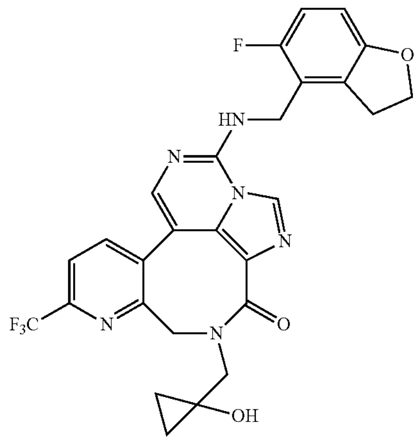 [SMILES: O=C1c2ncn3c(NCc4c(F)ccc5c4CCO5)ncc(c23)-c2ccc(C(F)(F)F)nc2CN1CC1(O)CC1] | 12-(((5-fluoro-2,3-dihydrobenzofuran-4-yl)methyl)amino)-4-((1-hydroxycyclopropyl)methyl)-7-(trifluoromethyl)-4,5-dihydro-3H-2,4,6,11,12a-pentaazabenzo[4,5]cycloocta[1,2,3-cd]inden-3-one |
| 45 | 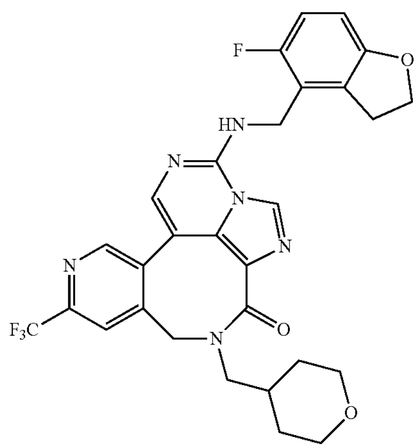 [SMILES: O=C1c2ncn3c(NCc4c(F)ccc5c4CCO5)ncc(c23)-c2cnc(C(F)(F)F)cc2CN1CC1CCOCC1] | 12-(((5-fluoro-2,3-dihydrobenzofuran-4-yl)methyl)amino)-4-((tetrahydro-2H-pyran-4-yl)methyl)-7-(trifluoromethyl)-4,5-dihydro-3H-2,4,8,11,12a-pentaazabenzo[4,5]cycloocta[1,2,3-cd]inden-3-one |
| 46 | 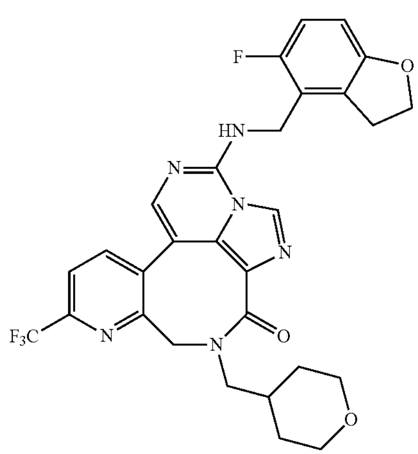 [SMILES: O=C1c2ncn3c(NCc4c(F)ccc5c4CCO5)ncc(c23)-c2ccc(C(F)(F)F)nc2CN1CC1CCOCC1] | 12-(((5-fluoro-2,3-dihydrobenzofuran-4-yl)methyl)amino)-4-((tetrahydro-2H-pyran-4-yl)methyl)-7-(trifluoromethyl)-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| 47 | 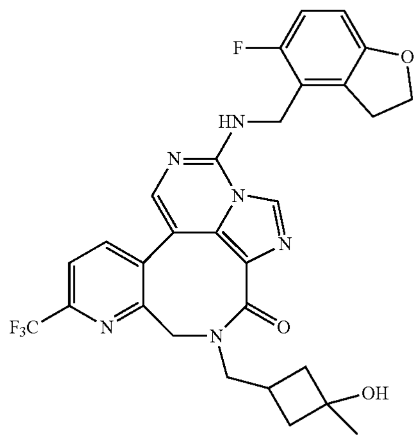 [SMILES: CC1(O)CC(CN2Cc3nc(C(F)(F)F)ccc3-c3cnc(NCc4c(F)ccc5c4CCO5)n4cnc(c34)C2=O)C1] | 12-(((5-fluoro-2,3-dihydrobenzofuran-4-yl)methyl)amino)-4-((3-hydroxy-3-methylcyclobutyl)methyl)-7-(trifluoromethyl)-4,5-dihydro-3H-2,4,6,11,12a-pentaazabenzo[4,5]cycloocta[1,2,3-cd]inden-3-one |
| 48 | 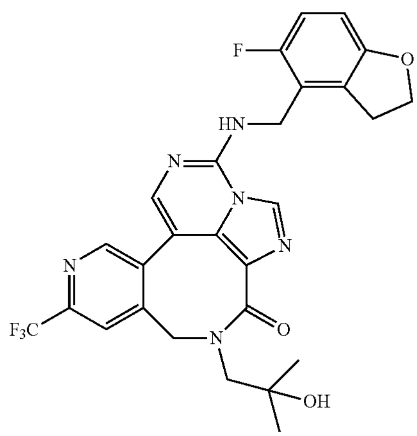 [SMILES: CC(C)(O)CN1Cc2cc(C(F)(F)F)ncc2-c2cnc(NCc3c(F)ccc4c3CCO4)n3cnc(c23)C1=O] | 12-(((5-fluoro-2,3-dihydrobenzofuran-4-yl)methyl)amino)-4-(2-hydroxy-2-methylpropyl)-7-(trifluoromethyl)-4,5-dihydro-3H-2,4,8,11,12a-pentaazabenzo[4,5]cycloocta[1,2,3-cd]inden-3-one |
| 49 | 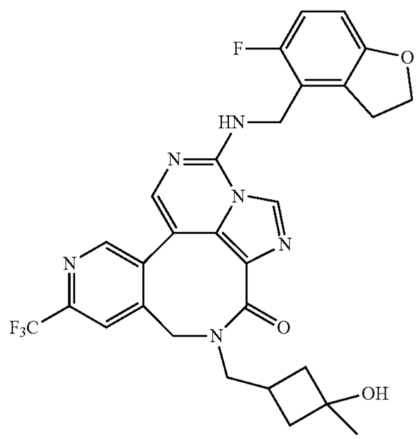 [SMILES: CC1(O)CC(CN2Cc3cc(C(F)(F)F)ncc3-c3cnc(NCc4c(F)ccc5c4CCO5)n4cnc(c34)C2=O)C1] | 12-(((5-fluoro-2,3-dihydrobenzofuran-4-yl)methyl)amino)-4-((3-hydroxy-3-methylcyclobutyl)methyl)-7-(trifluoromethyl)-4,5-dihydro-3H-2,4,8,11,12a-pentaazabenzo[4,5]cycloocta[1,2,3-cd]inden-3-one |

TABLE 1-continued

| Cpd. No. | Structure | Name |
|---|---|---|
| 50 | 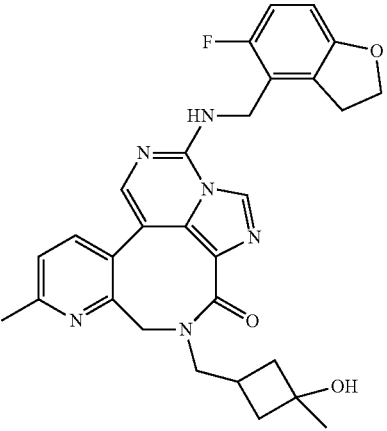 [SMILES: Cc1ccc2c(n1)CN(CC1CC(C)(O)C1)C(=O)c1ncn3c(NCc4c(F)ccc5c4CCO5)ncc-2c13] | 12-(((5-fluoro-2,3-dihydrobenzofuran-4-yl)methyl)amino)-4-((3-hydroxy-3-methylcyclobutyl)methyl)-7-methyl-4,5-dihydro-3H-2,4,6,11,12a-pentaazabenzo[4,5]cycloocta[1,2,3-cd]inden-3-one |
| 51 | 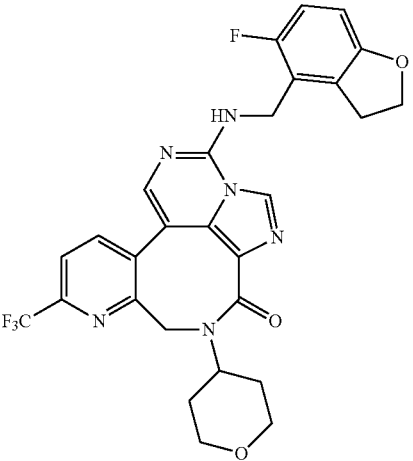 [SMILES: O=C1c2ncn3c(NCc4c(F)ccc5c4CCO5)ncc(c23)-c2ccc(C(F)(F)F)nc2CN1C1CCOCC1] | 12-(((5-fluoro-2,3-dihydrobenzofuran-4-yl)methyl)amino)-4-(tetrahydro-2H-pyran-4-yl)-7-(trifluoromethyl)-4,5-dihydro-3H-2,4,6,11,12a-pentaazabenzo[4,5]cycloocta[1,2,3-cd]inden-3-one |
| 52 | 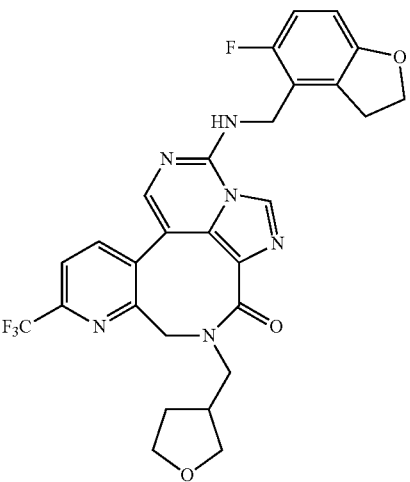 [SMILES: O=C1c2ncn3c(NCc4c(F)ccc5c4CCO5)ncc(c23)-c2ccc(C(F)(F)F)nc2CN1CC1CCOC1] | 12-(((5-fluoro-2,3-dihydrobenzofuran-4-yl)methyl)amino)-4-((tetrahydrofuran-3-yl)methyl)-7-(trifluoromethyl)-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| 53 | 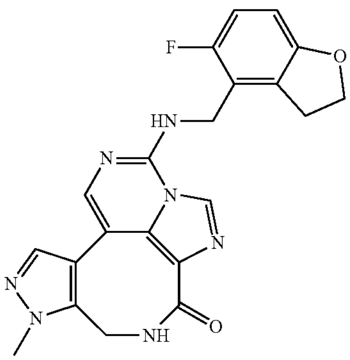 [SMILES: Cn1ncc2c1CNC(=O)c1ncn3c(NCc4c(F)ccc5c4CCO5)ncc-2c13] | 11-(((5-fluoro-2,3-dihydrobenzofuran-4-yl)methyl)amino)-6-methyl-5,6-dihydro-2,4,6,7,10,11a-hexaazacyclopenta[4,5]cycloocta[1,2,3-cd]inden-3(4H)-one |
| 54 | 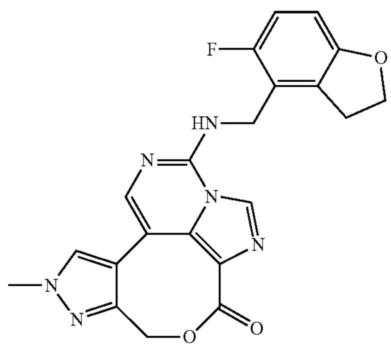 [SMILES: Cn1cc2c(n1)COC(=O)c1ncn3c(NCc4c(F)ccc5c4CCO5)ncc-2c13] | 11-(((5-fluoro-2,3-dihydrobenzofuran-4-yl)methyl)amino)-7-methyl-5,7-dihydro-3H-4-oxa-2,6,7,10,11a-pentaazacyclopenta[4,5]cycloocta[1,2,3-cd]inden-3-one |
| 55 | 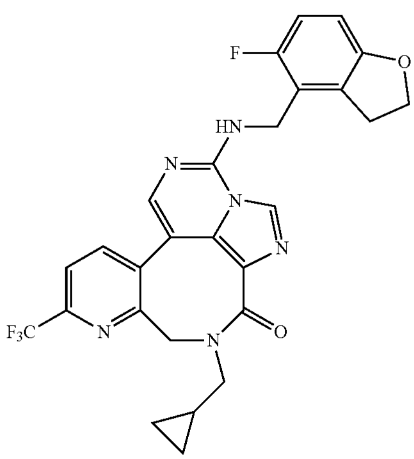 [SMILES: O=C1c2ncn3c(NCc4c(F)ccc5c4CCO5)ncc(c23)-c2ccc(C(F)(F)F)nc2CN1CC1CC1] | 4-(cyclopropylmethyl)-12-(((5-fluoro-2,3-dihydrobenzofuran-4-yl)methyl)amino)-7-(trifluoromethyl)-4,5-dihydro-3H-2,4,6,11,12a-pentaazabenzo[4,5]cycloocta[1,2,3-cd]inden-3-one |
| 56 | 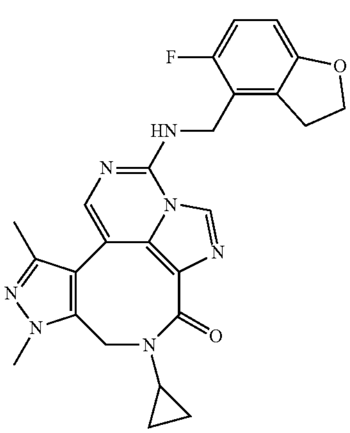 [SMILES: Cc1nn(C)c2c1-c1cnc(NCc3c(F)ccc4c3CCO4)n3cnc(c13)C(=O)N(C1CC1)C2] | 4-cyclopropyl-11-(((5-fluoro-2,3-dihydrobenzofuran-4-yl)methyl)amino)-6,8-dimethyl-5,6-dihydro-2,4,6,7,10,11a-hexaazacyclopenta[4,5]cycloocta[1,2,3-cd]inden-3(4H)-one |

TABLE 1-continued

| Cpd. No. | Structure | Name |
|---|---|---|
| 57 | 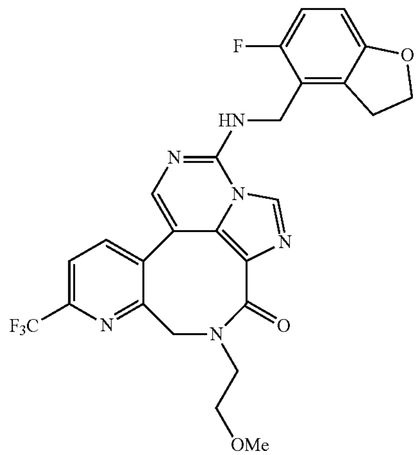 [SMILES: COCCN1Cc2nc(C(F)(F)F)ccc2-c2cnc(NCc3c(F)ccc4c3CCO4)n3cnc(c23)C1=O] | 12-(((5-fluoro-2,3-dihydrobenzofuran-4-yl)methyl)amino)-4-(2-methoxyethyl)-7-(trifluoromethyl)-4,5-dihydro-3H-2,4,6,11,12a-pentaazabenzo[4,5]cycloocta[1,2,3-cd]inden-3-one |
| 58 | 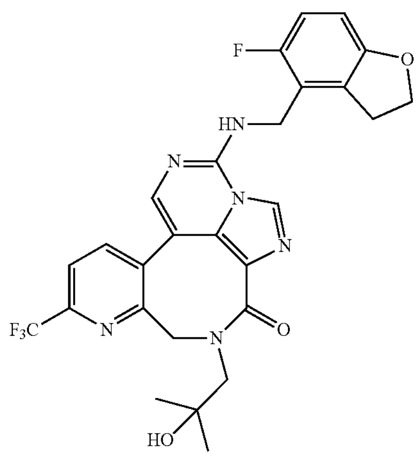 [SMILES: CC(C)(O)CN1Cc2nc(C(F)(F)F)ccc2-c2cnc(NCc3c(F)ccc4c3CCO4)n3cnc(c23)C1=O] | 12-(((5-fluoro-2,3-dihydrobenzofuran-4-yl)methyl)amino)-4-(2-hydroxy-2-methylpropyl)-7-(trifluoromethyl)-4,5-dihydro-3H-2,4,6,11,12a-pentaazabenzo[4,5]cycloocta[1,2,3-cd]inden-3-one |
| 59 | 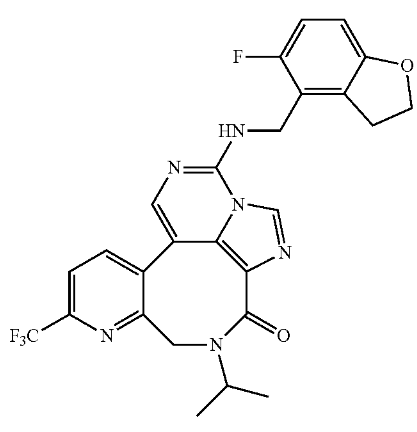 [SMILES: CC(C)N1Cc2nc(C(F)(F)F)ccc2-c2cnc(NCc3c(F)ccc4c3CCO4)n3cnc(c23)C1=O] | 12-(((5-fluoro-2,3-dihydrobenzofuran-4-yl)methyl)amino)-4-isopropyl-7-(trifluoromethyl)-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| 60 | 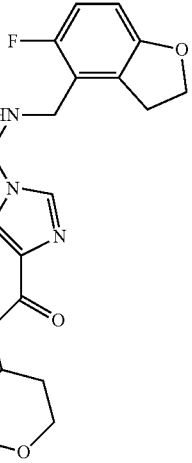 | 12-(((5-fluoro-2,3-dihydrobenzofuran-4-yl)methyl)amino)-4-(tetrahydro-2H-pyran-4-yl)-7-(trifluoromethyl)-4,5-dihydro-3H-2,4,11,12a-tetraazabenzo[4,5]cycloocta[1,2,3-cd]inden-3-one |
| 61 | 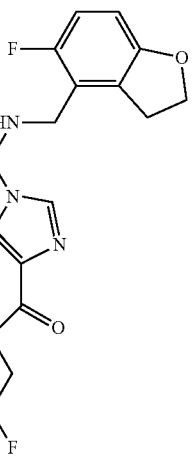 | 12-(((5-fluoro-2,3-dihydrobenzofuran-4-yl)methyl)amino)-4-(2-fluoroethyl)-7-(trifluoromethyl)-4,5-dihydro-3H-2,4,11,12a-tetraazabenzo[4,5]cycloocta[1,2,3-cd]inden-3-one |
| 62 | 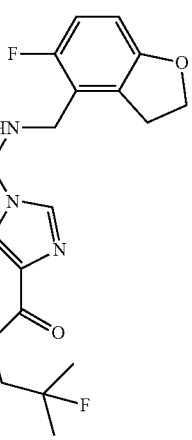 | 12-(((5-fluoro-2,3-dihydrobenzofuran-4-yl)methyl)amino)-4-(2-fluoro-2-methylpropyl)-7-(trifluoromethyl)-4,5-dihydro-3H-2,4,11,12a-tetraazabenzo[4,5]cycloocta[1,2,3-cd]inden-3-one |

TABLE 1-continued

| Cpd. No. | Structure | Name |
|---|---|---|
| 63 | 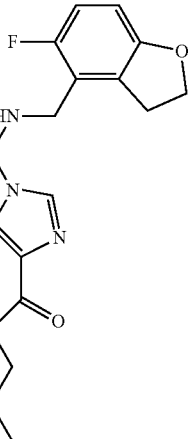 | 4-(2,2-difluoropropyl)-12-(((5-fluoro-2,3-dihydrobenzofuran-4-yl)methyl)amino)-7-(trifluoromethyl)-4,5-dihydro-3H-2,4,11,12a-tetraazabenzo[4,5]cycloocta[1,2,3-cd]inden-3-one |
| 64 | 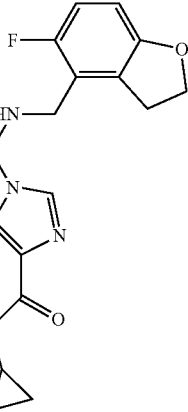 | 4-cyclopropyl-7-fluoro-12-(((5-fluoro-2,3-dihydrobenzofuran-4-yl)methyl)amino)-4,5-dihydro-3H-2,4,11,12a-tetraazabenzo[4,5]cycloocta[1,2,3-cd]inden-3-one |
| 65 | 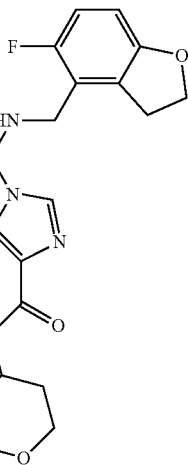 | 7-fluoro-12-(((5-fluoro-2,3-dihydrobenzofuran-4-yl)methyl)amino)-4-(tetrahydro-2H-pyran-4-yl)-4,5-dihydro-3H-2,4,11,12a-tetraazabenzo[4,5]cycloocta[1,2,3-cd]inden-3-one |

TABLE 1-continued

| Cpd. No. | Structure | Name |
|---|---|---|
| 66 | 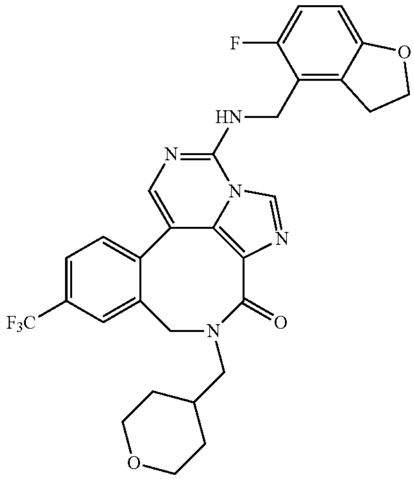 | 12-(((5-fluoro-2,3-dihydrobenzofuran-4-yl)methyl)amino)-4-((tetrahydro-2H-pyran-4-yl)methyl)-7-(trifluoromethyl)-4,5-dihydro-3H-2,4,11,12a-tetraazabenzo[4,5]cycloocta[1,2,3-cd]inden-3-one |
| 67 | 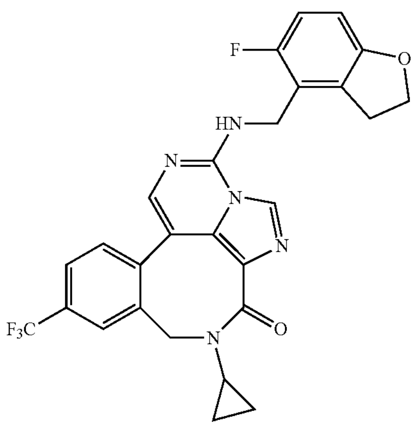 [SMILES: O=C1c2ncn3c(NCc4c(F)ccc5c4CCO5)ncc(c23)-c2ccc(C(F)(F)F)cc2CN1C1CC1] | 4-cyclopropyl-12-(((5-fluoro-2,3-dihydrobenzofuran-4-yl)methyl)amino)-7-(trifluoromethyl)-4,5-dihydro-3H-2,4,11,12a-tetraazabenzo[4,5]cycloocta[1,2,3-cd]inden-3-one |
| 68 | 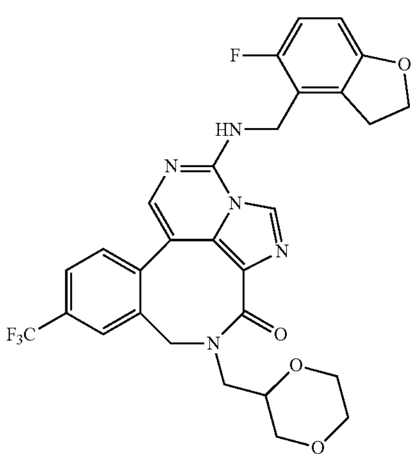 [SMILES: O=C1c2ncn3c(NCc4c(F)ccc5c4CCO5)ncc(c23)-c2ccc(C(F)(F)F)cc2CN1CC1COCCO1] | 4-((1,4-dioxan-2-yl)methyl)-12-(((5-fluoro-2,3-dihydrobenzofuran-4-yl)methyl)amino)-7-(trifluoromethyl)-4,5-dihydro-3H-2,4,11,12a-tetraazabenzo[4,5]cycloocta[1,2,3-cd]inden-3-one |

TABLE 1-continued

| Cpd. No. | Structure | Name |
|---|---|---|
| 69 | 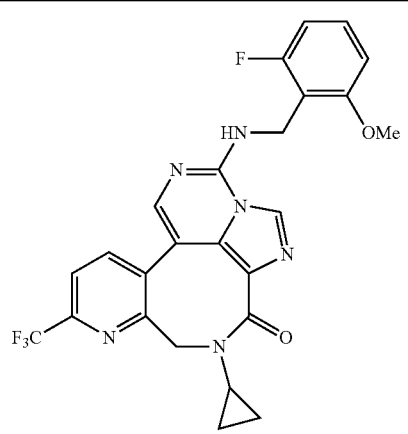 | 4-cyclopropyl-12-((2-fluoro-6-methoxybenzyl)amino)-7-(trifluoromethyl)-4,5-dihydro-3H-2,4,6,11,12a-pentaazabenzo[4,5]cycloocta[1,2,3-cd]inden-3-one |
| 70 | 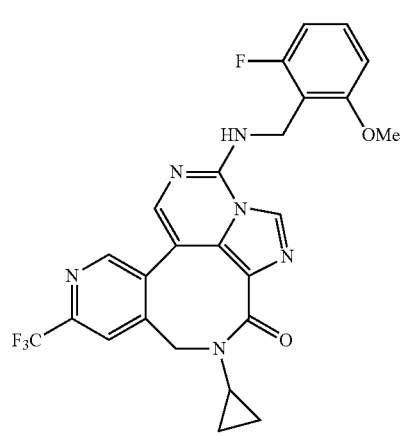 [SMILES: COc1cccc(F)c1CNc1ncc2c3c(ncn13)C(=O)N(C1CC1)Cc1cc(C(F)(F)F)ncc1-2] | 4-cyclopropyl-12-((2-fluoro-6-methoxybenzyl)amino)-7-(trifluoromethyl)-4,5-dihydro-3H-2,4,8,11,12a-pentaazabenzo[4,5]cycloocta[1,2,3-cd]inden-3-one |
| 71 | 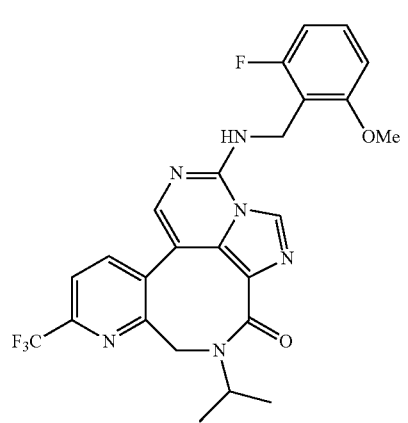 [SMILES: COc1cccc(F)c1CNc1ncc2c3c(ncn13)C(=O)N(C(C)C)Cc1nc(C(F)(F)F)ccc1-2] | 12-((2-fluoro-6-methoxybenzyl)amino)-4-isopropyl-7-(trifluoromethyl)-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| 72 | 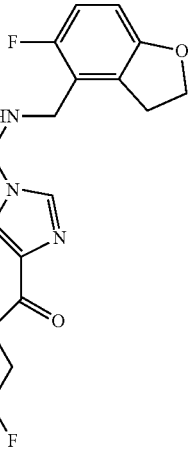 | 12-(((5-fluoro-2,3-dihydrobenzofuran-4-yl)methyl)amino)-4-(2-fluoroethyl)-7-(trifluoromethyl)-4,5-dihydro-3H-2,4,8,11,12a-pentaazabenzo[4,5]cycloocta[1,2,3-cd]inden-3-one |
| 73 | 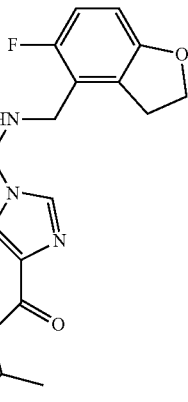 | 12-(((5-fluoro-2,3-dihydrobenzofuran-4-yl)methyl)amino)-4-isopropyl-7-(trifluoromethyl)-4,5-dihydro-3H-2,4,8,11,12a-pentaazabenzo[4,5]cycloocta[1,2,3-cd]inden-3-one |
| 74 | 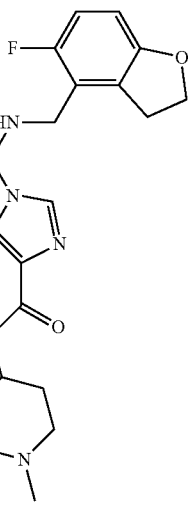 | 12-(((5-fluoro-2,3-dihydrobenzofuran-4-yl)methyl)amino)-4-(1-methylpiperidin-4-yl)-7-(trifluoromethyl)-4,5-dihydro-3H-2,4,11,12a-tetraazabenzo[4,5]cycloocta[1,2,3-cd]inden-3-one |

TABLE 1-continued

| Cpd. No. | Structure | Name |
|---|---|---|
| 75 | 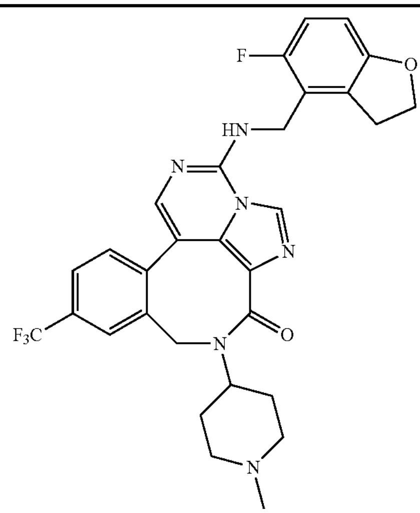 | 7-fluoro-12-(((5-fluoro-2,3-dihydrobenzofuran-4-yl)methyl)amino)-4-(1-methylpiperidin-4-yl)-4,5-dihydro-3H-2,4,11,12a-tetraazabenzo[4,5]cycloocta[1,2,3-cd]inden-3-one |
| 76 | 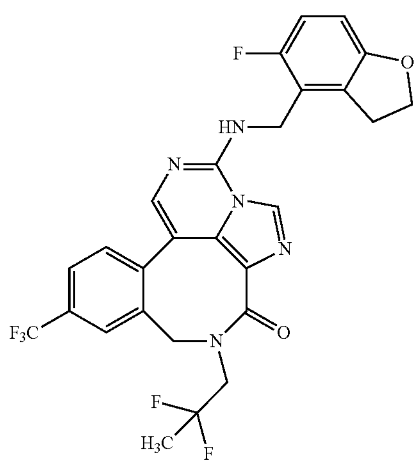 [SMILES: CC(F)(F)CN1Cc2cc(C(F)(F)F)ccc2-c2cnc(NCc3c(F)ccc4c3CCO4)n3cnc(c23)C1=O] | 4-(2,2-difluoropropyl)-7-fluoro-12-(((5-fluoro-2,3-dihydrobenzofuran-4-yl)methyl)amino)-4,5-dihydro-3H-2,4,11,12a-tetraazabenzo[4,5]cycloocta[1,2,3-cd]inden-3-one |
| 77 | 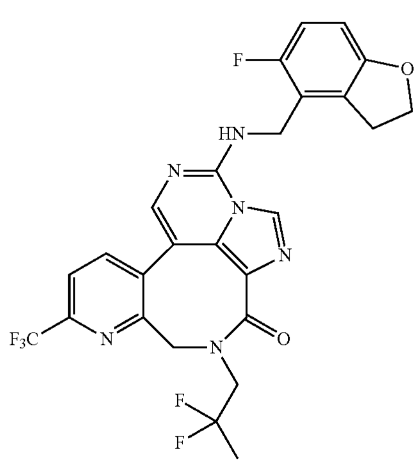 | 4-(2,2-difluoropropyl)-12-(((5-fluoro-2,3-dihydrobenzofuran-4-yl)methyl)amino)-7-(trifluoromethyl)-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| 78 | 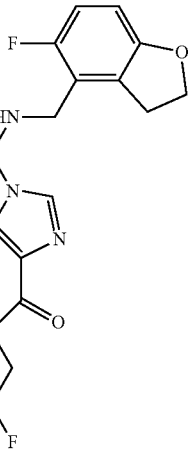 | 7-fluoro-12-(((5-fluoro-2,3-dihydrobenzofuran-4-yl)methyl)amino)-4-(2-fluoro-2-methylpropyl)-4,5-dihydro-3H-2,4,11,12a-tetraazabenzo[4,5]cycloocta[1,2,3-cd]inden-3-one |
| 79 | 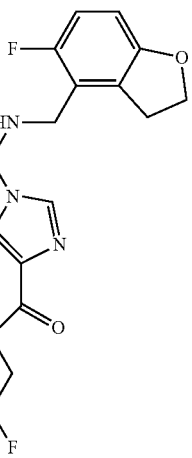 | 7-fluoro-12-(((5-fluoro-2,3-dihydrobenzofuran-4-yl)methyl)amino)-4-(2-fluoroethyl)-4,5-dihydro-3H-2,4,11,12a-tetraazabenzo[4,5]cycloocta[1,2,3-cd]inden-3-one |
| 80 | 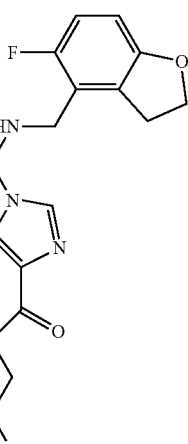 | 4-(2,2-difluoroethyl)-7-fluoro-12-(((5-fluoro-2,3-dihydrobenzofuran-4-yl)methyl)amino)-4,5-dihydro-3H-2,4,11,12a-tetraazabenzo[4,5]cycloocta[1,2,3-cd]inden-3-one |

TABLE 1-continued

| Cpd. No. | Structure | Name |
|---|---|---|
| 81 | 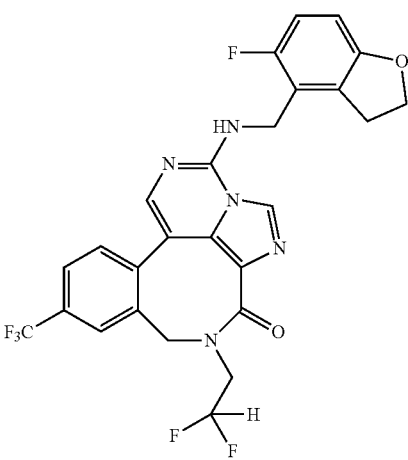 | 4-(2,2-difluoroethyl)-12-(((5-fluoro-2,3-dihydrobenzofuran-4-yl)methyl)amino)-7-(trifluoromethyl)-4,5-dihydro-3H-2,4,11,12a-tetraazabenzo[4,5]cycloocta[1,2,3-cd]inden-3-one |
| 82 | 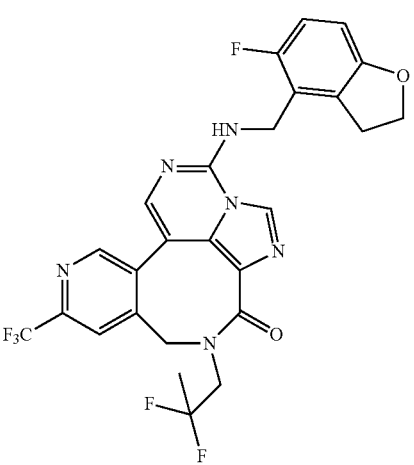 [SMILES: CC(F)(F)CN1Cc2cc(C(F)(F)F)ncc2-c2cnc(NCc3c(F)ccc4c3CCO4)n3cnc(c23)C1=O] | 4-(2,2-difluoropropyl)-12-(((5-fluoro-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one |
| 83 | 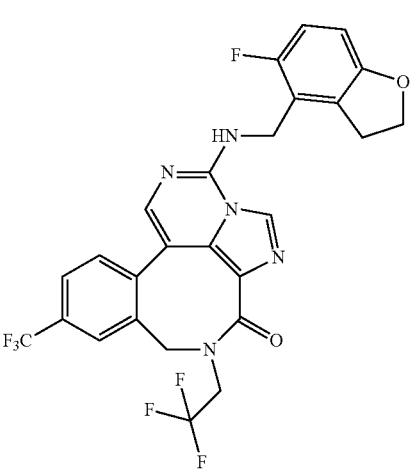 [SMILES: O=C1c2ncn3c(NCc4c(F)ccc5c4CCO5)ncc(c23)-c2ccc(C(F)(F)F)cc2CN1CC(F)(F)F] | 12-(((5-fluoro-2,3-dihydrobenzofuran-4-yl)methyl)amino)-4-(2,2,2-trifluoroethyl)-7-(trifluoromethyl)-4,5-dihydro-3H-2,4,11,12a-tetraazabenzo[4,5]cycloocta[1,2,3-cd]inden-3-one |

TABLE 1-continued

| Cpd. No. | Structure | Name |
|---|---|---|
| 84 | 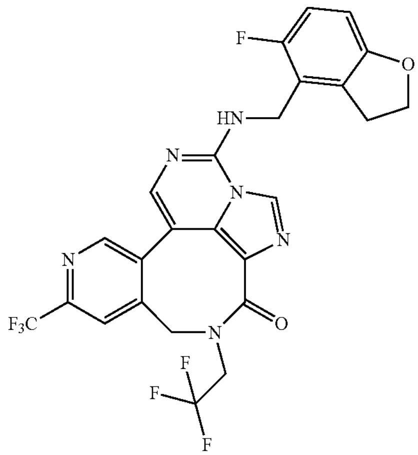 [SMILES: O=C1c2ncn3c(NCc4c(F)ccc5c4CCO5)ncc(c23)-c2cnc(C(F)(F)F)cc2CN1CC(F)(F)F] | 12-(((5-fluoro-2,3-dihydrobenzofuran-4-yl)methyl)amino)-4-(2,2,2-trifluoroethyl)-7-(trifluoromethyl)-4,5-dihydro-3H-2,4,8,11,12a-pentaazabenzo[4,5]cycloocta[1,2,3-cd]inden-3-one |
| 85 | 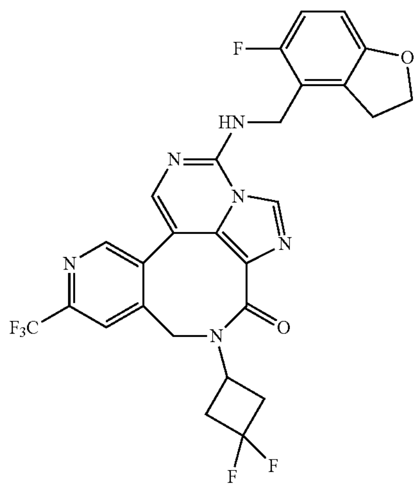 [SMILES: O=C1c2ncn3c(NCc4c(F)ccc5c4CCO5)ncc(c23)-c2cnc(C(F)(F)F)cc2CN1C1CC(F)(F)C1] | 4-(3,3-difluorocyclobutyl)-12-(((5-fluoro-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one |
| 86 | 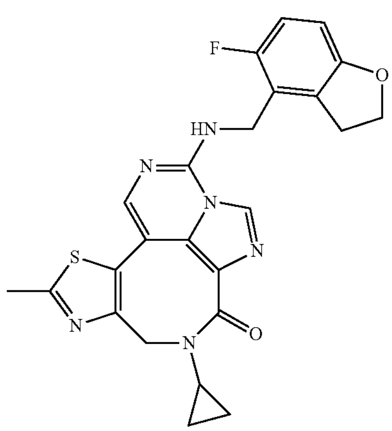 [SMILES: Cc1nc2c(s1)-c1cnc(NCc3c(F)ccc4c3CCO4)n3cnc(c13)C(=O)N(C1CC1)C2] | 4-cyclopropyl-11-(((5-fluoro-2,3-dihydrobenzofuran-4-yl)methyl)amino)-7-methyl-4,5-dihydro-3H-8-thia-2,4,6,10,11a-pentaazacyclopenta[4,5]cycloocta[1,2,3-cd]inden-3-one |

TABLE 1-continued

| Cpd. No. | Structure | Name |
| --- | --- | --- |
| 87 | 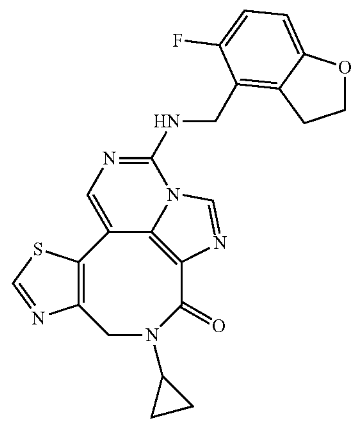 [SMILES: O=C1c2ncn3c(NCc4c(F)ccc5c4CCO5)ncc(c23)-c2scnc2CN1C1CC1] | 4-cyclopropyl-11-(((5-fluoro-2,3-dihydrobenzofuran-4-yl)methyl)amino)-4,5-dihydro-3H-8-thia-2,4,10,11a-tetraazacyclopenta[4,5]cycloocta[1,2,3-cd]inden-3-one |
| 88 | 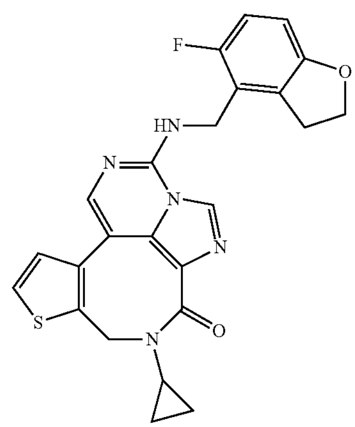 [SMILES: O=C1c2ncn3c(NCc4c(F)ccc5c4CCO5)ncc(c23)-c2ccsc2CN1C1CC1] | 4-cyclopropyl-11-(((5-fluoro-2,3-dihydrobenzofuran-4-yl)methyl)amino)-4,5-dihydro-3H-6-thia-2,4,10,11a-tetraazacyclopenta[4,5]cycloocta[1,2,3-cd]inden-3-one |
| 89 | 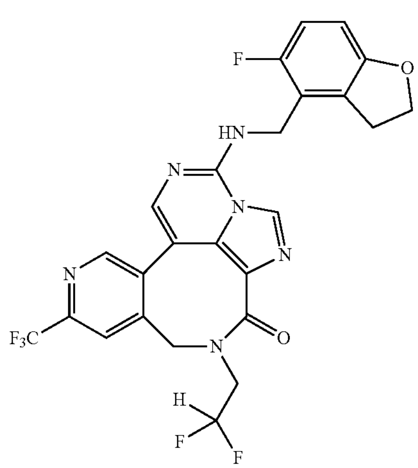 | 4-(2,2-difluoroethyl)-12-(((5-fluoro-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one |

TABLE 1-continued

| Cpd. No. | Structure | Name |
|---|---|---|
| 90 | 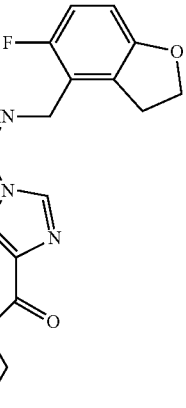 | 4-ethyl-12-(((5-fluoro-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one |
| 91 | 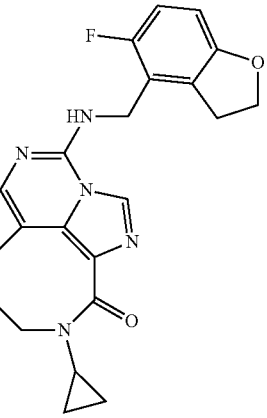 | 4-cyclopropyl-11-(((5-fluoro-2,3-dihydrobenzofuran-4-yl)methyl)amino)-7-(trifluoromethyl)-4,5-dihydro-3H-8-thia-2,4,6,10,11a-pentaazacyclopenta[4,5]cycloocta[1,2,3-cd]inden-3-one |
| 92 | 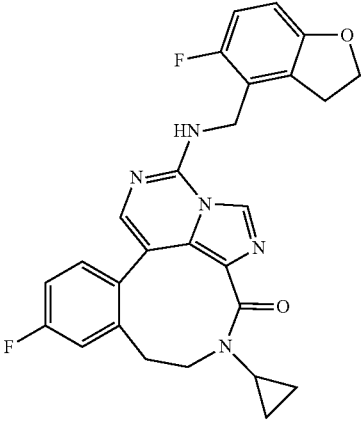 [SMILES: O=C1c2ncn3c(NCc4c(F)ccc5c4CCO5)ncc(c23)-c2ccc(F)cc2CCN1C1CC1] | 4-cyclopropyl-8-fluoro-13-(((5-fluoro-2,3-dihydrobenzofuran-4-yl)methyl)amino)-5,6-dihydro-2,4,12,13a-tetraazabenzo[4,5]cyclonona[1,2,3-cd]inden-3(4H)-one |

TABLE 1-continued

| Cpd. No. | Structure | Name |
|---|---|---|
| 93 | 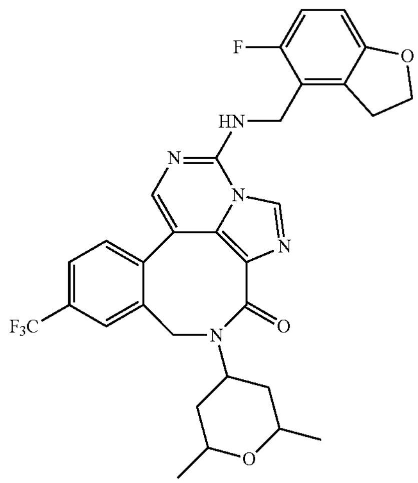 [SMILES: CC1CC(N2Cc3cc(C(F)(F)F)ccc3-c3cnc(NCc4c(F)ccc5c4CCO5)n4cnc(c34)C2=O)CC(C)O1] | 4-(2,6-dimethyltetrahydro-2H-pyran-4-yl)-12-(((5-fluoro-2,3-dihydrobenzofuran-4-yl)methyl)amino)-7-(trifluoromethyl)-4,5-dihydro-3H-2,4,11,12a-tetraazabenzo[4,5]cycloocta[1,2,3-cd]inden-3-one |
| 94 | 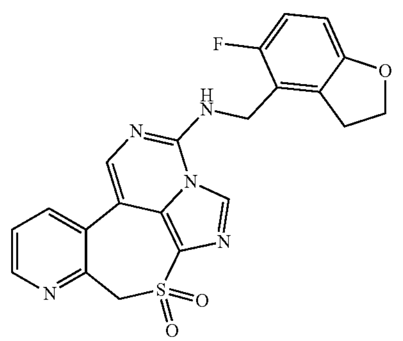 [SMILES: O=S1(=O)Cc2ncccc2-c2cnc(NCc3c(F)ccc4c3CCO4)n3cnc1c23] | 11-(((5-fluoro-2,3-dihydrobenzofuran-4-yl)methyl)amino)-4H-3-thia-2,5,10,11a-tetraazadibenzo[cd,f]azulene 3,3-dioxide |
| 95 | 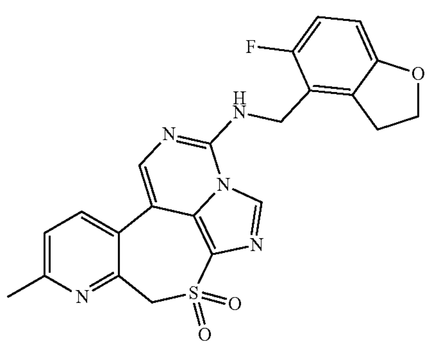 [SMILES: Cc1ccc2c(n1)CS(=O)(=O)c1ncn3c(NCc4c(F)ccc5c4CCO5)ncc-2c13] | 11-(((5-fluoro-2,3-dihydrobenzofuran-4-yl)methyl)amino)-6-methyl-4H-3-thia-2,5,10,11a-tetraazadibenzo[cd,f]azulene 3,3-dioxide |
| 96 | 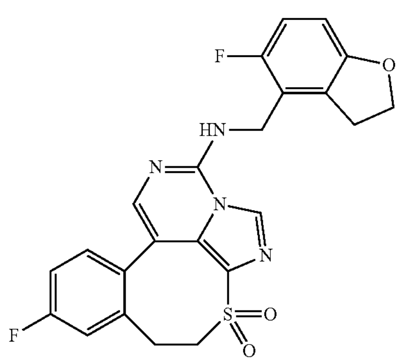 [SMILES: O=S1(=O)CCc2cc(F)ccc2-c2cnc(NCc3c(F)ccc4c3CCO4)n3cnc1c23] | 7-fluoro-12-(((5-fluoro-2,3-dihydrobenzofuran-4-yl)methyl)amino)-4,5-dihydro-3-thia-2,11,12a-triazabenzo[4,5]cycloocta[1,2,3-cd]indene 3,3-dioxide |

TABLE 1-continued

| Cpd. No. | Structure | Name |
|---|---|---|
| 97 | 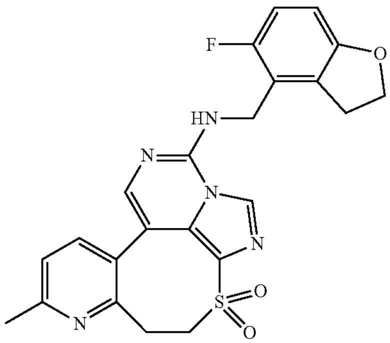 [SMILES: Cc1ccc2c(n1)CCS(=O)(=O)c1ncn3c(NCc4c(F)ccc5c4CCO5)ncc-2c13] | 12-(((5-fluoro-2,3-dihydrobenzofuran-4-yl)methyl)amino)-7-methyl-4,5-dihydro-3-thia-2,6,11,12a-tetraazabenzo[4,5]cycloocta[1,2,3-cd]indene 3,3-dioxide |
| 98 | 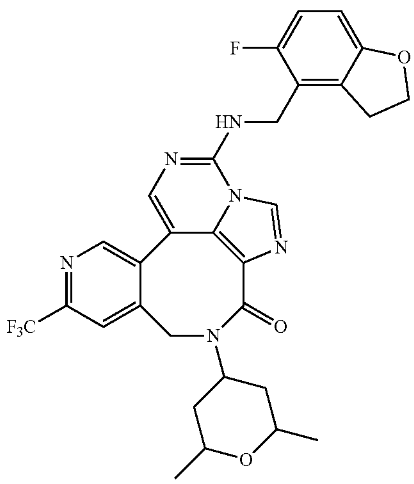 [SMILES: CC1CC(N2Cc3cc(C(F)(F)F)ncc3-c3cnc(NCc4c(F)ccc5c4CCO5)n4cnc(c34)C2=O)CC(C)O1] | 4-(2,6-dimethyltetrahydro-2H-pyran-4-yl)-12-(((5-fluoro-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one |
| 99 | 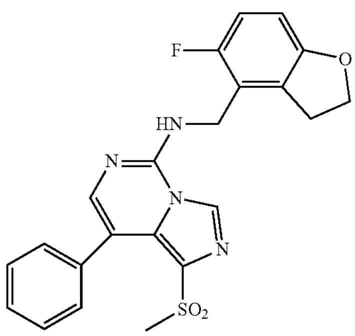 [SMILES: CS(=O)(=O)c1ncn2c(NCc3c(F)ccc4c3CCO4)ncc(-c3ccccc3)c12] | N-((5-fluoro-2,3-dihydrobenzofuran-4-yl)methyl)-1-(methylsulfonyl)-8-phenylimidazo[1,5-c]pyrimidin-5-amine |
| 100 | 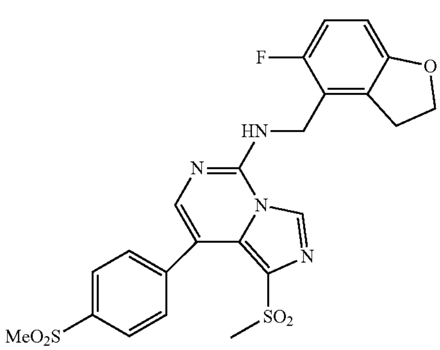 [SMILES: CS(=O)(=O)c1ccc(-c2cnc(NCc3c(F)ccc4c3CCO4)n3cnc(S(C)(=O)=O)c23)cc1] | N-((5-fluoro-2,3-dihydrobenzofuran-4-yl)methyl)-1-(methylsulfonyl)-8-(4-(methylsulfonyl)phenyl)imidazo[1,5-c]pyrimidin-5-amine |

TABLE 1-continued

| Cpd. No. | Structure | Name |
| --- | --- | --- |
| 101 | 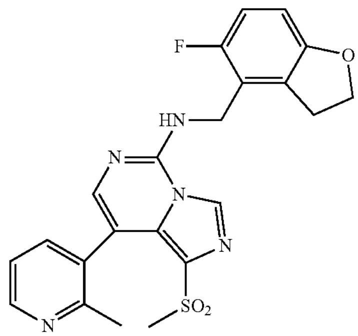 [SMILES: Cc1ncccc1-c1cnc(NCc2c(F)ccc3c2CCO3)n2cnc(S(C)(=O)=O)c12] | N-((5-fluoro-2,3-dihydrobenzofuran-4-yl)methyl)-8-(2-methylpyridin-3-yl)-1-(methylsulfonyl)imidazo[1,5-c]pyrimidin-5-amine |
| 102 | 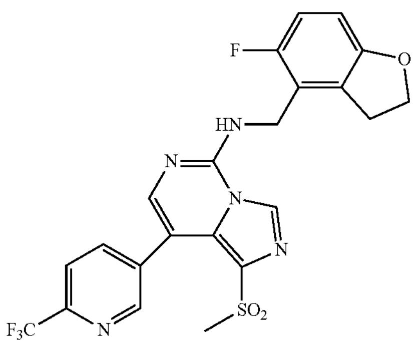 [SMILES: CS(=O)(=O)c1ncn2c(NCc3c(F)ccc4c3CCO4)ncc(-c3ccc(C(F)(F)F)nc3)c12] | N-((5-fluoro-2,3-dihydrobenzofuran-4-yl)methyl)-1-(methylsulfonyl)-8-(6-(trifluoromethyl)pyridin-3-yl)imidazo[1,5-c]pyrimidin-5-amine |
| 103 | 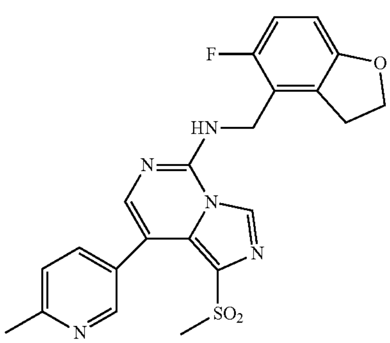 [SMILES: Cc1ccc(-c2cnc(NCc3c(F)ccc4c3CCO4)n3cnc(S(C)(=O)=O)c23)cn1] | N-((5-fluoro-2,3-dihydrobenzofuran-4-yl)methyl)-8-(6-methylpyridin-3-yl)-1-(methylsulfonyl)imidazo[1,5-c]pyrimidin-5-amine |
| 104 | 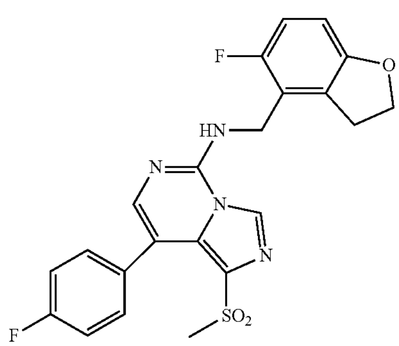 [SMILES: CS(=O)(=O)c1ncn2c(NCc3c(F)ccc4c3CCO4)ncc(-c3ccc(F)cc3)c12] | N-((5-fluoro-2,3-dihydrobenzofuran-4-yl)methyl)-8-(4-fluorophenyl)-1-(methylsulfonyl)imidazo[1,5-c]pyrimidin-5-amine |

TABLE 1-continued

| Cpd. No. | Structure | Name |
|---|---|---|
| 105 | 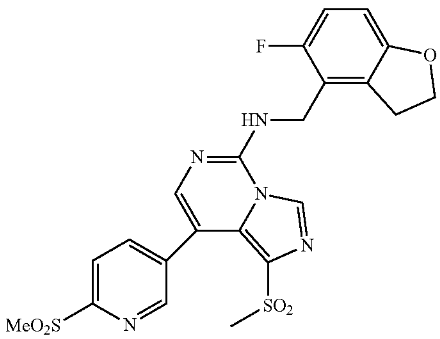 [SMILES: CS(=O)(=O)c1ccc(-c2cnc(NCc3c(F)ccc4c3CCO4)n3cnc(S(C)(=O)=O)c23)cn1] | N-((5-fluoro-2,3-dihydrobenzofuran-4-yl)methyl)-1-(methylsulfonyl)-8-(6-(methylsulfonyl)pyridin-3-yl)imidazo[1,5-c]pyrimidin-5-amine |
| 106 | 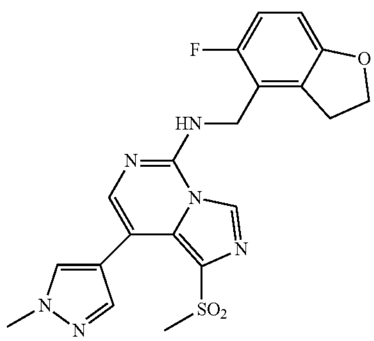 [SMILES: Cn1cc(-c2cnc(NCc3c(F)ccc4c3CCO4)n3cnc(S(C)(=O)=O)c23)cn1] | N-((5-fluoro-2,3-dihydrobenzofuran-4-yl)methyl)-8-(1-methyl-1H-pyrazol-4-yl)-1-(methylsulfonyl)imidazo[1,5-c]pyrimidin-5-amine |
| 107 | 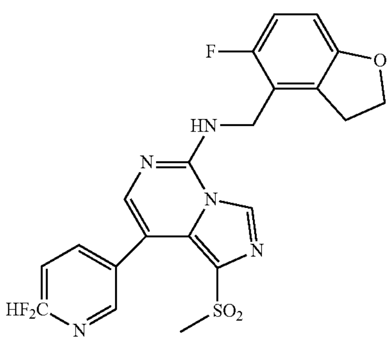 | 8-(6-(difluoromethyl)pyridin-3-yl)-N-((5-fluoro-2,3-dihydrobenzofuran-4-yl)methyl)-1-(methylsulfonyl)imidazo[1,5-c]pyrimidin-5-amine |
| 108 | 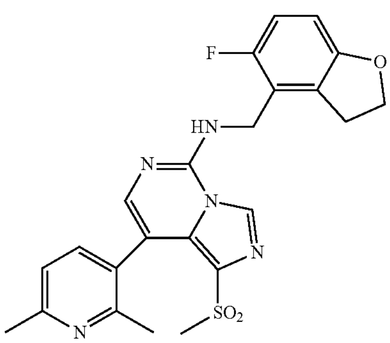 [SMILES: Cc1ccc(-c2cnc(NCc3c(F)ccc4c3CCO4)n3cnc(S(C)(=O)=O)c23)c(C)n1] | 8-(2,6-dimethylpyridin-3-yl)-N-((5-fluoro-2,3-dihydrobenzofuran-4-yl)methyl)-1-(methylsulfonyl)imidazo[1,5-c]pyrimidin-5-amine |

TABLE 1-continued

| Cpd. No. | Structure | Name |
|---|---|---|
| 109 | 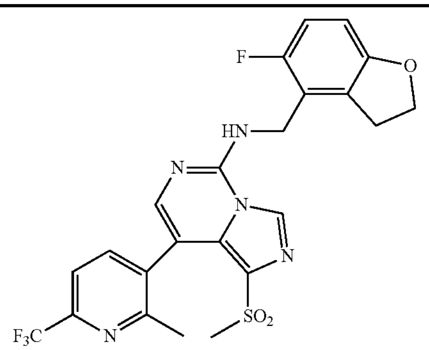 | N-((5-fluoro-2,3-dihydrobenzofuran-4-yl)methyl)-8-(2-methyl-6-(trifluoromethyl)pyridin-3-yl)-1-(methylsulfonyl)imidazo[1,5-c]pyrimidin-5-amine |
| 110 | 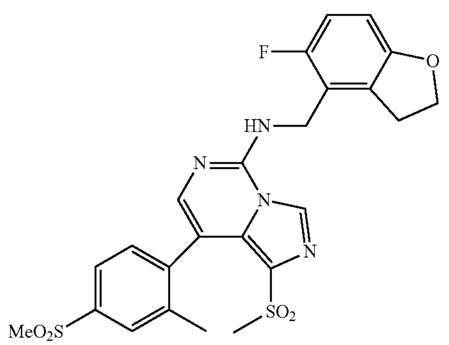 | N-((5-fluoro-2,3-dihydrobenzofuran-4-yl)methyl)-8-(2-methyl-4-(methylsulfonyl)phenyl)-1-(methylsulfonyl)imidazo[1,5-c]pyrimidin-5-amine |
| 111 | 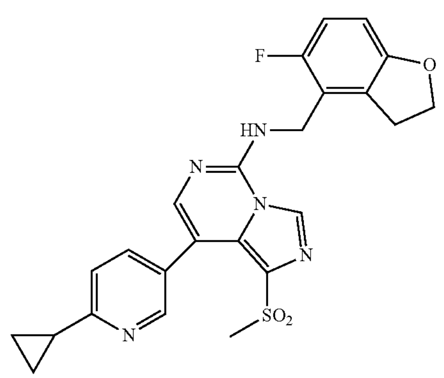 [SMILES: CS(=O)(=O)c1ncn2c(NCc3c(F)ccc4c3CCO4)ncc(-c3ccc(C4CC4)nc3)c12] | 8-(6-cyclopropylpyridin-3-yl)-N-((5-fluoro-2,3-dihydrobenzofuran-4-yl)methyl)-1-(methylsulfonyl)imidazo[1,5-c]pyrimidin-5-amine |
| 112 | 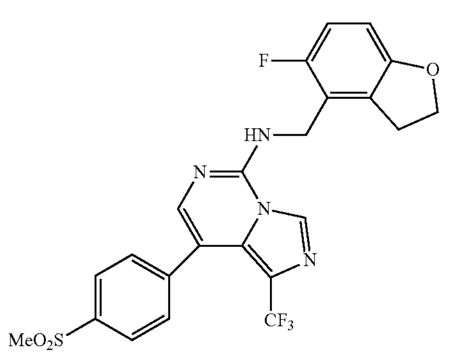 [SMILES: CS(=O)(=O)c1ccc(-c2cnc(NCc3c(F)ccc4c3CCO4)n3cnc(C(F)(F)F)c23)cc1] | N-((5-fluoro-2,3-dihydrobenzofuran-4-yl)methyl)-8-(4-(methylsulfonyl)phenyl)-1-(trifluoromethyl)imidazo[1,5-c]pyrimidin-5-amine |

TABLE 1-continued

| Cpd. No. | Structure | Name |
|---|---|---|
| 113 | 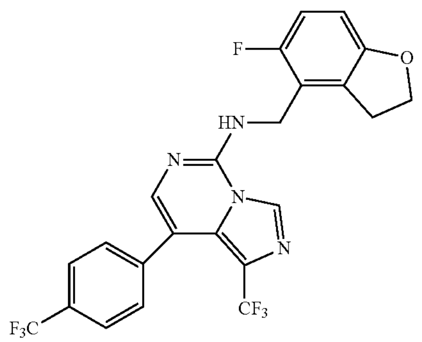 [SMILES: Fc1ccc2c(c1CNc1ncc(-c3ccc(C(F)(F)F)cc3)c3c(C(F)(F)F)ncn13)CCO2] | N-((5-fluoro-2,3-dihydrobenzofuran-4-yl)methyl)-1-(trifluoromethyl)-8-(4-(trifluoromethyl)phenyl)imidazo[1,5-c]pyrimidin-5-amine |
| 114 | 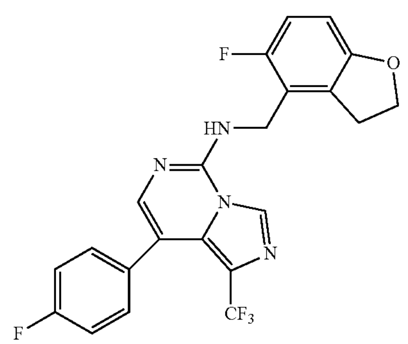 [SMILES: Fc1ccc(-c2cnc(NCc3c(F)ccc4c3CCO4)n3cnc(C(F)(F)F)c23)cc1] | N-((5-fluoro-2,3-dihydrobenzofuran-4-yl)methyl)-8-(4-fluorophenyl)-1-(trifluoromethyl)imidazo[1,5-c]pyrimidin-5-amine |
| 115 | 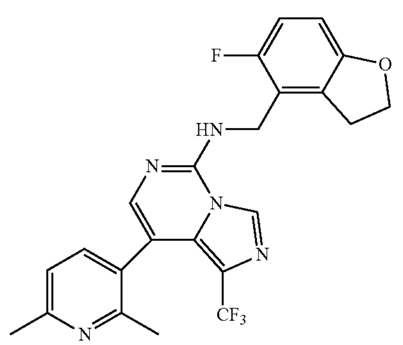 [SMILES: Cc1ccc(-c2cnc(NCc3c(F)ccc4c3CCO4)n3cnc(C(F)(F)F)c23)c(C)n1] | 8-(2,6-dimethylpyridin-3-yl)-N-((5-fluoro-2,3-dihydrobenzofuran-4-yl)methyl)-1-(trifluoromethyl)imidazo[1,5-c]pyrimidin-5-amine |
| 116 | 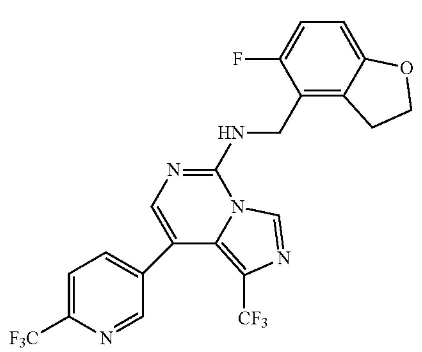 [SMILES: Fc1ccc2c(c1CNc1ncc(-c3ccc(C(F)(F)F)nc3)c3c(C(F)(F)F)ncn13)CCO2] | N-((5-fluoro-2,3-dihydrobenzofuran-4-yl)methyl)-1-(trifluoromethyl)-8-(6-(trifluoromethyl)pyridin-3-yl)imidazo[1,5-c]pyrimidin-5-amine |

TABLE 1-continued

| Cpd. No. | Structure | Name |
|---|---|---|
| 117 | 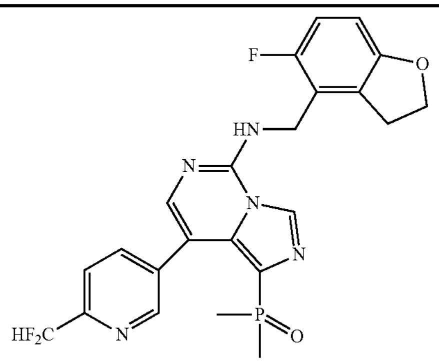 | (8-(6-(difluoromethyl)pyridin-3-yl)-5-(((5-fluoro-2,3-dihydrobenzofuran-4-yl)methyl)amino)imidazo[1,5-c]pyrimidin-1-yl)dimethylphosphine oxide |
| 118 | 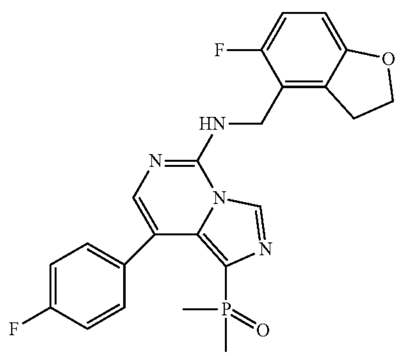 [SMILES: CP(C)(=O)c1ncn2c(NCc3c(F)ccc4c3CCO4)ncc(-c3ccc(F)cc3)c12] | (5-(((5-fluoro-2,3-dihydrobenzofuran-4-yl)methyl)amino)-8-(4-fluorophenyl)imidazo[1,5-c]pyrimidin-1-yl)dimethylphosphine oxide |
| 119 | 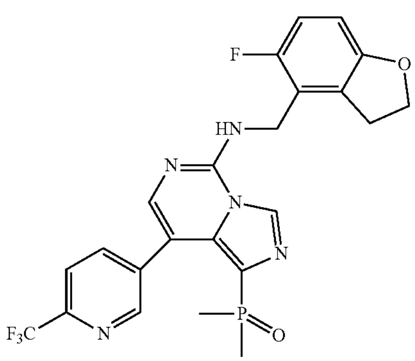 [SMILES: CP(C)(=O)c1ncn2c(NCc3c(F)ccc4c3CCO4)ncc(-c3ccc(C(F)(F)F)nc3)c12] | (5-(((5-fluoro-2,3-dihydrobenzofuran-4-yl)methyl)amino)-8-(6-(trifluoromethyl)pyridin-3-yl)imidazo[1,5-c]pyrimidin-1-yl)dimethylphosphine oxide |
| 120 | 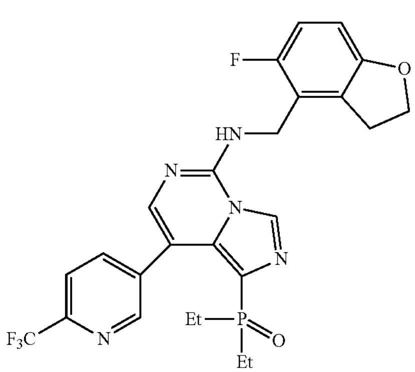 [SMILES: CCP(=O)(CC)c1ncn2c(NCc3c(F)ccc4c3CCO4)ncc(-c3ccc(C(F)(F)F)nc3)c12] | diethyl(5-(((5-fluoro-2,3-dihydrobenzofuran-4-yl)methyl)amino)-8-(6-(trifluoromethyl)pyridin-3-yl)imidazo[1,5-c]pyrimidin-1-yl)phosphine oxide |

TABLE 1-continued

| Cpd. No. | Structure | Name |
|---|---|---|
| 121 | 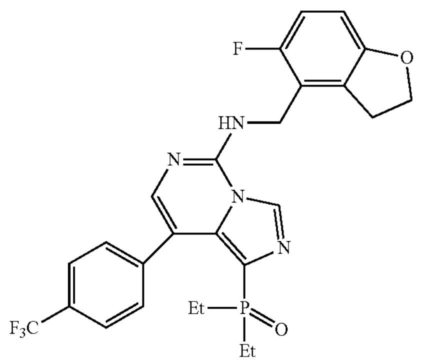 [SMILES: CCP(=O)(CC)c1ncn2c(NCc3c(F)ccc4c3CCO4)ncc(-c3ccc(C(F)(F)F)cc3)c12] | diethyl(5-(((5-fluoro-2,3-dihydrobenzofuran-4-yl)methyl)amino)-8-(4-(trifluoromethyl)phenyl)imidazo[1,5-c]pyrimidin-1-yl)phosphine oxide |
| 122 | 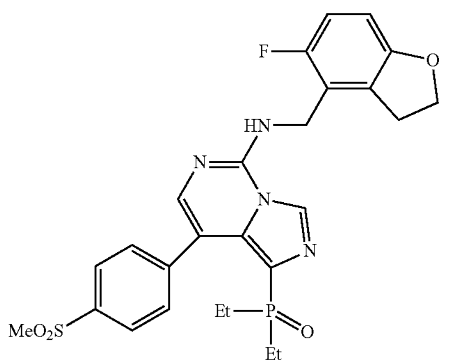 [SMILES: CCP(=O)(CC)c1ncn2c(NCc3c(F)ccc4c3CCO4)ncc(-c3ccc(S(C)(=O)=O)cc3)c12] | diethyl(5-(((5-fluoro-2,3-dihydrobenzofuran-4-yl)methyl)amino)-8-(4-(methylsulfonyl)phenyl)imidazo[1,5-c]pyrimidin-1-yl)phosphine oxide |
| 123 | 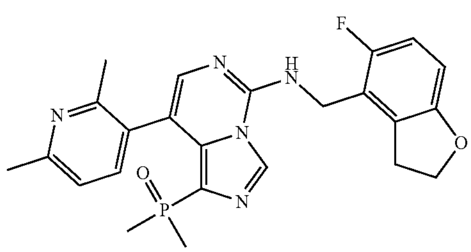 [SMILES: Cc1ccc(-c2cnc(NCc3c(F)ccc4c3CCO4)n3cnc(P(C)(C)=O)c23)c(C)n1] | (8-(2,6-dimethylpyridin-3-yl)-5-(((5-fluoro-2,3-dihydrobenzofuran-4-yl)methyl)amino)imidazo[1,5-c]pyrimidin-1-yl)dimethylphosphine oxide |
| 124 | 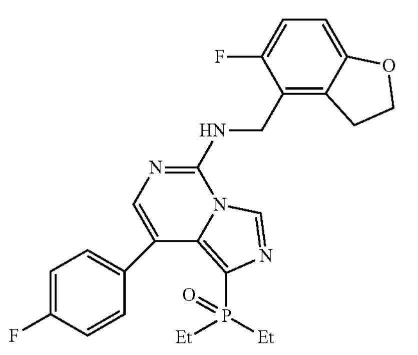 [SMILES: CCP(=O)(CC)c1ncn2c(NCc3c(F)ccc4c3CCO4)ncc(-c3ccc(F)cc3)c12] | diethyl(5-(((5-fluoro-2,3-dihydrobenzofuran-4-yl)methyl)amino)-8-(4-fluorophenyl)imidazo[1,5-c]pyrimidin-1-yl)phosphine oxide |
| 125 | 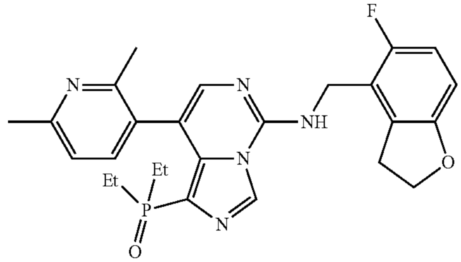 [SMILES: CCP(=O)(CC)c1ncn2c(NCc3c(F)ccc4c3CCO4)ncc(-c3ccc(C)nc3C)c12] | (8-(2,6-dimethylpyridin-3-yl)-5-(((5-fluoro-2,3-dihydrobenzofuran-4-yl)methyl)amino)imidazo[1,5-c]pyrimidin-1-yl)diethylphosphine oxide |

TABLE 1-continued

| Cpd. No. | Structure | Name |
|---|---|---|
| 126 | 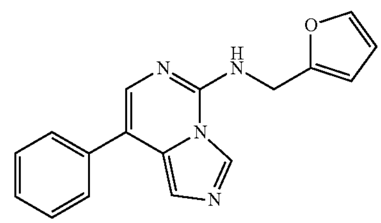 [SMILES: c1ccc(-c2cnc(NCc3ccco3)n3cncc23)cc1] | N-(furan-2-ylmethyl)-8-phenylimidazo[1,5-c]pyrimidin-5-amine |
| 127 | 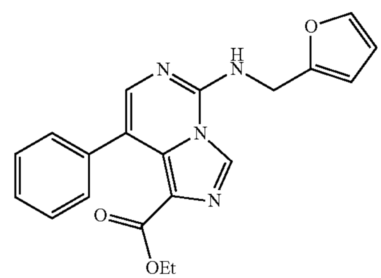 [SMILES: CCOC(=O)c1ncn2c(NCc3ccco3)ncc(-c3ccccc3)c12] | ethyl 5-((furan-2-ylmethyl)amino)-8-phenylimidazo[1,5-c]pyrimidine-1-carboxylate |
| 128 | 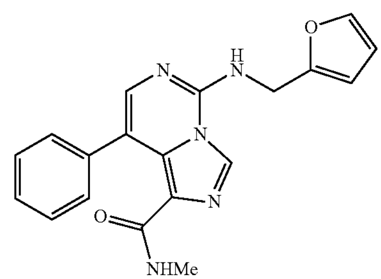 [SMILES: CNC(=O)c1ncn2c(NCc3ccco3)ncc(-c3ccccc3)c12] | 5-((furan-2-ylmethyl)amino)-N-methyl-8-phenylimidazo[1,5-c]pyrimidine-1-carboxamide |
| 129 | 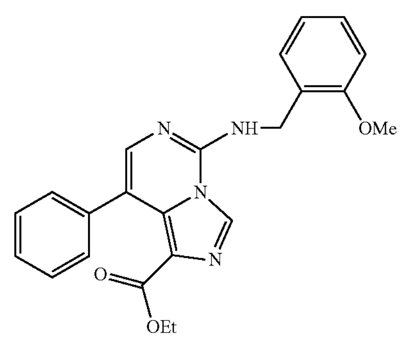 [SMILES: CCOC(=O)c1ncn2c(NCc3ccccc3OC)ncc(-c3ccccc3)c12] | ethyl 5-((2-methoxybenzyl)amino)-8-phenylimidazo[1,5-c]pyrimidine-1-carboxylate |
| 130 | 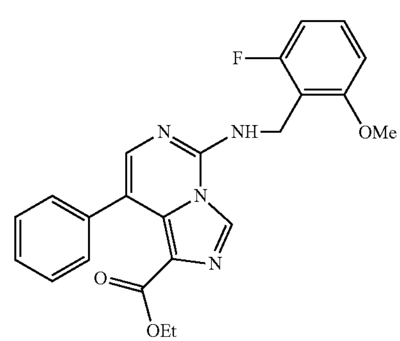 [SMILES: CCOC(=O)c1ncn2c(NCc3c(F)cccc3OC)ncc(-c3ccccc3)c12] | ethyl 5-((2-fluoro-6-methoxybenzyl)amino)-8-phenylimidazo[1,5-c]pyrimidine-1-carboxylate |

TABLE 1-continued

| Cpd. No. | Structure | Name |
|---|---|---|
| 131 | 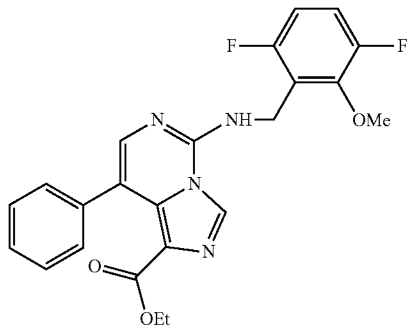 [SMILES: CCOC(=O)c1ncn2c(NCc3c(F)ccc(F)c3OC)ncc(-c3ccccc3)c12] | ethyl 5-((2,6-difluoro-3-methoxybenzyl)amino)-8-phenylimidazo[1,5-c]pyrimidine-1-carboxylate |
| 132 | 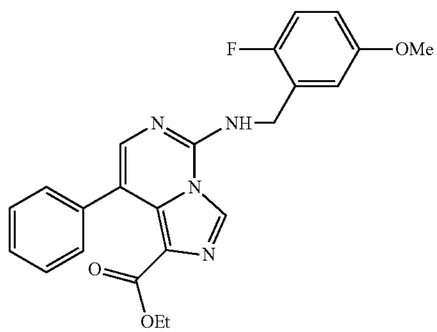 [SMILES: CCOC(=O)c1ncn2c(NCc3cc(OC)ccc3F)ncc(-c3ccccc3)c12] | ethyl 5-((2-fluoro-5-methoxybenzyl)amino)-8-phenylimidazo[1,5-c]pyrimidine-1-carboxylate |
| 133 | 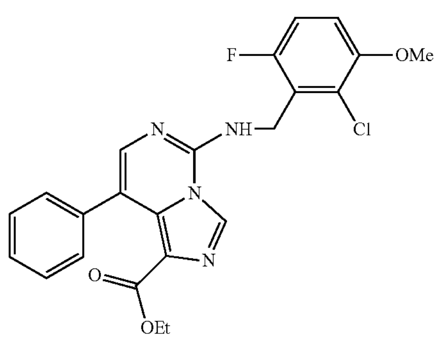 [SMILES: CCOC(=O)c1ncn2c(NCc3c(F)ccc(OC)c3Cl)ncc(-c3ccccc3)c12] | ethyl 5-((2-chloro-6-fluoro-3-methoxybenzyl)amino)-8-phenylimidazo[1,5-c]pyrimidine-1-carboxylate |
| 134 | 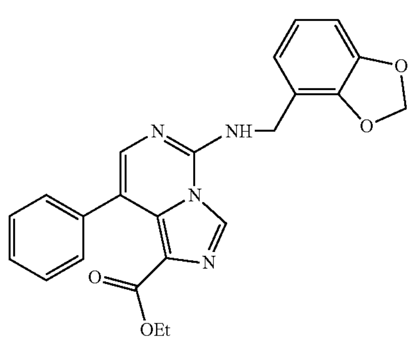 [SMILES: CCOC(=O)c1ncn2c(NCc3cccc4c3OCO4)ncc(-c3ccccc3)c12] | ethyl 5-((benzo[d][1,3]dioxol-4-ylmethyl)amino)-8-phenylimidazo[1,5-c]pyrimidine-1-carboxylate |

TABLE 1-continued

| Cpd. No. | Structure | Name |
|---|---|---|
| 135 | 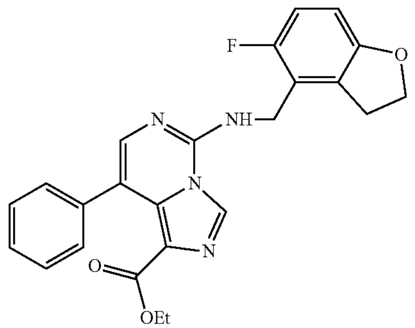 [SMILES: CCOC(=O)c1ncn2c(NCc3c(F)ccc4c3CCO4)ncc(-c3ccccc3)c12] | ethyl 5-(((5-fluoro-2,3-dihydrobenzofuran-4-yl)methyl)amino)-8-phenylimidazo[1,5-c]pyrimidine-1-carboxylate |
| 136 | 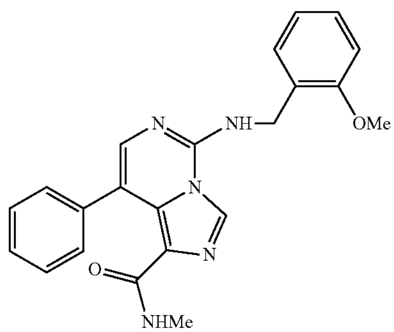 [SMILES: CNC(=O)c1ncn2c(NCc3ccccc3OC)ncc(-c3ccccc3)c12] | 5-((2-methoxybenzyl)amino)-N-methyl-8-phenylimidazo[1,5-c]pyrimidine-1-carboxamide |
| 137 | 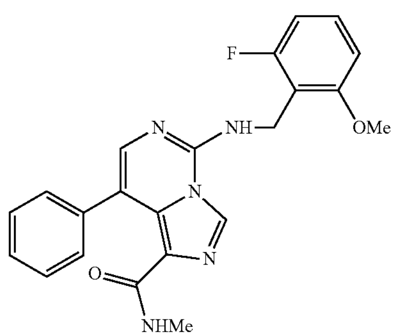 [SMILES: CNC(=O)c1ncn2c(NCc3c(F)cccc3OC)ncc(-c3ccccc3)c12] | 5-((2-fluoro-6-methoxybenzyl)amino)-N-methyl-8-phenylimidazo[1,5-c]pyrimidine-1-carboxamide |
| 138 | 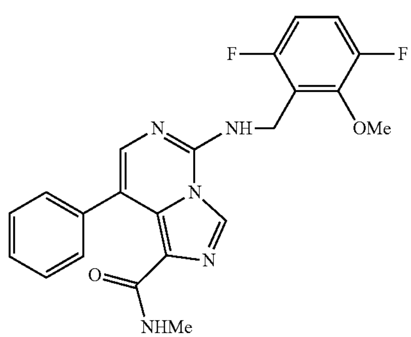 [SMILES: CNC(=O)c1ncn2c(NCc3c(F)ccc(F)c3OC)ncc(-c3ccccc3)c12] | 5-((3,6-difluoro-2-methoxybenzyl)amino)-N-methyl-8-phenylimidazo[1,5-c]pyrimidine-1-carboxamide |

TABLE 1-continued

| Cpd. No. | Structure | Name |
|---|---|---|
| 139 | 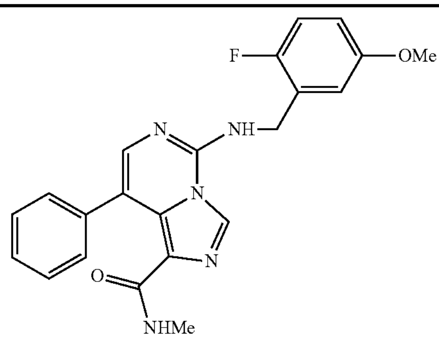 | 5-((2-fluoro-5-methoxybenzyl)amino)-N-methyl-8-phenylimidazo[1,5-c]pyrimidine-1-carboxamide |
| 140 | 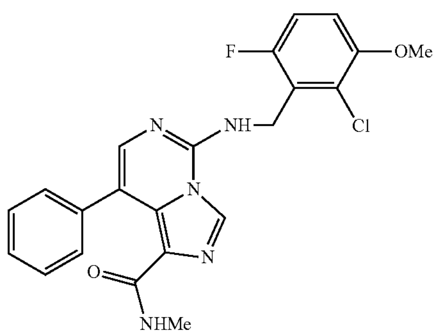 [SMILES: CNC(=O)c1ncn2c(NCc3c(F)ccc(OC)c3Cl)ncc(-c3ccccc3)c12] | 5-((2-chloro-6-fluoro-3-methoxybenzyl)amino)-N-methyl-8-phenylimidazo[1,5-c]pyrimidine-1-carboxamide |
| 141 | 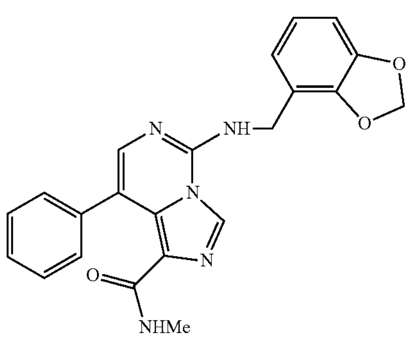 [SMILES: CNC(=O)c1ncn2c(NCc3cccc4c3OCO4)ncc(-c3ccccc3)c12] | 5-((benzo[d][1,3]dioxol-4-ylmethyl)amino)-N-methyl-8-phenylimidazo[1,5-c]pyrimidine-1-carboxamide |
| 142 | 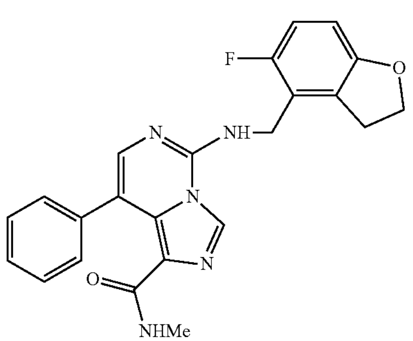 [SMILES: CNC(=O)c1ncn2c(NCc3c(F)ccc4c3CCO4)ncc(-c3ccccc3)c12] | 5-(((5-fluoro-2,3-dihydrobenzofuran-4-yl)methyl)amino)-N-methyl-8-phenylimidazo[1,5-c]pyrimidine-1-carboxamide |

TABLE 1-continued

| Cpd. No. | Structure | Name |
|---|---|---|
| 143 | 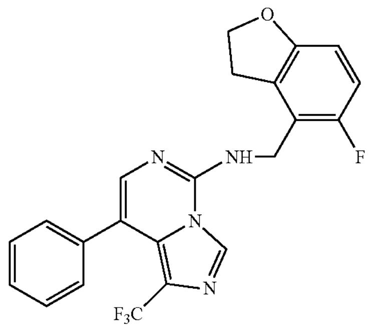 [SMILES: Fc1ccc2c(c1CNc1ncc(-c3ccccc3)c3c(C(F)(F)F)ncn13)CCO2] | N-((5-fluoro-2,3-dihydrobenzofuran-4-yl)methyl)-8-phenyl-1-(trifluoromethyl)imidazo[1,5-c]pyrimidin-5-amine |
| 144 | 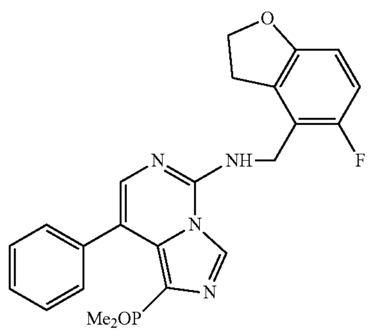 | (5-(((5-fluoro-2,3-dihydrobenzofuran-4-yl)methyl)amino)-8-phenylimidazo[1,5-c]pyrimidin-1-yl)dimethylphosphine oxide |
| 146 | 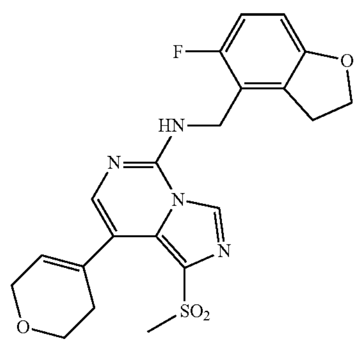 [SMILES: CS(=O)(=O)c1ncn2c(NCc3c(F)ccc4c3CCO4)ncc(C3=CCOCC3)c12] | 8-(3,6-dihydro-2H-pyran-4-yl)-N-((5-fluoro-2,3-dihydrobenzofuran-4-yl)methyl)-1-(methylsulfonyl)imidazo[1,5-c]pyrimidin-5-amine |
| 147 | 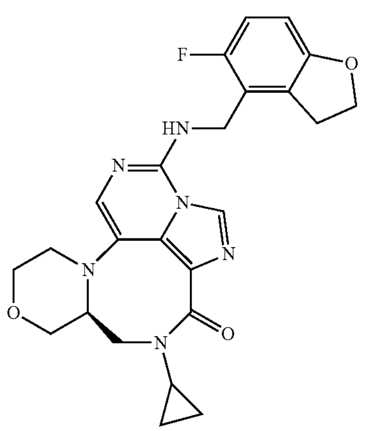 [SMILES: O=C1c2ncn3c(NCc4c(F)ccc5c4CCO5)ncc(c23)N2CCOC[C@@H]2CN1C1CC1] | (S)-4-cyclopropyl-12-(((5-fluoro-2,3-dihydrobenzofuran-4-yl)methyl)amino)-4,5,5a,6,8,9-hexahydro-3H-7-oxa-2,4,9a,11,12a-pentaazabenzo[4,5]cycloocta[1,2,3-cd]inden-3-one |

TABLE 1-continued

| Cpd. No. | Structure | Name |
|---|---|---|
| 148 | 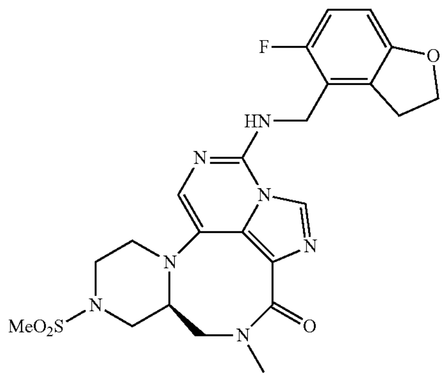 [SMILES: CN1C[C@H]2CN(S(C)(=O)=O)CCN2c2cnc(NCc3c(F)ccc4c3CCO4)n3cnc(c23)C1=O] | (S)-12-(((5-fluoro-2,3-dihydrobenzofuran-4-yl)methyl)amino)-4-methyl-7-(methylsulfonyl)-5,5a,6,7,8,9-hexahydro-2,4,7,9a,11,12a-hexaazabenzo[4,5]cycloocta[1,2,3-cd]inden-3(4H)-one |
| 149 | 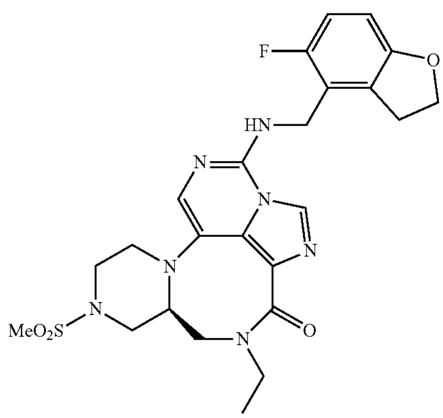 [SMILES: CCN1C[C@H]2CN(S(C)(=O)=O)CCN2c2cnc(NCc3c(F)ccc4c3CCO4)n3cnc(c23)C1=O] | (S)-4-ethyl-12-(((5-fluoro-2,3-dihydrobenzofuran-4-yl)methyl)amino)-7-(methylsulfonyl)-5,5a,6,7,8,9-hexahydro-2,4,7,9a,11,12a-hexaazabenzo[4,5]cycloocta[1,2,3-cd]inden-3(4H)-one |
| 150 | 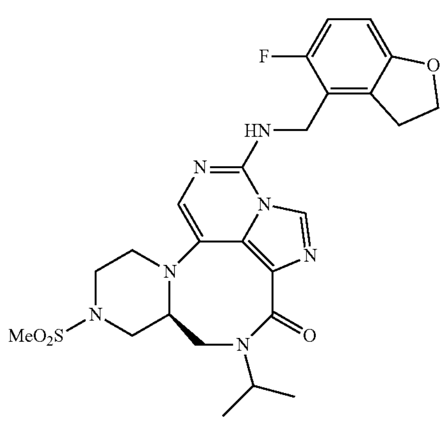 [SMILES: CC(C)N1C[C@H]2CN(S(C)(=O)=O)CCN2c2cnc(NCc3c(F)ccc4c3CCO4)n3cnc(c23)C1=O] | (S)-12-(((5-fluoro-2,3-dihydrobenzofuran-4-yl)methyl)amino)-4-isopropyl-7-(methylsulfonyl)-5,5a,6,7,8,9-hexahydro-2,4,7,9a,11,12a-hexaazabenzo[4,5]cycloocta[1,2,3-cd]inden-3(4H)-one |

TABLE 1-continued

| Cpd. No. | Structure | Name |
|---|---|---|
| 151 | 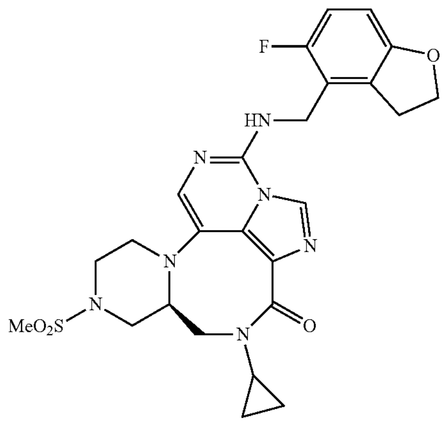 [SMILES: CS(=O)(=O)N1CCN2c3cnc(NCc4c(F)ccc5c4CCO5)n4cnc(c34)C(=O)N(C3CC3)C[C@H]2C1] | (S)-4-cyclopropyl-12-(((5-fluoro-2,3-dihydrobenzofuran-4-yl)methyl)amino)-7-(methylsulfonyl)-5,5a,6,7,8,9-hexahydro-2,4,7,9a,11,12a-hexaazabenzo[4,5]cycloocta[1,2,3-cd]inden-3(4H)-one |
| 152 | 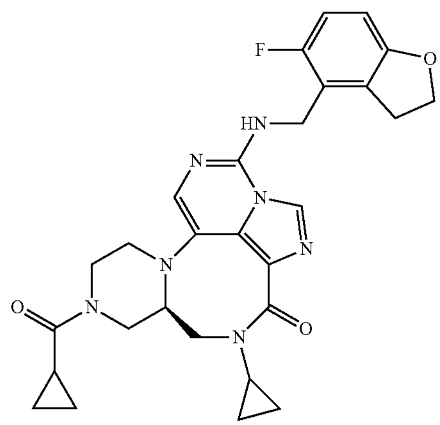 [SMILES: O=C(C1CC1)N1CCN2c3cnc(NCc4c(F)ccc5c4CCO5)n4cnc(c34)C(=O)N(C3CC3)C[C@H]2C1] | (R)-7-(cyclopropanecarbonyl)-4-cyclopropyl-12-(((5-fluoro-2,3-dihydrobenzofuran-4-yl)methyl)amino)-5,5a,6,7,8,9-hexahydro-2,4,7,9a,11,12a-hexaazabenzo[4,5]cycloocta[1,2,3-cd]inden-3(4H)-one |
| 153 | 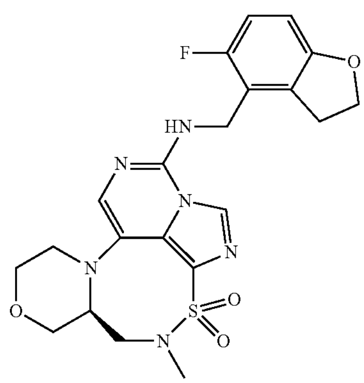 [SMILES: CN1C[C@H]2COCCN2c2cnc(NCc3c(F)ccc4c3CCO4)n3cnc(c23)S1(=O)=O] | (S)-12-(((5-fluoro-2,3-dihydrobenzofuran-4-yl)methyl)amino)-4-methyl-4,5,5a,6,8,9-hexahydro-7-oxa-3-thia-2,4,9a,11,12a-pentaazabenzo[4,5]cycloocta[1,2,3-cd]indene 3,3-dioxide |
| 154 | 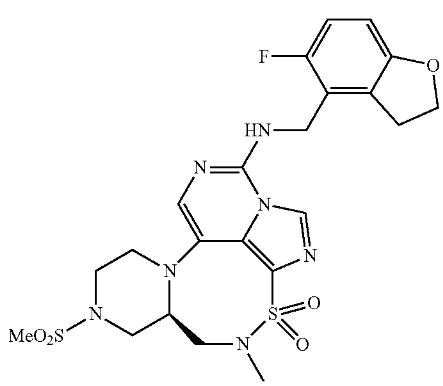 [SMILES: CN1C[C@H]2CN(S(C)(=O)=O)CCN2c2cnc(NCc3c(F)ccc4c3CCO4)n3cnc(c23)S1(=O)=O] | (S)-12-(((5-fluoro-2,3-dihydrobenzofuran-4-yl)methyl)amino)-4-methyl-7-(methylsulfonyl)-5,5a,6,7,8,9-hexahydro-4H-3-thia-2,4,7,9a,11,12a-hexaazabenzo[4,5]cycloocta[1,2,3-cd]indene 3,3-dioxide |

TABLE 1-continued

| Cpd. No. | Structure | Name |
|---|---|---|
| 155 | 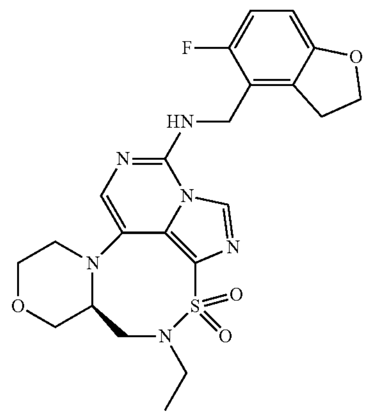 [SMILES: CCN1C[C@H]2COCCN2c2cnc(NCc3c(F)ccc4c3CCO4)n3cnc(c23)S1(=O)=O] | (S)-4-ethyl-12-(((5-fluoro-2,3-dihydrobenzofuran-4-yl)methyl)amino)-4,5,5a,6,8,9-hexahydro-7-oxa-3-thia-2,4,9a,11,12a-pentaazabenzo[4,5]cycloocta[1,2,3-cd]indene 3,3-dioxide |
| 156 | 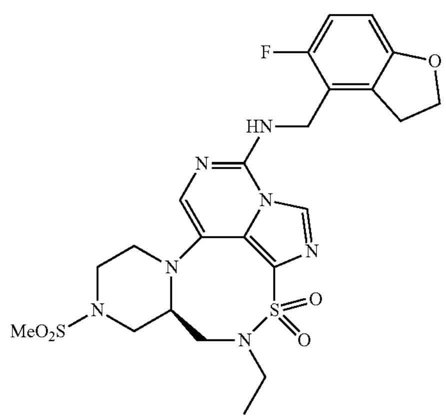 [SMILES: CCN1C[C@H]2CN(S(C)(=O)=O)CCN2c2cnc(NCc3c(F)ccc4c3CCO4)n3cnc(c23)S1(=O)=O] | (R)-4-ethyl-12-(((5-fluoro-2,3-dihydrobenzofuran-4-yl)methyl)amino)-7-(methylsulfonyl)-5,5a,6,7,8,9-hexahydro-4H-3-thia-2,4,7,9a,11,12a-hexaazabenzo[4,5]cycloocta[1,2,3-cd]indene 3,3-dioxide |
| 157 | 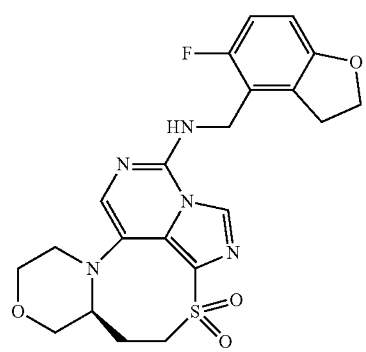 [SMILES: O=S1(=O)CC[C@H]2COCCN2c2cnc(NCc3c(F)ccc4c3CCO4)n3cnc1c23] | (S)-12-(((5-fluoro-2,3-dihydrobenzofuran-4-yl)methyl)amino)-4,5,5a,6,8,9-hexahydro-7-oxa-3-thia-2,9a,11,12a-tetraazabenzo[4,5]cycloocta[1,2,3-cd]indene 3,3-dioxide |
| 158 | 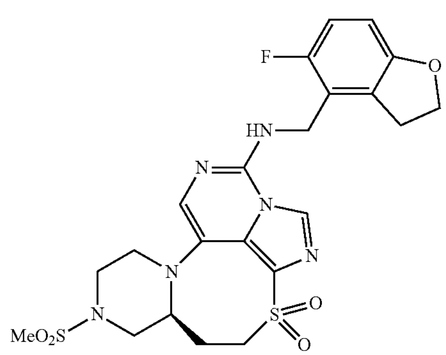 [SMILES: CS(=O)(=O)N1CCN2c3cnc(NCc4c(F)ccc5c4CCO5)n4cnc(c34)S(=O)(=O)CC[C@H]2C1] | (S)-12-(((5-fluoro-2,3-dihydrobenzofuran-4-yl)methyl)amino)-7-(methylsulfonyl)-5,5a,6,7,8,9-hexahydro-4H-3-thia-2,7,9a,11,12a-pentaazabenzo[4,5]cycloocta[1,2,3-cd]indene 3,3-dioxide |

TABLE 1-continued

| Cpd. No. | Structure | Name |
|---|---|---|
| 169 | 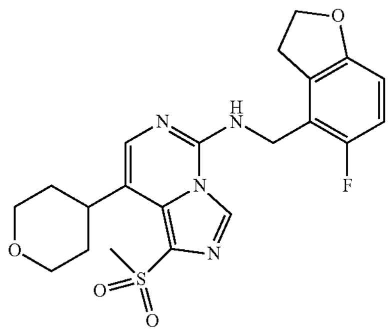 [SMILES: CS(=O)(=O)c1ncn2c(NCc3c(F)ccc4c3CCO4)ncc(C3CCOCC3)c12] | N-((5-fluoro-2,3-dihydrobenzofuran-4-yl)methyl)-1-(methylsulfonyl)-8-(tetrahydro-2H-pyran-4-yl)imidazo[1,5-c]pyrimidin-5-amine |
| 160 | 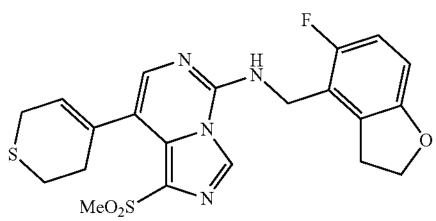 [SMILES: CS(=O)(=O)c1ncn2c(NCc3c(F)ccc4c3CCO4)ncc(C3=CCSCC3)c12] | 8-(3,6-dihydro-2H-thiopyran-4-yl)-N-((5-fluoro-2,3-dihydrobenzofuran-4-yl)methyl)-1-(methylsulfonyl)imidazo[1,5-c]pyrimidin-5-amine |
| 161 | 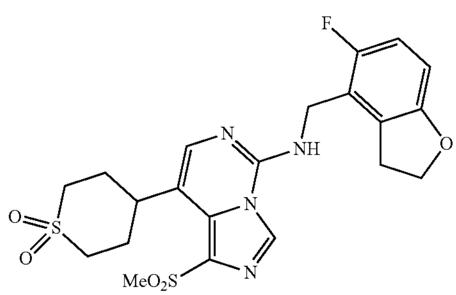 [SMILES: CS(=O)(=O)c1ncn2c(NCc3c(F)ccc4c3CCO4)ncc(C3CCS(=O)(=O)CC3)c12] | 4-(5-(((5-fluoro-2,3-dihydrobenzofuran-4-yl)methyl)amino)-1-(methylsulfonyl)imidazo[1,5-c]pyrimidin-8-yl)tetrahydro-2H-thiopyran 1,1-dioxide |
| 162 | 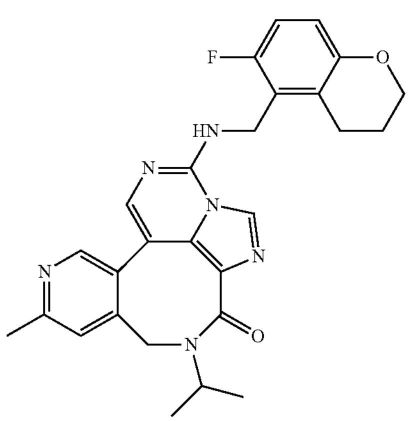 [SMILES: Cc1cc2c(cn1)-c1cnc(NCc3c(F)ccc4c3CCCO4)n3cnc(c13)C(=O)N(C(C)C)C2] | 12-(((6-fluorochroman-5-yl)methyl)amino)-4-isopropyl-7-methyl-4,5-dihydro-3H-2,4,8,11,12a-pentaazabenzo[4,5]cycloocta[1,2,3-cd]inden-3-one |

TABLE 1-continued
| Cpd. No. | Structure | Name |
|---|---|---|
| 163 | 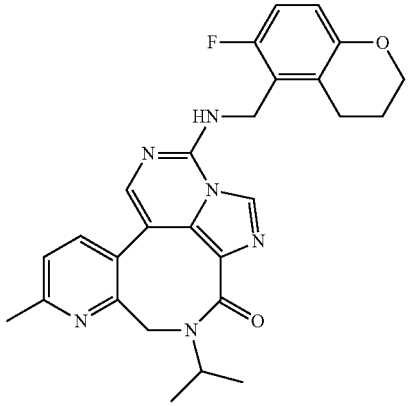 [SMILES: Cc1ccc2c(n1)CN(C(C)C)C(=O)c1ncn3c(NCc4c(F)ccc5c4CCCO5)ncc-2c13] | 12-(((6-fluorochroman-5-yl)methyl)amino)-4-isopropyl-7-methyl-4,5-dihydro-3H-2,4,6,11,12a-pentaazabenzo[4,5]cycloocta[1,2,3-cd]inden-3-one |
| 164 | 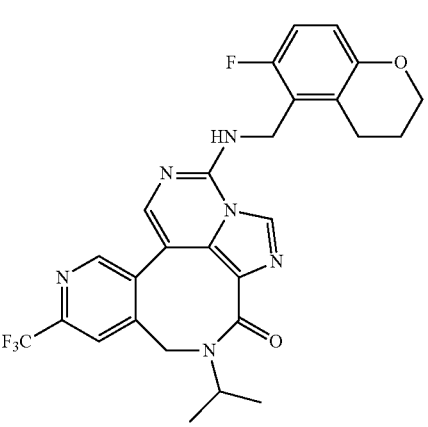 [SMILES: CC(C)N1Cc2cc(C(F)(F)F)ncc2-c2cnc(NCc3c(F)ccc4c3CCCO4)n3cnc(c23)C1=O] | 12-(((6-fluorochroman-5-yl)methyl)amino)-4-isopropyl-7-(trifluoromethyl)-4,5-dihydro-3H-2,4,8,11,12a-pentaazabenzo[4,5]cycloocta[1,2,3-cd]inden-3-one |
| 165 | 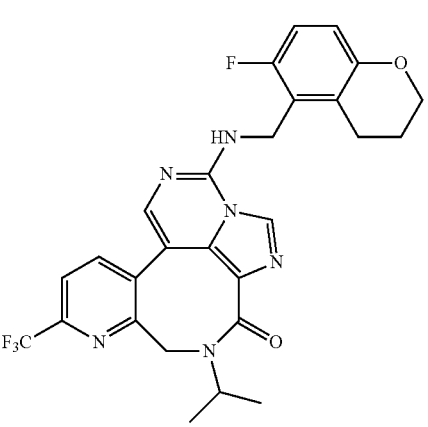 [SMILES: CC(C)N1Cc2nc(C(F)(F)F)ccc2-c2cnc(NCc3c(F)ccc4c3CCCO4)n3cnc(c23)C1=O] | 12-(((6-fluorochroman-5-yl)methyl)amino)-4-isopropyl-7-(trifluoromethyl)-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| 166 | 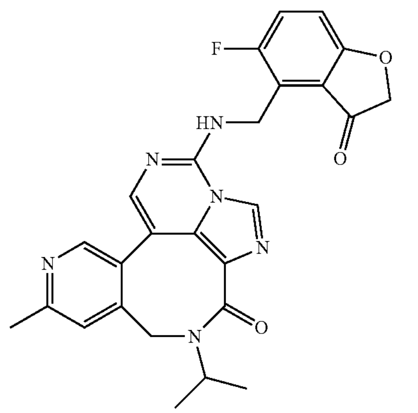 [SMILES: Cc1cc2c(cn1)-c1cnc(NCc3c(F)ccc4c3C(=O)CO4)n3cnc(c13)C(=O)N(C(C)C)C2] | 12-(((5-fluoro-3-oxo-2,3-dihydrobenzofuran-4-yl)methyl)amino)-4-isopropyl-7-methyl-4,5-dihydro-3H-2,4,8,11,12a-pentaazabenzo[4,5]cycloocta[1,2,3-cd]inden-3-one |
| 167 | 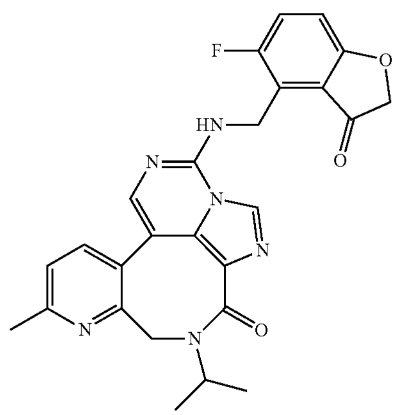 [SMILES: Cc1ccc2c(n1)CN(C(C)C)C(=O)c1ncn3c(NCc4c(F)ccc5c4C(=O)CO5)ncc-2c13] | 12-(((5-fluoro-3-oxo-2,3-dihydrobenzofuran-4-yl)methyl)amino)-4-isopropyl-7-methyl-4,5-dihydro-3H-2,4,6,11,12a-pentaazabenzo[4,5]cycloocta[1,2,3-cd]inden-3-one |
| 168 | 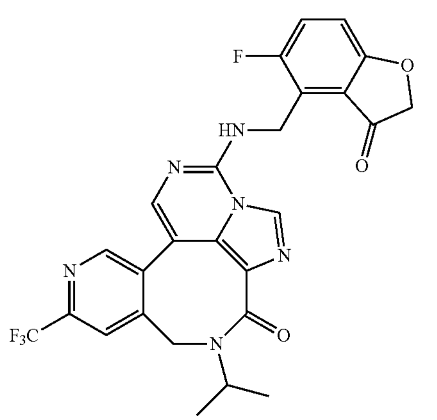 [SMILES: CC(C)N1Cc2cc(C(F)(F)F)ncc2-c2cnc(NCc3c(F)ccc4c3C(=O)CO4)n3cnc(c23)C1=O] | 12-(((5-fluoro-3-oxo-2,3-dihydrobenzofuran-4-yl)methyl)amino)-4-isopropyl-7-(trifluoromethyl)-4,5-dihydro-3H-2,4,8,11,12a-pentaazabenzo[4,5]cycloocta[1,2,3-cd]inden-3-one |

TABLE 1-continued

| Cpd. No. | Structure | Name |
|---|---|---|
| 169 | 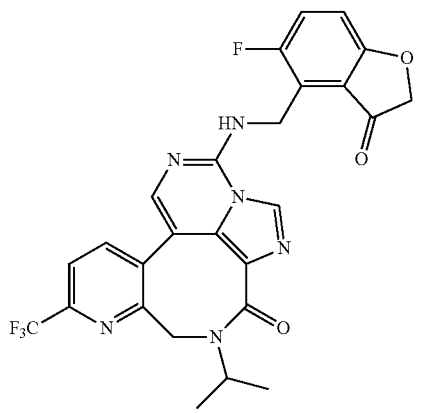 [SMILES: CC(C)N1Cc2nc(C(F)(F)F)ccc2-c2cnc(NCc3c(F)ccc4c3C(=O)CO4)n3cnc(c23)C1=O] | 12-(((5-fluoro-3-oxo-2,3-dihydrobenzofuran-4-yl)methyl)amino)-4-isopropyl-7-(trifluoromethyl)-4,5-dihydro-3H-2,4,6,11,12a-pentaazabenzo[4,5]cycloocta[1,2,3-cd]inden-3-one |
| 170 | 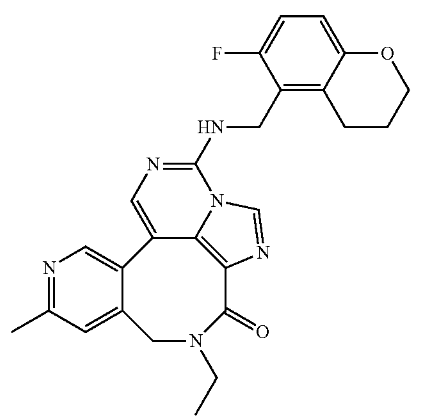 | 4-ethyl-12-(((6-fluorochroman-5-yl)methyl)amino)-7-methyl-4,5-dihydro-3H-2,4,8,11,12a-pentaazabenzo[4,5]cycloocta[1,2,3-cd]inden-3-one |
| 171 | 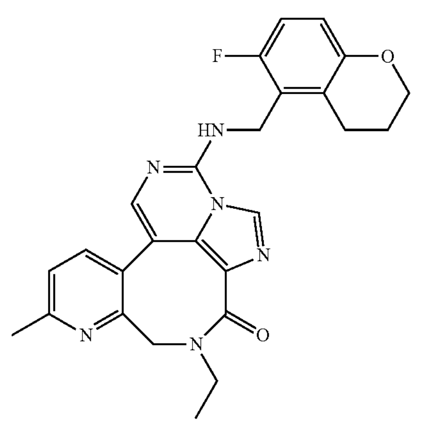 [SMILES: CCN1Cc2nc(C)ccc2-c2cnc(NCc3c(F)ccc4c3CCCO4)n3cnc(c23)C1=O] | 4-ethyl-12-(((6-fluorochroman-5-yl)methyl)amino)-7-methyl-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| 172 | 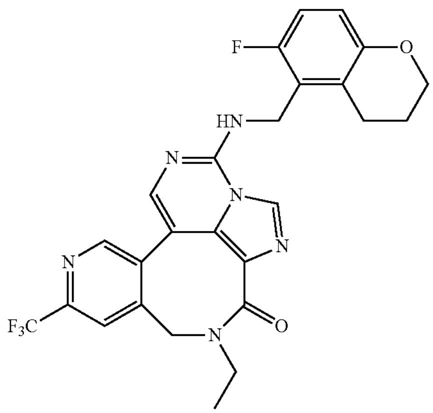 | 4-ethyl-12-(((6-fluorochroman-5-yl)methyl)amino)-7-(trifluoromethyl)-4,5-dihydro-3H-2,4,8,11,12a-pentaazabenzo[4,5]cycloocta[1,2,3-cd]inden-3-one |
| 173 | 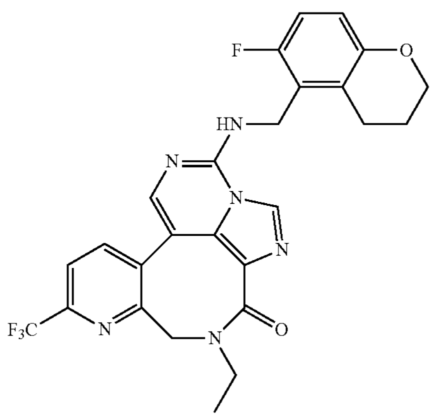 [SMILES: CCN1Cc2nc(C(F)(F)F)ccc2-c2cnc(NCc3c(F)ccc4c3CCCO4)n3cnc(c23)C1=O] | 4-ethyl-12-(((6-fluorochroman-5-yl)methyl)amino)-7-(trifluoromethyl)-4,5-dihydro-3H-2,4,6,11,12a-pentaazabenzo[4,5]cycloocta[1,2,3-cd]inden-3-one |
| 174 | 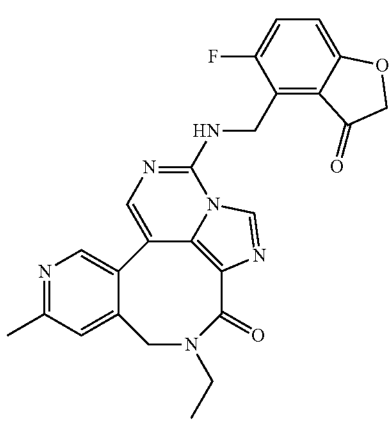 [SMILES: CCN1Cc2cc(C)ncc2-c2cnc(NCc3c(F)ccc4c3C(=O)CO4)n3cnc(c23)C1=O] | 4-ethyl-12-(((5-fluoro-3-oxo-2,3-dihydrobenzofuran-4-yl)methyl)amino)-7-methyl-4,5-dihydro-3H-2,4,8,11,12a-pentaazabenzo[4,5]cycloocta[1,2,3-cd]inden-3-one |

TABLE 1-continued

| Cpd. No. | Structure | Name |
|---|---|---|
| 175 | 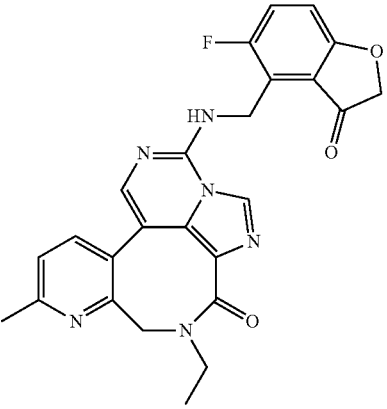 [SMILES: CCN1Cc2nc(C)ccc2-c2cnc(NCc3c(F)ccc4c3C(=O)CO4)n3cnc(c23)C1=O] | 4-ethyl-12-(((5-fluoro-3-oxo-2,3-dihydrobenzofuran-4-yl)methyl)amino)-7-methyl-4,5-dihydro-3H-2,4,6,11,12a-pentaazabenzo[4,5]cycloocta[1,2,3-cd]inden-3-one |
| 176 | 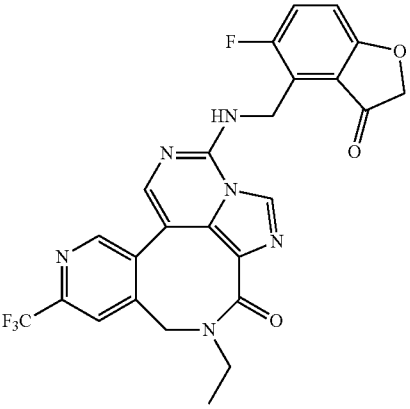 [SMILES: CCN1Cc2cc(C(F)(F)F)ncc2-c2cnc(NCc3c(F)ccc4c3C(=O)CO4)n3cnc(c23)C1=O] | 4-ethyl-12-(((5-fluoro-3-oxo-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one |
| 177 | 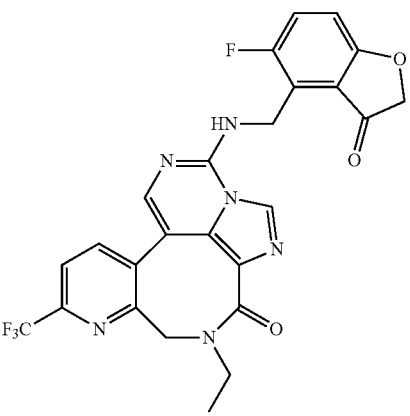 [SMILES: CCN1Cc2nc(C(F)(F)F)ccc2-c2cnc(NCc3c(F)ccc4c3C(=O)CO4)n3cnc(c23)C1=O] | 4-ethyl-12-(((5-fluoro-3-oxo-2,3-dihydrobenzofuran-4-yl)methyl)amino)-7-(trifluoromethyl)-4,5-dihydro-3H-2,4,6,11,12a-pentaazabenzo[4,5]cycloocta[1,2,3-cd]inden-3-one |
| 178 | 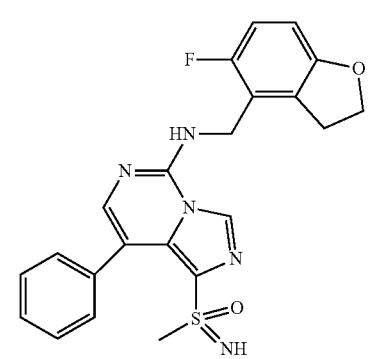 | (5-(((5-fluoro-2,3-dihydrobenzofuran-4-yl)methyl)amino)-8-phenylimidazo[1,5-c]pyrimidin-1-yl)(imino)(methyl)-l6-sulfanone |

TABLE 1-continued

| Cpd. No. | Structure | Name |
|---|---|---|
| 179 | 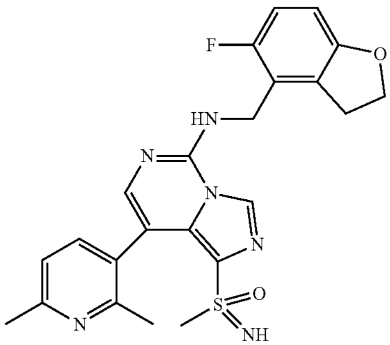 [SMILES: Cc1ccc(-c2cnc(NCc3c(F)ccc4c3CCO4)n3cnc(S(C)(=N)=O)c23)c(C)n1] | (8-(2,6-dimethylpyridin-3-yl)-5-(((5-fluoro-2,3-dihydrobenzofuran-4-yl)methyl)amino)imidazo[1,5-c]pyrimidin-1-yl)(imino)(methyl)-sulfanone |
| 180 | 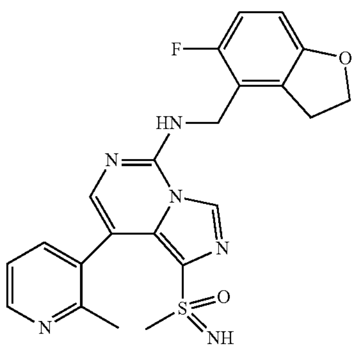 [SMILES: Cc1ncccc1-c1cnc(NCc2c(F)ccc3c2CCO3)n2cnc(S(C)(=N)=O)c12] | (5-(((5-fluoro-2,3-dihydrobenzofuran-4-yl)methyl)amino)-8-(2-methylpyridin-3-yl)imidazo[1,5-c]pyrimidin-1-yl)(imino)(methyl)-sulfanone |
| 181 | 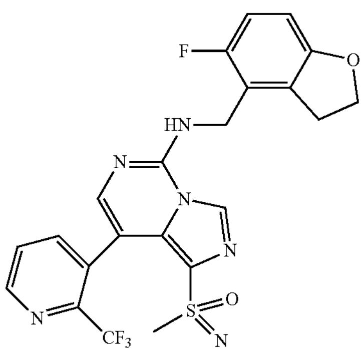 [SMILES: CS(=N)(=O)c1ncn2c(NCc3c(F)ccc4c3CCO4)ncc(-c3cccnc3C(F)(F)F)c12] | (5-(((5-fluoro-2,3-dihydrobenzofuran-4-yl)methyl)amino)-8-(2-(trifluoromethyl)pyridin-3-yl)imidazo[1,5-c]pyrimidin-1-yl)(imino)(methyl)-16-sulfanone |
| 182 | 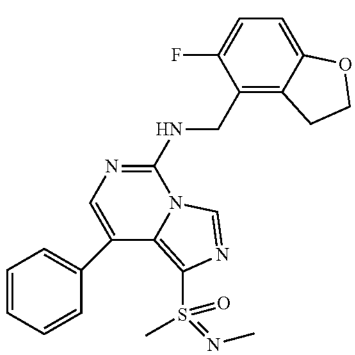 [SMILES: CN=S(C)(=O)c1ncn2c(NCc3c(F)ccc4c3CCO4)ncc(-c3ccccc3)c12] | (5-(((5-fluoro-2,3-dihydrobenzofuran-4-yl)methyl)amino)-8-phenylimidazo[1,5-c]pyrimidin-1-yl)(methyl)(methylimino)-16-sulfanone |

TABLE 1-continued

| Cpd. No. | Structure | Name |
|---|---|---|
| 183 | 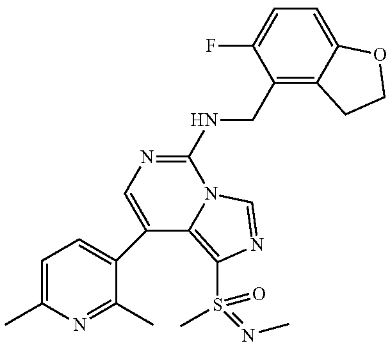 [SMILES: CN=S(C)(=O)c1ncn2c(NCc3c(F)ccc4c3CCO4)ncc(-c3ccc(C)nc3C)c12] | (8-(2,6-dimethylpyridin-3-yl)-5-(((5-fluoro-2,3-dihydrobenzofuran-4-yl)methyl)amino)imidazo[1,5-c]pyrimidin-1-yl)(methyl)(methylimino)-16-sulfanone |
| 184 | 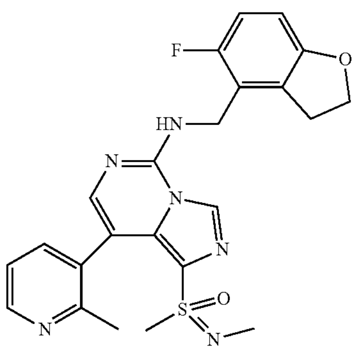 [SMILES: CN=S(C)(=O)c1ncn2c(NCc3c(F)ccc4c3CCO4)ncc(-c3cccnc3C)c12] | (5-(((5-fluoro-2,3-dihydrobenzofuran-4-yl)methyl)amino)-8-(2-methylpyridin-3-yl)imidazo[1,5-c]pyrimidin-1-yl)(methyl)(methylimino)-16-sulfanone |
| 185 | 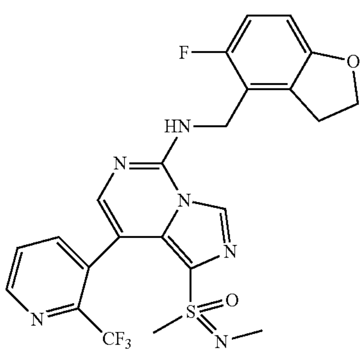 [SMILES: CN=S(C)(=O)c1ncn2c(NCc3c(F)ccc4c3CCO4)ncc(-c3cccnc3C(F)(F)F)c12] | (5-(((5-fluoro-2,3-dihydrobenzofuran-4-yl)methyl)amino)-8-(2-(trifluoromethyl)pyridin-3-yl)imidazo[1,5-c]pyrimidin-1-yl)(methyl)(methylimino)-16-sulfanone |
| 186 | 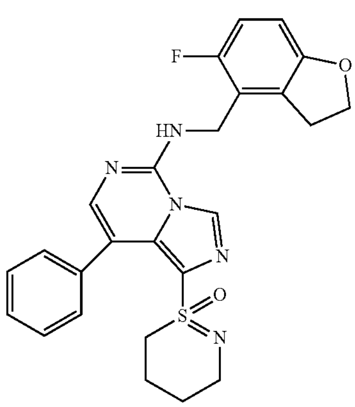 [SMILES: O=S1(c2ncn3c(NCc4c(F)ccc5c4CCO5)ncc(-c4ccccc4)c23)=NCCCC1] | 1-(5-(((5-fluoro-2,3-dihydrobenzofuran-4-yl)methyl)amino)-8-phenylimidazo[1,5-c]pyrimidin-1-yl)-3,4,5,6-tetrahydro-1,2-thiazine 1-oxide |

TABLE 1-continued

| Cpd. No. | Structure | Name |
|---|---|---|
| 187 | 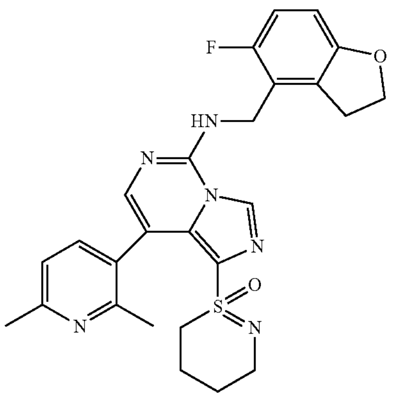 [SMILES: Cc1ccc(-c2cnc(NCc3c(F)ccc4c3CCO4)n3cnc(S4(=O)=NCCCC4)c23)c(C)n1] | 1-(8-(2,6-dimethylpyridin-3-yl)-5-(((5-fluoro-2,3-dihydrobenzofuran-4-yl)methyl)amino)imidazo[1,5-c]pyrimidin-1-yl)-3,4,5,6-tetrahydro-1,2-thiazine 1-oxide |
| 188 | 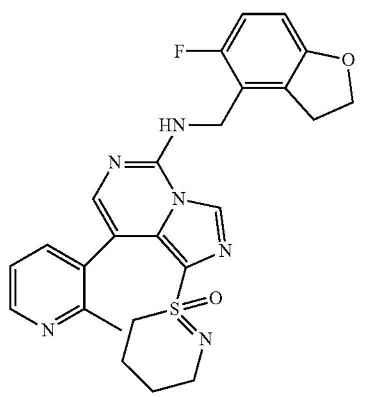 [SMILES: Cc1ncccc1-c1cnc(NCc2c(F)ccc3c2CCO3)n2cnc(S3(=O)=NCCCC3)c12] | 1-(5-(((5-fluoro-2,3-dihydrobenzofuran-4-yl)methyl)amino)-8-(2-methylpyridin-3-yl)imidazo[1,5-c]pyrimidin-1-yl)-3,4,5,6-tetrahydro-1,2-thiazine 1-oxide |
| 189 | 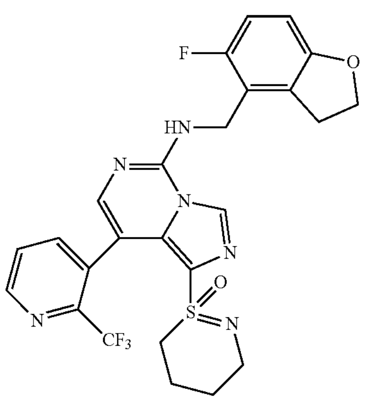 [SMILES: O=S1(c2ncn3c(NCc4c(F)ccc5c4CCO5)ncc(-c4cccnc4C(F)(F)F)c23)=NCCCC1] | 1-(5-(((5-fluoro-2,3-dihydrobenzofuran-4-yl)methyl)amino)-8-(2-(trifluoromethyl)pyridin-3-yl)imidazo[1,5-c]pyrimidin-1-yl)-3,4,5,6-tetrahydro-1,2-thiazine 1-oxide |
| E 1 | 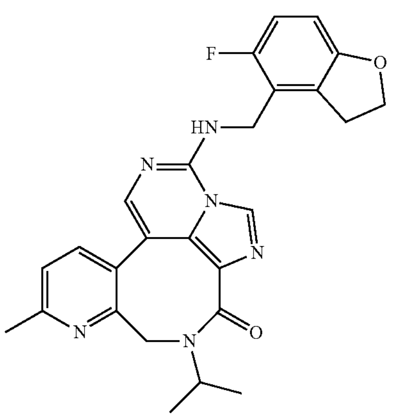 [SMILES: Cc1ccc2c(n1)CN(C(C)C)C(=O)c1ncn3c(NCc4c(F)ccc5c4CCO5)ncc-2c13] | 12-(((5-fluoro-2,3-dihydrobenzofuran-4-yl)methyl)amino)-4-isopropyl-7-methyl-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| E 2 | 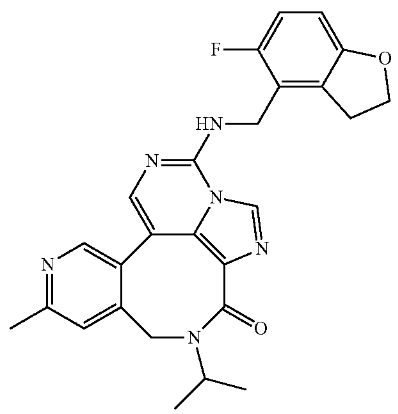 [SMILES: Cc1cc2c(cn1)-c1cnc(NCc3c(F)ccc4c3CCO4)n3cnc(c13)C(=O)N(C(C)C)C2] | 12-(((5-fluoro-2,3-dihydrobenzofuran-4-yl)methyl)amino)-4-isopropyl-7-methyl-4,5-dihydro-3H-2,4,8,11,12a-pentaazabenzo[4,5]cycloocta[1,2,3-cd]inden-3-one |
| E 3 | 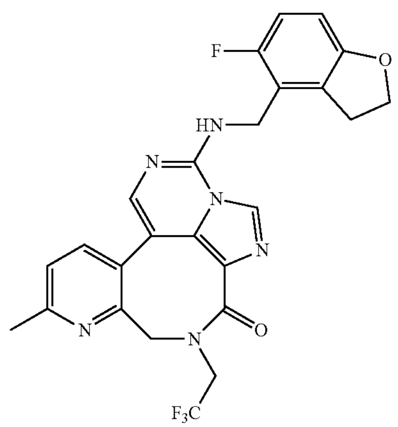 [SMILES: Cc1ccc2c(n1)CN(CC(F)(F)F)C(=O)c1ncn3c(NCc4c(F)ccc5c4CCO5)ncc-2c13] | 12-(((5-fluoro-2,3-dihydrobenzofuran-4-yl)methyl)amino)-7-methyl-4-(2,2,2-trifluoroethyl)-4,5-dihydro-3H-2,4,6,11,12a-pentaazabenzo[4,5]cycloocta[1,2,3-cd]inden-3-one |
| E 4 | 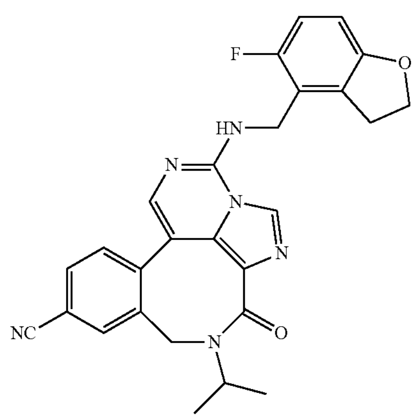 [SMILES: CC(C)N1Cc2cc(C#N)ccc2-c2cnc(NCc3c(F)ccc4c3CCO4)n3cnc(c23)C1=O] | 12-(((5-fluoro-2,3-dihydrobenzofuran-4-yl)methyl)amino)-4-isopropyl-3-oxo-4,5-dihydro-3H-2,4,11,12a-tetraazabenzo[4,5]cycloocta[1,2,3-cd]indene-7-carbonitrile |

TABLE 1-continued

| Cpd. No. | Structure | Name |
|---|---|---|
| E 5 | 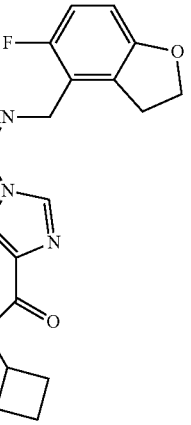 | 4-cyclobutyl-12-(((5-fluoro-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one |
| E 6 | 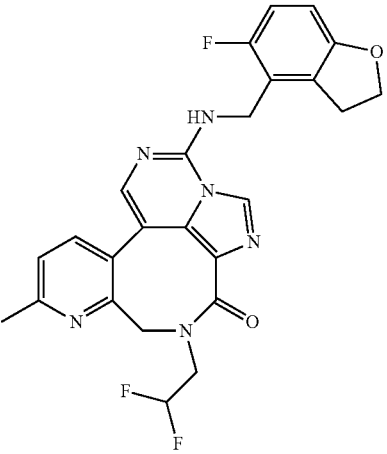 [SMILES: Cc1ccc2c(n1)CN(CC(F)F)C(=O)c1ncn3c(NCc4c(F)ccc5c4CCO5)ncc-2c13] | 4-(2,2-difluoroethyl)-12-(((5-fluoro-2,3-dihydrobenzofuran-4-yl)methyl)amino)-7-methyl-4,5-dihydro-3H-2,4,6,11,12a-pentaazabenzo[4,5]cycloocta[1,2,3-cd]inden-3-one |
| E 7 | 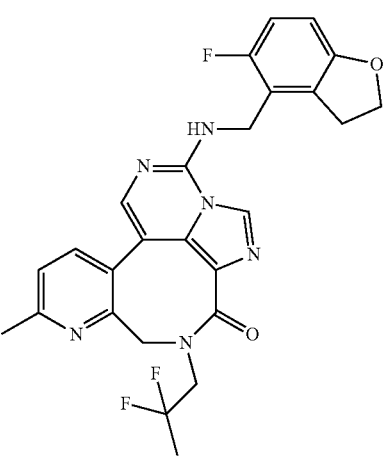 [SMILES: Cc1ccc2c(n1)CN(CC(C)(F)F)C(=O)c1ncn3c(NCc4c(F)ccc5c4CCO5)ncc-2c13] | 4-(2,2-difluoropropyl)-12-(((5-fluoro-2,3-dihydrobenzofuran-4-yl)methyl)amino)-7-methyl-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| E 8 | 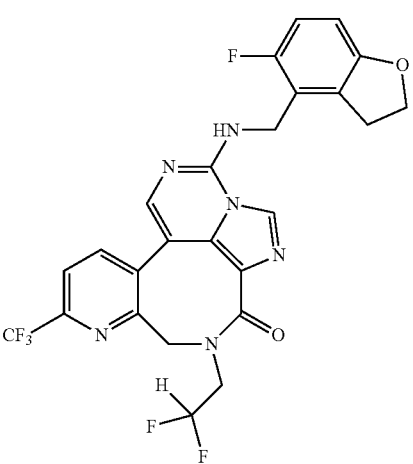 [SMILES: O=C1c2ncn3c(NCc4c(F)ccc5c4CCO5)ncc(c23)-c2ccc(C(F)(F)F)nc2CN1CC(F)F] | 4-(2,2-difluoroethyl)-12-(((5-fluoro-2,3-dihydrobenzofuran-4-yl)methyl)amino)-7-(trifluoromethyl)-4,5-dihydro-3H-2,4,6,11,12a-pentaazabenzo[4,5]cycloocta[1,2,3-cd]inden-3-one |
| E 9 | 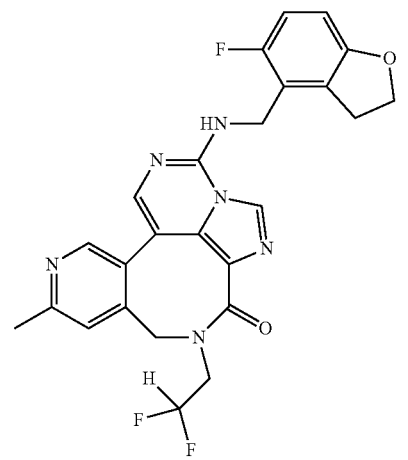 [SMILES: Cc1cc2c(cn1)-c1cnc(NCc3c(F)ccc4c3CCO4)n3cnc(c13)C(=O)N(CC(F)F)C2] | 4-(2,2-difluoroethyl)-12-(((5-fluoro-2,3-dihydrobenzofuran-4-yl)methyl)amino)-7-methyl-4,5-dihydro-3H-2,4,8,11,12a-pentaazabenzo[4,5]cycloocta[1,2,3-cd]inden-3-one |
| E 10 | 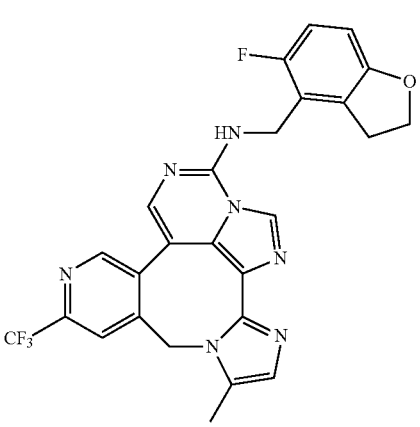 [SMILES: Cc1cnc2n1Cc1cc(C(F)(F)F)ncc1-c1cnc(NCc3c(F)ccc4c3CCO4)n3cnc-2c13] | N-((5-fluoro-2,3-dihydrobenzofuran-4-yl)methyl)-5-methyl-8-(trifluoromethyl)-6H-2,3,5a,9,12,13a-hexaazabenzo[4,5]cyclopenta[7,8]cycloocta[1,2,3-cd]inden-13-amine |

TABLE 1-continued

| Cpd. No. | Structure | Name |
|---|---|---|
| E 11 | 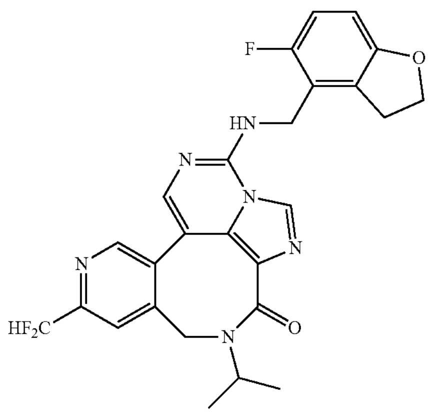 | 7-(difluoromethyl)-12-(((5-fluoro-2,3-dihydrobenzofuran-4-yl)methyl)amino)-4-isopropyl-4,5-dihydro-3H-2,4,8,11,12a-pentaazabenzo[4,5]cycloocta[1,2,3-cd]inden-3-one |
| E 12 | 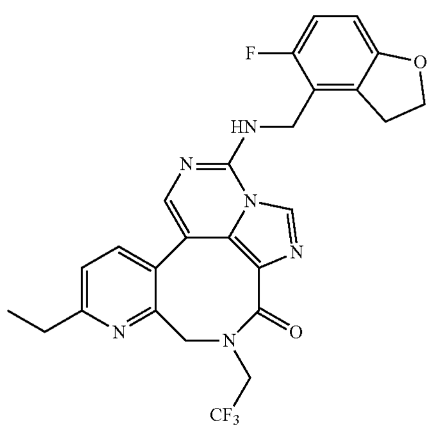 | 7-ethyl-12-(((5-fluoro-2,3-dihydrobenzofuran-4-yl)methyl)amino)-4-(2,2,2-trifluoroethyl)-4,5-dihydro-3H-2,4,6,11,12a-pentaazabenzo[4,5]cycloocta[1,2,3-cd]inden-3-one |
| E 13 | 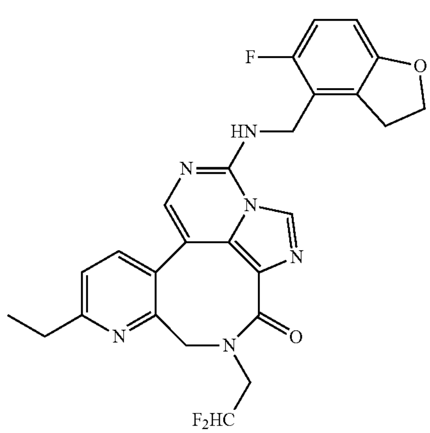 | 4-(2,2-difluoroethyl)-7-ethyl-12-(((5-fluoro-2,3-dihydrobenzofuran-4-yl)methyl)amino)-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| E 14 | 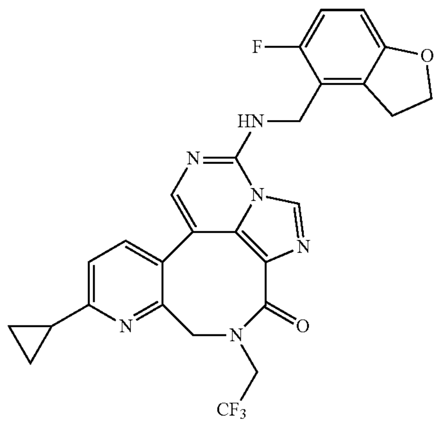 [SMILES: O=C1c2ncn3c(NCc4c(F)ccc5c4CCO5)ncc(c23)-c2ccc(C3CC3)nc2CN1CC(F)(F)F] | 7-cyclopropyl-12-(((5-fluoro-2,3-dihydrobenzofuran-4-yl)methyl)amino)-4-(2,2,2-trifluoroethyl)-4,5-dihydro-3H-2,4,6,11,12a-pentaazabenzo[4,5]cycloocta[1,2,3-cd]inden-3-one |
| E 15 | 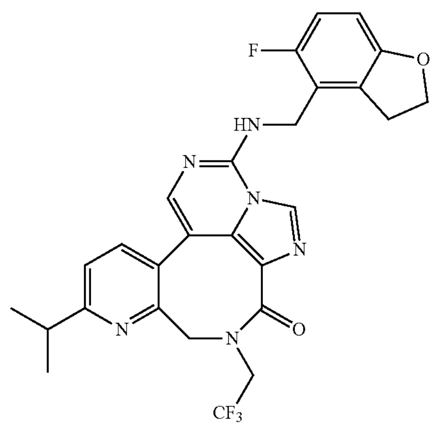 [SMILES: CC(C)c1ccc2c(n1)CN(CC(F)(F)F)C(=O)c1ncn3c(NCc4c(F)ccc5c4CCO5)ncc-2c13] | 12-(((5-fluoro-2,3-dihydrobenzofuran-4-yl)methyl)amino)-7-isopropyl-4-(2,2,2-trifluoroethyl)-4,5-dihydro-3H-2,4,6,11,12a-pentaazabenzo[4,5]cycloocta[1,2,3-cd]inden-3-one |
| E 16 | 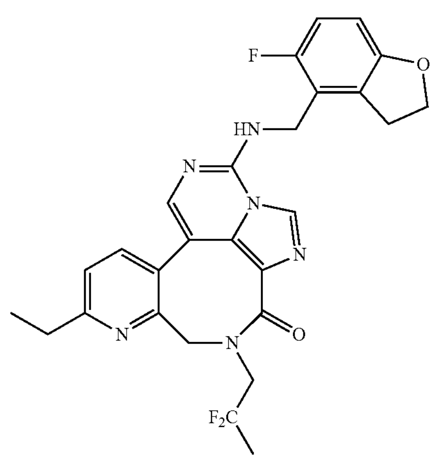 [SMILES: CCc1ccc2c(n1)CN(CC(C)(F)F)C(=O)c1ncn3c(NCc4c(F)ccc5c4CCO5)ncc-2c13] | 4-(2,2-difluoropropyl)-7-ethyl-12-(((5-fluoro-2,3-dihydrobenzofuran-4-yl)methyl)amino)-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| E 17 | 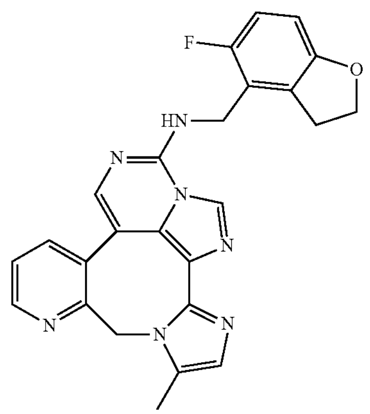 [SMILES: Cc1cnc2n1Cc1ncccc1-c1cnc(NCc3c(F)ccc4c3CCO4)n3cnc-2c13] | N-((5-fluoro-2,3-dihydrobenzofuran-4-yl)methyl)-5-methyl-6H-2,3,5a,7,12,13a-hexaazabenzo[4,5]cyclopenta[7,8]cycloocta[1,2,3-cd]inden-13-amine |
| E 18 | 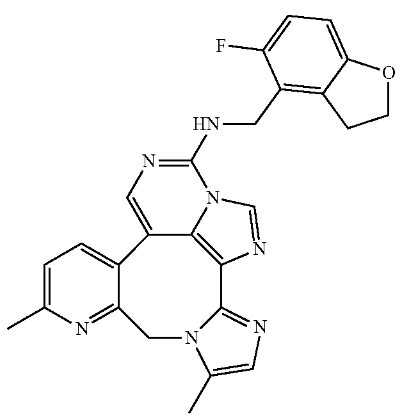 [SMILES: Cc1ccc2c(n1)Cn1c(C)cnc1-c1ncn3c(NCc4c(F)ccc5c4CCO5)ncc-2c13] | N-((5-fluoro-2,3-dihydrobenzofuran-4-yl)methyl)-5,8-dimethyl-6H-2,3,5a,7,12,13a-hexaazabenzo[4,5]cyclopenta[7,8]cycloocta[1,2,3-cd]inden-13-amine |
| E 19 | 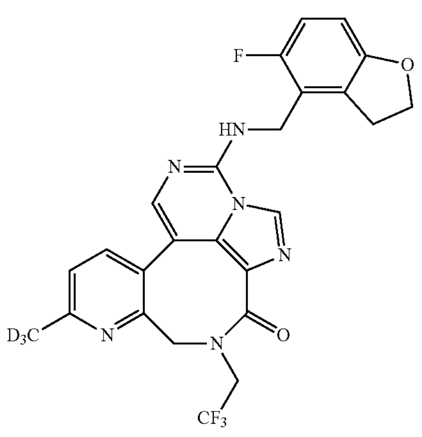 [SMILES: [2H]C([2H])([2H])c1ccc2c(n1)CN(CC(F)(F)F)C(=O)c1ncn3c(NCc4c(F)ccc5c4CCO5)ncc-2c13] | 12-(((5-fluoro-2,3-dihydrobenzofuran-4-yl)methyl)amino)-7-(methyl-d3)-4-(2,2,2-trifluoroethyl)-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| E 20 | 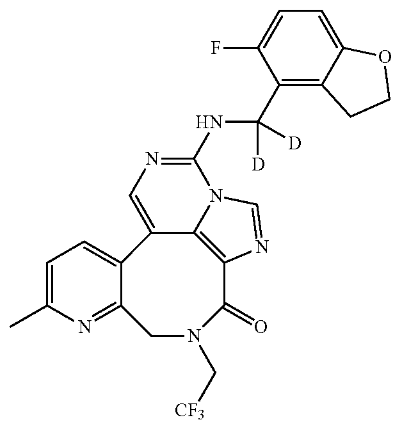 [SMILES: [2H]C([2H])(Nc1ncc2c3c(ncn13)C(=O)N(CC(F)(F)F)Cc1nc(C)ccc1-2)c1c(F)ccc2c1CCO2] | 12-(((5-fluoro-2,3-dihydrobenzofuran-4-yl)methyl-d2)amino)-7-methyl-4-(2,2,2-trifluoroethyl)-4,5-dihydro-3H-2,4,6,11,12a-pentaazabenzo[4,5]cycloocta[1,2,3-cd]inden-3-one |
| E 21 | 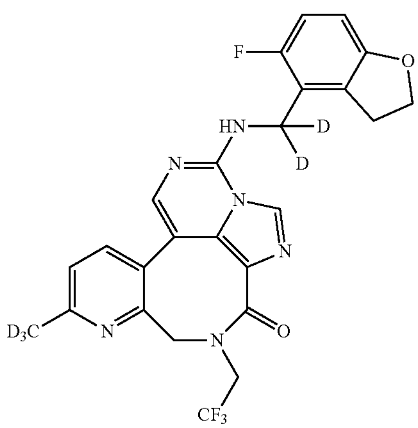 [SMILES: [2H]C([2H])([2H])c1ccc2c(n1)CN(CC(F)(F)F)C(=O)c1ncn3c(NC([2H])([2H])c4c(F)ccc5c4CCO5)ncc-2c13] | 12-(((5-fluoro-2,3-dihydrobenzofuran-4-yl)methyl-d2)amino)-7-(methyl-d3)-4-(2,2,2-trifluoroethyl)-4,5-dihydro-3H-2,4,6,11,12a-pentaazabenzo[4,5]cycloocta[1,2,3-cd]inden-3-one |
| E 22 | 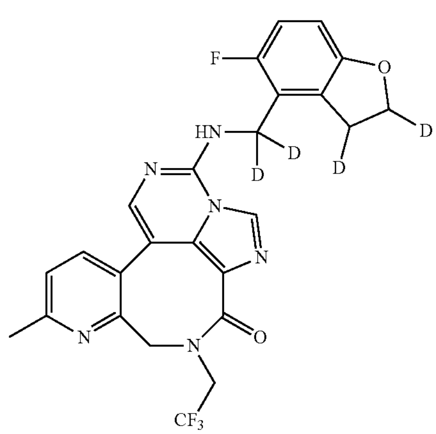 [SMILES: [2H]C1Oc2ccc(F)c(C([2H])([2H])Nc3ncc4c5c(ncn35)C(=O)N(CC(F)(F)F)Cc3nc(C)ccc3-4)c2C1[2H]] | 12-(((5-fluoro-2,3-dihydrobenzofuran-4-yl-2,3-d2)methyl-d2)amino)-7-methyl-4-(2,2,2-trifluoroethyl)-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| E 23 | 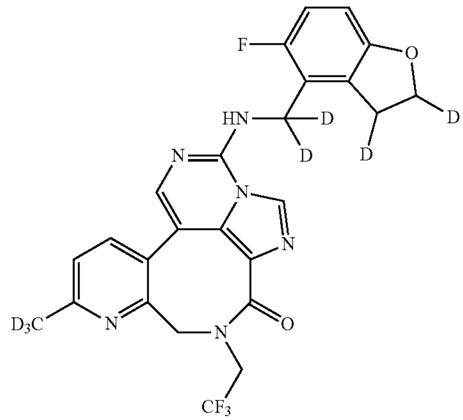 [SMILES: [2H]C1Oc2ccc(F)c(C([2H])([2H])Nc3ncc4c5c(ncn35)C(=O)N(CC(F)(F)F)Cc3nc(C([2H])([2H])[2H])ccc3-4)c2C1[2H]] | 12-(((5-fluoro-2,3-dihydrobenzofuran-4-yl-2,3-d2)methyl-d2)amino)-7-(methyl-d3)-4-(2,2,2-trifluoroethyl)-4,5-dihydro-3H-2,4,6,11,12a-pentaazabenzo[4,5]cycloocta[1,2,3-cd]inden-3-one |
| E 24 | 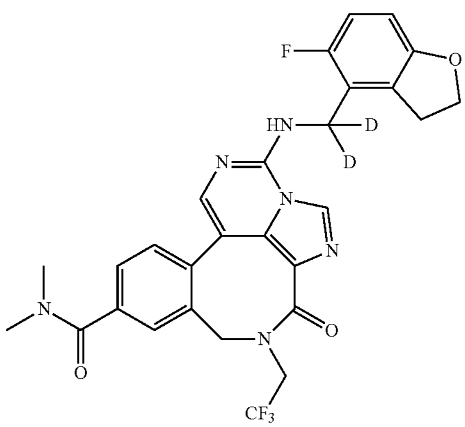 [SMILES: [2H]C([2H])(Nc1ncc2c3c(ncn13)C(=O)N(CC(F)(F)F)Cc1cc(C(=O)N(C)C)ccc1-2)c1c(F)ccc2c1CCO2] | 12-(((5-fluoro-2,3-dihydrobenzofuran-4-yl)methyl-d2)amino)-N,N-dimethyl-3-oxo-4-(2,2,2-trifluoroethyl)-4,5-dihydro-3H-2,4,11,12a-tetraazabenzo[4,5]cycloocta[1,2,3-cd]indene-7-carboxamide |
| E 25 | 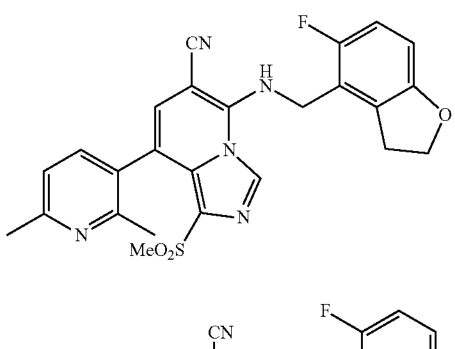 | 8-(2,6-dimethylpyridin-3-yl)-5-(((5-fluoro-2,3-dihydrobenzofuran-4-yl)methyl)amino)-1-(methylsulfonyl)imidazo[1,5-a]pyridine-6-carbonitrile |
| E 26 | 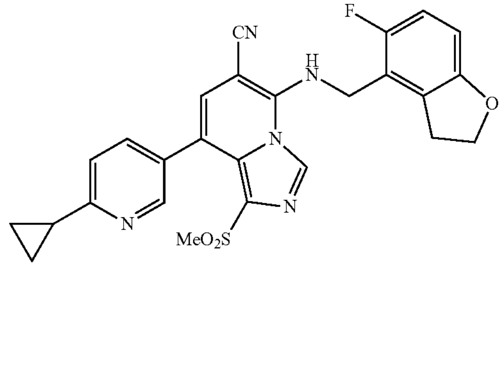 [SMILES: CS(=O)(=O)c1ncn2c(NCc3c(F)ccc4c3CCO4)c(C#N)cc(-c3ccc(C4CC4)nc3)c12] | 8-(6-cyclopropylpyridin-3-yl)-5-(((5-fluoro-2,3-dihydrobenzofuran-4-yl)methyl)amino)-1-(methylsulfonyl)imidazo[1,5-a]pyridine-6-carbonitrile |

TABLE 1-continued

| Cpd. No. | Structure | Name |
|---|---|---|
| E 27 | 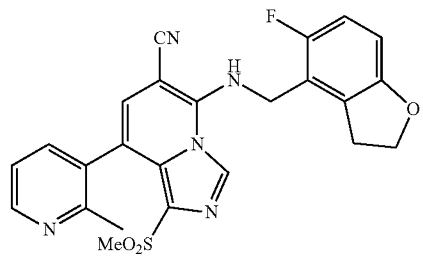 [SMILES: Cc1ncccc1-c1cc(C#N)c(NCc2c(F)ccc3c2CCO3)n2cnc(S(C)(=O)=O)c12] | 5-(((5-fluoro-2,3-dihydrobenzofuran-4-yl)methyl) amino)-8-(2-methylpyridin-3-yl)-1-(methylsulfonyl)imidazo[1,5-a]pyridine-6-carbonitrile |
| E 28 | 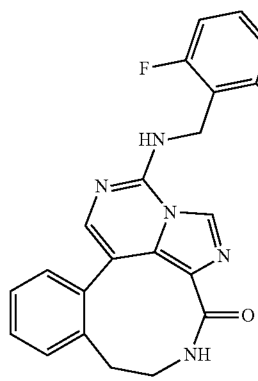 | 13-(((5-fluoro-2,3-dihydrobenzofuran-4-yl)methyl)amino)-5,6-dihydro-2,4,12,13a-tetraazabenzo[4,5]cyclonona[1,2,3-cd]inden-3(4H)-one |
| E 29 | 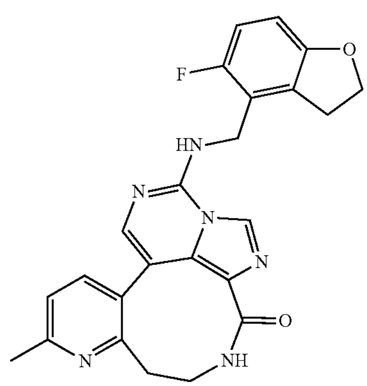 [SMILES: Cc1ccc2c(n1)CCNC(=O)c1ncn3c(NCc4c(F)ccc5c4CCO5)ncc-2c13] | 13-(((5-fluoro-2,3-dihydrobenzofuran-4-yl)methyl)amino)-8-methyl-5,6-dihydro-2,4,7,12,13a-pentaazabenzo[4,5]cyclonona[1,2,3-cd]inden-3(4H)-one |
| E 30 | 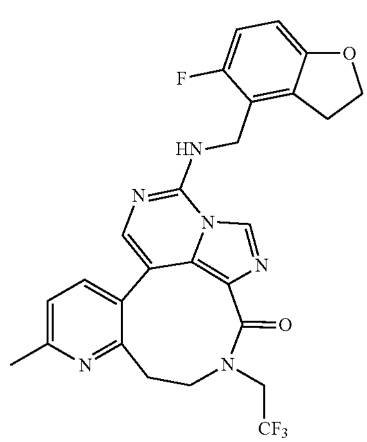 [SMILES: Cc1ccc2c(n1)CCN(CC(F)(F)F)C(=O)c1ncn3c(NCc4c(F)ccc5c4CCO5)ncc-2c13] | 13-(((5-fluoro-2,3-dihydrobenzofuran-4-yl)methyl)amino)-8-methyl-4-(2,2,2-trifluoroethyl)-5,6-dihydro-2,4,7,12,13a-pentaazabenzo[4,5]cyclonona[1,2,3-cd]inden-3(4H)-one |

TABLE 1-continued

| Cpd. No. | Structure | Name |
|---|---|---|
| E 31 | 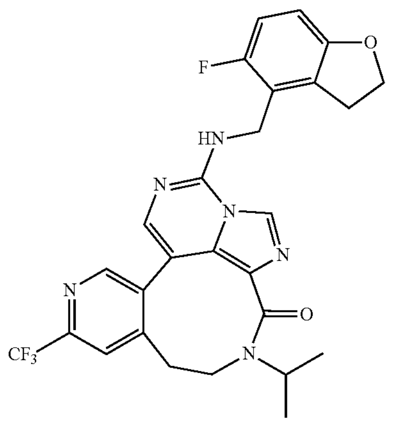 [SMILES: CC(C)N1CCc2cc(C(F)(F)F)ncc2-c2cnc(NCc3c(F)ccc4c3CCO4)n3cnc(c23)C1=O] | 13-(((5-fluoro-2,3-dihydrobenzofuran-4-yl)methyl)amino)-4-isopropyl-8-(trifluoromethyl)-5,6-dihydro-2,4,9,12,13a-pentaazabenzo[4,5]cyclonona[1,2,3-cd]inden-3(4H)-one |
| E 32 | 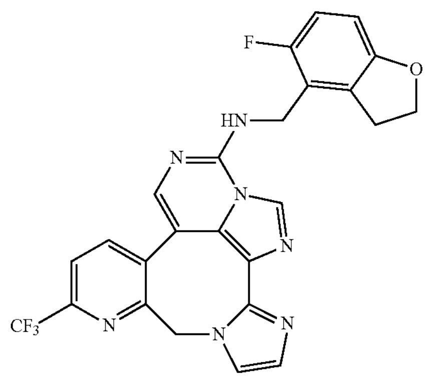 [SMILES: Fc1ccc2c(c1CNc1ncc3c4c(ncn14)-c1nccn1Cc1nc(C(F)(F)F)ccc1-3)CCO2] | N-((5-fluoro-2,3-dihydrobenzofuran-4-yl)methyl)-8-(trifluoromethyl)-6H-2,3,5a,7,12,13a-hexaazabenzo[4,5]cyclopenta[7,8]cycloocta[1,2,3-cd]inden-13-amine |
| E 33 | 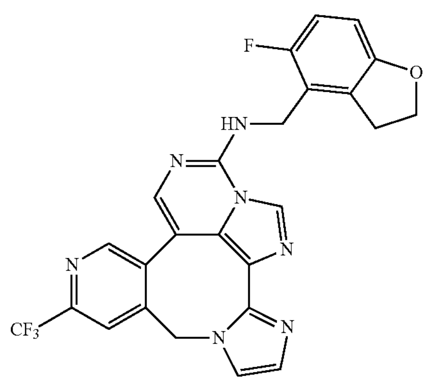 [SMILES: Fc1ccc2c(c1CNc1ncc3c4c(ncn14)-c1nccn1Cc1cc(C(F)(F)F)ncc1-3)CCO2] | N-((5-fluoro-2,3-dihydrobenzofuran-4-yl)methyl)-8-(trifluoromethyl)-6H-2,3,5a,9,12,13a-hexaazabenzo[4,5]cyclopenta[7,8]cycloocta[1,2,3-cd]inden-13-amine |
| E 34 | 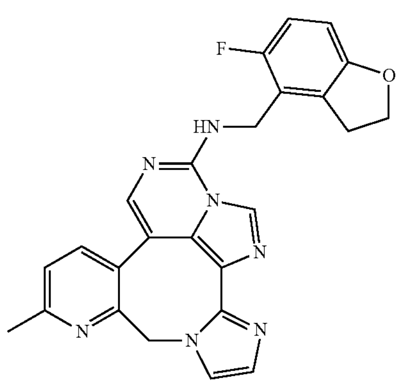 [SMILES: Cc1ccc2c(n1)Cn1ccnc1-c1ncn3c(NCc4c(F)ccc5c4CCO5)ncc-2c13] | N-((5-fluoro-2,3-dihydrobenzofuran-4-yl)methyl)-8-methyl-6H-2,3,5a,7,12,13a-hexaazabenzo[4,5]cyclopenta[7,8]cycloocta[1,2,3-cd]inden-13-amine |

TABLE 1-continued

| Cpd. No. | Structure | Name |
|---|---|---|
| E 35 | 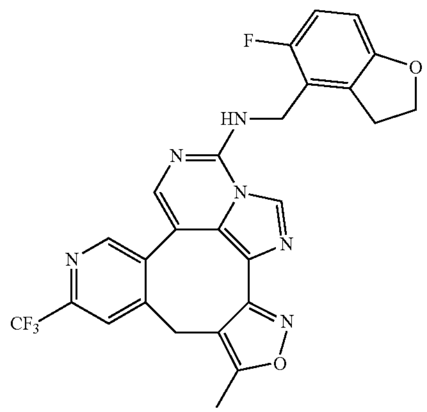 [SMILES: Cc1onc2c1Cc1cc(C(F)(F)F)ncc1-c1cnc(NCc3c(F)ccc4c3CCO4)n3cnc-2c13] | N-((5-fluoro-2,3-dihydrobenzofuran-4-yl)methyl)-5-methyl-8-(trifluoromethyl)-6H-4-oxa-2,3,9,12,13a-pentaazabenzo[4,5]cyclopenta[7,8]cycloocta[1,2,3-cd]inden-13-amine |
| E 36 | 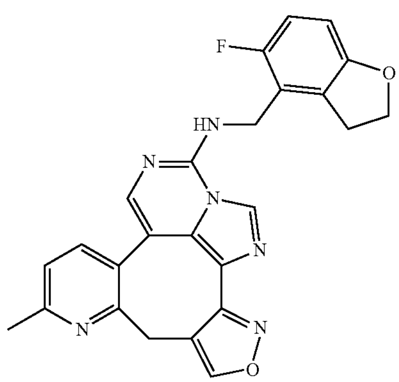 [SMILES: Cc1ccc2c(n1)Cc1conc1-c1ncn3c(NCc4c(F)ccc5c4CCO5)ncc-2c13] | N-((5-fluoro-2,3-dihydrobenzofuran-4-yl)methyl)-8-methyl-6H-4-oxa-2,3,7,12,13a-pentaazabenzo[4,5]cyclopenta[7,8]cycloocta[1,2,3-cd]inden-13-amine |
| E 37 | 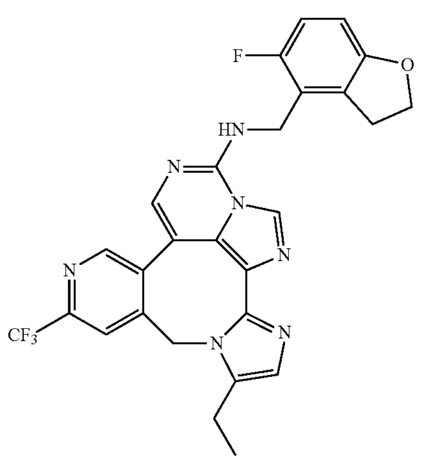 [SMILES: CCc1cnc2n1Cc1cc(C(F)(F)F)ncc1-c1cnc(NCc3c(F)ccc4c3CCO4)n3cnc-2c13] | 5-ethyl-N-((5-fluoro-2,3-dihydrobenzofuran-4-yl)methyl)-8-(trifluoromethyl)-6H-2,3,5a,9,12,13a-hexaazabenzo[4,5]cyclopenta[7,8]cycloocta[1,2,3-cd]inden-13-amine |

TABLE 1-continued

| Cpd. No. | Structure | Name |
|---|---|---|
| E 38 | 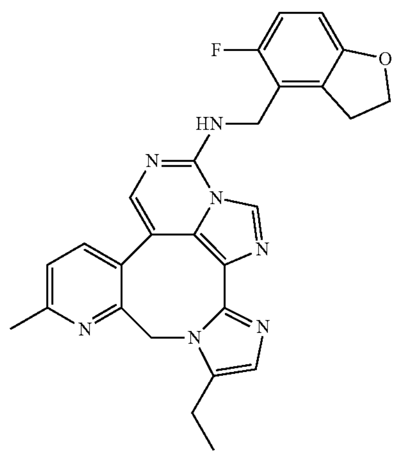 [SMILES: CCc1cnc2n1Cc1nc(C)ccc1-c1cnc(NCc3c(F)ccc4c3CCO4)n3cnc-2c13] | 5-ethyl-N-((5-fluoro-2,3-dihydrobenzofuran-4-yl)methyl)-8-methyl-6H-2,3,5a,7,12,13a-hexaazabenzo[4,5]cyclopenta[7,8]cycloocta[1,2,3-cd]inden-13-amine |
| E 39 | 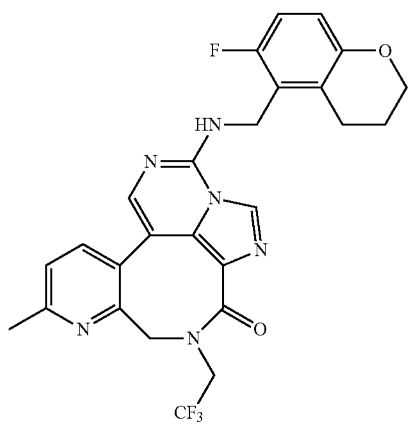 [SMILES: Cc1ccc2c(n1)CN(CC(F)(F)F)C(=O)c1ncn3c(NCc4c(F)ccc5c4CCCO5)ncc-2c13] | 12-(((6-fluorochroman-5-yl)methyl)amino)-7-methyl-4-(2,2,2-trifluoroethyl)-4,5-dihydro-3H-2,4,6,11,12a-pentaazabenzo[4,5]cycloocta[1,2,3-cd]inden-3-one |
| E 40 | 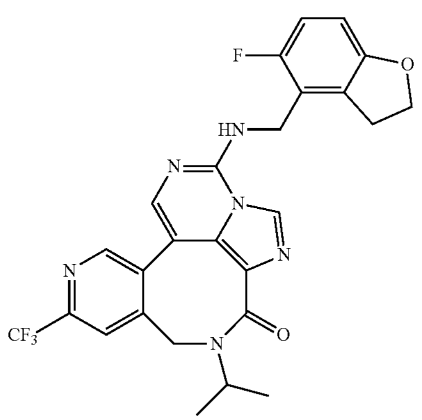 [SMILES: CC(C)N1Cc2cc(C(F)(F)F)ncc2-c2cnc(NCc3c(F)ccc4c3CCO4)n3cnc(c23)C1=O] | 12-(((5-fluoro-2,3-dihydrobenzofuran-4-yl)methyl)amino)-4-isopropyl-7-(trifluoromethyl)-4,5-dihydro-3H-2,4,8,11,12a-pentaazabenzo[4,5]cycloocta[1,2,3-cd]inden-3-one |

TABLE 1-continued

| Cpd. No. | Structure | Name |
|---|---|---|
| E 41 | 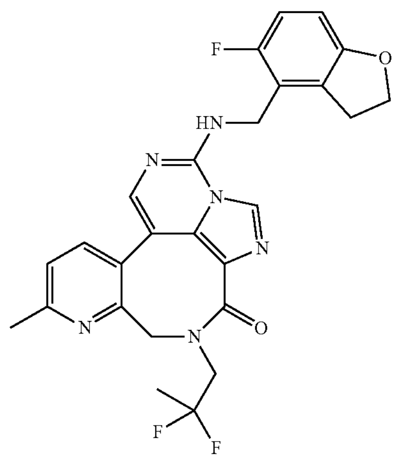 [SMILES: Cc1ccc2c(n1)CN(CC(C)(F)F)C(=O)c1ncn3c(NCc4c(F)ccc5c4CCO5)ncc-2c13] | 4-(2,2-difluoropropyl)-12-(((5-fluoro-2,3-dihydrobenzofuran-4-yl)methyl)amino)-7-methyl-4,5-dihydro-3H-2,4,6,11,12a-pentaazabenzo[4,5]cycloocta[1,2,3-cd]inden-3-one |
| E 42 | 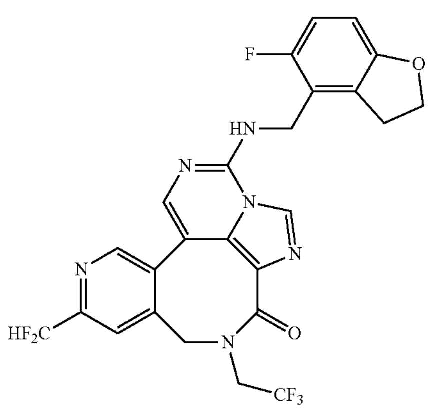 | 7-(difluoromethyl)-12-(((5-fluoro-2,3-dihydrobenzofuran-4-yl)methyl)amino)-4-(2,2,2-trifluoroethyl)-4,5-dihydro-3H-2,4,8,11,12a-pentaazabenzo[4,5]cycloocta[1,2,3-cd]inden-3-one |
| E 43 | 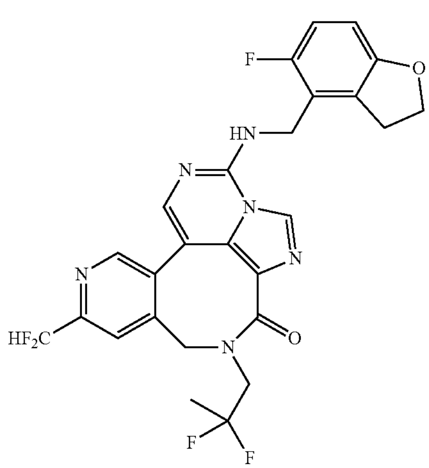 | 7-(difluoromethyl)-4-(2,2-difluoropropyl)-12-(((5-fluoro-2,3-dihydrobenzofuran-4-yl)methyl)amino)-4,5-dihydro-3H-2,4,8,11,12a-pentaazabenzo[4,5]cycloocta[1,2,3-cd]inden-3-one |

TABLE 1-continued

| Cpd. No. | Structure | Name |
|---|---|---|
| E 44 | 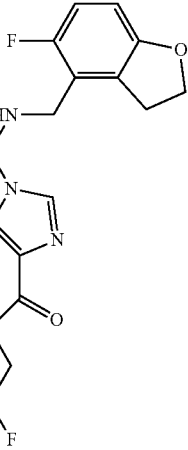 | 4-(2,2-difluoroethyl)-7-(difluoromethyl)-12-(((5-fluoro-2,3-dihydrobenzofuran-4-yl)methyl)amino)-4,5-dihydro-3H-2,4,8,11,12a-pentaazabenzo[4,5]cycloocta[1,2,3-cd]inden-3-one |
| E 45 | 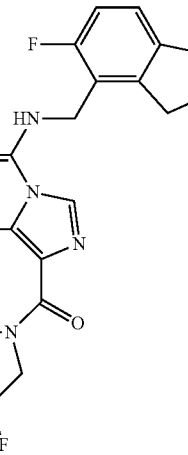 | 12-(((5-fluoro-2,3-dihydrobenzofuran-4-yl)methyl)amino)-7-(tetrahydro-2H-pyran-4-yl)-4-(2,2,2-trifluoroethyl)-4,5-dihydro-3H-2,4,6,11,12a-pentaazabenzo[4,5]cycloocta[1,2,3-cd]inden-3-one |
| E 46 | 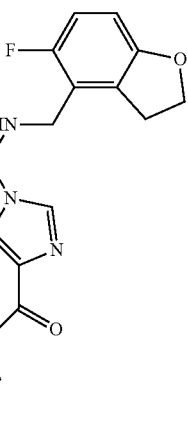 | 7-(tert-butyl)-12-(((5-fluoro-2,3-dihydrobenzofuran-4-yl)methyl)amino)-4-(2,2,2-trifluoroethyl)-4,5-dihydro-3H-2,4,8,11,12a-pentaazabenzo[4,5]cycloocta[1,2,3-cd]inden-3-one |

TABLE 1-continued

| Cpd. No. | Structure | Name |
|---|---|---|
| E 47 | 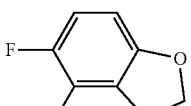 | 4-(2,2-difluoroethyl)-12-(((5-fluoro-2,3-dihydrobenzofuran-4-yl)methyl)amino)-7-isopropyl-4,5-dihydro-3H-2,4,6,11,12a-pentaazabenzo[4,5]cycloocta[1,2,3-cd]inden-3-one |
| E 48 | 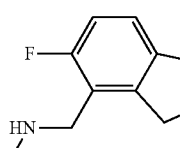 | 7-(1,4-dioxan-2-yl)-12-(((5-fluoro-2,3-dihydrobenzofuran-4-yl)methyl)amino)-4-(2,2,2-trifluoroethyl)-4,5-dihydro-3H-2,4,6,11,12a-pentaazabenzo[4,5]cycloocta[1,2,3-cd]inden-3-one |
| E 49 | 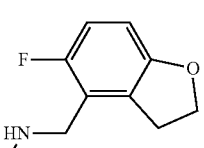 | 7-((1,4-dioxan-2-yl)methyl)-12-(((5-fluoro-2,3-dihydrobenzofuran-4-yl)methyl)amino)-4-(2,2,2-trifluoroethyl)-4,5-dihydro-3H-2,4,6,11,12a-pentaazabenzo[4,5]cycloocta[1,2,3-cd]inden-3-one |

TABLE 1-continued

| Cpd. No. | Structure | Name |
|---|---|---|
| E 50 | 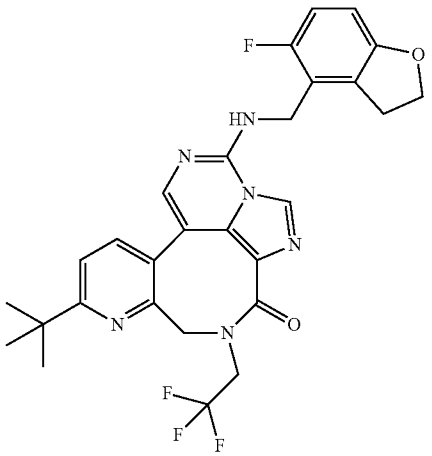 [SMILES: CC(C)(C)c1ccc2c(n1)CN(CC(F)(F)F)C(=O)c1ncn3c(NCc4c(F)ccc5c4CCO5)ncc-2c13] | 7-(tert-butyl)-12-(((5-fluoro-2,3-dihydrobenzofuran-4-yl)methyl)amino)-4-(2,2,2-trifluoroethyl)-4,5-dihydro-3H-2,4,6,11,12a-pentaazabenzo[4,5]cycloocta[1,2,3-cd]inden-3-one |
| E 51 | 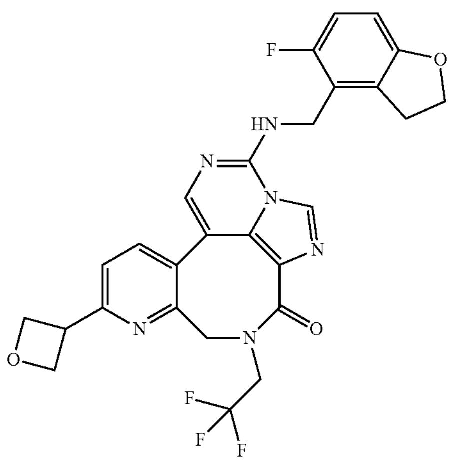 [SMILES: O=C1c2ncn3c(NCc4c(F)ccc5c4CCO5)ncc(c23)-c2ccc(C3COC3)nc2CN1CC(F)(F)F] | 12-(((5-fluoro-2,3-dihydrobenzofuran-4-yl)methyl)amino)-7-(oxetan-3-yl)-4-(2,2,2-trifluoroethyl)-4,5-dihydro-3H-2,4,6,11,12a-pentaazabenzo[4,5]cycloocta[1,2,3-cd]inden-3-one |
| E 52 | 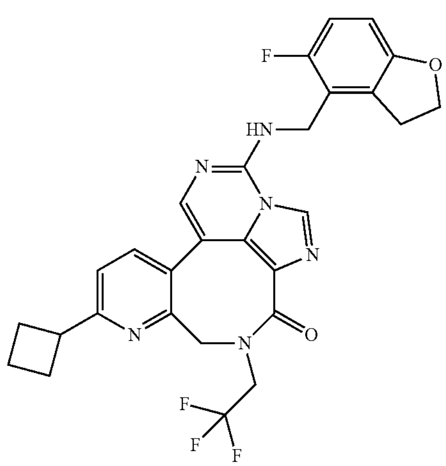 [SMILES: O=C1c2ncn3c(NCc4c(F)ccc5c4CCO5)ncc(c23)-c2ccc(C3CCC3)nc2CN1CC(F)(F)F] | 7-cyclobutyl-12-(((5-fluoro-2,3-dihydrobenzofuran-4-yl)methyl)amino)-4-(2,2,2-trifluoroethyl)-4,5-dihydro-3H-2,4,6,11,12a-pentaazabenzo[4,5]cycloocta[1,2,3-cd]inden-3-one |

In another embodiment, Compounds of the Disclosure are compounds of Formula I selected from group consisting of:
4-ethyl-12-(((5-fluoro-2,3-dihydrobenzofuran-4-yl)methyl) amino)-7-(trifluoromethyl)-4,5-dihydro-3H-2,4,8,11,12a-pentaazabenzo[4,5]cycloocta[1,2,3-cd]inden-3-one;
12-(((5-fluoro-2,3-dihydrobenzofuran-4-yl)methyl)amino)-4-(2,2,2-trifluoroethyl)-7-(trifluoromethyl)-4,5-dihydro-3H-2,4,8,11,12a-pentaazabenzo[4,5]cycloocta[1,2,3-cd]inden-3-one;
4-cyclopropyl-12-(((5-fluoro-2,3-dihydrobenzofuran-4-yl) methyl)amino)-7-(trifluoromethyl)-4,5-dihydro-3H-2,4,8,11,12a-pentaazabenzo[4,5]cycloocta[1,2,3-cd]inden-3-one;
12-(((5-fluoro-2,3-dihydrobenzofuran-4-yl)methyl)amino)-4-isopropyl-7-(trifluoromethyl)-4,5-dihydro-3H-2,4,8,11,12a-pentaazabenzo[4,5]cycloocta[1,2,3-cd]inden-3-one; and
11-(((5-fluoro-2,3-dihydrobenzofuran-4-yl)methyl)amino)-6-methyl-4H-3-thia-2,5,10,11a-tetraazadibenzo[cd,f]azulene 3,3-dioxide,
or a pharmaceutically acceptable salt or solvate thereof.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with a suitable acid. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, J. Pharmaceut. Sci., 93(3):601-611 (2004), which describes the preparation of solvates of fluconazole with ethyl acetate and with water. Similar preparation of solvates, hemisolvates, hydrates, and the like are described by E. C. van Tonder et al., AAPS Pharm. Sci. Tech., 5(1):Article 12 (2004), and A. L. Bingham et al., Chem. Commun. 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvate in a crystal of the solvate.

II. Intermediates of the Disclosure

The disclosure also provides synthetic intermediates, collectively referred to as "Intermediates of the Disclosure," that can be used to prepare Compounds of the Disclosure.

In one embodiment, Intermediates of the Disclosure are compounds of Formula I, wherein:
$R^3$ is $R^{3a}$;
$R^4$ is $R^{4a}$;
$R^{3a}$ is selected from group consisting of substituted aryl, substituted 5- to 10-membered heteroaryl, and substituted 4- to 8-membered heterocyclo;
wherein at least one of the aryl, 5- to 10-membered heteroaryl, or 4- to 8-membered heterocyclo substituents are amino, hydroxyalkyl, or (amino)alkyl; and
$R^{4a}$ is halo or —C(=O)O$R^{11a}$, or a pharmaceutically acceptable salt or solvate thereof.

In one embodiment, Intermediates of the Disclosure are compounds of Formula XVII:

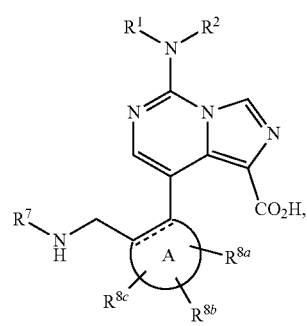

XVII wherein

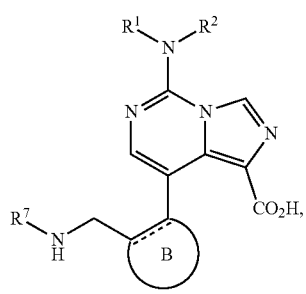

is phenyl, 5-membered heteroaryl, or 6-membered heteroaryl; and $R^1$, $R^2$, $R^7$, $R^{8a}$, $R^{8b}$, $R^{8c}$, and $\rlap{=}{=}$ are as defined in connection with Formula I, or a pharmaceutically acceptable salt or solvate thereof.

In another embodiment, Intermediates of the Disclosure are compounds of Formula XVIII:

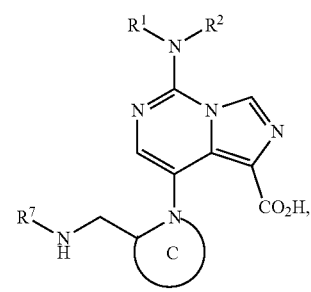
XVIII wherein

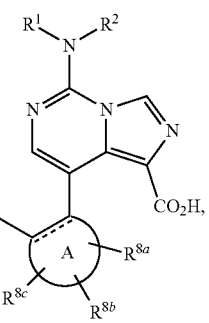

B is optionally substituted 3- to 8-membered cycloalkyl or optionally substituted 4- to 8-membered heterocyclo; and $R^1$, $R^2$, $R^7$, and $\rlap{=}{=}$ are as defined in connection with Formula I, or a pharmaceutically acceptable salt or solvate thereof.

In another embodiment, Intermediates of the Disclosure are compounds of Formula XIX:

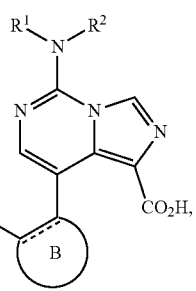
XIX wherein

C is optionally substituted 4- to 8-membered heterocyclo; and $R^1$, $R^2$, and $R^7$, are as defined in connection with Formula I, or a pharmaceutically acceptable salt or solvate thereof.

In one embodiment, Intermediates of the Disclosure are compounds of Formula XX:

XX wherein

A is phenyl, 5-membered heteroaryl, or 6-membered heteroaryl; and $R^1$, $R^2$, $R^{8a}$, $R^{8b}$, $R^{8c}$, and $\rlap{=}{=}$ are as defined in connection with Formula I, or a pharmaceutically acceptable salt or solvate thereof.

In another embodiment, Intermediates of the Disclosure are compounds of Formula XXI:

XXI wherein

B is optionally substituted 3- to 8-membered cycloalkyl or optionally substituted 4- to 8-membered heterocyclo; and $R^1$, $R^2$, and $\rlap{=}{=}$ are as defined in connection with Formula I, or a pharmaceutically acceptable salt or solvate thereof.

In another embodiment, Intermediates of the Disclosure are compounds of Formula XXII:

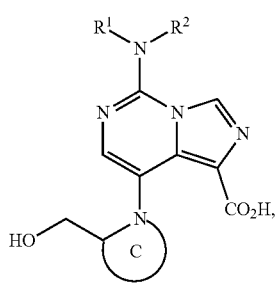 XXII wherein is optionally substituted 4- to 8-membered heterocyclo; and $R^1$, and $R^2$, are as defined in connection with Formula I, or a pharmaceutically acceptable salt or solvate thereof.

Exemplary Intermediates of the Disclosure include, but are not limited to, E 12-8 and E 12-9 of EXAMPLE 1, E 16-1 and E-16-2 of EXAMPLE 2, E 3-1 of EXAMPLE 3, E 36-6 and E 36-7 of EXAMPLE 4, E 10-8 of EXAMPLE 5, E 95-3 of EXAMPLE 6, E-2211.2 and E-2211.3 of EXAMPLE 26, E-2189.1 and E-2189.2 of EXAMPLE 27, and E-2206.2 and E-2206.3 of EXAMPLE 28.

III. Methods of Preparing Compounds and Intermediates of the Disclosure

The disclosure also provides methods of preparing Compounds of the Disclosure and/or Intermediates of the Disclosure.

Exemplary methods of preparing Compounds of the Disclosure and/or Intermediates of the Disclosure are provided in EXAMPLES 1-6 and 17.

IV. Methods of Treating Disease with Compounds of the Disclosure

Compounds of the Disclosure inhibit EED and are thus useful in the treatment or prevention of a variety of diseases and conditions. In particular, Compounds of the Disclosure are useful in methods of treating or preventing a disease or condition wherein inhibition of EED provides a benefit. Foremost among these diseases and conditions are cancers and proliferative diseases. In one embodiment, such a cancer is referred to as a "EED-mediated cancer." EED-mediated cancers are known in the art. The therapeutic methods of this disclosure comprise administering a therapeutically effective amount of a Compound of the Disclosure to a subject, e.g., human, in need thereof. The present methods also encompass optionally administering an optional therapeutic agent to the subject in addition to the Compound of the Disclosure. The optional therapeutic agent is selected from drugs known as useful in treating the disease or condition afflicting the subject in need thereof, e.g., a chemotherapeutic agent and/or radiation known as useful in treating a particular cancer.

In another embodiment, the present disclosure relates to a method of treating an individual suffering from a disease or condition wherein inhibition of EED provides a benefit, the method comprising administering a therapeutically effective amount of a Compound of the Disclosure.

Since Compounds of the Disclosure are inhibitors of EED protein, a number of diseases and conditions mediated by EED can be treated by employing these compounds. The present disclosure is thus directed generally to a method for treating a condition or disorder responsive to EED inhibition in a subject, e.g., a human subject, suffering from, or at risk of suffering from, the condition or disorder, the method comprising administering to the subject an effective amount of one or more Compounds of the Disclosure.

In another embodiment, the present disclosure is directed to a method of inhibiting EED in a subject in need thereof, said method comprising administering to the subject an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, an optional therapeutic agent, packaged separately or together, and an insert having instructions for using these active agents.

In one embodiment, a Compound of the Disclosure is administered in conjunction with an optional therapeutic agent useful in the treatment of a disease or condition wherein inhibition of EED provides a benefit. The optional therapeutic agent is different from the Compound of the Disclosure. A Compound of the Disclosure and the optional therapeutic agent can be administered simultaneously or sequentially to achieve the desired effect. In addition, the Compound of the Disclosure and optional therapeutic agent can be administered from a single composition or two separate compositions.

The optional therapeutic agent is administered in an amount to provide its desired therapeutic effect. The effective dosage range for each optional therapeutic agent is known in the art, and the optional therapeutic agent is administered to an individual in need thereof within such established ranges.

A Compound of the Disclosure and the optional therapeutic agent can be administered together as a single-unit dose or separately as multi-unit doses, wherein the Compound of the Disclosure is administered before the optional therapeutic agent or vice versa. One or more doses of the Compound of the Disclosure and/or one or more dose of the optional therapeutic agent can be administered. The Compound of the Disclosure therefore can be used in conjunction with one or more optional therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human subject is treated with a Compound of the Disclosure, or a pharmaceutical composition comprising a Compound of the Disclosure, wherein the compound is administered in an amount sufficient to inhibit EED protein in the subject.

In another aspect, the present disclosure provides a method of treating cancer in a subject comprising administering a therapeutically effective amount of a Compound of the Disclosure. While not being limited to a specific mechanism, in some embodiments, Compounds of the Disclosure treat cancer by inhibiting EED. Examples of treatable cancers include, but are not limited to, any one or more of the cancers of Table 3.

TABLE 3

| | | | |
|---|---|---|---|
| adrenal cancer | acinic cell carcinoma | acoustic neuroma | acral lentigious melanoma |
| acrospiroma | acute eosinophilic leukemia | acute erythroid leukemia | acute lymphoblastic leukemia |
| acute megakaryoblastic leukemia | acute monocytic leukemia | acute promyelocytic leukemia | adenocarcinoma |
| adenoid cystic carcinoma | adenoma | adenomatoid odontogenic tumor | adenosquamous carcinoma |
| adipose tissue neoplasm | adrenocortical carcinoma | adult T-cell leukemia/lymphoma | aggressive NK-cell leukemia |
| AIDS-related lymphoma | alveolar rhabdomyosarcoma | alveolar soft part sarcoma | ameloblastic fibroma |
| anaplastic large cell lymphoma | anaplastic thyroid cancer | angioimmunoblastic T-cell lymphoma | angiomyolipoma |
| angiosarcoma | astrocytoma | atypical teratoid rhabdoid tumor | B-cell chronic lymphocytic leukemia |
| B-cell prolymphocytic leukemia | B-cell lymphoma | basal cell carcinoma | biliary tract cancer |
| bladder cancer | blastoma | bone cancer | Brenner tumor |
| Brown tumor | Burkitt's lymphoma | breast cancer | brain cancer |
| carcinoma | carcinoma in situ | carcinosarcoma | cartilage tumor |
| cementoma | myeloid sarcoma | chondroma | chordoma |
| choriocarcinoma | choroid plexus papilloma | clear-cell sarcoma of the kidney | craniopharyngioma |
| cutaneous T-cell lymphoma | cervical cancer | colorectal cancer | Degos disease |
| desmoplastic small round cell tumor | diffuse large B-cell lymphoma | dysembryoplastic neuroepithelial tumor | dysgerminoma |
| embryonal carcinoma | endocrine gland neoplasm | endodermal sinus tumor | enteropathy-associated T-cell lymphoma |
| esophageal cancer | fetus in fetu | fibroma | fibrosarcoma |
| follicular lymphoma | follicular thyroid cancer | ganglioneuroma | gastrointestinal cancer |
| germ cell tumor | gestational choriocarcinoma | giant cell fibroblastoma | giant cell tumor of the bone |
| glial tumor | glioblastoma multiforme | glioma | gliomatosis cerebri |
| glucagonoma | gonadoblastoma | granulosa cell tumor | gynandroblastoma |
| gallbladder cancer | gastric cancer | hairy cell leukemia | hemangioblastoma |
| head and neck cancer | hemangiopericytoma | hematological cancer | hepatoblastoma |
| hepatosplenic T-cell lymphoma | Hodgkin's lymphoma | non-Hodgkin's lymphoma | invasive lobular carcinoma |
| intestinal cancer | kidney cancer | laryngeal cancer | lentigo maligna |
| lethal midline carcinoma | leukemia | leydig cell tumor | liposarcoma |
| lung cancer | lymphangioma | lymphangiosarcoma | lymphoepithelioma |
| lymphoma | acute lymphocytic leukemia | acute myelogeous leukemia | chronic lymphocytic leukemia |
| liver cancer | small cell lung cancer | non-small cell lung cancer | MALT lymphoma |
| malignant fibrous histiocytoma | malignant peripheral nerve sheath tumor | malignant triton tumor | mantle cell lymphoma |
| marginal zone B-cell lymphoma | mast cell leukemia | mediastinal germ cell tumor | medullary carcinoma of the breast |
| medullary thyroid cancer | medulloblastoma | melanoma | meningioma |
| merkel cell cancer | mesothelioma | metastatic urothelial carcinoma | mixed Mullerian tumor |
| mucinous tumor | multiple myeloma | muscle tissue neoplasm | mycosis fungoides |
| myxoid liposarcoma | myxoma | myxosarcoma | nasopharyngeal carcinoma |
| neurinoma | neuroblastoma | neurofibroma | neuroma |
| nodular melanoma | ocular cancer | oligoastrocytoma | oligodendroglioma |
| oncocytoma | optic nerve sheath meningioma | optic nerve tumor | oral cancer |
| osteosarcoma | ovarian cancer | Pancoast tumor | papillary thyroid cancer |
| paraganglioma | pinealoblastoma | pineocytoma | pituicytoma |
| pituitary adenoma | pituitary tumor | plasmacytoma | polyembryoma |
| precursor T- | primary central | primary effusion | preimary peritoneal |

TABLE 3-continued

| | | | |
|---|---|---|---|
| lymphoblastic lymphoma | nervous system lymphoma | lymphoma | cancer |
| prostate cancer | pancreatic cancer | pharyngeal cancer | pseudomyxoma periotonei |
| renal cell carcinoma | renal medullary carcinoma | retinoblastoma | rhabdomyoma |
| rhabdomyosarcoma | Richter's transformation | rectal cancer | sarcoma |
| Schwannomatosis | seminoma | Sertoli cell tumor | sex cord-gonadal stromal tumor |
| signet ring cell carcinoma | skin cancer | small blue round cell tumors | small cell carcinoma |
| soft tissue sarcoma | somatostatinoma | soot wart | spinal tumor |
| splenic marginal zone lymphoma | squamous cell carcinoma | synovial sarcoma | Sezary's disease |
| small intestine cancer | squamous carcinoma | stomach cancer | T-cell lymphoma |
| testicular cancer | thecoma | thyroid cancer | transitional cell carcinoma |
| throat cancer | urachal cancer | urogenital cancer | urothelial carcinoma |
| uveal melanoma | uterine cancer | verrucous carcinoma | visual pathway glioma |
| vulvar cancer | vaginal cancer | Waldenstrom's macroglobulinemia | Warthin's tumor |
| Wilms' tumor | | | |

In another embodiment, the cancer is a solid tumor. In another embodiment, the cancer a hematological cancer. Exemplary hematological cancers include, but are not limited to, the cancers listed in Table 4. In another embodiment, the hematological cancer is acute lymphocytic leukemia, chronic lymphocytic leukemia (including B-cell chronic lymphocytic leukemia), or acute myeloid leukemia.

TABLE 4

| | |
|---|---|
| acute lymphocytic leukemia (ALL) | acute eosinophilic leukemia |
| acute myeloid leukemia (AML) | acute erythroid leukemia |
| chronic lymphocytic leukemia (CLL) | acute lymphoblastic leukemia |
| small lymphocytic lymphoma (SLL) | acute megakaryoblastic leukemia |
| multiple myeloma (MM) | acute monocytic leukemia |
| Hodgkins lymphoma (HL) | acute promyelocytic leukemia |
| non-Hodgkin's lymphoma (NHL) | acute myelogeous leukemia |
| mantle cell lymphoma (MCL) | B-cell prolymphocytic leukemia |
| marginal zone B-cell lymphoma | B-cell lymphoma |
| splenic marginal zone lymphoma | MALT lymphoma |
| follicular lymphoma (FL) | precursor T-lymphoblastic lymphoma |
| Waldenstrom's macroglobulinemia (WM) | T-cell lymphoma |
| diffuse large B-cell lymphoma (DLBCL) | mast cell leukemia |
| marginal zone lymphoma (MZL) | adult T cell leukemia/lymphoma |
| hairy cell leukemia (HCL) | aggressive NK-cell leukemia |
| Burkitt's lymphoma (BL) | angioimmunoblastic T-cell lymphoma |
| Richter's transformation | |

In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the subject, and ultimately is determined by the attendant physician. Dosage amounts and intervals can be adjusted individually to provide plasma levels of the Compound of the Disclosure that are sufficient to maintain the desired therapeutic effects. The desired dose can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, about 0.05, about 0.5, about 5, about 10, about 20, about 30, about 40, about 50, about 100, about 150, about 200, about 250, about 300, about 350, about 400, about 450, or about 500 milligrams, including all doses between 0.005 and 500 milligrams.

The dosage of a composition containing a Compound of the Disclosure, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 g/kg, about µg/kg, about 25 µg/kg, about 50 g/kg, about 75

µg/kg, about 100 µg/kg, about 125 µg/kg, about 150 µg/kg, about 175 µg/kg, about 200 µg/kg, about 225 µg/kg, about 250 µg/kg, about 275 g/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 g/kg, about 675 µg/kg, about 700 µg/kg, about 725 µg/kg, about 750 µg/kg, about 775 µg/kg, about 800 µg/kg, about 825 µg/kg, about 850 ag/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual subject, which can vary with the age, weight, and response of the particular subject.

Compounds of the Disclosure typically are administered in admixture with a pharmaceutical carrier to give a pharmaceutical composition selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, PA, 19th ed. 1995. Such carriers enable the active agents to be formulated as tablets, pills, dragees, capsules, liquids, gels, syrups, slurries, suspensions and the like, for oral ingestion by a subject to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

V. Optional Therapeutic Agents

In some therapeutic methods and uses of the disclosure, a Compound of the Disclosure is administered to a subject having a disease, disorder, or condition, e.g., cancer, as a single agent. In other therapeutic methods and uses of the disclosure, a Compound of the Disclosure is administered to a subject having a disease, disorder, or condition, e.g., cancer, in combination with one or more optional therapeutic agents. In one embodiment, a Compound of the Disclosure is administered in combination with one optional therapeutic agent. In another embodiment, a Compound of the Disclosure is administered in combination with two optional therapeutic agents. In another embodiment, a Compound of the Disclosure is administered in combination with three optional therapeutic agents. Optional therapeutic agents useful in treating cancer patients include those known in the art as well as those developed in the future.

Optional therapeutic agents are administered in an amount to provide their desired therapeutic effect. The effective dosage range for each optional therapeutic agent is known in the art, and the optional therapeutic agent is administered to an individual in need thereof within such established ranges.

A Compound of the Disclosure and the optional therapeutic agent(s) can be administered together as a single-unit dose or separately as multi-unit doses, and in any order, e.g., wherein a Compound of the Disclosure is administered before the optional therapeutic agent(s), or vice versa. One or more doses of a Compound of the Disclosure and the optional therapeutic agent(s) can be administered to the subject.

In one embodiment, the optional therapeutic agent is an immune checkpoint inhibitor. Immune checkpoint inhibitors are therapies that blockade immune system inhibitor checkpoints. Immune checkpoints can be stimulatory or inhibitory. Blockade of inhibitory immune checkpoint activates immune system function and can be used for cancer immunotherapy. Pardoll, Nature Reviews. Cancer 12:252-64 (2012). Tumor cells turn off activated T cells when they attach to specific T-cell receptors. Immune checkpoint inhibitors prevent tumor cells from attaching to T cells, which results in T cells remaining activated. In effect, the coordinated action by cellular and soluble components combats pathogens and injuries by cancers. The modulation of immune system pathways may involve changing the expression or the functional activity of at least one component of the pathway to then modulate the response by the immune system. U.S. 2015/0250853. Examples of immune checkpoint inhibitors include PD-1 inhibitors, PD-L1 inhibitors, CTLA-4 inhibitors, LAG3 inhibitors, TIM3 inhibitors, cd47 inhibitors, and B7-H1 inhibitors. Thus, in one embodiment, the immune checkpoint inhibitor is selected from the group consisting of a PD-1 inhibitor, a PD-L1 inhibitor, a CTLA-4 inhibitor, a LAG3 inhibitor, a TIM3 inhibitor, and a cd47 inhibitor.

In another embodiment, the immune checkpoint inhibitor is a programmed cell death (PD-1) inhibitor. PD-1 is a T-cell coinhibitory receptor that plays a pivotal role in the ability of tumor cells to evade the host's immune system. Blockage of interactions between PD-1 and PD-L1, a ligand of PD-1, enhances immune function and mediates antitumor activity. Examples of PD-1 inhibitors include antibodies that specifically bind to PD-1. Particular anti-PD-1 antibodies include, but are not limited to nivolumab, pembrolizumab, STI-A1014, pidilzumab, and cemiplimab-rwlc. For a general discussion of the availability, methods of production, mechanism of action, and clinical studies of anti-PD-1 antibodies, see U.S. 2013/0309250, U.S. Pat. Nos. 6,808, 710, 7,595,048, 8,008,449, 8,728,474, 8,779,105, 8,952,136, 8,900,587, 9,073,994, 9,084,776, and Naido et al., British Journal of Cancer 111:2214-19 (2014).

In another embodiment, the immune checkpoint inhibitor is a PD-L1 (also known as B7-H1 or CD274) inhibitor. Examples of PD-L1 inhibitors include antibodies that specifically bind to PD-L1. Particular anti-PD-L1 antibodies include, but are not limited to, avelumab, atezolizumab, durvalumab, and BMS-936559. For a general discussion of the availability, methods of production, mechanism of action, and clinical studies, see U.S. Pat. No. 8,217,149, U.S. 2014/0341917, U.S. 2013/0071403, WO 2015036499, and Naido et al., British Journal of Cancer 111:2214-19 (2014).

In another embodiment, the immune checkpoint inhibitor is a CTLA-4 inhibitor. CTLA-4, also known as cytotoxic T-lymphocyte antigen 4, is a protein receptor that downregulates the immune system. CTLA-4 is characterized as a "brake" that binds costimulatory molecules on antigen-presenting cells, which prevents interaction with CD28 on T cells and also generates an overtly inhibitory signal that constrains T cell activation. Examples of CTLA-4 inhibitors include antibodies that specifically bind to CTLA-4. Particular anti-CTLA-4 antibodies include, but are not limited to, ipilimumab and tremelimumab. For a general discussion of the availability, methods of production, mechanism of action, and clinical studies, see U.S. Pat. Nos. 6,984,720, 6,207,156, and Naido et al., British Journal of Cancer 111:2214-19 (2014).

In another embodiment, the immune checkpoint inhibitor is a LAG3 inhibitor. LAG3, Lymphocyte Activation Gene 3, is a negative co-stimulatory receptor that modulates T cell homeostatis, proliferation, and activation. In addition, LAG3 has been reported to participate in regulatory T cells (Tregs) suppressive function. A large proportion of LAG3 molecules are retained in the cell close to the microtubule-organizing center, and only induced following antigen specific T cell activation. U.S. 2014/0286935. Examples of LAG3 inhibitors include antibodies that specifically bind to LAG3. Particular anti-LAG3 antibodies include, but are not limited to, GSK2831781. For a general discussion of the availability, methods of production, mechanism of action, and studies, see, U.S. 2011/0150892, U.S. 2014/0093511, U.S. 20150259420, and Huang et al., Immunity 21:503-13 (2004).

In another embodiment, the immune checkpoint inhibitor is a TIM3 inhibitor. TIM3, T-cell immunoglobulin and mucin domain 3, is an immune checkpoint receptor that functions to limit the duration and magnitude of $T_H 1$ and $T_C 1$ T-cell responses. The TIM3 pathway is considered a target for anticancer immunotherapy due to its expression on dysfunctional CD8$^+$ T cells and Tregs, which are two reported immune cell populations that constitute immunosuppression in tumor tissue. Anderson, Cancer Immunology Research 2:393-98 (2014). Examples of TIM3 inhibitors include antibodies that specifically bind to TIM3. For a general discussion of the availability, methods of production, mechanism of action, and studies of TIM3 inhibitors, see U.S. 20150225457, U.S. 20130022623, U.S. Pat. No. 8,522,156, Ngiow et al., Cancer Res 71: 6567-71 (2011), Ngiow, et al., Cancer Res 71:3540-51 (2011), and Anderson, Cancer Immunology Res 2:393-98 (2014).

In another embodiment, the immune checkpoint inhibitor is a cd47 inhibitor. See Unanue, E. R., PNAS 110:10886-87 (2013).

The term "antibody" is meant to include intact monoclonal antibodies, polyclonal antibodies, multispecific antibodies formed from at least two intact antibodies, and antibody fragments, so long as they exhibit the desired biological activity. In another embodiment, "antibody" is meant to include soluble receptors that do not possess the Fc portion of the antibody. In one embodiment, the antibodies are humanized monoclonal antibodies and fragments thereof made by means of recombinant genetic engineering.

Another class of immune checkpoint inhibitors include polypeptides that bind to and block PD-1 receptors on T-cells without triggering inhibitor signal transduction. Such peptides include B7-DC polypeptides, B7-H1 polypeptides, B7-1 polypeptides and B7-2 polypeptides, and soluble fragments thereof, as disclosed in U.S. Pat. No. 8,114,845.

Another class of immune checkpoint inhibitors include compounds with peptide moieties that inhibit PD-1 signaling. Examples of such compounds are disclosed in U.S. Pat. No. 8,907,053 and have the structure:

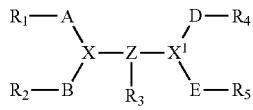

or a pharmaceutically acceptable salt thereof, wherein the compound comprises at least 5 amino acids useful as therapeutic agents capable of inhibiting the PD-1 signaling pathway.

Another class of immune checkpoint inhibitors include inhibitors of certain metabolic enzymes, such as indoleamine 2,3 dioxygenase (IDO), which is expressed by infiltrating myeloid cells and tumor cells, and isocitrate dehydrogenase (IDH), which is mutated in leukemia cells. Mutants of the IDH enzyme lead to increased levels of 2-hydroxyglutarate (2-HG), which prevent myeloid differentiation. Stein et al., Blood 130:722-31 (2017); Wouters, Blood 130:693-94 (2017). Particular mutant IDH blocking agents include, but are not limited to, ivosidenib and enasidenib mesylate. Dalle and DiNardo, Ther Adv Hematol 9(7):163-73 (2018); Nassereddine et al., Onco Targets Ther 12:303-08 (2018). The IDO enzyme inhibits immune responses by depleting amino acids that are necessary for anabolic functions in T cells or through the synthesis of particular natural ligands for cytosolic receptors that are able to alter lymphocyte functions. Pardoll, Nature Reviews. Cancer 12:252-64 (2012); Löb, Cancer Immunol Immunother 58:153-57 (2009). Particular IDO blocking agents include, but are not limited to, levo-1-methyl typtophan (L-1MT) and 1-methyltryptophan (1MT). Qian et al., Cancer Res 69:5498-504 (2009); and Löb et al., Cancer Immunol Immunother 58:153-7 (2009).

In one embodiment, the immune checkpoint inhibitor is nivolumab, pembrolizumab, pidilizumab, STI-A1110, avelumab, atezolizumab, durvalumab, STI-A1014, ipilimumab, tremelimumab, GSK2831781, BMS-936559 or MED14736.

In another embodiment, the optional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat and panobinostat lactate.

In another embodiment, the optional therapeutic agent is a chemotherapeutic agent or other anti-proliferative agent that can be administered in combination with a Compound of the Disclosure to treat cancer. Examples of conventional therapies and anticancer agents that can be used in combination with a Compound of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved biologic therapy or chemotherapy, e.g., a treatment regimen that uses drugs to stop the growth of cancer cells, either by killing the cells or by stopping them from dividing. Chemotherapy may be given by mouth, injection, or infusion, or on the skin, depending on the type and stage of the cancer being treated.

Nonlimiting exemplary antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent, e.g., temozolomide; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include steroids, such as atamestane, exemestane, and formestane, and non-steroids, such as aminoglutethimide, roglethimide, pyridoglutethimide, trilostane, testolactone, ketoconazole, vorozole, fadrozole, anastrozole, and letrozole.

Nonlimiting anti-estrogens include tamoxifen, fulvestrant, raloxifene, and raloxifene hydrochloride. Anti-androgens include, but are not limited to, bicalutamide and apalutamide. Gonadorelin agonists include, but are not limited to, abarelix, goserelin, and goserelin acetate.

Nonlimiting exemplary topoisomerase I inhibitors include topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; discodermolides; cochicine and epothilones and derivatives thereof.

Nonlimiting exemplary alkylating agents include cyclophosphamide, ifosfamide, melphalan, trabectedin, and nitrosoureas, such as carmustine and lomustine.

Nonlimiting exemplary matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Nonlimiting exemplary mTOR inhibitors include compounds that inhibit the mammalian target of rapamycin (mTOR) and possess antiproliferative activity such as sirolimus, everolimus, CCI-779, and ABT578.

Nonlimiting exemplary antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Nonlimiting exemplary platin compounds include carboplatin, cis-platin, cisplatinum, and oxaliplatin.

Nonlimiting exemplary methionine aminopeptidase inhibitors include bengamide or a derivative thereof and PPI-2458.

Nonlimiting exemplary bisphosphonates include etridonic acid, clodronic acid, tiludronic acid, pamidronic acid, alendronic acid, ibandronic acid, risedronic acid, and zoledronic acid.

Nonlimiting exemplary heparanase inhibitors include compounds that target, decrease, or inhibit heparin sulfate degradation, such as PI-88 and OGT2115.

Nonlimiting exemplary compounds which target, decrease, or inhibit the oncogenic activity of Ras include farnesyl transferase inhibitors, such as L-744832, DK8G557, tipifarnib, and lonafarnib.

Nonlimiting exemplary telomerase inhibitors include compounds that target, decrease, or inhibit the activity of telomerase, such as compounds that inhibit the telomerase receptor, such as telomestatin.

Nonlimiting exemplary proteasome inhibitors include compounds that target, decrease, or inhibit the activity of the proteasome including, but not limited to, bortezomib. In some embodiments, the proteasome inhibitor is carfilzomib or ixazomib.

Nonlimiting exemplary FMS-like tyrosine kinase inhibitors, which are compounds targeting, decreasing or inhibiting the activity of FMS-like tyrosine kinase receptors (Flt-3R), include gilteritinib, interferon, I-β-D-arabinofuransylcytosine (ara-c), and bisulfan; and ALK inhibitors, which are compounds that target, decrease, or inhibit anaplastic lymphoma kinase, include alectinib, brigatinib, and lorlatinib.

Nonlimiting exemplary Flt-3 inhibitors include PKC412, midostaurin, a staurosporine derivative, SU11248, MLN518, and gilteritinib.

Nonlimiting exemplary HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino, 17-demethoxygeldanamycin (17AAG), a geldanamycin derivative; other geldanamycin related compounds; radicicol and HDAC inhibitors.

Nonlimiting exemplary protein tyrosine kinase and/or serine and/or threonine kinase inhibitors or lipid kinase inhibitors, include a) a compound targeting, decreasing, or inhibiting the activity of the platelet-derived growth factor-receptors (PDGFR), such as a compound that targets, decreases, or inhibits the activity of PDGFR, including olaratumab and N-phenyl-2-pyrimidine-amine derivatives, such as imatinib, SU101, SU6668, and GFB-111; b) a compound targeting, decreasing, or inhibiting the activity of the fibroblast growth factor-receptors (FGFR), such as erdafitinib and lenvatinib; c) a compound targeting, decreasing, or inhibiting the activity of the insulin-like growth factor receptor I (IGF-IR), such as brigatinib; d) a compound targeting, decreasing, or inhibiting the activity of the vascular endothelial growth factor-receptors (VEGFR), such as lenvatinib; e) a compound targeting, decreasing, or inhibiting the activity of the Trk receptor tyrosine kinase family, or ephrin B4 inhibitors, such as larotrectinib; f) a compound targeting, decreasing, or inhibiting the activity of the Ax1 receptor tyrosine kinase family; g) a compound targeting, decreasing, or inhibiting the activity of the Ret receptor tyrosine kinase, such as alectinib; h) a compound targeting, decreasing, or inhibiting the activity of the Kit/SCFR receptor tyrosine kinase, such as imatinib; i) a compound targeting, decreasing, or inhibiting the activity of the c-Kit receptor tyrosine kinases, such as imatinib; j) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; k) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; abemaciclib; binimetinib; cobimetinib; encorafenib; neratinib; palbociclib; ribociclib; l) a compound targeting, decreasing or inhibiting the activity of a protein-tyrosine kinase, such as acalabrutinib, imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl) methyl]amino}-benzoic acid adamantyl ester; NSC 680410, adaphostin); m) a compound targeting, decreasing, or inhibiting the activity of the epidermal growth factor family of receptor tyrosine kinases (EGFR, ErbB2, ErbB3, ErbB4 as homo- or heterodimers) and their mutants, such as brigatinib, CP 358774, ZD 1839, ZM 105180; trastuzumab, cetuximab, gefitinib, erlotinib, osimertinib, dacomitinib, necitumumab, neratinib, OSI-774, Cl-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; n) a compound targeting, decreasing or inhibiting the activity of a phosphatidylinositol 3-kinase (PI3K), such as alpelisib, copanlisib, and duvelisib; and o) a compound targeting, decreasing, or inhibiting the activity of the c-Met receptor.

Nonlimiting exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a Compound of the Disclosure include: avastin, daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, porfimer sodium, anecortave, triamcinolone, hydrocortisone, 11-a-epihydrocotisol, cortexolone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

A number of suitable optional therapeutic, e.g., anticancer, agents are contemplated for use in the therapeutic methods provided herein. Indeed, the methods provided herein can include, but are not limited to, administration of numerous optional therapeutic agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of optional therapeutic agents such as chemotherapeutic compounds and anticancer therapies suitable for co-administration with the disclosed compounds are known to those skilled in the art.

In certain embodiments, anticancer agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-$R^1$ or TRAIL-$R^2$); kinase inhibitors (e.g., epidermal growth factor receptor (EGFR) kinase inhibitor). Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, apalutamide, bicalutamide, finasteride, aminoglutethamide, ketoconazole, and corticosteroids); BCL-2 inhibitors (e.g., venetoclax); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the therapeutic methods provided herein include administering to a subject having cancer (a cancer patient) therapeutically effective amounts of a Compound of the Disclosure, an immune checkpoint inhibitor, and at least one additional optional therapeutic agent, e.g., an anti-hyperproliferative or antineoplastic agent selected from alkylating agents, antimetabolites, and natural products (e.g., herbs and other plant and/or animal derived compounds).

Alkylating agents suitable for use in the present methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimidazolecarboxamide).

In some embodiments, antimetabolites suitable for use in the present methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the methods of the present disclosure include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the therapeutic methods of the present disclosure. For example, the U.S. Food and Drug Administration (FDA) maintains a formulary of oncolytic agents approved for use in the United States. International counterpart agencies to the FDA maintain similar formularies. Those skilled in the art will appreciate that the "product labels" required on all U.S. approved chemotherapeutics describe approved indications, dosing information, toxicity data, and the like, for the exemplary agents.

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calaspargase pegol-mknl, calcitriol, CCI-779, CDB-2914, cefixime, cetuximab, CG0070, cilengitide, clofarabine, combretastatin A4 phosphate, CP-675,206, CP-724,714, CpG 7909, curcumin, daratumumab, decitabine, DENSPM, dinutuximab, doxercalciferol, E7070, E7389, ecteinascidin 743, efaproxiral, eflornithine, EKB-569, elotuzumab, enzastaurin, erlotinib, exisulind, fenretinide, flavopiridol, fludarabine, flutamide, fotemustine, FR901228, G17DT, galiximab, gefitinib, genistein, glasdegib, glufosfamide, GTI-2040, histrelin, HKI-272, homoharringtonine, HSPPC-96, hu14.18-interleukin-2 fusion protein, HuMax-CD4, iloprost, imiquimod, infliximab, inotuzumab ozogamicin, interleukin-12, IPI-504, irofulven, ixabepilone, lapatinib, lenalidomide, lestaurtinib, leuprolide, LMB-9 immunotoxin, lonafarnib, luniliximab, lutetium Lu 177 dotatate, mafosfamide, MB07133, MDX-010, MLN2704, mogamulizumab-kpkc, monoclonal antibody 3F8, monoclonal antibody J591, motexafin, moxetumomab pasudotox-tdfk, MS-275, MVA-MUC1-IL2, nilutamide, niraparib, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, polatuzumab vedotin-piiq, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, rucaparib, S-1, S-8184, satraplatin, SB-, 15992, SGN-0010, SGN-40, sonidegib, sorafenib, SR31747A, ST1571, SU011248, suberoylanilide hydroxamic acid, suramin, tagraxofusp-erzs, talabostat, talampanel, talazoparib, tariquidar, temsirolimus, TGFa-PE38 immunotoxin, thalidomide, thymalfasin, tipifarnib, tirapazamine, TLK286, trabectedin, trifluridine and tipiracil hydrochloride, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

In one embodiment, the optional therapeutic agent comprises one of the anti-cancer drugs or anti-cancer drug combinations listed in Table 5.

TABLE 5

| | | | |
|---|---|---|---|
| Abemaciclib | Abiraterone Acetate | Abraxane (Paclitaxel Albumin-stabilized Nanoparticle Formulation) | ABVD |
| ABVE | ABVE-PC | AC | Acalabrutinib |
| AC-T | Actemra (Tocilizumab) | Adcetris (Brentuximab Vedotin) | ADE |
| Ado-Trastuzumab Emtansine | Adriamycin (Doxorubicin Hydrochloride) | Afatinib Dimaleate | Afinitor (Everolimus) |
| Akynzeo (Netupitant and Palonosetron Hydrochloride) | Aldara (Imiquimod) | Aldesleukin | Alecensa (Alectinib) |
| Alectinib | Alemtuzumab | Alimta (Pemetrexed Disodium) | Aliqopa (Copanlisib Hydrochloride) |
| Alkeran for Injection (Melphalan Hydrochloride) | Alkeran Tablets (Melphalan) | Aloxi (Palonosetron Hydrochloride) | Alunbrig (Brigatinib) |
| Ameluz (Aminolevulinic Acid) | Amifostine | Aminolevulinic Acid | Anastrozole |
| Apalutamide | Aprepitant | Aranesp (Darbepoetin Alfa) | Aredia (Pamidronate Disodium) |
| Arimidex (Anastrozole) | Aromasin (Exemestane) | Arranon (Nelarabine) | Arsenic Trioxide |
| Arzerra (Ofatumumab) | Asparaginase Erwinia chrysanthemi | Atezolizumab | Avastin (Bevacizumab) |
| Avelumab | Axicabtagene Ciloleucel | Axitinib | Azacitidine |
| Azedra (Iobenguane I 131) | Bavencio (Avelumab) | BEACOPP | Beleodaq (Belinostat) |
| Belinostat | Bendamustine Hydrochloride | Bendeka (Bendamustine Hydrochloride) | BEP |
| Besponsa (Inotuzumab Ozogamicin) | Bevacizumab | Bexarotene | Bicalutamide |
| BiCNU (Carmustine) | Binimetinib | Bleomycin | Blinatumomab |
| Blincyto (Blinatumomab) | Bortezomib | Bosulif (Bosutinib) | Bosutinib |

TABLE 5-continued

| | | | |
|---|---|---|---|
| Braftovi (Encorafenib) | Brentuximab Vedotin | Brigatinib | BuMel |
| Busulfan | Busulfex (Busulfan) | Cabazitaxel | Cabometyx (Cabozantinib-S-Malate) |
| Cabozantinib-S-Malate | CAF | Calquence (Acalabrutinib) | Campath (Alemtuzumab) |
| Camptosar (Irinotecan Hydrochloride) | Capecitabine | CAPOX | Carac (Fluorouracil--Topical) |
| Carboplatin | CARBOPLATIN-TAXOL | Carfilzomib | Carmustine |
| Carmustine Implant | Casodex (Bicalutamide) | CEM | Cemiplimab-rwlc |
| Ceritinib | Cerubidine (Daunorubicin Hydrochloride) | Cervarix (Recombinant HPV Bivalent Vaccine) | Cetuximab |
| CEV | Chlorambucil | CHLORAMBUCIL-PREDNISONE | CHOP |
| Cisplatin | Cladribine | Clofarabine | Clolar (Clofarabine) |
| CMF | Cobimetinib | Cometriq (Cabozantinib-S-Malate) | Copanlisib Hydrochloride |
| COPDAC | Copiktra (Duvelisib) | COPP | COPP-ABV |
| Cosmegen (Dactinomycin) | Cotellic (Cobimetinib) | Crizotinib | CVP |
| Cyclophosphamide | Cyramza (Ramucirumab) | Cytarabine | Cytarabine Liposome |
| Cytosar-U (Cytarabine) | Dabrafenib | Dacarbazine | Dacogen (Decitabine) |
| Dacomitinib | Dactinomycin | Daratumumab | Darbepoetin Alfa |
| Darzalex (Daratumumab) | Dasatinib | Daunorubicin Hydrochloride | Daunorubicin Hydrochloride and Cytarabine Liposome |
| Decitabine | Defibrotide Sodium | Defitelio (Defibrotide Sodium) | Degarelix |
| Denileukin Diftitox | Denosumab | DepoCyt (Cytarabine Liposome) | Dexamethasone |
| Dexr azoxane Hydrochloride | Dinutuximab | Docetaxel | Doxil (Doxorubicin Hydrochloride Liposome) |
| Doxorubicin Hydrochloride | Doxorubicin Hydrochloride Liposome | Dox-SL (Doxorubicin Hydrochloride Liposome) | Durvalumab |
| Duvelisib | Efudex (Fluorouracil--Topical) | Eligard (Leuprolide Acetate) | Elitek (Rasburicase) |
| Ellence (Epirubicin Hydrochloride) | Elotuzumab | Eloxatin (Oxaliplatin) | Eltrombopag Olamine |
| Emend (Aprepitant) | Empliciti (Elotuzumab) | Enasidenib Mesylate | Encorafenib |
| Enzalutamide | Epirubicin Hydrochloride | EPOCH | Epoetin Alfa |
| Epogen (Epoetin Alfa) | Erbitux (Cetuximab) | Eribulin Mesylate | Erivedge (Vismodegib) |
| Erleada (Apalutamide) | Erlotinib Hydrochloride | Erwinaze (Asparaginase Erwinia chrysanthemi) | Ethyol (Amifostine) |
| Etopophos (Etoposide Phosphate) | Etoposide | Etoposide Phosphate | Evacet (Doxorubicin Hydrochloride Liposome) |
| Everolimus | Evista (Raloxifene Hydrochloride) | Evomela (Melphalan Hydrochloride) | Exemestane |
| 5-FU (Fluorouracil Injection) | 5-FU (Fluorouracil--Topical) | Fareston (Toremifene) | Farydak (Panobinostat lactate) |
| Faslodex (Fulvestrant) | FEC | Femara (Letrozole) | Filgrastim |
| Firmagon (Degarelix) | Fludarabine Phosphate | Fluoroplex (Fluorouracil--Topical) | Fluorouracil Injection |
| Fluorouracil--Topical | Flutamide | FOLFIRI | FOLFIRI-BEVACIZUMAB |
| FOLFIRI-CETUXIMAB | FOEFIRINOX | FOLFOX | Folotyn (Pralatrexate) |

TABLE 5-continued

| | | | |
|---|---|---|---|
| Fostamatinib Disodium | FU-LV | Fulvestrant | Fusilev (Leucovorin Calcium) |
| Gardasil (Recombinant HPV Quadrivalent Vaccine) | Gardasil 9 (Recombinant HPV Nonavalent Vaccine) | Gazyva (Obinutuzumab) | Gefitinib |
| Gemcitabine Hydrochloride | GEMCITABINE-CISPLATIN | GEMCITABINE-OXALIPLATIN | Gemtuzumab Ozogamicin |
| Gemzar (Gemcitabine Hydrochloride) | Gilotrif (Afatinib Dimaleate) | Gleevec (Imatinib Mesylate) | Gliadel Wafer (Carmustine Implant) |
| Glucarpidase | Goserelin Acetate | Granisetron | Granisetron Hydrochloride |
| Granix (Filgrastim) | Halaven (Eribulin Mesylate) | Hemangeol (Propranolol Hydrochloride) | Herceptin (Trastuzumab) |
| HPV Bivalent Vaccine, Recombinant | HPV Nonavalent Vaccine, Recombinant | HPV Quadrivalent Vaccine, Recombinant | Hycamtin (Topotecan Hydrochloride) |
| Hydrea (Hydroxyurea) | Hydroxyurea | Hyper-CVAD | Ibrance (Palbociclib) |
| Ibritumomab Tiuxetan | Ibrutinib | ICE | Iclusig (Ponatinib Hydrochloride) |
| Idarubicin Hydrochloride | Idelalisib | Idhifa (Enasidenib Mesylate) | Ifex (Ifosfamide) |
| Ifosfamide | IL-2 (Aldesleukin) | Imatinib Mesylate | Imbruvica (Ibrutinib) |
| Imfinzi (Durvalumab) | Imiquimod | Imlygic (Talimogene Laherparepvec) | Inlyta (Axitinib) |
| Inotuzumab Ozogamicin | Interferon Alfa-2b, Recombinant | Interleukin-2 (Aldesleukin) | Intron A (Recombinant Interferon Alfa-2b) |
| Iobenguane I 131 | Ipilimumab | Iressa (Gefitinib) | Irinotecan Hydrochloride |
| Irinotecan Hydrochloride Liposome | Istodax (Romidepsin) | Ivosidenib | Ixabepilone |
| Ixazomib Citrate | Ixempra (Ixabepilone) | Jakafi (Ruxolitinib Phosphate) | JEB |
| Jevtana (Cabazitaxel) | Kadcyla (Ado-Trastuzumab Emtansine) | Kepivance (Palifermin) | Keytruda (Pembrolizumab) |
| Kisqali (Ribociclib) | Kymriah (Tisagenlecleucel) | Kyprolis (Carfilzomib) | Lanreotide Acetate |
| Lapatinib Ditosylate | Larotrectinib Sulfate | Lartruvo (Olaratumab) | Lenalidomide |
| Lenvatinib Mesylate | Lenvima (Lenvatinib Mesylate) | Letrozole | Leucovorin Calcium |
| Leukeran (Chlorambucil) | Leuprolide Acetate | Levulan Kerastik (Aminolevulinic Acid) | Libtayo (Cemiplimab-rwlc) |
| LipoDox (Doxorubicin Hydrochloride Liposome) | Lomustine | Lonsurf (Trifluridine and Tipiracil Hydrochloride) | Lorbrena (Lorlatinib) |
| Lorlatinib | Lumoxiti (Moxetumomab Pasudotox-tdfk) | Lupron (Leuprolide Acetate) | Lupron Depot (Leuprolide Acetate) |
| Lutathera (Lutetium Lu 177-Dotatate) | Lutetium (Lu 177-Dotatate) | Lynparza (Olaparib) | Marqibo (Vincristine Sulfate Liposome) |
| Matulane (Procarbazine Hydrochloride) | Mechlorethamine Hydrochloride | Megestrol Acetate | Mekinist (Trametinib) |
| Mektovi (Binimetinib) | Melphalan | Melphalan Hydrochloride | Mercaptopurine |
| Mesna | Mesnex (Mesna) | Methotrexate | Methylnaltrexone Bromide |
| Midostaurin | Mitomycin C | Mitoxantrone Hydrochloride | Mogamulizumab-kpkc |
| Moxetumomab Pasudotox-tdfk | Mozobil (Plerixafor) | Mustargen (Mechlorethamine Hydrochloride) | MVAC |
| Myleran (Busulfan) | Mylotarg (Gemtuzumab Ozogamicin) | Nanoparticle Paclitaxel (Paclitaxel Albumin-stabilized Nanoparticle Formulation) | Navelbine (Vinorelbine Tartrate) |

TABLE 5-continued

| | | | |
|---|---|---|---|
| Necitumumab | Nelarabine | Neratinib Maleate | Nerlynx (Neratinib Maleate) |
| Netupitant and Palonosetron Hydrochloride | Neulasta (Pegfilgrastim) | Neupogen (Filgrastim) | Nexavar (Sorafenib Tosylate) |
| Nilandron (Nilutamide) | Nilotinib | Nilutamide | Ninlaro (Ixazomib Citrate) |
| Niraparib Tosylate Monohydrate | Nivolumab | Nplate (Romiplostim) | Obinutuzumab |
| Odomzo (Sonidegib) | OEPA | Ofatumumab | OFF |
| Olaparib | Olaratumab | Omacetaxine Mepesuccinate | Oncaspar (Pegaspargase) |
| Ondansetron Hydrochloride | Onivyde (Irinotecan Hydrochloride Liposome) | Ontak (Denileukin Diftitox) | Opdivo (Nivolumab) |
| OPPA | Osimertinib | Oxaliplatin | Paclitaxel |
| Paclitaxel Albumin-stabilized Nanoparticle Formulation | PAD | Palbociclib | Palifermin |
| Palonosetron Hydrochloride | Palonosetron Hydrochloride and Netupitant | Pamidronate Disodium | Panitumumab |
| Panobinostat Lactate | Pazopanib Hydrochloride | PCV | PEB |
| Pegaspargase | Pegfilgrastim | Peginterferon Alfa-2b | PEG-Intron (Peginterferon Alfa-2b) |
| Pembrolizumab | Pemetrexed Disodium | Perjeta (Pertuzumab) | Pertuzumab |
| Plerixafor | Pomalidomide | Pomalyst (Pomalidomide) | Ponatinib Hydrochloride |
| Portrazza (Necitumumab) | Poteligeo (Mogamulizumab-kpkc) | Pralatrexate | Prednisone |
| Procarbazine Hydrochloride | Procrit (Epoetin Alfa) | Proleukin (Aldesleukin) | Prolia (Denosumab) |
| Promacta (Eltrombopag Olamine) | Propranolol Hydrochloride | Provenge (Sipuleucel-T) | Purinethol (Mercaptopurine) |
| Purixan (Mercaptopurine) | Radium 223 Dichloride | Raloxifene Hydrochloride | Ramucirumab |
| Rasburicase | R-CHOP | R-CVP | Recombinant Human Papillomavirus (HPV) Bivalent Vaccine |
| Recombinant Human Papillomavirus (HPV) Nonavalent Vaccine | Recombinant Human Papillomavirus (HPV) Quadrivalent Vaccine | Recombinant Interferon Alfa-2b | Regorafenib |
| Relistor (Methylnaltrexone Bromide) | R-EPOCH | Retacrit (Epoetin Alfa) | Revlimid (Lenalidomide) |
| Rheumatrex (Methotrexate) | Ribociclib | R-ICE | Rituxan (Rituximab) |
| Rituxan Hycela (Rituximab and Hyaluronidase Human) | Rituximab | Rituximab and Hyaluronidase Human | Rolapitant Hydrochloride |
| Romidepsin | Romiplostim | Rubidomycin (Daunorubicin Hydrochloride) | Rubraca (Rucaparib Camsylate) |
| Rucaparib Camsylate | Ruxolitinib Phosphate | Rydapt (Midostaurin) | Sancuso (Granisetron) |
| Sclerosol Intrapleural Aerosol (Talc) | Siltuximab | Sipuleucel-T | Somatuline Depot (Lanreotide Acetate) |
| Sonidegib | Sorafenib Tosylate | Sprycel (Dasatinib) | STANFORD V |
| Sterile Talc Powder (Talc) | Steritalc (Talc) | Stivarga (Regorafenib) | Sunitinib Malate |
| Sustol (Granisetron) | Sutent (Sunitinib Malate) | Sylatron (Peginterferon Alfa-2b) | Sylvant (Siltuximab) |

TABLE 5-continued

| | | | |
|---|---|---|---|
| Synribo (Omacetaxine Mepesuccinate) | Tabloid (Thioguanine) | TAC | Tafinlar (Dabrafenib) |
| Tagrisso (Osimertinib) | Talc | Talimogene Laherparepvec | Tamoxifen Citrate |
| Tarabine PFS (Cytarabine) | Tarceva (Erlotinib Hydrochloride) | Targretin (Bexarotene) | Tasigna (Nilotinib) |
| Tavalisse (Fostamatinib Disodium) | Taxol (Paclitaxel) | Taxotere (Docetaxel) | Tecentriq (Atezolizumab) |
| Temodar (Temozolomide) | Temozolomide | Temsirolimus | Thalidomide |
| Thalomid (Thalidomide) | Thioguanine | Thiotepa | Tibsovo (Ivosidenib) |
| Tisagenlecleucel | Tocilizumab | Tolak (Fluorouracil--Topical) | Topotecan Hydrochloride |
| Toremifene | Torisel (Temsirolimus) | Totect (Dexrazoxane Hydrochloride) | TPF |
| Trabectedin | Trametinib | Trastuzumab | Treanda (Bendamustine Hydrochloride) |
| Trexall (Methotrexate) | Trifluridine and Tipiracil Hydrochloride | Trisenox (Arsenic Trioxide) | Tykerb (Lapatinib Ditosylate) |
| Unituxin (Dinutuximab) | Uridine Triacetate | VAC | Valrubicin |
| Valstar (Valrubicin) | Vandetanib | VAMP | Varubi (Rolapitant Hydrochloride) |
| Vectibix (Panitumumab) | VeIP | Velcade (Bortezomib) | Vemurafenib |
| Venclexta (Venetoclax) | Venetoclax | Verzenio (Abemaciclib) | Vidaza (Azacitidine) |
| Vinblastine Sulfate | Vincristine Sulfate | Vincristine Sulfate Liposome | Vinorelbine Tartrate |
| VIP | Vismodegib | Vistogard (Uridine Triacetate) | Vitrakvi (Larotrectinib Sulfate) |
| Vizimpro (Dacomitinib) | Voraxaze (Glucarpidase) | Vorinostat | Votrient (Pazopanib Hydrochloride) |
| Vyxeos (Daunorubicin Hydrochloride and Cytarabine Liposome) | Xalkori (Crizotinib) | Xeloda (Capecitabine) | XELIRI |
| XELOX | Xgeva (Denosumab) | Xofigo (Radium 223 Dichloride) | Xtandi (Enzalutamide) |
| Yervoy (Ipilimumab) | Yescarta (Axicabtagene Ciloleucel) | Yondelis (Trabectedin) | Zaltrap (Ziv-Aflibercept) |
| Zarxio (Filgrastim) | Zejula (Niraparib Tosylate Monohydrate) | Zelboraf (Vemurafenib) | Zevalin (Ibritumomab Tiuxetan) |
| Zinecard (Dexr azoxane Hydrochloride) | Ziv-Aflibercept | Zofran (Ondansetron Hydrochloride) | Zoladex (Goserelin Acetate) |
| Zoledronic Acid | Zolinza (Vorinostat) | Zometa (Zoledronic Acid) | Zydelig (Idelalisib) |
| Zykadia (Ceritinib) | Zytiga (Abiraterone Acetate) | | |

The disclosure provides the following particular embodiments in connection with treating a disease in a subject.

Embodiment I. A method of treating a subject, the method comprising administering to the subject a therapeutically effective amount of a Compound of the Disclosure, wherein the subject has cancer, a chronic autoimmune disorder, an inflammatory condition, a proliferative disorder, sepsis, or a viral infection.

Embodiment II. The method Embodiment I, wherein the subject has cancer.

Embodiment III. The method of Embodiment II, wherein the cancer is any one or more of the cancers of Table 3.

Embodiment IV. The method of Embodiment II, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment V. The method of Embodiment II, wherein the cancer is any one or more of the cancers of Table 4

Embodiment VI. The method of any one of Embodiments I-V further comprising administering a therapeutically effective amount of an optional therapeutic agent useful in the treatment of the disease or condition, e.g., an immune checkpoint inhibitor or other anticancer agent.

Embodiment VII. The method of any one of Embodiments I-VI, wherein the Compound of the Disclosure is a compound of any one of Formulae I-XI, XI-A, XI-B, XII, XII-A, XII-B, XIII, XIII-A, XIII-B, XIV, XIV-A, XIV-B, XV, XV-A, or XV-B, or a pharmaceutically acceptable salt or solvate thereof.

Embodiment VIII. The method of any one of Embodiments I-VI, wherein the Compound of the Disclosure is a compound of Formula XVI, or a pharmaceutically acceptable salt or solvate thereof.

Embodiment IX. A pharmaceutical composition comprising a Compound of the Disclosure and a pharmaceutically acceptable excipient for use in treating cancer, a chronic autoimmune disorder, an inflammatory condition, a proliferative disorder, sepsis, or a viral infection.

Embodiment X. The pharmaceutical composition of Embodiment IX for use in treating cancer.

Embodiment XI. The pharmaceutical composition of Embodiment X, wherein the cancer is any one or more of the cancers of Table 3.

Embodiment XII. The pharmaceutical composition of Embodiment X, wherein the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XIII. The pharmaceutical composition of Embodiment X, wherein the cancer is any one or more of the cancers of Table 4.

Embodiment XIV. The pharmaceutical composition of any one of Embodiments IX-XIII, wherein the Compound of the Disclosure is a compound of any one of Formulae I-XI, XI-A, XI-B, XII, XII-A, XII-B, XIII, XIII-A, XIII-B, XIV, XIV-A, XIV-B, XV, XV-A, or XV-B, or a pharmaceutically acceptable salt or solvate thereof.

Embodiment XV. The pharmaceutical composition of any one of Embodiments IX-XIII, wherein the Compound of the Disclosure is a compound of Formula XVI, or a pharmaceutically acceptable salt or solvate thereof.

Embodiment XVI. A Compound of the Disclosure for use in treatment of cancer, a chronic autoimmune disorder, an inflammatory condition, a proliferative disorder, sepsis, or a viral infection.

Embodiment XVII. The compound of Embodiment XVI for use in treating cancer.

Embodiment XVIII. The compound of Embodiment XVII, wherein the cancer is any one or more of the cancers of Table 3.

Embodiment XIX. The compound of Embodiment XVII, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XX. The compound of Embodiment XVII, wherein the cancer is any one or more of the cancers of Table 4.

Embodiment XXI. The compound of any one of Embodiments XVI-XX, wherein the Compound of the Disclosure is a compound of any one of Formulae I-XI, XI-A, XI-B, XII, XII-A, XII-B, XIII, XIII-A, XIII-B, XIV, XIV-A, XIV-B, XV, XV-A, or XV-B, or a pharmaceutically acceptable salt or solvate thereof.

Embodiment XXII. The compound of any one of Embodiments XVI-XX, wherein the Compound of the Disclosure is a compound of Formula XVI, or a pharmaceutically acceptable salt or solvate thereof.

Embodiment XXIII. Use of a Compound of the Disclosure for the manufacture of a medicament for treatment of cancer, a chronic autoimmune disorder, an inflammatory condition, a proliferative disorder, sepsis, or a viral infection.

Embodiment XXIV. The use of Embodiment XXIII for the treatment of cancer.

Embodiment XXV. The use of Embodiment XXIV, wherein the cancer is any one or more of the cancers of Table 3.

Embodiment XXVI. The use of Embodiment XXIII, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XXVII. The use of Embodiment XXIV, wherein the cancer is any one or more of the cancers of Table 4.

Embodiment XXVIII. The use of any one of Embodiments XXIII-XXVII, wherein the Compound of the Disclosure is a compound of any one of Formulae I-XI, XI-A, XI-B, XII, XII-A, XII-B, XIII, XIII-A, XIII-B, XIV, XIV-A, XIV-B, XV, XV-A, or XV-B, or a pharmaceutically acceptable salt or solvate thereof.

Embodiment XXIX. The use of any one of Embodiments XXIII-XXVII, wherein the Compound of the Disclosure is a compound of Formula XVI, or a pharmaceutically acceptable salt or solvate thereof.

Embodiment XXX. A method of inhibiting EED protein within a cell of a subject in need thereof, the method comprising administering to the subject a compound of any one of Formulae I-XI, XI-A, XI-B, XII, XII-A, XII-B, XIII, XIII-A, XIII-B, XIV, XIV-A, XIV-B, XV, XV-A, or XV-B, or a pharmaceutically acceptable salt or solvate thereof.

Embodiment XXXI. A method of inhibiting EED protein within a cell of a subject in need thereof, the method comprising administering to the subject a compound of Formula XVI, or a pharmaceutically acceptable salt or solvate thereof.

V. Kits of the Disclosure

In another embodiment, the present disclosure provides kits which comprise a Compound of the Disclosure (or a composition comprising a Compound of the Disclosure)

packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure, e.g., the method of any one of Embodiments I-VI. In one embodiment, the compound or composition is packaged in a unit dosage form. The kit further can include a device suitable for administering the composition according to the intended route of administration.

VI. Definitions

The term "a disease or condition wherein inhibition of EED provides a benefit" and the like pertains to a disease or condition in which EED is important or necessary, e.g., for the onset, progress, expression of that disease or condition, or a disease or a condition which is known to be treated by an EED inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by a EED inhibitor for any particular cell type, for example, by assays which conveniently can be used to assess the activity of particular compounds. See, e.g., Yue and Turkson, Expert Opinion Invest Drugs 18:45-56 (2009).

The term "EED" refers to embryonic ectoderm development protein. See Moritz and Trievel, J. Biol. Chem. 293 (36):13805-13814 (2018).

The term "optional therapeutic agent" refers to a therapeutic agent different from a Compound of the Disclosure and that is known to treat the disease or condition of interest. For example, when a cancer is the disease or condition of interest, the optional therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. Compounds of the Disclosure are inhibitors of EED and can be used in treating or preventing diseases and conditions wherein inhibition of EED provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to a subject in need thereof. In the case of a cancer or other proliferation disorder, the therapeutically effective amount of the agent may reduce (i.e., retard to some extent or stop) unwanted cellular proliferation; reduce the number of cancer cells; reduce the tumor size; inhibit (i.e., retard to some extent or stop) cancer cell infiltration into peripheral organs; inhibit (i.e., retard to some extent or stop) tumor metastasis; inhibit, to some extent, tumor growth; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and subject to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to a subject in a sequence and sufficiently close in time so as to provide the desired therapeutic effect and can act in concert. For example, a Compound of the Disclosure can be administered at the same time or sequentially in any order at different points in time as an optional therapeutic agent. A Compound of the Disclosure and the optional therapeutic agent can be administered separately, in any appropriate form and by any suitable route. When a Compound of the Disclosure and the optional therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an optional therapeutic agent treatment modality (e.g., radiotherapy), to a subject in need thereof. In various embodiments, a Compound of the Disclosure and the optional therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "halo" as used herein by itself or as part of another group refers to —Cl, —F, —Br, or —I.

The term "nitro" as used herein by itself or as part of another group refers to —$NO_2$.

The term "cyano" as used herein by itself or as part of another group refers to —CN.

The term "hydroxy" as herein used by itself or as part of another group refers to —OH.

The term "alkyl" as used herein by itself or as part of another group refers to a straight- or branched-chain aliphatic hydrocarbon containing one to twelve carbon atoms, i.e., a $C_1$-$C_{12}$ alkyl, or the number of carbon atoms designated, e.g., a $C_1$ alkyl such as methyl, a $C_2$ alkyl such as ethyl, etc. In one embodiment, the alkyl is a $C_1$-$C_{10}$ alkyl. In another embodiment, the alkyl is a $C_1$-$C_6$ alkyl. In another embodiment, the alkyl is a $C_1$-$C_4$alkyl. In another embodiment, the alkyl is a $C_1$-$C_3$ alkyl, i.e., methyl, ethyl, propyl, or isopropyl. Non-limiting exemplary $C_1$-$C_{12}$ alkyl groups include methyl, ethyl, propyl, isopropyl, butyl, sec-butyl, tert-butyl, iso-butyl, 3-pentyl, hexyl, heptyl, octyl, nonyl, and decyl. In another embodiment, one or more of the hydrogen atoms of the alkyl group are replaced by deuterium atoms, i.e., the alkyl group is isotopically-labeled with deuterium. A non-limiting exemplarly deteuterated alkyl group is —$CD_3$.

The term "optionally substituted alkyl" as used herein by itself or as part of another group refers to an alkyl group that is either unsubstituted or substituted with one, two, or three substituents, wherein each substituent is independently nitro, haloalkoxy, aryloxy, aralkyloxy, alkylthio, sulfonamido, alkylcarbonyl, arylcarbonyl, alkylsulfonyl, arylsulfonyl, ureido, guanidino, carbamate, carboxy, alkoxycarbonyl, carboxyalkyl, —N($R^{56a}$)C(=O)$R^{56b}$, —N($R^{56c}$)S(=O)$_2R^{56d}$, —C(=O)$R^{57}$, —S(=O)$R^{56e}$, or —S(=O)$_2R^{58}$; wherein:

$R^{56a}$ is hydrogen or alkyl;

$R^{56b}$ is alkyl, haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{56c}$ is hydrogen or alkyl;

$R^{56d}$ is alkyl, haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{56e}$ is alkyl, haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{57}$ is haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, or optionally substituted heteroaryl; and $R^{58}$ is haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, or optionally substituted heteroaryl. Non-limiting exemplary optionally substituted alkyl groups include —CH($CO_2$Me)$CH_2CO_2$Me and —CH($CH_3$)$CH_2$N(H)C(=O)O($CH_3$)$_3$.

The term "alkenyl" as used herein by itself or as part of another group refers to an alkyl group containing one, two, or three carbon-to-carbon double bonds. In one embodiment, the alkenyl group is a $C_2$-$C_6$ alkenyl group. In another embodiment, the alkenyl group is a $C_2$-$C_4$ alkenyl group. In another embodiment, the alkenyl group has one carbon-to-carbon double bond. Non-limiting exemplary alkenyl groups include ethenyl, propenyl, isopropenyl, butenyl, sec-butenyl, pentenyl, and hexenyl.

The term "optionally substituted alkenyl" as used herein by itself or as part of another refers to an alkenyl group that is either unsubstituted or substituted with one, two or three substituents, wherein each substituent is independently halo, nitro, cyano, hydroxy, amino (e.g., alkylamino, dialkylamino), haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted cycloalkyl, alkenyl, alkynyl, optionally substituted aryl, optionally substituted heteroaryl, or optionally substituted heterocyclo. Non-limiting exemplary optionally substituted alkenyl groups include —CH=CHPh.

The term "alkynyl" as used herein by itself or as part of another group refers to an alkyl group containing one, two, or three carbon-to-carbon triple bonds. In one embodiment, the alkynyl is a $C_2$-$C_6$ alkynyl. In another embodiment, the alkynyl is a $C_2$-$C_4$ alkynyl. In another embodiment, the alkynyl has one carbon-to-carbon triple bond. Non-limiting exemplary alkynyl groups include ethynyl, propynyl, butynyl, 2-butynyl, pentynyl, and hexynyl groups.

The term "optionally substituted alkynyl" as used herein by itself or as part of another group refers to an alkynyl group that is either unsubstituted or substituted with one, two or three substituents, wherein each substituent is independently halo, nitro, cyano, hydroxy, amino, e.g., alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted cycloalkyl, alkenyl, alkynyl, optionally substituted aryl, optionally substituted heteroaryl, or optionally substituted heterocyclo. Non-limiting exemplary optionally substituted alkynyl groups include —C≡CPh and —CH(Ph)C≡CH.

The term "haloalkyl" as used herein by itself or as part of another group refers to an alkyl group substituted by one or more fluorine, chlorine, bromine, and/or iodine atoms. In one embodiment, the alkyl is substituted by one, two, or three fluorine and/or chlorine atoms. In another embodiment, the alkyl is substituted by one, two, or three fluorine atoms. In another embodiment, the alkyl is a $C_1$-$C_6$ alkyl. In another embodiment, the alkyl is a $C_1$-$C_4$ alkyl. In another embodiment, the alkyl group is a $C_1$ or $C_2$ alkyl. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

The terms "hydroxyalkyl" or "(hydroxy)alkyl" as used herein by themselves or as part of another group refer to an alkyl group substituted with one, two, or three hydroxy groups. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. In another embodiment, the hydroxyalkyl is a monohydroxyalkyl group, i.e., substituted with one hydroxy group. In another embodiment, the hydroxyalkyl group is a dihydroxyalkyl group, i.e., substituted with two hydroxy groups. Non-limiting exemplary (hydroxyl)alkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

The term "alkoxy" as used herein by itself or as part of another group refers to an alkyl group attached to a terminal oxygen atom. In one embodiment, the alkyl is a $C_1$-$C_6$ alkyl and resulting alkoxy is thus referred to as a "$C_1$-$C_6$ alkoxy." In another embodiment, the alkyl is a $C_1$-$C_4$ alkyl group. Non-limiting exemplary alkoxy groups include methoxy, ethoxy, and tert-butoxy.

The term "haloalkoxy" as used herein by itself or as part of another group refers to a haloalkyl group attached to a terminal oxygen atom. In one embodiment, the haloalkyl group is a $C_1$-$C_6$ haloalkyl. In another embodiment, the haloalkyl group is a $C_1$-$C_4$ haloalkyl group. Non-limiting exemplary haloalkoxy groups include fluoromethoxy, difluoromethoxy, trifluoromethoxy, and 2,2,2-trifluoroethoxy.

The term "alkylthio" as used herein by itself or as part of another group refers to an alkyl group attached to a terminal sulfur atom. In one embodiment, the alkyl group is a $C_1$-$C_4$ alkyl group. Non-limiting exemplary alkylthio groups include —SCH$_3$, and —SCH$_2$CH$_3$.

The terms "alkoxyalkyl" or "(alkoxy)alkyl" as used herein by themselves or as part of another group refers to an alkyl group substituted with one alkoxy group. In one embodiment, the alkoxy is a $C_1$-$C_6$ alkoxy. In another embodiment, the alkoxy is a $C_1$-$C_4$ alkoxy. In another embodiment, the alkyl is a $C_1$-$C_6$ alkyl. In another embodiment, the alkyl is a $C_1$-$C_4$ alkyl. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

The term "heteroalkyl" as used by itself or part of another group refers to unsubstituted straight- or branched-chain aliphatic hydrocarbons containing from three to twenty chain atoms, i.e., 3- to 20-membered heteroalkyl, or the number of chain atoms designated, wherein at least one —CH$_2$— is replaced with at least one of —O—, —N(H)—, —N(C$_1$-C$_4$ alkyl)-, or —S—. The —O—, —N(H)—, —N(C$_1$-C$_4$ alkyl)-, or —S— can independently be placed at any interior position of the aliphatic hydrocarbon chain so long as each —O—, —N(H)—, —N(C$_1$-C$_4$ alkyl)-, and —S— group is separated by at least two —CH$_2$— groups. In one embodiment, one —CH$_2$— group is replaced with one —O— group. In another embodiment, two —CH$_2$— groups are replaced with two —O— groups. In another embodiment, three —CH$_2$— groups are replaced with three —O— groups. In another embodiment, four —CH$_2$— groups are replaced with four —O— groups. Non-limiting exemplary heteroalkyl groups include —CH$_2$OCH$_3$, —CH$_2$OCH$_2$CH$_2$CH$_3$, —CH$_2$CH$_2$CH$_2$OCH$_3$, —CH$_2$CH$_2$OCH$_2$CH$_2$OCH$_2$CH$_3$, —CH$_2$CH$_2$OCH$_2$CH$_2$OCH$_2$CH$_2$OCH$_2$CH$_3$.

The term "cycloalkyl" as used herein by itself or as part of another group refers to saturated and partially unsaturated, e.g., containing one or two double bonds, monocyclic, bicyclic, or tricyclic aliphatic hydrocarbons containing three to twelve carbon atoms, i.e., a $C_{3-12}$ cycloalkyl, or the number of carbons designated, e.g., a $C_3$ cycloalkyl such a cyclopropyl, a $C_4$ cycloalkyl such as cyclobutyl, etc. In one embodiment, the cycloalkyl is bicyclic, i.e., it has two rings. In another embodiment, the cycloalkyl is monocyclic, i.e., it has one ring. In another embodiment, the cycloalkyl is a $C_{3-8}$ cycloalkyl. In another embodiment, the cycloalkyl is a $C_{3-6}$ cycloalkyl, i.e., cyclopropyl, cyclobutyl, cyclopentyl, or cyclohexyl. In another embodiment, the cycloalkyl is a $C_5$ cycloalkyl, i.e., cyclopentyl. In another embodiment, the cycloalkyl is a $C_6$ cycloalkyl, i.e., cyclohexyl. Non-limiting exemplary $C_{3-12}$ cycloalkyl groups include cyclopropyl, cyclobutyl, cyclopentyl, cyclohexyl, cycloheptyl, cyclooctyl, norbornyl, decalin, adamantyl, cyclohexenyl, and spiro[3.3]heptane.

The term "optionally substituted cycloalkyl" as used herein by itself or as part of another group refers to a cycloalkyl group that is either unsubstituted or substituted with one, two, or three substituents, wherein each substituent is independently halo, nitro, cyano, hydroxy, amino (e.g., —NH$_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N(R$^{56a}$)C(=O)R$^{56b}$, —N(R$^{56c}$)S(=O)$_2$R$^{56d}$, —C(=O)R$^{57}$, —S(=O)R$^{56e}$, —S(=O)$_2$R$^{58}$, or —OR$^{59}$, wherein R$^{56a}$, R$^{56b}$, R$^{56c}$, R$^{56d}$, R$^{56e}$, R$^{57}$, and R$^{58}$ are as defined in connection with the term "optionally substituted alkyl" and R$^{59}$ is (hydroxy)alkyl or (amino)alkyl. The term optionally substituted cycloalkyl also includes cycloalkyl groups having fused optionally substituted aryl or optionally substituted heteroaryl groups such as

201

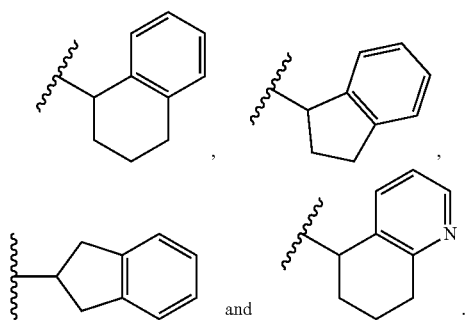

Non-limiting exemplary optionally substituted cycloalkyl groups include:

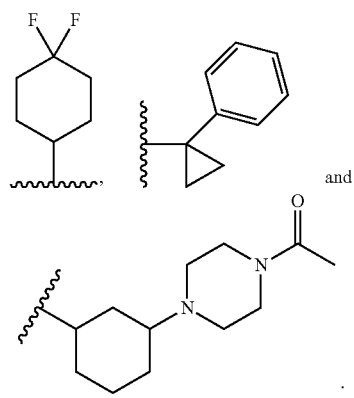

The term "heterocyclo" as used herein by itself or as part of another group refers to saturated and partially unsaturated, e.g., containing one or two double bonds, monocyclic, bicyclic, or tricyclic groups containing three to fourteen ring members, i.e., a 3- to 14-membered heterocyclo, comprising one, two, three, or four heteroatoms. Each heteroatom is independently oxygen, sulfur, or nitrogen. Each sulfur atom is independently oxidized to give a sulfoxide, i.e., S(=O), or sulfone, i.e., S(=O)$_2$.

The term heterocyclo includes groups wherein one or more —CH$_2$— groups is replaced with one or more —C(=O)— groups, including cyclic ureido groups such as imidazolidinyl-2-one, cyclic amide groups such as pyrrolidin-2-one or piperidin-2-one, and cyclic carbamate groups such as oxazolidinyl-2-one.

The term heterocyclo also includes groups having fused optionally substituted aryl or optionally substituted heteroaryl groups such as indoline, indolin-2-one, 2,3-dihydro-1H-pyrrolo[2,3-c]pyridine, 2,3,4,5-tetrahydro-1H-benzo[d]azepine, or 1,3,4,5-tetrahydro-2H-benzo[d]azepin-2-one.

In one embodiment, the heterocyclo group is a 4- to 8-membered cyclic group containing one ring and one or two oxygen atoms, e.g., tetrahydrofuran or tetrahydropyran, or one or two nitrogen atoms, e.g., pyrrolidine, piperidine, or piperazine, or one oxygen and one nitrogen atom, e.g., morpholine, and, optionally, one —CH$_2$— group is replaced with one —C(=O)— group, e.g., pyrrolidin-2-one or piperazin-2-one. In another embodiment, the heterocyclo group is a 5- to 8-membered cyclic group containing one ring and one or two nitrogen atoms and, optionally, one —CH$_2$— group is replaced with one —C(=O)— group. In another embodiment, the heterocyclo group is a 5- or 6-membered cyclic group containing one ring and one or two nitrogen atoms and, optionally, one —CH$_2$— group is replaced with one —C(=O)— group. In another embodiment, the heterocyclo group is a 8- to 12-membered cyclic group containing two rings and one or two nitrogen atoms. The heterocyclo can be linked to the rest of the molecule through any available carbon or nitrogen atom. Non-limiting exemplary heterocyclo groups include:

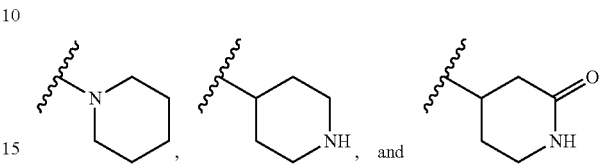

The term "optionally substituted heterocyclo" as used herein by itself or part of another group refers to a heterocyclo group that is either unsubstituted or substituted with one to four substituents, wherein each substituent is independently halo, nitro, cyano, hydroxy, amino, (e.g., —NH$_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N(R$^{56a}$)C(=O)R$^{56b}$, —N(R$^{56c}$)S(=O)$_2$R$^{56d}$, —C(=O)R$^{57}$, —S(=O)R$^{56e}$, —S(=O)$_2$R$^{58}$, or —OR$^{59}$, wherein R$^{56a}$, R$^{56b}$, R$^{56c}$, R$^{56d}$, R$^{56e}$, R$^{57}$, R$^{58}$, and R$^{59}$ are as defined in connection with the term "optionally substituted cycloalkyl." Substitution may occur on any available carbon or nitrogen atom of the heterocyclo group. Non-limiting exemplary optionally substituted heterocyclo groups include:

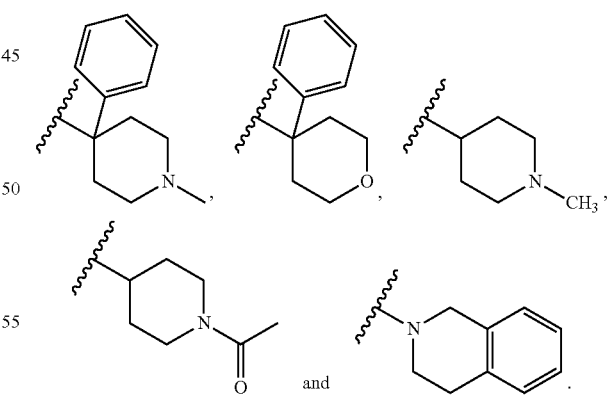

The term "aryl" as used herein by itself or as part of another group refers to an aromatic ring system having six to fourteen carbon atoms, i.e., C$_6$-C$_{14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl. In another embodiment, the aryl group is phenyl.

The term "optionally substituted aryl" as used herein by itself or as part of another group refers to aryl that is either unsubstituted or substituted with one to five substituents, wherein the substituents are each independently halo, nitro, cyano, hydroxy, amino, (e.g., —NH$_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N(R$^{56a}$)C(=O)R$^{56b}$, —N(R$^{56c}$)S(=O)$_2$R$^{56d}$, —C(=O)R$^{57}$, —S(=O)R$^{56e}$, —S(=O)$_2$R$^{58}$, or —OR$^{59}$, wherein R$^{56a}$, R$^{56b}$, R$^{56c}$, R$^{56d}$, R$^{56e}$, R$^{57}$, R$^{58}$, and R$^{59}$ are as defined in connection with the term "optionally substituted cycloalkyl."

In one embodiment, the optionally substituted aryl is an optionally substituted phenyl. In another embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary optionally substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, 3-chloro-4-fluorophenyl, and 2-phenylpropan-2-amine. The term optionally substituted aryl includes aryl groups having fused optionally substituted cycloalkyl groups and fused optionally substituted heterocyclo groups. Non-limiting examples include: 2,3-dihydro-1H-inden-1-yl, 1,2,3,4-tetrahydronaphthalen-1-yl, 1,3,4,5-tetrahydro-2H-benzo[c]azepin-2-yl, 1,2,3,4-tetrahydroisoquinolin-1-yl, and 2-oxo-2,3,4,5-tetrahydro-1H-benzo[d]azepin-1-yl.

The term "heteroaryl" as used herein by itself or as part of another group refers to monocyclic and bicyclic aromatic ring systems having five to 14 fourteen ring members, i.e., a 5- to 14-membered heteroaryl, comprising one, two, three, or four heteroatoms. Each heteroatom is independently oxygen, sulfur, or nitrogen. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term heteroaryl also includes N-oxides. A non-limiting exemplary N-oxide is pyridyl N-oxide.

The term "optionally substituted heteroaryl" as used herein by itself or as part of another group refers to a heteroaryl that is either unsubstituted or substituted with one to four substituents, wherein the substituents are independently halo, nitro, cyano, hydroxy, amino, (e.g., —NH$_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N(R$^{56a}$)C(=O)R$^{56b}$, —N(R$^{56c}$)S(=O)$_2$R$^{56d}$, —C(=O)R$^{57}$, —S(=O)R$^{56e}$, —S(=O)$_2$R$^{58}$, or —OR$^{59}$, wherein R$^{56a}$, R$^{56b}$, R$^{56c}$, R$^{56d}$, R$^{56e}$, R$^{57}$, R$^{58}$, and R$^{59}$ are as defined in connection with the term "optionally substituted cycloalkyl."

In one embodiment, the optionally substituted heteroaryl has two substituents. In another embodiment, the optionally substituted heteroaryl has one substituent. Any available carbon or nitrogen atom can be substituted.

The term "5-membered heteroarylenyl" as used herein by itself or part of another group refers to a divalent form of an optionally substituted 5-membered heteroaryl group. In one embodiment, the heteroarylenyl is a substituted 5-membered heteroarylenyl. In one embodiment, the heteroarylenyl is an unsubstituted 5-membered heteroarylenyl. Non-limiting exemplary 5-membered heteroarylenyls include:

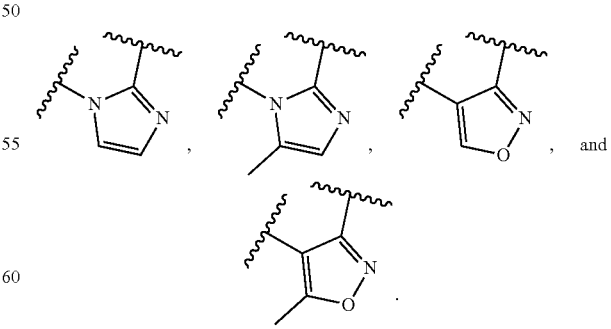

The term "aryloxy" as used herein by itself or as part of another group refers to an optionally substituted aryl attached to a terminal oxygen atom. A non-limiting exemplary aryloxy group is PhO—.

The term "heteroaryloxy" as used herein by itself or as part of another group refers to an optionally substituted heteroaryl attached to a terminal oxygen atom. A non-limiting exemplary aryloxy group is pyridyl-O—.

The term "aralkyloxy" as used herein by itself or as part of another group refers to an aralkyl attached to a terminal oxygen atom. A non-limiting exemplary aralkyloxy group is PhCH$_2$O—.

The term "(cyano)alkyl" as used herein by itself or as part of another group refers to an alkyl substituted with one, two, or three cyano groups. In one embodiment, the alkyl is substituted with one cyano group. In another embodiment, the alkyl is a $C_1$-$C_6$ alkyl In another embodiment, the alkyl is a $C_1$-$C_4$ alkyl. Non-limiting exemplary (cyano)alkyl groups include —CH$_2$CH$_2$CN and —CH$_2$CH$_2$CH$_2$CN.

The term "(cycloalkyl)alkyl" as used herein by itself or as part of another group refers to an alkyl substituted with one or two optionally substituted cycloalkyl groups. In one embodiment, the cycloalkyl group(s) is an optionally substituted $C_3$-$C_6$ cycloalkyl. In another embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. In another embodiment, the alkyl is substituted with one optionally substituted cycloalkyl group. In another embodiment, the alkyl is substituted with two optionally substituted cycloalkyl groups. Non-limiting exemplary (cycloalkyl)alkyl groups include:

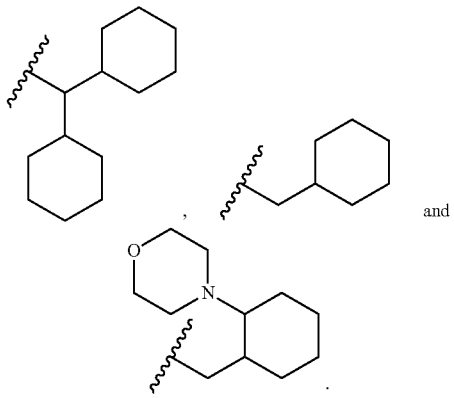

The term "sulfonamido" as used herein by itself or as part of another group refers to a radical of the formula —SO$_2$NR$^{50a}$R$^{50b}$, wherein R$^{50a}$ and R$^{50b}$ are each independently hydrogen, alkyl, optionally substituted cycloalkyl, optionally substituted heterocyclo, optionally substituted aryl, or optionally substituted heteroaryl; or R$^{50a}$ and R$^{50b}$ taken together with the nitrogen to which they are attached form a 3- to 8-membered optionally substituted heterocyclo group. Non-limiting exemplary sulfonamido groups include —SO$_2$NH$_2$, —SO$_2$N(H)CH$_3$, and —SO$_2$N(H)Ph.

The term "carboxamido" as used herein by itself or as part of another group refers to a radical of the formula —C(=O)NR$^{50c}$R$^{50d}$, wherein R$^{50c}$ and R$^{50d}$ are each independently hydrogen, alkyl, optionally substituted cycloalkyl, optionally substituted heterocyclo, optionally substituted aryl, or optionally substituted heteroaryl; or R$^{50c}$ and R$^{50d}$ taken together with the nitrogen to which they are attached form a 3- to 8-membered optionally substituted heterocyclo group. Non-limiting exemplary carboxamido groups include —C(=O)NH$_2$, —C(=O)(H)CH$_3$, and —C(=O)N(CH$_3$)$_2$.

The term "alkylcarbonyl" as used herein by itself or as part of another group refers to a carbonyl group, i.e., —C(=O)—, substituted by an alkyl group. In one embodiment, the alkyl is a $C_1$-$C_4$ alkyl. A non-limiting exemplary alkylcarbonyl group is —COCH$_3$.

The term "arylcarbonyl" as used herein by itself or as part of another group refers to a carbonyl group, i.e., —C(=O)—, substituted by an optionally substituted aryl group. A non-limiting exemplary arylcarbonyl group is —COPh.

The term "alkylsulfonyl" as used herein by itself or as part of another group refers to a sulfonyl group, i.e., —SO$_2$—, substituted by an alkyl group. A non-limiting exemplary alkylsulfonyl group is —SO$_2$CH$_3$.

The term "arylsulfonyl" as used herein by itself or as part of another group refers to a sulfonyl group, i.e., —SO$_2$—, substituted by an optionally substituted aryl group. A non-limiting exemplary arylsulfonyl group is —SO$_2$Ph.

The term "mercaptoalkyl" as used herein by itself or as part of another group refers to an alkyl substituted by a —SH group.

The term "carboxy" as used by itself or as part of another group refers to a radical of the formula —C(=O)OH.

The term "ureido" as used herein by itself or as part of another group refers to a radical of the formula —NR$^{51a}$—C(=O)—NR$^{51b}$R$^{51c}$, wherein R$^{51a}$ is hydrogen or alkyl; and R$^{51b}$ and R$^{51c}$ are each independently hydrogen, alkyl, optionally substituted cycloalkyl, optionally substituted heterocyclo, optionally substituted aryl, or optionally substituted heteroaryl, or R$^{51b}$ and R$^{51c}$ taken together with the nitrogen to which they are attached form a 4- to 8-membered optionally substituted heterocyclo group. Non-limiting exemplary ureido groups include —NH—C(C=O)—NH$_2$ and —NH—C(C=O)—NHCH$_3$.

The term "guanidino" as used herein by itself or as part of another group refers to a radical of the formula —NR$^{52a}$—C(=NR$^{53}$)—NR$^{52b}$R$^{52c}$, wherein R$^{52a}$ is hydrogen or alkyl; R$^{52b}$ and R$^{53c}$ are each independently hydrogen, alkyl, optionally substituted cycloalkyl, optionally substituted heterocyclo, optionally substituted aryl, or optionally substituted heteroaryl; or R$^{52b}$ and R$^{52c}$ taken together with the nitrogen to which they are attached form a 4- to 8-membered optionally substituted heterocyclo group; and R$^{53}$ is hydrogen, alkyl, cyano, alkylsulfonyl, alkylcarbonyl, carboxamido, or sulfonamido. Non-limiting exemplary guanidino groups include —NH—C(C=NH)—NH$_2$, —NH—C(C=NCN)—NH$_2$, and —NH—C(C=NH)—NHCH$_3$.

The term "(heterocyclo)alkyl" as used herein by itself or as part of another group refers to an alkyl substituted with one, two, or three optionally substituted heterocyclo groups. In one embodiment, the alkyl is substituted with one optionally substituted 5- to 8-membered heterocyclo group. In another embodiment, alkyl is a $C_1$-$C_6$ alkyl. In another embodiment, alkyl is a $C_1$-$C_4$ alkyl. The heterocyclo group can be linked to the alkyl group through a carbon or nitrogen atom. Non-limiting exemplary (heterocyclo)alkyl groups include:

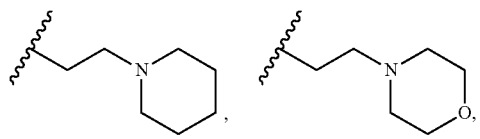

-continued

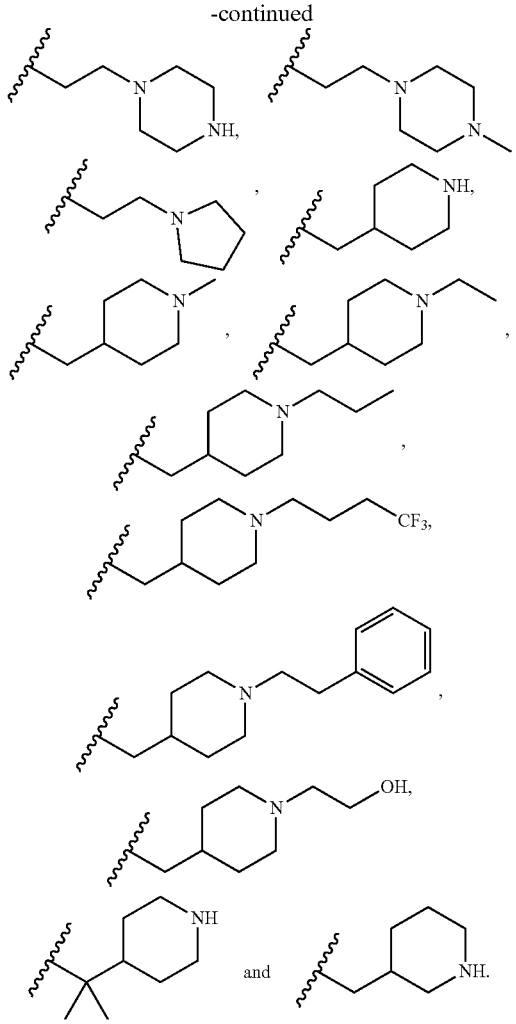

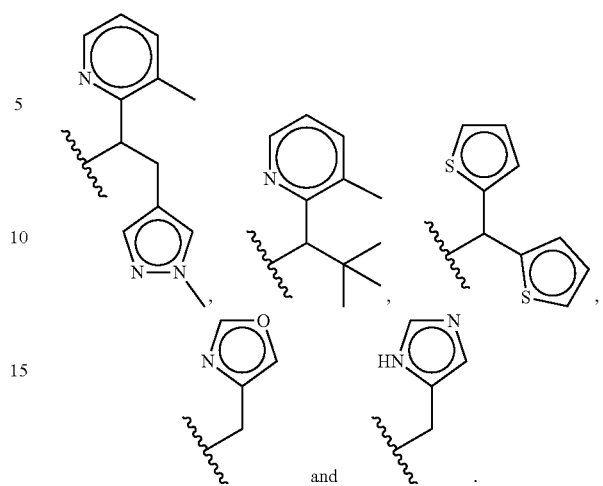

and

The term "carbamate" as used herein by itself or as part of another group refers to a radical of the formula —NR$^{54a}$—C(=O)—OR$^{54b}$, wherein R$^{54a}$ is hydrogen or alkyl, and R$^{54b}$ is hydrogen, alkyl, optionally substituted cycloalkyl, optionally substituted heterocyclo, optionally substituted aryl, or optionally substituted heteroaryl. A non-limiting exemplary carbamate group is —NH—(C=O)—OtBu.

The term "(heteroaryl)alkyl" as used herein by itself or as part of another group refers to an alkyl substituted with one or two optionally substituted heteroaryl groups. In one embodiment, the alkyl group is substituted with one optionally substituted 5- to 14-membered heteroaryl group. In another embodiment, the alkyl group is substituted with two optionally substituted 5- to 14-membered heteroaryl groups. In another embodiment, the alkyl group is substituted with one optionally substituted 5- to 9-membered heteroaryl group. In another embodiment, the alkyl group is substituted with two optionally substituted 5- to 9-membered heteroaryl groups. In another embodiment, the alkyl group is substituted with one optionally substituted 5- or 6-membered heteroaryl group. In another embodiment, the alkyl group is substituted with two optionally substituted 5- or 6-membered heteroaryl groups. In one embodiment, the alkyl group is a $C_1$-$C_6$ alkyl. In another embodiment, the alkyl group is a $C_1$-$C_4$ alkyl. In another embodiment, the alkyl group is a $C_1$ or $C_2$ alkyl. Non-limiting exemplary (heteroaryl)alkyl groups include:

The terms "aralkyl" or "(aryl)alkyl" as used herein by themselves or as part of another group refers to an alkyl substituted with one, two, or three optionally substituted aryl groups. In one embodiment, the alkyl is substituted with one optionally substituted aryl group. In another embodiment, the alkyl is substituted with two optionally substituted aryl groups. In one embodiment, the aryl is an optionally substituted phenyl or optionally substituted naphthyl. In another embodiment, the aryl is an optionally substituted phenyl. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (aryl)alkyl groups include benzyl, phenethyl, —CHPh$_2$, and —CH(4-F-Ph)$_2$.

The term "amido" as used herein by itself or as part of another group refers to a radical of formula —C(=O)NR$^{60a}$R$^{60b}$, wherein R$^{60a}$ and R$^{60b}$ are each independently hydrogen, optionally substituted alkyl, optionally substituted alkenyl, optionally substituted alkynyl, haloalkyl, (alkoxy)alkyl, (hydroxy)alkyl, (cyano)alkyl, optionally substituted cycloalkyl, optionally substituted heterocyclo, optionally substituted aryl, optionally substituted heteroaryl, (aryl)alkyl, (cycloalkyl)alkyl, (heterocyclo)alkyl, or (heteroaryl)alkyl; or R$^{60a}$ and R$^{60b}$ taken together with the nitrogen to which they are attached from a 4- to 8-membered optionally substituted heterocyclo group. In one embodiment, R$^{60a}$ and R$^{60b}$ are each independently hydrogen or $C_1$-$C_6$ alkyl.

The term "amino" as used by itself or as part of another group refers to a radical of the formula —NR$^{55a}$R$^{55b}$, wherein R$^{55a}$ and R$^{55b}$ are independently hydrogen, optionally substituted alkyl, haloalkyl, (hydroxy)alkyl, (alkoxy)alkyl, (amino)alkyl, heteroalkyl, optionally substituted cycloalkyl, optionally substituted heterocyclo, optionally substituted aryl, optionally substituted heteroaryl, (aryl)alkyl, (cycloalkyl)alkyl, (heterocyclo)alkyl, or (heteroaryl)alkyl.

In one embodiment, the amino is —NH$_2$.

In another embodiment, the amino is an "alkylamino," i.e., an amino group wherein R$^{55a}$ is $C_{1-6}$ alkyl and R$^{55b}$ is hydrogen. In one embodiment, R$^{55a}$ is $C_1$-$C_4$ alkyl. Non-limiting exemplary alkylamino groups include —N(H)CH$_3$ and —N(H)CH$_2$CH$_3$.

In another embodiment, the amino is a "dialkylamino," i.e., an amino group wherein R$^{55a}$ and R$^{55b}$ are each independently $C_{1-6}$ alkyl. In one embodiment, R$^{55a}$ and R$^{55b}$ are each independently $C_1$-$C_4$ alkyl. Non-limiting exemplary dialkylamino groups include —N(CH$_3$)$_2$ and —N(CH$_3$)CH$_2$CH(CH$_3$)$_2$.

In another embodiment, the amino is a "hydroxyalkylamino," i.e., an amino group wherein $R^{55a}$ is (hydroxy)alkyl and $R^{55b}$ is hydrogen or $C_1$-$C_4$ alkyl.

In another embodiment, the amino is a "cycloalkylamino," i.e., an amino group wherein $R^{55a}$ is optionally substituted cycloalkyl and $R^{55b}$ is hydrogen or $C_1$-$C_4$ alkyl.

In another embodiment, the amino is a "aralkylamino," i.e., an amino group wherein $R^{55a}$ is aralkyl and $R^{55b}$ is hydrogen or $C_1$-$C_4$ alkyl. Non-limiting exemplary aralkylamino groups include —N(H)CH$_2$Ph, —N(H)CHPh$_2$, and —N(CH$_3$)CH$_2$Ph.

In another embodiment, the amino is a "(cycloalkyl)alkylamino," i.e., an amino group wherein $R^{55a}$ is (cycloalkyl)alkyl and $R^{55b}$ is hydrogen or $C_1$-$C_4$ alkyl. Non-limiting exemplary (cycloalkyl)alkylamino groups include:

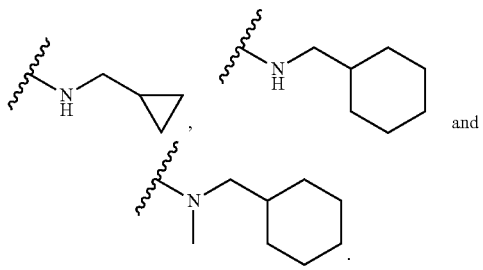

In another embodiment, the amino is a "(heterocyclo)alkylamino," i.e., an amino group wherein $R^{55a}$ is (heterocyclo)alkyl and $R^{55b}$ is hydrogen or $C_1$-$C_4$ alkyl. Non-limiting exemplary (heterocyclo)alkylamino groups include:

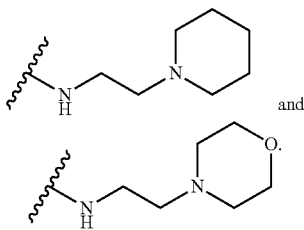

The term "(amino)alkyl" as used herein by itself or as part of another group refers to an alkyl substituted with one amino group. In one embodiment, the amino group is —NH$_2$. In one embodiment, the amino group is an alkylamino. In another embodiment, the amino group is a dialkylamino. In another embodiment, the alkyl is a $C_1$-$C_6$ alkyl. In another embodiment, the alkyl is a $C_1$-$C_4$ alkyl. Non-limiting exemplary (amino)alkyl groups include —CH$_2$NH$_2$, —CH$_2$CH$_2$N(H)CH$_3$, —CH$_2$CH$_2$N(CH$_3$)$_2$, —CH$_2$N(H)cyclopropyl, —CH$_2$N(H)cyclobutyl, and —CH$_2$N(H)cyclohexyl, and —CH$_2$CH$_2$CH$_2$N(H)CH$_2$Ph and —CH$_2$CH$_2$CH$_2$N(H)CH$_2$(4-CF$_3$-Ph).

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H (or deuterium (D)), $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, e.g., $^3$H, $^{11}$C, and $^{14}$C. In one embodiment, provided is a compound wherein substantially all of the atoms at a position within the Compound of the Disclosure are replaced by an atom having a different atomic mass or mass number. In another embodiment, provided is a compound wherein substantially all of the atoms at a position within the Compound of the Disclosure are replaced by deuterium atoms, e.g., all of the hydrogen atoms of a —CH$_3$ group are replaced by deuterium atoms to give a —CD$_3$ group. In another embodiment, provided is a compound wherein a portion of the atoms at a position within the Compound of the disclosure are replaced, i.e., the Compound of the Disclosure is enriched at a position with an atom having a different atomic mass or mass number. In another embodiment, provided is a compound wherein none of the atoms of the Compound of the Disclosure are replaced by an atom having a different atomic mass or mass number. Isotopically-labelled Compounds of the Disclosure can be prepared by methods known in the art.

Compounds of the Disclosure may contain one or more asymmetric centers and may thus give rise to enantiomers, diastereomers, and other stereoisomeric forms. The present disclosure encompasses the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also encompassed by the present disclosure.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive. In one embodiment, Compounds of the Disclosure are racemic.

The term "absolute configuration" refers to the spatial arrangement of the atoms of a chiral molecular entity (or group) and its stereochemical description, e.g., R or S.

The stereochemical terms and conventions used in the specification are meant to be consistent with those described in Pure & Appl. Chem 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.
The term "about," as used herein, includes the recited number±10%. Thus, "about 10" means 9 to 11.
EXAMPLES
Example 1
Synthesis of 12-(((5-fluoro-2,3-dihydrobenzofuran-4-yl)methyl)amino)-3H,5H-4-oxa-2,6,11,12a-tetraazabenzo[4,5]cycloocta[1,2,3-cd]inden-3-one (Cpd. No. 12)
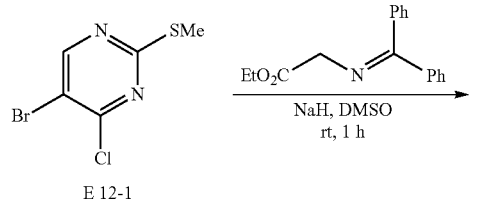
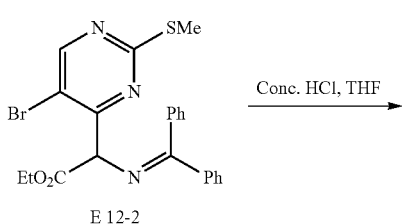
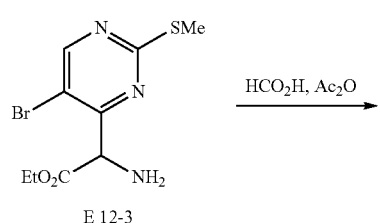
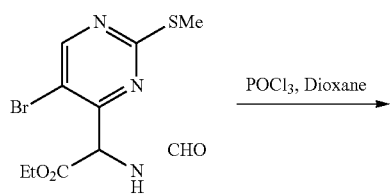
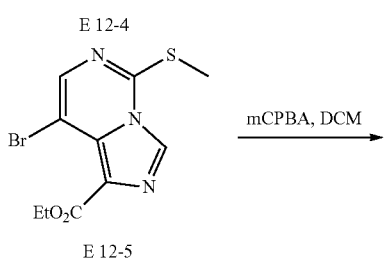
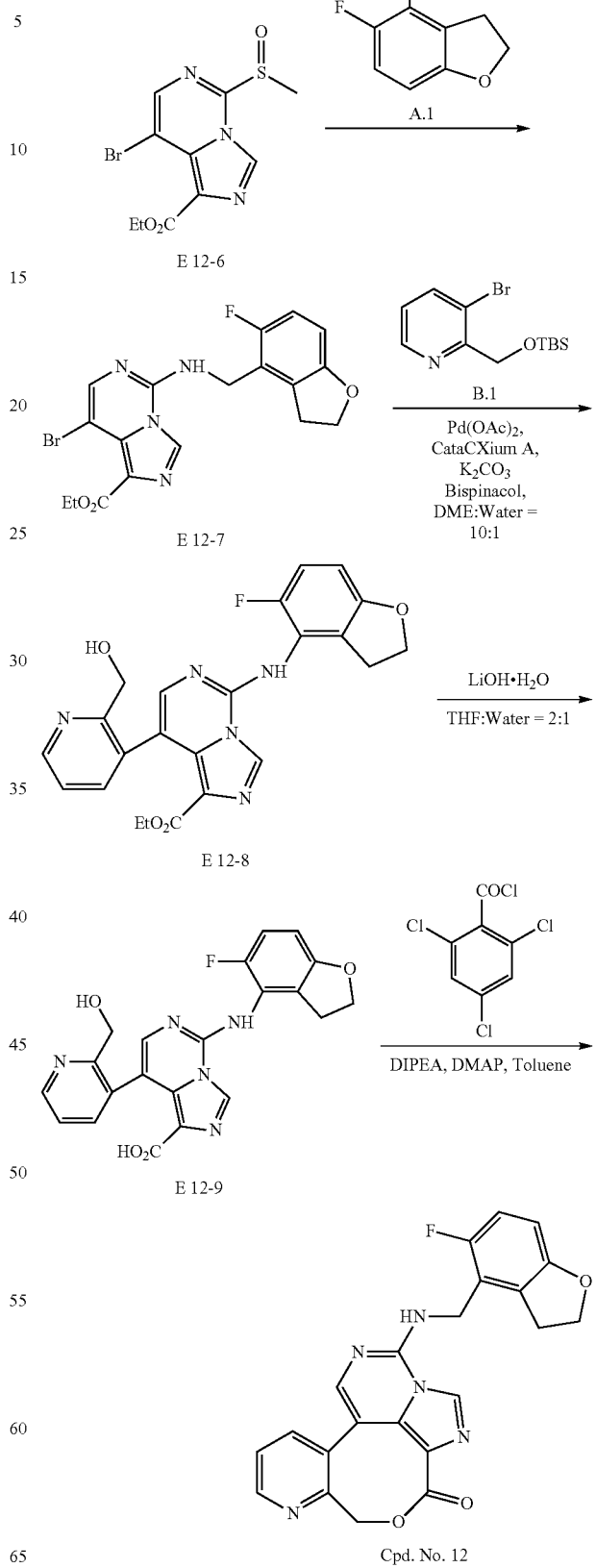

A solution of ethyl 2-(diphenylmethyleneamino)acetate (18.4 g, 69 mmol) in DMSO (50 ml) was added dropwise at 0° C. to a suspension of NaH (60%) (5.0 g, 125.5 mmol) in 70 ml of anhydrous DMSO. The reaction mixture turned orange immediately. After 5 min ethyl 2-((diphenylmethylene)amino)acetate (15 g, 62.7 mmol) in 50 ml DMSO was added dropwise. The mixture was stirred at room temperature for 2 h. After that the reaction mixture was quenched by careful addition of aq. $NH_4Cl$ solution. The mixture was extracted then with ethyl acetate, washed with brine, dried and concentrated and used as crude for the next step. LC-MS: [M+H]+=470.01.

To a solution of compound E 12-2 (crude, 5.0 g, 10.6 mmol) in THF (50 ml) was added 10 ml 3 N HCl in water at 0° C. The mixture was stirred at room temperature for 1 h and the reaction mixture was concentrated followed by basification to pH 8~9 with aq. $Na_2CO_3$ solution. The mixture was extracted with DCM, washed with brine. Concentration under reduced pressure followed by purification by flash chromatography (0-100% EtOAc/Hexane) gave the desired compound E 12-3 in 80% overall yield. LC-MS: [M+H]+=305.95.

A mixture of HCOOH (4 ml) and $Ac_2O$ (4 ml) was heated at 50° C. for 1 h. The reaction mixture was cooled to room temperature and added to a solution of ethyl 2-amino-2-(methylthio) pyrimidin-4-yl) acetate (compound E 12-3, 2.0 g, 6.55 mmol) in 20 ml of DCM. The mixture was stirred at room temperature for 2 h. After completion of the reaction, the mixture was concentrated. The mixture was extracted with DCM (2×50 ml), washed successively with water (20 ml), and brine (10 ml). The organic phase was dried ($Na_2SO_4$), filtered and concentrated to afford the crude title compound E 12-4 as an oil, which was used for the next steps without further purification. LC-MS: [M+H]+=334.05.

To a solution of compound E 12-4 (2.0 g, crude) in dioxane (20 ml) was added $POCl_3$ (1.5 ml) dropwise. The reaction mixture was heated under reflux for 4 h. The mixture was cooled to rt and concentrated. Ice cooled water (50 ml) was added, and the mixture was adjusted to pH 8 with satd. aq. $NaHCO_3$. The mixture was extracted with DCM (2×50 ml), washed with brine (10 ml), dried ($Na_2SO_4$) and filtered. The filtrate was concentrated, and the residue was purified by silica gel column chromatography (eluted with 50-100% EtOAc/Hexane) to afford the title compound E 12-5 as a white solid (1.42 g, 4.59 mmol) in 70% overall yield in two steps. LC-MS: [M+H]+=315.70. $^1$H NMR (400 MHz, DMSO $d_6$): 8.67 (s, 1H), 7.99 (s, 1H), 4.33 (q, 2H), 2.76 (s, 3H), 1.34 (t, 3H).

To a solution of compound E 12-5 (567 mg, 1.8 mmol, 1.0 eq.) in DCM (18 ml) was added m-CPBA (464 mg, 2.7 mmol, <77%, 1.5 eq.) at 0° C. After 45 min, $Et_3N$ (1 ml, 7.6 mmol, 4 eq.) was added at 0° C. and stirred for 2 min, followed by addition of compound A.1 (300 mg, 1.8 mmol). The reaction mixture was then stirred at room temperature for 3 h. After that the reaction mixture was concentrated and the residue was purified by silica gel column chromatography (eluted with 50-100% EtOAc/Hexane) to afford E 12-7 (429 mg, 0.99 mmol) in 55% yield. LC-MS: [M+H]+=434.03. $^1$H NMR (400 MHz, DMSO-$d_6$) δ 8.75 (s, 1H), 8.65 (t, J=5.1 Hz, 1H), 7.68 (s, 1H), 6.94 (t, J=9.5 Hz, 1H), 6.70 (dd, J=8.7, 3.9 Hz, 1H), 4.68 (d, J=5.0 Hz, 2H), 4.54 (t, J=8.7 Hz, 2H), 4.29 (q, J=7.1 Hz, 2H), 3.27 (t, J=8.8 Hz, 2H), 1.32 (t, J=7.1 Hz, 3H).

Palladium (II) acetate (70 mg, 0.31 mmol, 0.1 eq.) and cataCXium A (221 mg, 0.62 mmol, 0.2 eq.) were mixed together in DME (2.0 ml, degassed) and resulting solution was added via pipette to a stirred solution of compound E 12-7 (1.34 g, 3.1 mmol, 1.0 eq.), compound B.1 (1.86 g, 6.2 mmol, 2.0 eq.), bis-pinacolatediboron (1.6 g, 6.2 mmol, 2.0 eq.) and $K_2CO_3$ (1.71 g, 12.4 mmol, 4.0 eq.) in DME/$H_2O$ (10:1, 22 ml, degassed) at 70° C. The reaction mixture was the stirred for 12 h. After that the reaction mixture was concentrated and extracted with ethyl acetate (2×50 ml), washed with water and brine, and then dried over $Na_2SO_4$. The mixture was concentrated, and residue was purified by HPLC to afford the desired compound, which on treatment of TFA/DCM afforded the desired compound E 12-8 (719 mg, 1.55 mmol) as a white solid in 50% yield. LC-MS: [M+H]+=464.16.

A mixture of E 12-8 (40 mg, 0.090 mmol, 1 equiv.) and LiOH (20 mg, 0.90 mmol, 10 eq.) in THF (4 ml) and water (1.0 ml) was heated at 70° C. for overnight. 3 N aq. HCl was added drop wise at 0° C. until pH 2-3. The mixture was concentrated, and residue was purified by HPLC to afford the title compound E 12-9 (35 mg, 0.081 mmol) as a white solid in 90% yield. LC-MS: [M+H]+=436.13.

To a cloudy mixture of 2,4,6-trichlorobenzoyl chloride (24 mg, 0.01 mmol, 1.5 eq.), DIPEA (85 mg, 0.66 mmol, 10.0 eq.), and DMAP (4 mg, 0.033 mmol, 0.5 eq.) in toluene (2 ml) was added a clear solution of secoacid E 12-9 (31 mg, 0.066 mmol) in toluene (1 ml) slowly via cannula. After 2 h, the reaction mixture was concentrated. The crude product was extracted with ethyl acetate (2×10 ml), washed in brine, and dried over $Na_2SO_4$. The mixture was concentrated, and residue was purified by HPLC to afford Cpd. No. 12 (16 mg, 0.039 mmol) as a white solid in 60% yield. LC-MS: [M+H]+=418.12. $^1$H NMR (400 MHz, Acetone-$d_6$) δ 8.77 (s, 1H), 8.66 (d, J=4.7 Hz, 1H), 8.20 (s, 1H), 8.04 (d, J=7.9 Hz, 1H), 7.75 (s, 1H), 7.56 (dd, J=8.0, 4.6 Hz, 1H), 6.90 (t, J=9.4 Hz, 1H), 6.67 (dd, J=8.6, 3.8 Hz, 1H), 6.04 (s, 1H), 5.08 (s, 1H), 4.90 (s, 2H), 4.59 (t, J=8.6 Hz, 2H), 3.49 (t, J=8.6 Hz, 2H).

Example 2

12-(((5-fluoro-2,3-dihydrobenzofuran-4-yl)methyl) amino)-4,5-dihydro-3H-2,4,6,11,12a-pentaazabenzo [4,5]cycloocta[1,2,3-cd]inden-3-one (Cpd. No. 16)

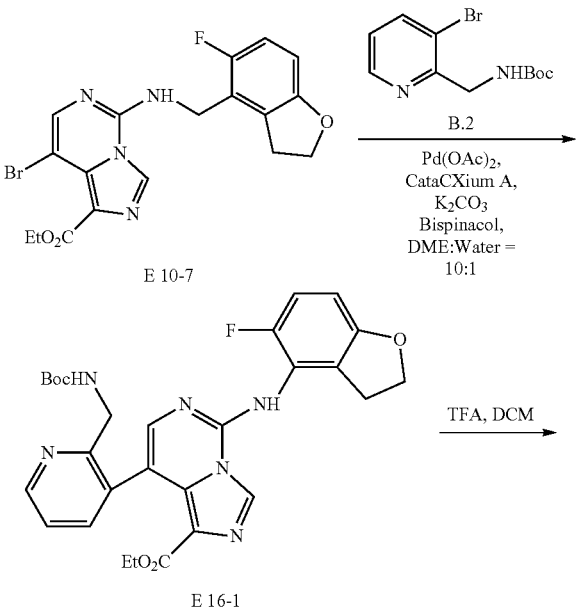

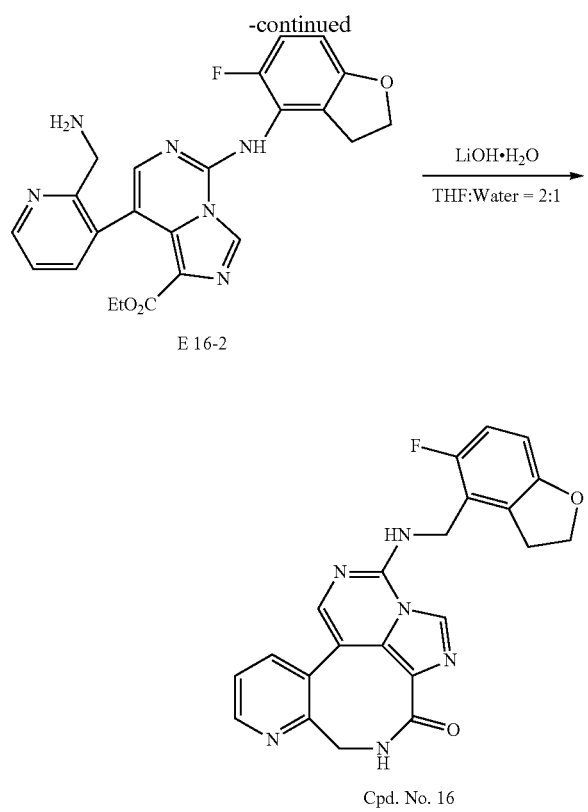

E 16-2

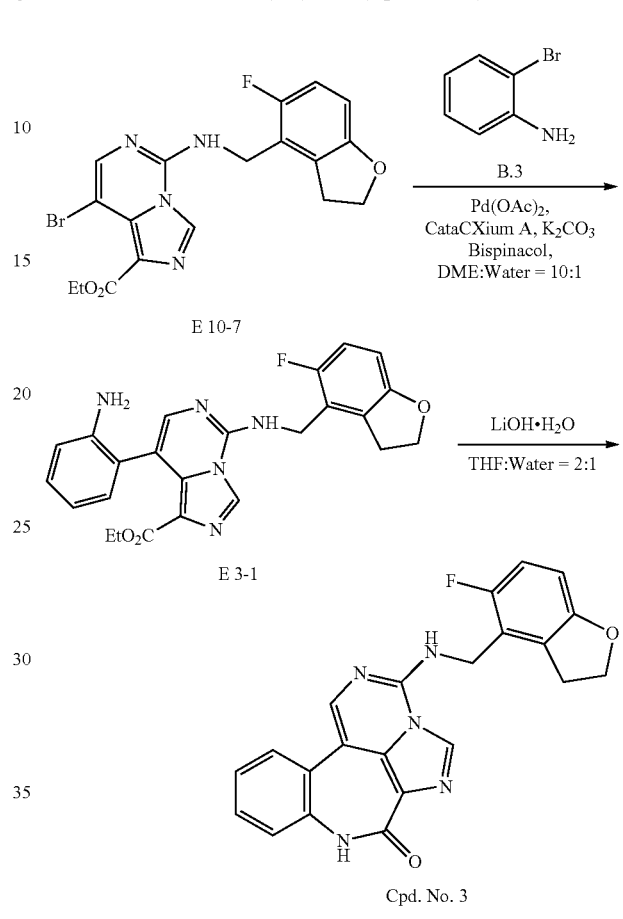

Cpd. No. 16

Palladium (II) acetate (70 mg, 0.31 mmol, 0.1 eq.) and cataCXium A (221 mg, 0.62 mmol, 0.2 eq.) were mixed together in DME (2.0 ml, degassed) and resulting solution was added via pipette to a stirred solution of compound E 10-7 (1.34 g, 3.1 mmol, 1.0 eq.), compound B.2 (1.77 g, 6.2 mmol, 2.0 eq.), bis-pinacolatediboron (1.6 g, 6.2 mmol, 2.0 eq.) and $K_2CO_3$ (1.71 g, 12.4 mmol, 4.0 eq.) in DME/$H_2O$ (10:1, 22 ml, degassed) at 70° C. The reaction mixture was the stirred for 12 h. After that the reaction mixture was concentrated and extracted with ethyl acetate (2×50 ml), washed with water and brine, and then dried over $Na_2SO_4$. The mixture was concentrated, and residue was purified by HPLC to afford the title compound E 16-1 (871 mg, 1.55 mmol) as a white solid in 50% yield. LC-MS: [M+H]+=563.16.

Compound E 16-1 was treated with 25% TFA/DCM at room temperature for 1 h, after that the volatiles were removed in vacuo. The crude was diluted with ethyl acetate, washed with satd. aq. $Na_2CO_3$, then brine. The organic layer was over $Na_2SO_4$ and concentrated in vacuo to provide the compound E 16-2, which was used as crude for the next step.

A mixture of E 16-2 (40 mg, 0.09 mmol, 1 eq.) and LiOH (20 mg, 0.90 mmol, 10 eq.) in THF (4 ml) and water (1.0 ml) was heated at 70° C. for overnight. 3 N aq. HCl was added drop wise at 0° C. until pH 2-3. The mixture was concentrated, and residue was purified by HPLC to afford Cpd. No. 16 as a white solid in 90% yield. LC-MS: [M+H]+=416.14. $^1$H NMR (400 MHz, DMSO-$d_6$) δ 8.82 (s, 1H), 8.65 (t, J=5.1 Hz, 1H), 8.54 (dd, J=4.8, 1.6 Hz, 1H), 8.47 (s, 1H), 7.92 (dd, J=7.8, 1.6 Hz, 1H), 7.53-7.48 (m, 2H), 6.96 (dd, J=10.3, 8.7 Hz, 1H), 6.72 (dd, J=8.7, 3.9 Hz, 1H), 4.98-4.94 (m, 1H), 4.75 (s, 2H), 4.57-4.53 (m, 2H), 4.03 (m, 1H), 3.35 (t, J=8.7 Hz, 2H).

Example 3

Synthesis of 11-(((5-fluoro-2,3-dihydrobenzofuran-4-yl)methyl)amino)-2,4,10,11a-tetraazadibenzo[cd,f]azulen-3(4H)-one (Cpd. No. 3)

Palladium (II) acetate (70 mg, 0.31 mmol, 0.1 eq.) and cataCXium A (221 mg, 0.62 mmol, 0.2 eq.) were mixed together in DME (2.0 ml, degassed) and resulting solution was added via pipette to a stirred solution of compound E 10-7 (1.34 g, 3.1 mmol, 1.0 eq.), compound B.3 (1.05 g, 6.2 mmol, 2.0 eq.), bis-pinacolatediboron (1.6 g, 6.2 mmol, 2.0 eq.) and $K_2CO_3$ (1.71 g, 12.4 mmol, 4.0 eq.) in DME/$H_2O$ (10:1, 22 ml, degassed) at 70° C. The reaction mixture was the stirred for 12 h. After that the reaction mixture was concentrated and extracted with ethyl acetate (2×50 ml), washed with water and brine, and then dried over $Na_2SO_4$. The mixture was concentrated, and residue was purified by HPLC to afford the title compound E 3-1 (692 mg, 1.55 mmol) as a white solid in 50% yield. LC-MS: [M+H]+=563.16.

A mixture of E 3-1 (40 mg, 0.090 mmol, 1 eq.) and LiOH (20 mg, 0.90 mmol, 10 eq.) in THF (4 ml) and water (1.0 ml) was heated at 70° C. for overnight. 3 N aq. HCl was added drop wise at 0° C. until pH 2-3. The mixture was concentrated, and residue was purified by HPLC to afford the Cpd. No. 3 (32 mg, 0.081 mmol) as a white solid in 90% yield. LC-MS: [M+H]+=402.13. $^1$H NMR (400 MHz, DMSO-$d_6$) δ 9.50 (s, 1H), 8.67 (s, 1H), 8.53 (t, J=5.1 Hz, 1H), 7.99 (s, 1H), 7.88-7.80 (m, 1H), 7.19 (dd, J=6.1, 1.6 Hz, 2H), 7.02 (ddd, J=8.3, 6.1, 2.4 Hz, 1H), 6.96 (dd, J=10.3, 8.7 Hz, 1H), 6.71 (dd, J=8.6, 3.9 Hz, 1H), 4.73 (d, J=4.8 Hz, 2H), 4.56 (t, J=8.7 Hz, 2H), 3.31 (d, J=8.5 Hz, 2H).

Example 4
Synthesis of 4-cyclopropyl-12-(((5-fluoro-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one (Cpd. No. 36)
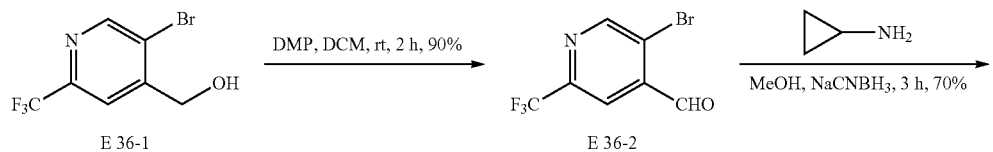
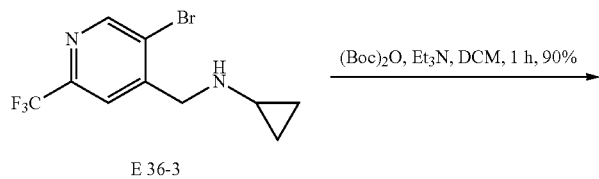
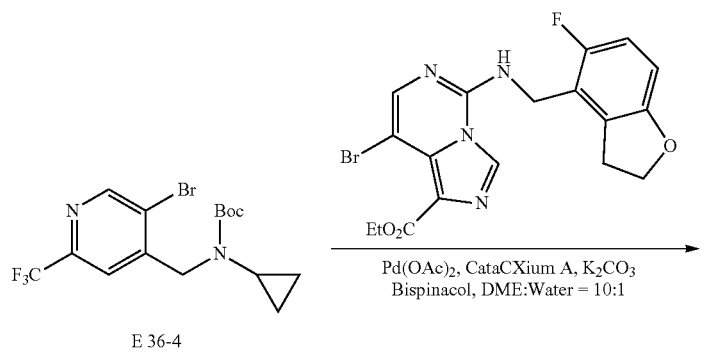
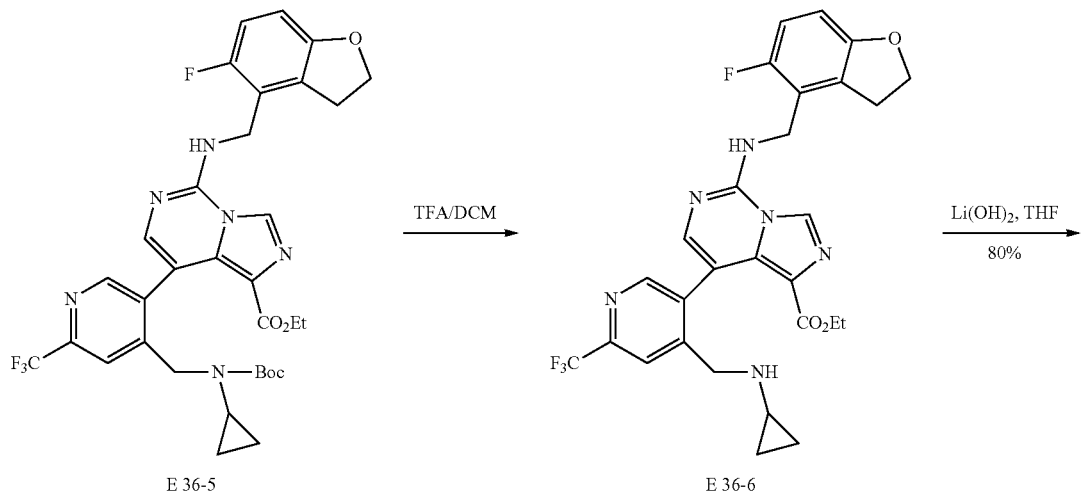

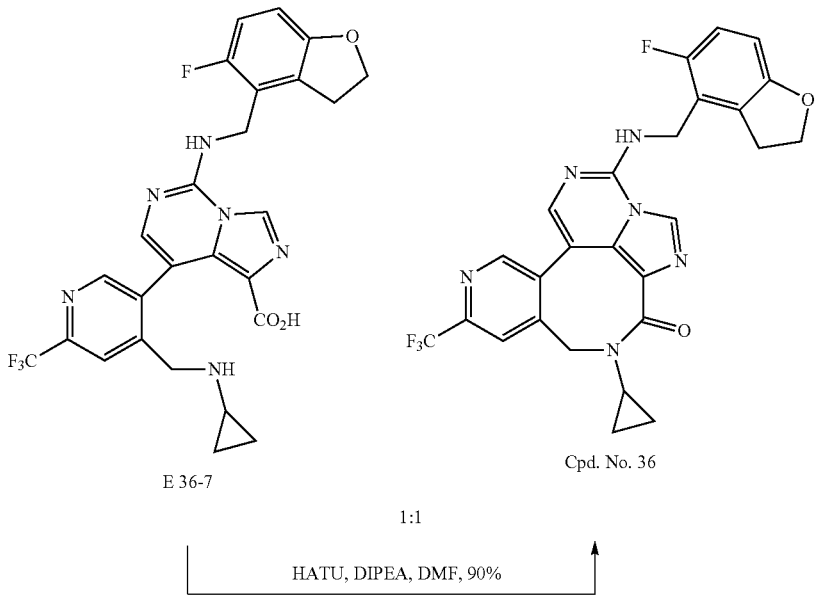

E 36-7

1:1

HATU, DIPEA, DMF, 90%

Cpd. No. 36

An aliquot of (5-bromo-2-(trifluoromethyl)pyridin-4-yl) methanol (E 36-1) was dissolved in dry DCM (~0.2 M), then to this solution 1.5 eq. of Dess-Martin periodinane was added and the reaction mixture is allowed to stirring for 1 h, monitored via TLC. Upon completion quenched with saturated $NH_4Cl$ solution, then extracted with DCM and washed with water and brine. The organic layers were collected and combined, washed with brine, dried over anhydrous $Na_2SO_4$, and concentrated in vacuo. Purification was performed on silica gel normal phase column chromatography with increasing amounts of ethyl acetate in hexanes to afford the desired aldehyde E 36-2 (yield ~90%).

To the obtained aldehyde was added methanol (~0.2 M), followed by 2.2 eq. of cyclopropanamine, 2 eq. of Na(CN)$BH_3$ and 2 eq. of acetic acid under ice bath. Then remove the ice bath and reaction mixture is allowed to stir for 3 h, monitored via TLC. Upon completion, the reaction mixture was concentrated, and residue was purified by HPLC to afford the title compound E 36-3 in 70% yield. LC-MS: [M+H]+=294.99.

To the obtained secondary amine was added 1.5 eq. of (Boc)$_2$O, dissolved by dry DCM (~0.2 M), then followed by 3 eq of TEA, the reaction mixture is allowed to stir for 1 h, monitored via TLC. Upon completion it was quenched with saturated $NH_4Cl$ solution, then extracted with DCM and washed with brine. The organic layers were collected and combined, dried over anhydrous $Na_2SO_4$, and concentrated in vacuo. Purification was performed on silica gel normal phase column chromatography with increasing amounts of ethyl acetate in hexanes to afford the Boc protected secondary amine E 36-4 (yield ~90%). LC-MS: [M+H]+=395.10.

Palladium (II) acetate (0.1 eq.) and cataCXium A (0.2 eq.) were mixed together in DME (0.5 ml, degassed) and resulting solution was added via pipette to a mixture of ethyl 8-bromo-5-(((5-fluoro-2,3-dihydrobenzofuran-4-yl)methyl) amino) imidazo[1,5-c]pyrimidine-1-carboxylate (1 eq.), the Boc protected secondary amine E 36-4 (2 eq.), bis-pinacolatediboron (2.0 eq.) and $K_2CO_3$ (4.0 eq.) in DME/$H_2O$ (10:1, 10 ml, degassed) at 70° C. The reaction mixture was the stirred for 12 h. After that the reaction mixture was concentrated and extracted with ethyl acetate (2×50 ml), washed with water and brine, and then dried over $Na_2SO_4$. The mixture was concentrated, and residue was purified by HPLC to afford the title compound E 36-5 in 40% yield. LC-MS: [M+H]+=671.25.

Compound E 36-5 was treated with 25% TFA/DCM at 0° C. for 1 h, after that the volatiles were removed in vacuo, which was used as crude (E 36-6) for the next step. LC-MS: [M+H]+=571.25.

A mixture of compound E 36-6 (1 eq.) and LiOH (10 eq.) in THF (10 ml/mmol) and water (5 ml/mmol) was heated at 70° C. for overnight. The mixture was concentrated, and residue was then purified by prep-HPLC to afford E 36 and compound E 36-7 in ~1:1 ratio.

To a mixture of compound E 36-7 (1 eq.) and HATU (2 eq.) in DMF (5 ml/mmol) was added DIPEA (5 eq.). The reaction mixture is allowed to stir overnight. Then it was concentrated, and the residue was purified by prep-HPLC to Cpd. No. 36. The combined yield for both compounds is ~90%. LC-MS: [M+H]+=525.15. $^1$H NMR (400 MHz, methanol-d$_4$) δ 8.84 (s, 1H), 8.74 (s, 1H), 7.86 (s, 1H), 7.70 (s, 1H), 6.86 (t, J=9.6 Hz, 1H), 6.65 (dd, J=8.7, 4.0 Hz, 1H), 5.42 (d, J=14.7 Hz, 1H), 4.81 (d, J=6.1 Hz, 2H), 4.59 (t, J=8.9 Hz, 2H), 4.37 (d, J=14.9 Hz, 1H), 3.42 (t, J=8.7 Hz, 2H), 2.55 (s, 1H), 1.16 (s, 1H), 1.00 (d, J=5.5 Hz, 2H), 0.94-0.77 (m, 1H).

Example 5

Synthesis of N-((5-fluoro-2,3-dihydrobenzofuran-4-yl)methyl)-3H,5H-4-oxa-2,6,11,12a-tetraazabenzo[4,5]cycloocta[1,2,3-cd]inden-12-amine (Cpd. No. 2)

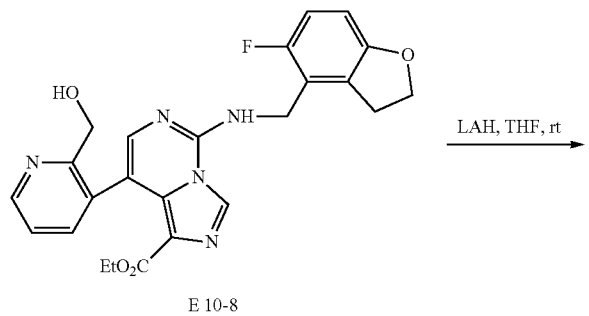

Compound E 10-8 (25 mg, 0.053 mmol) in 2 ml of THF was treated with LAH (0.2 ml 1M solution of LAH in THF) at 0° C. After that temperature was increased to 50° C. and stirred overnight. After cooling to room temperature, the reaction was slowly quenched with satd. $Na_2SO_4$ at 0° C. It was then filtered and washed several times with ethyl acetate. Purification by flash chromatography (0-10% MeOH in DCM) gives Cpd. No. 2 (10 mg, 0.024 mmol) in 50% yield. LC-MS: [M+H]+=404.14.

Example 6

Synthesis of 11-(((5-fluoro-2,3-dihydrobenzofuran-4-yl)methyl)amino)-6-methyl-4H-3-thia-2,5,10,11a-tetraazadibenzo[cd,f]azulene 3,3-dioxide (Cpd. No. 95)

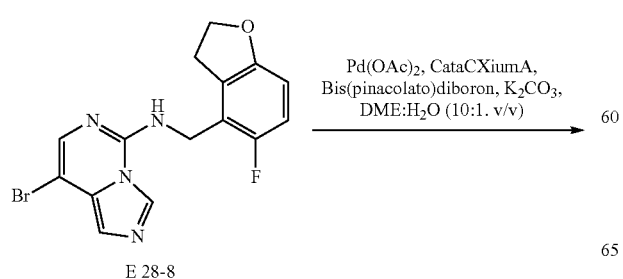

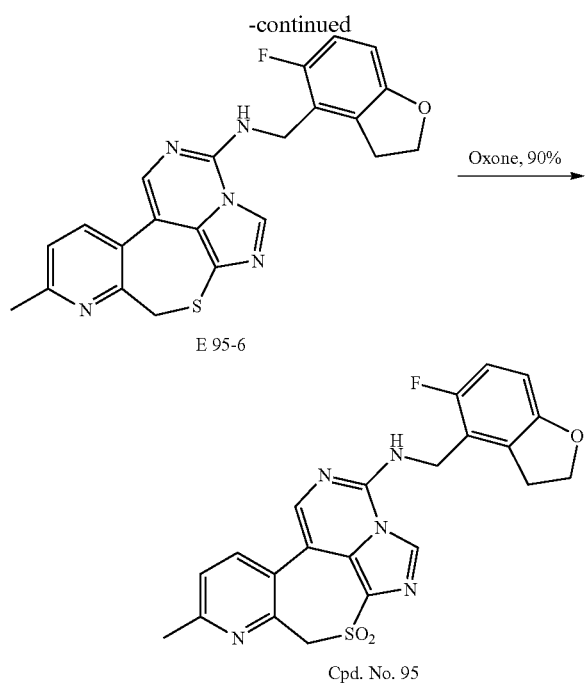

E 95-6

Cpd. No. 95

Synthesis of 8-(2-(((tert-butyldimethylsilyl)oxy)methyl)-6-methylpyridin-3-yl)-N-((5-fluoro-2,3-dihydrobenzofuran-4-yl)methyl)imidazol[1,5-c]pyrimidin-5-amine (E 95-1)

8-bromo-N-((5-fluoro-2,3-dihydrobenzofuran-4-yl)methyl)imidazo[1,5-c]pyrimidin-5-amine (795 mg, 2.19 mmol), 3-bromo-2-(((tert-butyldimethylsilyl)oxy)methyl)-6-methylpyridine (1.393 g, 4.38 mmol), palladium (II) acetate (0.1 eq.), cataCXium A (0.2 eq.), bis-pinacolatediboron (2.0 eq.) and $K_2CO_3$ (5.0 eq.) were mixed together in DME:water (10:1, 17.4 ml, degassed) under $N_2$ atmosphere. The reaction mixture was stirred for 12 h at 70° C. After that the reaction mixture was concentrated and extracted with ethyl acetate (2×200 ml), washed with water and brine, and then dried over $Na_2SO_4$. The mixture was concentrated, and the residue was purified by HPLC to afford the title compound E 95-1 (304 mg, 0.585 mmol) in 38% yield. LC-MS: [M+H]+=520.30.

Synthesis of 8-(2-(((tert-butyldimethylsilyl)oxy)methyl)-6-methylpyridin-3-yl)-N-((5-fluoro-2,3-dihydrobenzofuran-4-yl)methyl)-1-iodoimidazo[1,5-c]pyrimidin-5-amine (E 95-2)

To a solution of 8-(2-(((tert-butyldimethylsilyl)oxy)methyl)-6-methylpyridin-3-yl)-N-((5-fluoro-2,3-dihydrobenzofuran-4-yl)methyl)imidazo[1,5-c]pyrimidin-5-amine (304 mg, 0.585 mmol) in DMF (5 ml) at 0° C. was added NIS (125 mg, 0.95 mmol), and stirred at room temperature for 15 mins. The mixture was extracted with EA (4×50 ml), washed with brine (30 ml), dried ($Na_2SO_4$) and filtered. The filtrate was concentrated, and the residue was purified by column chromatography (silica gel, eluted with 20-80% EtOAc/Hexane) to afford E 95-2 as a yellow solid (190 mg, 0.29 mmol, 50%). LC-MS: [M+H]+=646.21.

Synthesis of (3-(5-(((5-fluoro-2,3-dihydrobenzofuran-4-yl)methyl)amino)-1-iodoimidazo[1,5-c]pyrimidin-8-yl)-6-methylpyridin-2-yl)methanol (E 95-3)

To a solution of 8-(2-(((tert-butyldimethylsilyl)oxy)methyl)-6-methylpyridin-3-yl)-N-((5-fluoro-2,3-dihydrobenzofuran-4-yl)methyl)-1-iodoimidazo[1,5-c]pyrimidin-5-amine (190 mg, 0.29 mmol) in THF (6 ml) was added TBAF (3 ml), and stirred at room temperature overnight. Upon completion the mixture was extracted with EA (3×60 ml), washed with brine (30 ml), dried over $Na_2SO_4$ and filtered. The filtrate was concentrated, and the residue was purified by column chromatography (silica gel, eluted with 0-15% MeOH/DCM) to afford E 95-3 (125 mg, 0.24 mmol, 80%). LC-MS: [M+H]+=532.19.

Synthesis of S-((3-(5-(((5-fluoro-2,3-dihydrobenzofuran-4-yl)methyl)amino)-1-iodoimidazo[1,5-c]pyrimidin-8-yl)-6-methylpyridin-2-yl)methyl) ethanethioate (E 95-4)

MsCl (41 mg, 0.352 mmol) in THF (0.5 ml) was added dropwise to a solution of (3-(5-(((5-fluoro-2,3-dihydrobenzofuran-4-yl)methyl)amino)-1-iodoimidazo[1,5-c]pyrimidin-8-yl)-6-methylpyridin-2-yl)methanol (125 mg, 0.24 mmol) and $Et_3N$ (36 mg, 0.352 mmol) in THF (2 ml) at 0° C. A white ppt of $Et_3N$ hydrochloride formed immediately. The reaction mixture was stirred for 2-3 hrs, upon completion potassium thioacetate (81 mg, 0.704 mmol) in DMF (1.0 ml) was added, resulting in an orange solution which tuned red after several hours. The reaction was monitored via UPLC, upon completion the reaction mixture was stopped and concentrated, then dissolved in DCM. This mixture solution was washed with saturated LiCl twice, followed by water and brine. The saturated LiCl, brine and water washes were combined and separately back-extracted with ethyl acetate. All organic layers are combined, dried over $Na_2SO_4$, filtered and concentrated to dark oil. Flash chromatography (silica gel, eluted with 20-100% EtOAc/Hexane) to afford E 95-4 as a yellow solid (78 mg, 0.13 mmol, 56%). LC-MS: [M+H]+=590.03.

Synthesis of 8,8'-((disulfanediylbis(methylene))bis(6-methylpyridine-2,3-diyl))bis(N-((5-fluoro-2,3-dihydrobenzofuran-4-yl)methyl)-1-iodoimidazo[1,5-c]pyrimidin-5-amine) (E 95-5)

To a solution of S-((3-(5-(((5-fluoro-2,3-dihydrobenzofuran-4-yl)methyl)amino)-1-iodoimidazo[1,5-c]pyrimidin-8-yl)-6-methylpyridin-2-yl)methyl) ethanethioate (78 mg, 0.13 mmol) in methanol (5.0 ml, degassed) was added 0.9 eq. of NaOMe (7 mg, 0.12 mmol) under $N_2$ atmosphere. The reaction mixture was refluxed at 80° C. for an hour. Flash chromatography (silica gel, eluted with 20-100% EtOAc/Hexane) to afford E 95-5 as a yellow solid (57 mg, 0.052 mmol, 79%). LC-MS: [M/2+H]+=547.14.

Synthesis of N-((5-fluoro-2,3-dihydrobenzofuran-4-yl)methyl)-6-methyl-4H-3-thia-2,5,10,11a-tetraazadibenzo[cd,f]azulen-11-amine (E 95-6)

To a solution of 8,8'-((disulfanediylbis(methylene))bis(6-methylpyridine-2,3-diyl))bis(N-((5-fluoro-2,3-dihydrobenzofuran-4-yl)methyl)-1-iodoimidazo[1,5-c]pyrimidin-5-amine) (57 mg, 0.052 mmol) in DMF (3.0 ml, degassed) was added 1.2 eq. of TCEP (18 mg, 0.0626 mmol) under $N_2$ atmosphere. The reaction mixture was stirred at room temperature for 24 hrs. The reaction was monitored by UPLC. Upon completion it was purified by reverse phase HPLC to afford E 95-6 as a pale yellow solid (38 mg, 0.091 mmol, 87%). LC-MS: [M+H]+=420.15.

Synthesis of 11-(((5-fluoro-2,3-dihydrobenzofuran-4-yl)methyl)amino)-6-methyl-4H-3-thia-2,5,10,11a-tetraazadibenzo[cd,f]azulene 3,3-dioxide (E 95)

To a solution of N-((5-fluoro-2,3-dihydrobenzofuran-4-yl)methyl)-6-methyl-4H-3-thia-2,5,10,11a-tetraazadibenzo[cd,f]azulen-11-amine (38 mg, 0.091 mmol) in a mixed solvent of MeOH:H₂O:THF (4.0 mL, 5:5:10) was added 5 eq. of oxone (279 mg, 0.45 mmol). The reaction mixture was stirred for 5 hours. Upon completion reverse phase HPLC afforded Cpd. No. 95 as a pale yellow solid (17 mg, 0.038 mmol, 41%). LC-MS: [M+H]+=452.25.

Example 7

Synthesis of (5-fluoro-2,3-dihydrobenzofuran-4-yl)methanamine (A.1)

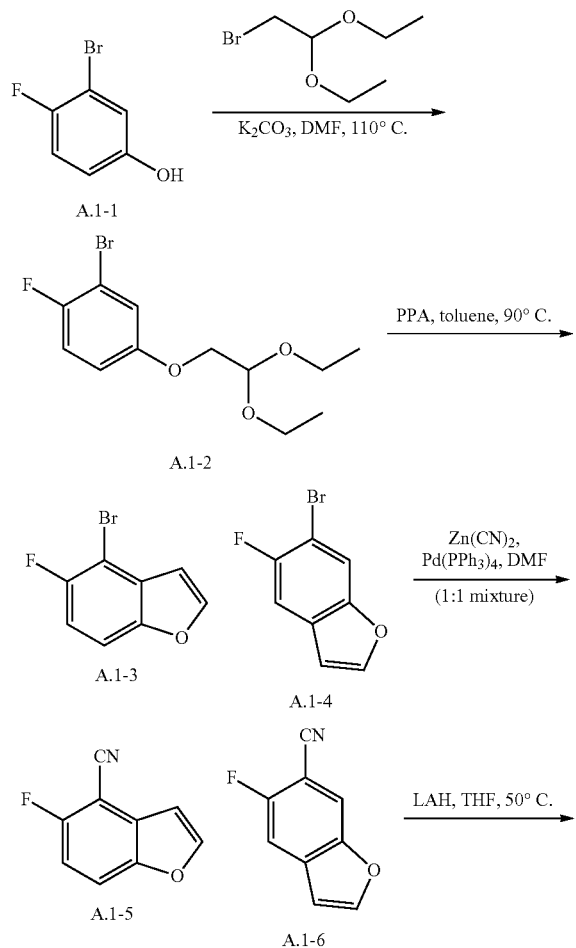

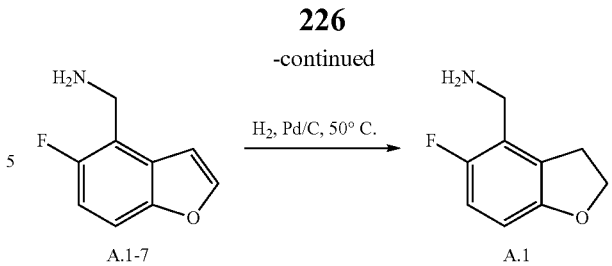

To a solution of 3-bromo-4-fluoro phenol (A.1-1, 50 g, 0.26 mol, 1 eq.) and 2-bromo-1,1-diethoxyethane (67 g, 0.34 mol, 1.3 eq.) in 250 ml DMF was added $K_2CO_3$ (109 g, 0.78 mol, 3 eq.) in one portion. The suspension was heated at 110° C. and stirred overnight under $N_2$. After cooling to room temperature, the reaction was diluted with water and extracted with ethyl acetate (2×500 ml). The combined organic phase was washed with brine and dried over anhydrous $Na_2SO_4$. The residue was purified on silica gel (0-10% EtOAc/Hexane) to give the title compound (A.1-2) as yellow oil (60.12 g, 196 mmol, 75% yield). LC-MS: [M+H]+=307.02. ¹H NMR (400 MHz, methanol-d₄) δ 7.13 (d, 1H), 7.04 (dd, 1H), 6.84 (dd, 1H), 4.82 (t, 1H), 3.97 (d, 2H), 3.78 (q, 2H), 3.65 (q, 2H), 1.27 (t, 6H).

To a solution of PPA (132.4 g, 0.39 mol) and toluene (300 ml) heated at 100° C. and compound A.1-2 (81 g, 0.26 mol) in 50 ml toluene was added slowly. The reaction mixture was heated at 100° C. for 4 h. After cooling to room temperature, 400 ml of ice water was added and extracted with hexane twice. The combined organic phase was washed with brine and dried over anhydrous $Na_2SO_4$. The residue was purified on silica gel (0-10% EtOAc/Hexane) to give the title compound (A.1-3, A.1-4) as inseparable diastereomeric mixture in 45% overall yield. LC-MS: [M+H]+=214.94.

To a solution of A.1-3 and A.1-4 (31 g, 0.144 mol) and Zn(CN)₂ (25.3 g, 0.216 mol) in 100 ml of DMF was added Pd(PPh₃)₄ (16.2 g, 14 mmol). The reaction mixture was degassed with $N_2$ and stirred under $N_2$ atmosphere for 24 h at 100° C. After cooling to room temperature, water was added and extracted with ethyl acetate (2×100 ml). The combined organic phase was washed with brine and dried over anhydrous $Na_2SO_4$. The residue was purified on silica gel (0-20% EtOAc/Hexane) to separate the desired isomer (A.1-5) as a white solid. The structure was confirmed using NMR. LC-MS: [M+H]+=162.02. Compound A.1-5: ¹H NMR (400 MHz, methanol-d₄) δ 8.10 (dd, 1H), 7.89 (dd, 1H), 7.30 (dd, 1H), 7.07 (d, 1H).

Desired isomer A.1-5 (2.3 g, 14.55 mmol) in 10 ml of THF was treated with LAH (36 ml 1M solution of LAH in THF) at 0° C. After that temperature was increased to 50° C. and stirred overnight. After cooling to room temperature, the reaction was slowly quenched with satd. $Na_2SO_4$ at 0° C. It was the filtered and washed several times with ethyl acetate. Purification by flash chromatography (0-10% MeOH in DCM containing 1% trimethylamine) gives the desired compound A.1-7 (1.63 g, 10.1 mmol) in 70% yield. LC-MS: [M+H]+=166.02.

To a solution of compound A.1-7 (1 g, 6.02 mmol) in MeOH (50 ml) was added Pd/C (100 mg, 10% wt). The reaction mixture was degassed with $H_2$ and stirred under $H_2$ atmosphere for 6 h at 40° C. The mixture was then filtered through celite, and washed with MeOH. Concentration under reduced pressure followed by purification by flash chromatography (0-10% MeOH in DCM containing 1% trimethylamine) gives the desired compound intermediate A.1 (859 mg, 5.11 mmol) in 85% yield. LC-MS: [M+H]+=168.07. ¹H NMR (400 MHz, methanol-$d_4$): 6.81 (dd, 1H), 6.59 (dd, 1H), 4.56 (t, 2H), 3.77 (s, 2H), 3.27 (t, 2H).

Example 8

Synthesis of 3-bromo-2-(((tert-butyldimethylsilyl)oxy)methyl)-6-methylpyridine (B.4)

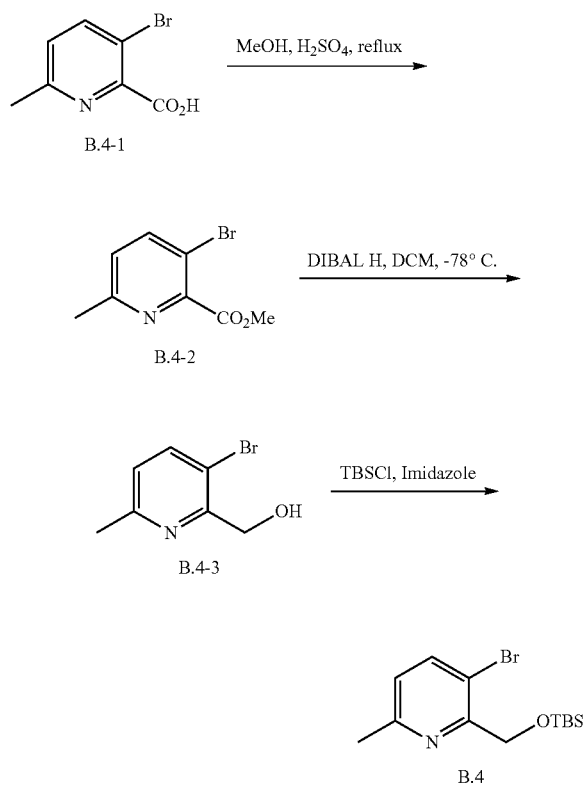

$H_2SO_4$ (1.2 mL, 23.4 mmol, 1.0 eq.) was added to a solution of 3-bromo-6-methylpicolinic acid (B.4-1, 5.0 g, 23.4 mmol, 1.0 eq.) in MeOH (50 ml). The resulting solution was stirred for 14 h while the temperature was maintained at reflux in an oil bath. The mixture was cooled to room temperature and concentrated under vacuum. The residue was dissolved in ethyl acetate (50 ml) and washed with water and satd. aq. NaCl (2×100 ml), dried over anhydrous $Na_2SO_4$ and concentrated under vacuum. The residue was purified by silica gel column and eluted with EtOAc/Hexane (1:5) to yield methyl 3-bromo-6-methylpicolinate (B.4-2, 4.7 g) in 90% yield. LC-MS [M+H]+=229.97.

To a solution of methyl 3-bromo-6-methylpicolinate (B.4-2, 520 mg, 2.28 mmol) in DCM (15 ml) at −60° C., DIBAL-H (4.6 ml, 4.60 mmol, 1 M in cyclohexane) was added dropwise. The reaction mixture was maintained at −60° C. to −15° C. for 30 min, then was allowed to rise to room temperature and stirred for another 12 h. The reaction mixture was cooled to 0° C. again, and was quenched with satd. aq. $NH_4Cl$ (50 ml). The resulting mixture was extracted with DCM (3×100 ml), washed with brine (50 ml), dried ($Na_2SO_4$), filtered, and concentrated. The residue was purified by silica gel column and eluted with EtOAc/Hexane (1:3) to afford the title compound (B.4-3) as a colorless liquid (1.36 mmol, 273 mg, 60%). LC-MS [M+H]+=201.97.

A solution of (3-bromo-6-methylpyridin-2-yl)methanol (B.4-3, 273 mg, 1.36 mmol), imidazole (138 mg, 2.04 mmol), and TBSCl (300 mg, 2.04 mmol) in DCM (10 ml) was stirred at room temperature for 3 h. $H_2O$ (5 ml) was added and the layers separated. The aq. phase was extracted with DCM (2×20 ml) and the combined organic extracts were dried ($Na_2SO_4$) and the solvent removed under reduced pressure. The residue was purified by silica gel column and eluted with EtOAc/Hexane (1:5) to afford the title compound (B.4, 1.22 mmol, 386 mg, 90%) as a colorless liquid. LC-MS [M+H]+=316.06.

Example 9

Synthesis of tert-butyl (2-bromo-5-(trifluoromethyl)benzyl)carbamate (B.5)

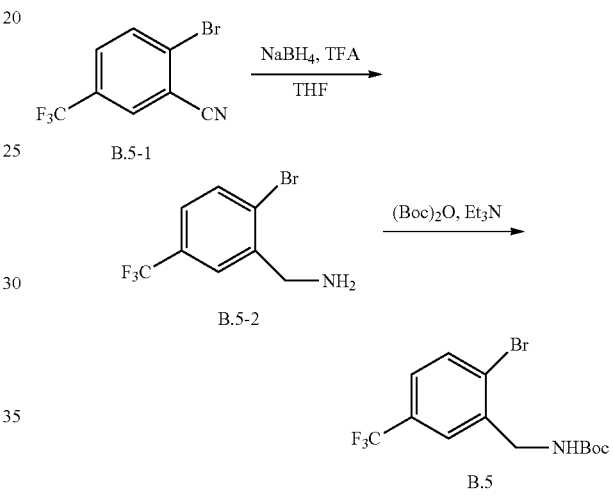

$NaBH_4$ (0.66 g, 14.81 mmol) was charged to a 100 ml flask followed by anhydrous THF 20 ml. The mixture was cooled in an ice-water bath. TFA (1.5 ml) was added to THF (4 ml) at that temperature for 0.5 h. The ice-water bath was removed and the resulting mixture was stirred at room temperature for 2 h. 2-Bromo-5-trifluoromethyl-benzonitrile (B.5-1, 2 g, 8.0 mmol) was dissolved in THF (10 ml). The TFA/$NaBH_4$ mixture was again cooled in an ice-water bath and the nitrile solution was added over 0.5 h. The mixture was allowed to reach ambient temperature while stirring for 16 h. LC analysis of an aliquot revealed completion of reaction. The mixture was cooled in an ice bath and 10 ml methanol was added slowly. Volatiles were removed in vacuo and ethyl acetate (50 ml) was added. This mixture was washed with water (10 ml). The aq. layer was washed with ethyl acetate (10 ml) and the combined organic layer were washed with brine (10 ml), dried over $Na_2SO_4$, filtered, and concentrated. The residue was purified by purified by reverse phase combiflash (eluted with 1-20% acetonitrile/$H_2O$) to afford the title compound (B.5-2, 1.6 g, 80%) as a colorless liquid. LC-MS [M+H]+=256.96.

Compound (B.5-2, 512 mg, 2 mmol) is stirred at room temperature for 3 h with $(Boc)_2O$ (0.51 g, 2.4 mmol, 1.2 eq.) and $Et_3N$ (2 eq., 4 mmol, 380 mg) in 20 ml DCM. After that the residue was purified by column chromatography using 0-50% EtOAc/Hexane to give desired compound (B.5, 560 mg) 80% overall yield. LC-MS [M+H]+=355.16.

Example 10

Synthesis of 3-bromo-2-(((tert-butyldimethylsilyl)oxy)methyl)-6-(trifluoromethyl)pyridine (B.6)

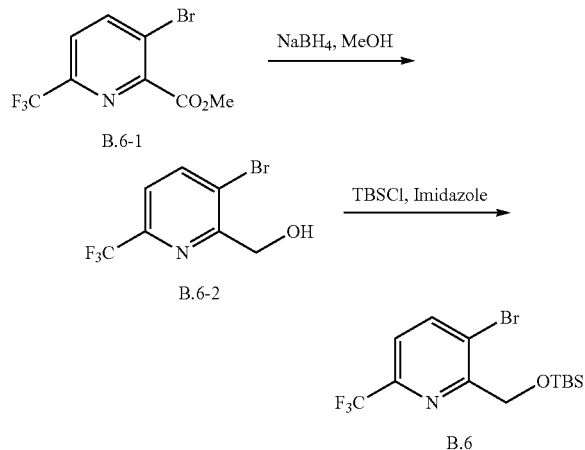

To a solution of methyl 3-bromo-6-(trifluoromethyl)picolinate (B.6-1, 1 g, 3.53 mmol) in MeOH (50 ml) at 0° C. was added NaBH$_4$ (671 mg, 17.65 mmol). The reaction mixture was stirred at room temperature overnight, followed by concentration under reduced pressure. The resultant residue was dissolved in ethyl acetate (50 ml), washed with aq. NH$_4$Cl (3×20 ml), dried over Na$_2$SO$_4$, filtered, and concentrated to afford the title compound. The residue was purified by column chromatography (eluted with 0-50% EtOAc/Hexane) to afford the title compound (B.6-2, 3.17 mmol, 806 mg, 90%) as a colorless liquid. LC-MS [M+H]+=255.95.

TBS protection was accomplished as in EXAMPLE 8. LC-MS [M+H]+=370.03.

Example 11

Synthesis of tert-butyl ((5-bromo-2-(trifluoromethyl)pyridin-4-yl)methyl)carbamate (B.7)

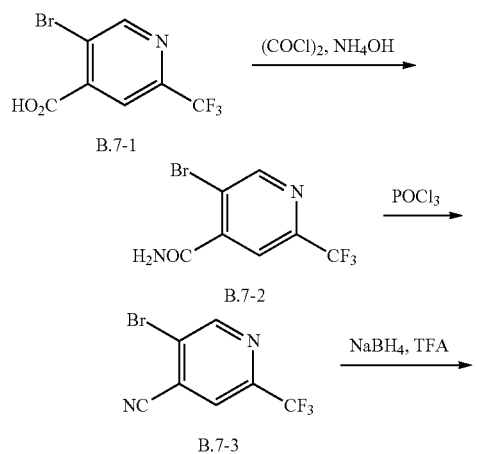

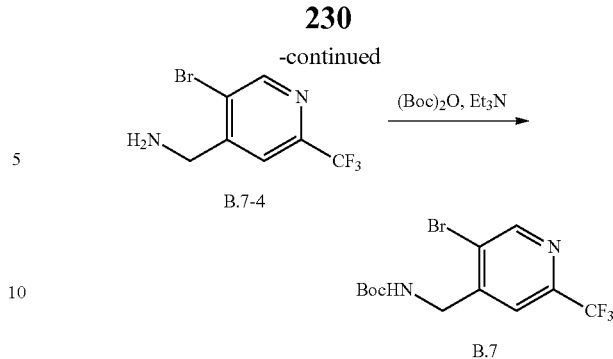

To a 500 ml round bottom flask equipped with a stir bar, condenser and nitrogen inlet was charged 38.9 g (144 mmol) of 5-bromo-2-trifluoromethyl-isonicotinic acid. To the solid was added 250 ml of anhydrous DCM followed by 13.2 ml (151 mmol, 1.05 eq.) oxalyl chloride. To the mixture was added 0.5 ml of anhydrous DMF and the mixture was stirred at ambient temperature for 2 h. The solvent was removed in vacuo. To a 1 lit Erlenmeyer flask equipped with a stir bar in an ice-bath was charged 500 ml of aq. NH$_4$OH. To the chilled solution was added dropwise the crude acid chloride. The residue was transferred with a small amount of acetonitrile. The mixture was stirred for 20 minutes following addition. The resulting precipitate was collected by filtration and washed with water. The filter cake was dried in vacuo at 45° C. affording 5-bromo-2-trifluoromethyl-isonicotinamide (B.7-2, 118 mmol, 31.52 g, 82% yield) as an off-white solid. LC-MS [M+H]+=269.95.

To a 100 mL round bottom equipped with a stir bar, condenser and nitrogen inlet was charged 5.2 g (19.3 mmol) of 5-bromo-2-trifluoromethylisonicotinamide (B.7-2). The solid was diluted with 12 ml of POCl$_3$. The mixture was heated at 70° C. for 3 h. The mixture was cooled to room temperature and poured onto ice. The mixture was neutralized with the careful addition of 50% sodium hydroxide. The resulting off-white solid was collected by filtration, washed with water and dried in vacuo at 50° C. for 18 h. This afforded 4.5 g of 5-bromo-2-trifluoromethyl-isonicotinonitrile (B.7-3, 4.53 g, 18.1 mmol) as an off-white solid in a 94% yield. LC-MS [M+H]+=250.95. $^1$H NMR (CDCl$_3$): δ, 9.03 (s, 1H), 7.91 (s, 1H).

Reduction of nitrile and Boc protection was accomplished as in EXAMPLE 9.

Example 12

Synthesis of tert-butyl ((3-bromo-6-methylpyridin-2-yl)methyl)carbamate (B.8)

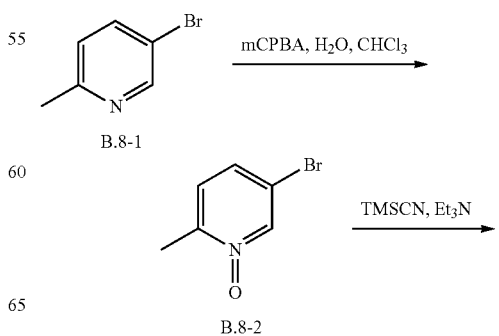

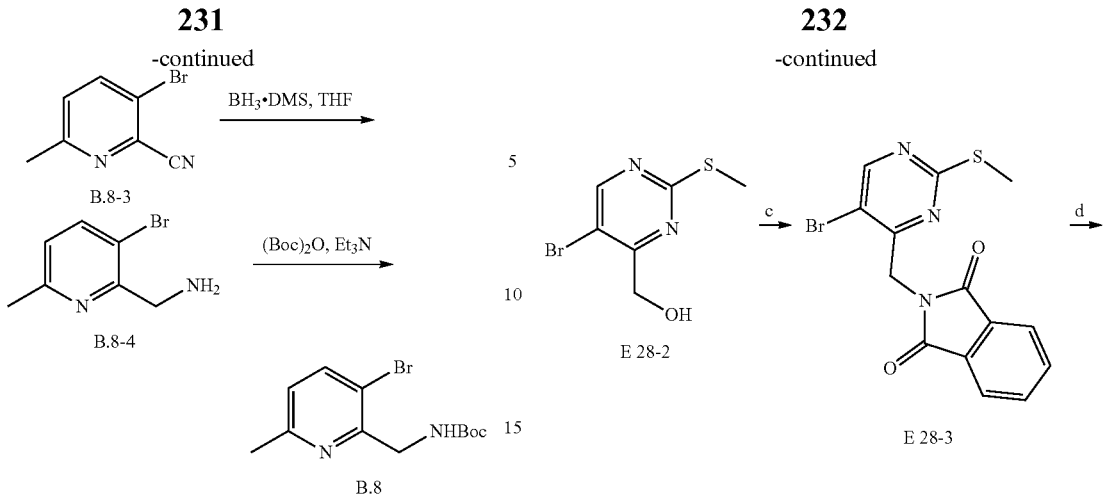

To a solution of 5-bromo-2-methylpyridine (B.8-1, 510 mg, 3.0 mmol, 1.0 eq.) in CHCl₃ (8 ml, 0.38 M) was added 77% mCPBA (5.44 g, 12.0 mmol, 4.0 eq.) and heated at 60° C. for 20 h. After cooling to room temperature, Ca(OH)₂ (1.5 g, 15.9 mmol, 5.3 eq.) was added, and the resulting precipitate was stirred for 30 minutes. The precipitate was filtered and washed with 3:1 CHCl₃/methanol. The filtrate was concentrated in vacuo to give a solid, which was stirred in 30% ethyl acetate in hexane and filtered to give the desired N-oxide. The filtrate was concentrated in vacuo, and the residue was purified by column chromatography using 0-100% ethyl acetate in hexane to give more of the desired N-oxide (B.8-2, 410 mg, 2.4 mmol).

To a solution of 5-bromo-2-methylpyridine 1-oxide (B.8-2, 372 mg, 2.0 mmol) in acetonitrile (10 ml, 0.2 M) was added trimethylsilyl cyanide (TMSCN) (793 mg, 8.0 mmol, 4.0 eq.) and triethylamine (606 mg, 6.0 mmol, 3.0 eq.). The reaction was heated at 100° C. overnight. After cooling to room temperature, the solvent was concentrated in vacuo, and the residue was purified by column chromatography using 0-50% ethyl acetate in hexane to give 3-bromo-6-methylpicolinonitrile (B.8-3, 273 mg, 1.4 mmol, 70% yield).

3-bromo-6-methylpicolinonitrile (B.8-3, 273 mg, 1.4 mmol) was dissolved in 15 ml of dry THF. While stirring the solution, 3.5 ml of BH₃.DMS complex (2M) (5 eq.) was added dropwise. The mixture was then stirred overnight and then quenched by slow addition of 30 ml MeOH at 0° C. After stirring for 1 h, the organic layers were then concentrated under reduced pressure followed by purification by flash chromatography (0-10% MeOH in DCM containing 1% trimethylamine) affords the desired compound (B.8-4, 199 mg, 0.98 mmol, 70% yield).

Boc protection was accomplished as in EXAMPLE 9.

Example 13

Synthesis of N-(furan-2-ylmethyl)-8-phenylimidazo[1,5-c]pyrimidin-5-amine (Cpd. No. 126)

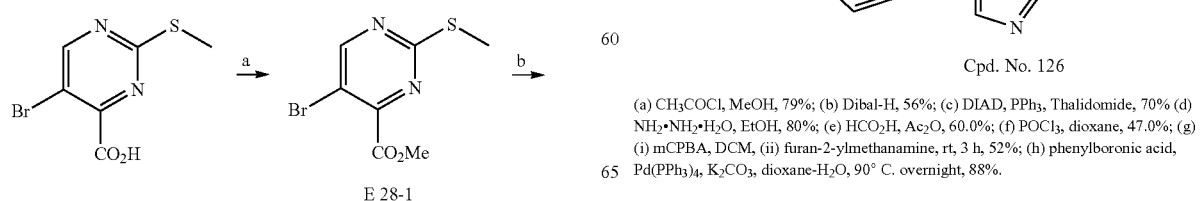

(a) CH₃COCl, MeOH, 79%; (b) Dibal-H, 56%; (c) DIAD, PPh₃, Thalidomide, 70% (d) NH₂·NH₂·H₂O, EtOH, 80%; (e) HCO₂H, Ac₂O, 60.0%; (f) POCl₃, dioxane, 47.0%; (g) (i) mCPBA, DCM, (ii) furan-2-ylmethanamine, rt, 3 h, 52%; (h) phenylboronic acid, Pd(PPh₃)₄, K₂CO₃, dioxane-H₂O, 90° C. overnight, 88%.

Synthesis of Methyl 5-bromo-2-(methylthio)pyrimidine-4-carboxylate (E 28-1)

Acetyl chloride (3.1 mL, 43.8 mmol) was added drop wise to methanol (50 ml) at 0-5° C. The resulting mixture was stirred at this temperature for 5 min, and 5-bromo-2-(methylthio)pyrimidine-4-carboxylic acid (5.5 g, 22.2 mmol) was added. The reaction mixture was heated to reflux for 1 h then cooled to room temperature. The reaction mixture was poured into satd. aq. NaHCO$_3$ solution (100 ml). The mixture was extracted with DCM (3×100 ml), washed with water (50 ml), dried (Na$_2$SO$_4$), filtered and concentrated, and the residue was re-crystalized from petroleum ether to give the title compound (E 28-1) as a yellow solid (4.6 g, 34.6 mmol) in 79% yield. LC-MS: [M+H]+=263.10.

Synthesis of (5-Bromo-2-(methylthio)pyrimidin-4-yl)methanol (E 28-2)

To a solution of methyl 5-bromo-2-(methylthio)pyrimidine-4-carboxylate (E 28-1, 600 mg, 2.28 mmol) in DCM (15 ml) at −60° C., DIBAL-H (4.6 ml, 4.60 mmol, 1 M in cyclohexane) was added drop wise. The reaction mixture was maintained at −60 to −15° C. for 30 min, and then was allowed to rise to room temperature and stirred for another 12 h. The reaction mixture was cooled to 0° C. again, and was quenched with satd. aq. NH$_4$Cl (50 ml). The resulting mixture was extracted with DCM (3×100 ml), washed with brine (50 ml), dried (Na$_2$SO$_4$), filtered, and concentrated. The residue was purified by column chromatography (eluted with 0-50% EtOAc/Hexane) to afford the title compound (E 28-2) as a yellow solid (300 mg) in 56% yield. LC-MS: [M+H]+=235.02.

Synthesis of 2-((5-bromo-2-(methylthio)pyrimidin-4-yl)methyl)isoindoline-1,3-dione (E 28-3)

A THF solution (10 ml) of (5-bromo-2-(methylthio)pyrimidin-4-yl)methanol (1.69 g, 7.22 mmol), phthalimide (1.27 g, 8.66 mmol) and triphenylphosphine (2.19 g, 10.84 mmol) was mixed with DIAD (1.88 g, 10.84 mmol) under cooling with ice and stirred at room temperature for overnight. After completion of the reaction, it was diluted with ethyl acetate, and the organic layer was washed with saturated brine, dried over Na$_2$SO$_4$ and evaporated under reduced pressure. The residue was purified by column chromatography (eluted with with 0-50% EtOAc/Hexane) to afford the desired product (E 28-3, 479 mg) in 70% yield. LC-MS: [M+H]+=363.12.

Synthesis of (5-bromo-2-(methylthio)pyrimidin-4-yl)methanamine (E 28-4)

2-((5-bromo-2-(methylthio)pyrimidin-4-yl)methyl)isoindoline-1,3-dione (910 mg, 2.51 mmol) in ethanol (10 ml) was stirred with NH$_2$NH$_2$·H$_2$O (0.16 ml, 5.02 mmol) at room temperature for 4 h. After completion of the reaction, the solid was filtered off with ethanol, and the filtrate was evaporated under reduced pressure. It was purified by reverse phase combi flash (eluted with 0-20% acetonitrile/H$_2$O) to afford the title compound (E 28-4) as a colorless liquid in 80% yield. LC-MS: [M+H]+=236.10

Synthesis of N-((5-bromo-2-(methylthio)pyrimidin-4-yl)methyl)formamide (E 28-5)

A mixture of HCO$_2$H (4 ml) and Ac$_2$O (4 ml) was heated at 50° C. for 1 h. The reaction mixture was cooled to room temperature and added to a solution of 5-bromo-2-(methylthio)pyrimidin-4-yl)methanamine (1.52 g, 6.55 mmol) in 20 ml of DCM. The mixture was stirred at room temperature for 2 h. After completion of the reaction, the mixture was concentrated. The mixture was extracted with DCM (2×50 ml), washed successively with water (20 ml), and brine (10 ml). The organic phase was dried (Na$_2$SO$_4$), filtered and concentrated to afford the crude title compound (E 28-5) as an oil, which was used for the next steps without further purification. LC-MS: [M+H]+=262.12.

Synthesis of 8-Bromo-5-(methylthio)imidazo[1,5-c]pyrimidine (E 28-6)

To a solution of N-((5-bromo-2-(methylthio)pyrimidin-4-yl)methyl)formamide (800 mg, 3.06 mmol) in dioxane (30 ml) was added POCl$_3$ (0.43 ml, 4.60 mmol) drop wise. The reaction mixture was heated under reflux for 2 h. An ice-water (50 ml) was added, and the mixture was adjusted to pH 8 with satd. aq. NaHCO$_3$. The mixture was extracted with DCM (4×50 ml), washed with brine (30 ml), dried (Na$_2$SO$_4$) and filtered. The filtrate was concentrated, and the residue was purified by column chromatography (silica gel, eluted with 0-50% EtOAc/Hexane) to afford the title compound (E 28-6) as a yellow solid (350 mg, 47.0%). LC-MS: [M+H]+=244.0.

Synthesis of 8-bromo-N-(furan-2-ylmethyl)imidazo[1,5-c]pyrimidin-5-amine (E 28-7)

To a solution of compound E 28-6 (439 mg, 1.8 mmol, 1.0 eq.) in DCM (18 ml) was added m-CPBA (464 mg, 2.7 mmol, <77%, 1.5 eq.) at 0° C. After 45 min, Et$_3$N (1 ml, 7.6 mmol, 4 eq.) was added at 0° C. and stirred for 2 min, followed by addition of furan-2-ylmethanamine (175 mg, 1.8 mmol). The reaction mixture was then stirred at room temperature for 3 h. After that the reaction mixture was concentrated and the residue was purified by silica gel column chromatography (eluted with 50-100% EtOAc/Hexane) to afford the title compound E 28-7 (274 mg, 0.93 mmol) in 52% yield. LC-MS: [M+H]+=294.12.

Synthesis of N-(furan-2-ylmethyl)-8-phenylimidazo[1,5-c]pyrimidin-5-amine (Cpd. No. 126)

To a solution of 8-bromo-N-(furan-2-ylmethyl)imidazo[1,5-c]pyrimidin-5-amine (160 mg, 0.55 mmol) in mixed solvent (dioxane/water=10 ml:2.5 ml) were added potassium carbonate (227 mg, 1.64 mmol), phenylboronic acid (168 mg, 0.82 mmol), and Pd(PPh$_3$)$_4$ (63 mg, 0.055 mmol). The resulting mixture was stirred under N$_2$ at 90° C. for overnight. The mixture was then cooled to room temperature, and solvent was removed in vacuo. The residue was purified with silica gel chromatography (eluted with 0-10% MeOH/DCM) to Cpd. No. 126 (159 mg, 0.34 mmol) in 80% yield. LC-MS: [M+H]+=291.11; $^1$H NMR (400 MHz, CDCl$_3$) δ 10.13 (s, 1H), 7.66 (s, 1H), 7.61 (d, J=1.0 Hz, 1H), 7.57-7.51 (m, 4H), 7.51-7.45 (m, 1H), 7.37 (dd, J=1.8, 0.8 Hz, 1H), 6.41 (dd, J=3.2, 0.8 Hz, 1H), 6.34 (dd, J=3.2, 1.8 Hz, 1H), 4.89 (s, 2H).

Example 14

Synthesis of N-((5-fluoro-2,3-dihydrobenzofuran-4-yl)methyl)-1-(methylsulfonyl)-8-phenylimidazo[1,5-c]pyrimidin-5-amine (Cpd. No. 99), N-((5-fluoro-2,3-dihydrobenzofuran-4-yl)methyl)-8-phenyl-1-(trifluoromethyl)imidazo[1,5-c]pyrimidin-5-amine (Cpd. No. 143) and (5-(((5-fluoro-2,3-dihydrobenzofuran-4-yl)methyl)amino)-8-phenylimidazo[1,5-c]pyrimidin-1-yl)dimethylphosphine oxide (Cpd. No. 144)

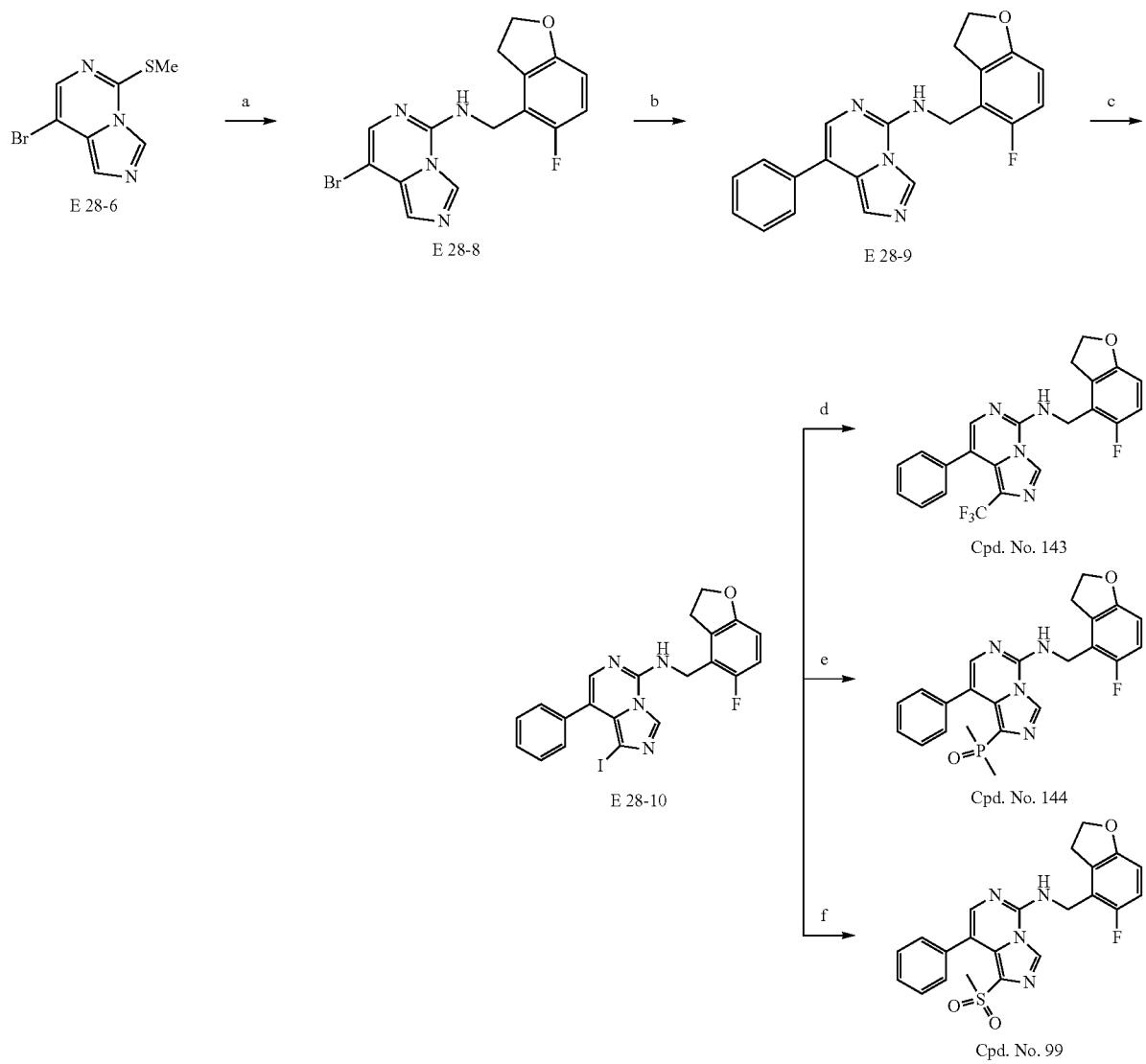

(a) (5-fluoro-2,3-dihydrobenzofuran-4-yl)methanamine, 40° C., 24 h, 60%; (b) phenylboronic acid, Pd(PPh₃)₄, K₂CO₃, dioxane-H₂O, 90° C. overnight, 88%; (c) NIS, DMF, 0° C., 70%; (d) methyl 2,2-difluoro-2-(fluorosulfonyl)acetate, CuI, PdCl₂(dppf)Cl₂, DMF, 90° C. 42%; (e) dimethylphosphine oxide, Pd(dba)₃, xantphos, Et₃N, dioxane, 40%; (f) MeSO₂Na, CuI, DMSO, 50%

Synthesis of 8-bromo-N-((5-fluoro-2,3-dihydrobenzofuran-4-yl)methyl)imidazo[1,5-c]pyrimidin-5-amine (E 28-8)

A mixture of 8-bromo-5-(methylthio)imidazo[1,5-c]pyrimidine (E 28-6, 1.0 g, 4.1 mmol) and (5-fluoro-2,3-dihydrobenzofuran-4-yl)methanamine (1.41 g, 8.2 mmol) was heated at 40° C. and stirred for 24 h. After cooling to room temperature, the crude mixture was purified by reverse phase combi flash (eluted with 0-70% acetonitrile/H₂O) to afford the title compound (E 28-8) as a yellow solid in 60% yield. LC-MS: [M+H]+=363.01; ¹H NMR (400 MHz, methanol-d₄) δ 8.58 (s, 1H), 7.38 (s, 1H), 7.32 (s, 1H), 6.91-6.80 (m, 1H), 6.65 (dd, J=8.7, 3.9 Hz, 1H), 4.74 (s, 2H), 4.62-4.52 (m, 2H), 3.37 (s, 2H).

Synthesis of N-((5-fluoro-2,3-dihydrobenzofuran-4-yl)methyl)-8-phenylimidazo[1,5-c]pyrimidin-5-amine (E 28-9)

To a solution of 8-bromo-N-((5-fluoro-2,3-dihydrobenzofuran-4-yl)methyl)imidazo[1,5-c]pyrimidin-5-amine (200 mg, 0.55 mmol) in mixed solvent (dioxane:water=10 ml:2.5 ml) were added potassium carbonate (227 mg, 1.64 mmol), phenylboronic acid (168 mg, 0.82 mmol), and Pd(PPh$_3$)$_4$ (63 mg, 0.055 mmol). The resulting mixture was stirred under N$_2$ at 90° C. for overnight. The mixture was then cooled to room temperature, and solvent was removed in vacuo. The residue was purified with silica gel chromatography eluted with 0-10% MeOH/DCM to afford title compound E 28-9 (174 mg, 0.34 mmol) in 88% yield. LC-MS: [M+H]+=361.13.

Synthesis of N-((5-fluoro-2,3-dihydrobenzofuran-4-yl)methyl)-1-iodo-8-phenylimidazo[1,5-c]pyrimidin-5-amine (E 28-10)

To a solution of N-((5-fluoro-2,3-dihydrobenzofuran-4-yl)methyl)-8-phenylimidazo[1,5-c]pyrimidin-5-amine (500 mg, 1.38 mmol) in DMF (10 ml) at 0° C. was added NIS (278 mg, 1.24 mmol), and stirred at room temperature for 15 mins. The mixture was extracted with DCM (4×50 ml), washed with brine (30 ml), dried (Na$_2$SO$_4$) and filtered. The filtrate was concentrated, and the residue was purified by column chromatography (silica gel, eluted with 20-50% EtOAc/Hexane) to afford the title compound (E 28-10) as a yellow solid (610 mg, 1.26 mmol, 70%). LC-MS: [M+H]+=487.03

Synthesis of N-((5-fluoro-2,3-dihydrobenzofuran-4-yl)methyl)-8-phenyl-1-(trifluoromethyl)imidazo[1,5-c]pyrimidin-5-amine (Cpd. No. 143)

A solution of N-((5-fluoro-2,3-dihydrobenzofuran-4-yl)methyl)-1-iodo-8-phenylimidazo[1,5-c]pyrimidin-5-amine (50 mg, 0.1 mmol) in DMF (5 ml) was added to a mixture of copper (I) iodide (190 mg, 1.0 mmol), methyl 2,2-difluoro-2-(fluorosulfonyl)acetate (192 mg, 1.0 mmol), and PdCl$_2$(dppf)Cl$_2$ (7 mg, 0.01 mmol). The reaction was stirred at 90° C. for overnight, and then cooled down to room temperature and quenched by pouring into water. The mixture was filtered and the filtrate was extracted with diethyl ether. The ethereal extract was concentrated, and residue was purified by HPLC to afford Cpd. No. 143 (16 mg, 0.04 mmol) in 42% yield. LC-MS: [M+H]+=429.12. $^1$H NMR (400 MHz, DMSO-d$_6$) δ 8.85 (s, 1H), 8.61 (s, 1H), 7.44-7.31 (m, 6H), 6.94 (t, J=8.8 Hz, 1H), 6.71 (dd, J=8.4, 4.0 Hz, 1H), 4.73 (d, 2H), 4.54 (t, J=8.8 Hz, 2H), 3.31 (t, J=8.8 Hz, 2H).

Synthesis of (5-(((5-fluoro-2,3-dihydrobenzofuran-4-yl)methyl)amino)-8-phenylimidazo[1,5-c]pyrimidin-1-yl)dimethylphosphine oxide (Cpd. No. 144)

To a solution of N-((5-fluoro-2,3-dihydrobenzofuran-4-yl)methyl)-1-iodo-8-phenylimidazo[1,5-c]pyrimidin-5-amine (50 mg, 0.1 mmol) in 2 ml of dioxane was added dimethylphosphine oxide (22 mg, 0.3 mmol), Pd(dba)$_3$ (9 mg, 0.01 mmol), xantphos (6 mg, 0.01 mmol), and Et$_3$N (0.2 ml). The mixture was purged with argon, and heated at 100° C. for overnight. The mixture was concentrated, and residue was purified by HPLC to afford Cpd. No. 144 (17 mg, 0.04 mmol) in 40% yield. LC-MS: [M+H]+=437.14. $^1$H NMR (400 MHz, DMSO-d$_6$) δ 8.85 (s, 1H), 8.52 (s, 1H), 7.58-7.56 (m, 2H), 7.42-7.41 (m, 2H), 7.29 (s, 1H), 6.94 (t, J=9.2 Hz, 1H), 6.70 (dd, J=8.4, 4.0 Hz, 1H), 4.73 (d, J=4.0 Hz, 2H), 4.54 (t, J=8.8 Hz, 2H), 3.31 (t, J=8.8 Hz, 2H), 1.21 (s, 1H), 1.18 (s, 1H).

N-((5-fluoro-2,3-dihydrobenzofuran-4-yl)methyl)-1-(methylsulfonyl)-8-phenylimidazo[1,5-c]pyrimidin-5-amine (Cpd. No. 99)

A mixture of compound E 28-10 (50 mg, 0.1 mmol), MeSO$_2$Na (30 mg. 0.3 mmol), and CuI (57 mg. 0.3 mmol) in DMSO (2 ml) was bubbled with N$_2$ for 5 mins, and the sealed tube was then heated in a microwave reactor at 120° C. for 20 min, and then at 100° C. for 3 h. The mixture was concentrated, and residue was purified by HPLC to afford Cpd. No. 99 (21 mg, 0.05 mmol) in 50% yield. $^1$H NMR (400 MHz, CDCl$_3$) δ 8.60 (s, 1H), 7.55-7.35 (m, 6H), 6.77 (dd, J=10.1, 8.7 Hz, 1H), 6.61 (dd, J=8.7, 3.9 Hz, 1H), 4.82 (s, 2H), 4.61 (t, J=8.7 Hz, 2H), 3.40 (t, J=8.7 Hz, 2H), 2.86 (s, 3H). LC-MS: [M+H]+=439.12.

Example 15

Synthesis of ethyl 5-((furan-2-ylmethyl)amino)-8-phenylimidazo[1,5-c]pyrimidine-1-carboxylate (Cpd. No. 127) and 5-((furan-2-ylmethyl)amino)-N-methyl-8-phenylimidazo[1,5-c]pyrimidine-1-carboxamide (Cpd. No. 128)

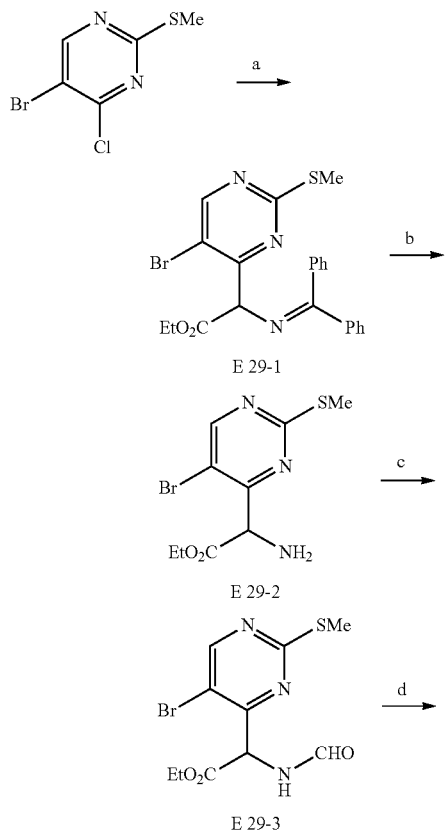

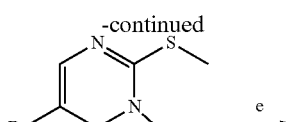

E 29-4

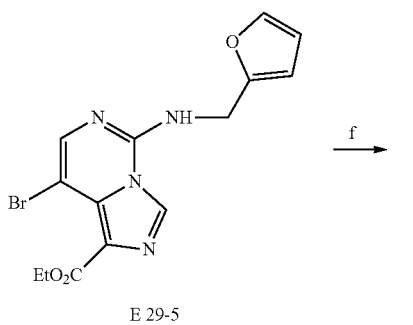

E 29-5

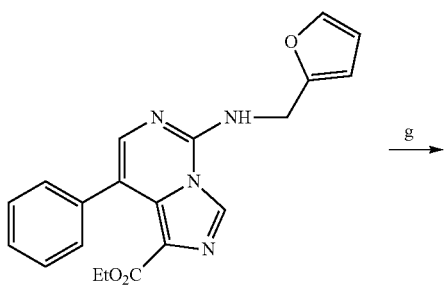

Cpd. No. 127

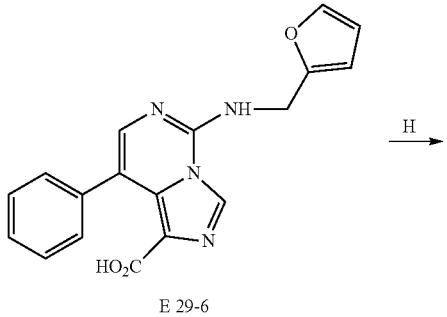

E 29-6

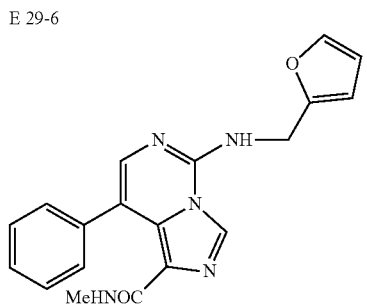

Cpd. No. 128

(a) ethyl 2-(diphenylmethyleneamino)acetate, NaH, rt, 2 h; (b) 3N HCl in THF, rt, 1 h, 70%; (c) HCO₂H, Ac₂O, rt, 2 h; (d) POCl₃, Dioxane, reflux, 4 h, 70%; (e) (i) mCPBA, DCM, (ii) furan-2-ylmethanamine, rt, 3 h, 55%; (f) phenylboronic acid, Pd(PPh₃)₄, K₂CO₃, dioxane-H₂O, 90° C. overnight, 90%; (g) Li(OH)₂,THF—H₂O, 90%; (h) NHMe·HCl, DIPEA, HATU, 90%

Synthesis of ethyl 2-(5-bromo-2-(methylthio)pyrimidin-4-yl)-2-((diphenylmethylene)amino)acetate (E 29-1)

A solution of ethyl 2-(diphenylmethyleneamino)acetate (18.4 g, 69 mmol) in DMSO (50 ml) was added dropwise at 0° C. to a suspension of NaH (60%) (5.0 g, 125.5 mmol) in 70 ml of anhydrous DMSO. The reaction mixture turned orange immediately. After 5 min later 5-bromo-4-chloro-2-(methylthio)pyrimidine (15 g, 62.7 mmol) in 50 mL DMSO was added dropwise. The mixture was then stirred at room temperature for 2 h. After that the reaction mixture was quenched by careful addition of aq. NH₄Cl solution. The mixture was extracted then with ethyl acetate, washed with brine, dried and concentrated and used as crude for the next step. LC-MS: [M+H]+=470.01.

Synthesis of ethyl 2-amino-2-(5-bromo-2-(methylthio)pyrimidin-4-yl)acetate (E 29-2)

To a solution of compound E 29-1 (crude, 5.0 g, 10.6 mmol) in THF (50 ml) was added 10 ml 3 N HCl in water at 0° C. The mixture was stirred at room temperature for 1 h and the reaction mixture was then concentrated followed by basification to pH 8~9 with aq. Na₂CO₃ solution. The mixture was extracted with DCM, washed with brine. Concentration under reduced pressure followed by purification by flash chromatography (0-100% EtOAc/Hexane) gives the desired compound 8-2 (2.26 g) in 70% overall yield. LC-MS: [M+H]+=305.95.

Synthesis of ethyl 2-(5-bromo-2-(methylthio)pyrimidin-4-yl)-2-formamidoacetate (E 29-3)

A mixture of HCO₂H (4 ml) and Ac₂O (4 ml) was heated at 50° C. for 1 h. The reaction mixture was cooled to room temperature and added to a solution of ethyl 2-amino-2-(methylthio) pyrimidin-4-yl) acetate (2.0 g, 6.55 mmol) in 20 ml of DCM. The mixture was stirred at room temperature for 2 h. After completion of the reaction, the mixture was concentrated. The mixture was extracted with DCM (2×50 ml), washed successively with water (20 ml), and brine (10 ml). The organic phase was dried (Na₂SO₄), filtered and concentrated to afford the crude title compound E 29-3 as an oil, which was used for the next steps without further purification. LC-MS: [M+H]+=334.05.

Synthesis of ethyl 8-bromo-5-(methylthio)imidazo[1,5-c]pyrimidine-1-carboxylate (E 29-4)

To a solution of compound E 29-3 (2.0 g, crude) in dioxane (20 ml) was added POCl₃ (1.5 ml) dropwise. The reaction mixture was heated under reflux for 4 h. The mixture was cooled to room temperature and concentrated. Ice cooled water (50 ml) was added, and the mixture was adjusted to pH 8 with satd. aq. NaHCO₃. The mixture was extracted with DCM (2×50 ml), washed with brine (10 ml), dried (Na₂SO₄) and filtered. The filtrate was concentrated, and the residue was purified by silica gel column chromatography (eluted with 50-100% EtOAc/Hexane) to afford the title compound E 29-4 as a white solid (1.42 g, 4.59 mmol) in 70% overall yield in two steps. LC-MS: [M+H]+=315.70.

¹H NMR (400 MHz, DMSO d₆): 8.67 (s, 1H), 7.99 (s, 1H), 4.33 (q, 2H), 2.76 (s, 3H), 1.34 (t, 3H).

Synthesis of ethyl 8-bromo-5-((furan-2-ylmethyl)amino)imidazo[1,5-c]pyrimidine-1-carboxylate (E 29-5)

To a solution of compound E 29-4 (567 mg, 1.8 mmol, 1.0 eq.) in DCM (18 ml) was added m-CPBA (464 mg, 2.7 mmol, <77%, 1.5 eq.) at 0° C. After 45 min, Et₃N (1 ml, 7.6 mmol, 4 eq.) was added at 0° C. and stirred for 2 min, followed by addition of furan-2-ylmethanamine (175 mg, 1.8 mmol). The reaction mixture was then stirred at room temperature for 3 h. After that the reaction mixture was concentrated and the residue was purified by silica gel column chromatography (eluted with 50-100% EtOAc/Hexane) to afford the title compound E 29-5 (361 mg, 0.99 mmol) in 55% yield. LC-MS: [M+H]+=365.017. ¹H NMR (400 MHz, MeOD) δ 8.58 (s, 1H), 7.70 (d, J=2.1 Hz, 1H), 7.47 (dd, J=1.8, 1.0 Hz, 1H), 6.39 (dt, J=3.2, 1.1 Hz, 2H), 4.78 (t, J=0.9 Hz, 2H), 4.46-4.36 (m, 2H), 1.43-1.35 (m, 3H).

Synthesis of ethyl 5-((furan-2-ylmethyl)amino)-8-phenylimidazo[1,5-c]pyrimidine-1-carboxylate (Cpd. No. 127)

To a solution of ethyl 8-bromo-5-((furan-2-ylmethyl)amino)imidazo[1,5-c]pyrimidine-1-carboxylate (200 mg, 0.55 mmol) in mixed solvent (dioxane:water=10 ml:2.5 ml) were added potassium carbonate (227 mg, 1.64 mmol), phenylboronic acid (168 mg, 0.82 mmol), and Pd(PPh₃)₄ (63 mg, 0.055 mmol). The resulting mixture was stirred under N₂ at 90° C. for overnight. The mixture was then cooled to room temperature, and solvent was removed in vacuo. The residue was purified with silica gel chromatography eluted with 0-10% MeOH/DCM to afford Cpd. No. 127 (159 mg, 0.34 mmol) in 80% yield. LC-MS: [M+H]+=363.017. ¹H NMR (400 MHz, CDCl₃) δ 8.81 (s, 1H), 7.49 (d, J=1.0 Hz, 1H), 7.41 (d, J=6.7 Hz, 3H), 7.34 (dq, J=3.3, 1.7 Hz, 3H), 6.35 (d, J=3.2 Hz, 1H), 6.30 (dt, J=3.1, 1.4 Hz, 1H), 4.87 (s, 2H), 3.87 (q, J=7.1 Hz, 2H), 0.88 (t, J=7.1 Hz, 3H).

Synthesis of 5-((furan-2-ylmethyl)amino)-8-phenylimidazo[1,5-c]pyrimidine-1-carboxylic acid (E 29-6)

A mixture of E 29 (40 mg, 0.11 mmol, 1 equiv.) and LiOH (26 mg, 1.10 mmol, 10 eq.) in THF (4 ml) and water (2.0 ml) was heated at 70° C. for overnight. 3 N aq. HCl was added drop wise at 0° C. until pH 2-3. The mixture was concentrated, and residue was purified by HPLC to afford the title compound E 29-6 (33 mg, 0.099 mmol) in 90% yield. LC-MS: [M+H]+=335.10.

Synthesis of N-(furan-2-ylmethyl)-1-(((methylamino)oxy)carbonyl)-8-phenylimidazo[1,5-c]pyrimidin-5-amine (Cpd. No. 128)

To a solution of compound E 29-6 (10 mg, 0.029 mmol) in DMF (1 ml) was added methylamine hydrochloride (4 mg, 0.058 mmol) and diisopropylethylamine (50 µL, 0.29 mmol). The reaction mixture was stirred at room temperature for 10 minutes and then HATU (11 mg, 0.029 mmol) was added. The reaction mixture was allowed to warm to room temperature, stirred at room temperature overnight. The mixture was concentrated, and residue was purified by HPLC to afford Cpd. No. 128 (9 mg, 0.026 mmol) in 90% yield. LC-MS: [M+H]+=348.13. ¹H NMR (400 MHz, CDCl₃) δ 9.22 (s, 1H), 7.55-7.43 (m, 3H), 7.38-7.30 (m, 3H), 6.40 (s, 1H), 6.36 (s, 1H), 6.31 (brs, 1H), 4.86 (s, 2H), 2.54 (s, 3H).

Example 16

Synthesis of –(3,6-dihydro-2H-pyran-4-yl)-N-((5-fluoro-2,3-dihydrobenzofuran-4-yl)methyl)-1-(methylsulfonyl)imidazo[1,5-c]pyrimidin-5-amine (Cpd. No. 146) 8-(3,6-dihydro-2H-pyran-4-yl)-N-((5-fluoro-2,3-dihydrobenzofuran-4-yl)methyl)-1-(methylsulfonyl)imidazo[1,5-c]pyrimidin-5-amine (Cpd. No. 169)

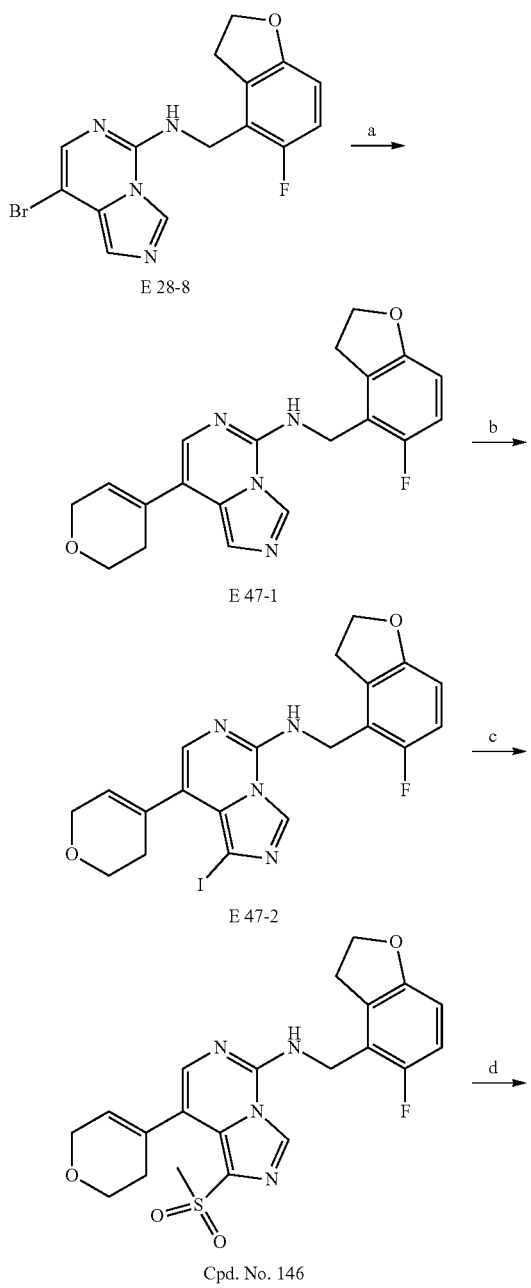

E 28-8

E 47-1

E 47-2

Cpd. No. 146

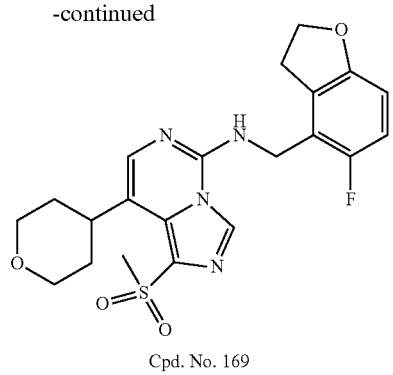

Cpd. No. 169

Synthesis of 8-(3,6-dihydro-2H-pyran-4-yl)-N-((5-fluoro-2,3-dihydrobenzofuran-4-yl)methyl)imidazo[1,5-c]pyrimidin-5-amine (E 47-1)

To a solution (dioxane:water=10 ml:2.5 ml) compound E 28-8 (250 mg, 0.69 mmol), 3,6-dihydro-2H-pyran-4-boronic acid pinacol ester (290 mg, 1.38 mmol), Pd(PPh$_3$)$_4$ (80 mg, 0.069 mmol), 285 mg of Na$_2$CO$_3$ was added. The resulting mixture was stirred under N$_2$ at 90° C. for overnight. The mixture was then cooled to room temperature, and solvent was removed in vacuo and purified by column chromatography (DCM:MeOH=20:1) to obtain the title compound E 47-1 as white solid in 80% yield. LC-MS: [1M+H]+=366.14.

Synthesis of 8-(3,6-dihydro-2H-pyran-4-yl)-N-((5-fluoro-2,3-dihydrobenzofuran-4-yl)methyl)-1-iodo-imidazo[1,5-c]pyrimidin-5-amine (E 47-2)

To a solution of compound E 47-1 (160 mg, 0.43 mmol) in DMF (4 ml) at 0° C. was added NIS (82 mg, 0.4 mmol), and stirred at room temperature for 15 mins. The mixture was extracted with DCM (4×50 ml), washed with brine (30 ml), dried (Na$_2$SO$_4$) and filtered. The filtrate was concentrated, and the residue was purified by column chromatography (silica gel, eluted with 20-50% EtOAc/Hexane) to afford the title compound (E 47-2) in 60% yield (127 mg, 0.25 mmol, 70%). LC-MS: [M+H]+=493.04

Synthesis of 8-(3,6-dihydro-2H-pyran-4-yl)-N-((5-fluoro-2,3-dihydrobenzofuran-4-yl)methyl)-1-(methylsulfonyl)imidazo[1,5-c]pyrimidin-5-amine (Cpd. No. 146)

A mixture of compound E 47-2 (50 mg, 0.1 mmol), MeSO$_2$Na (30 mg. 0.3 mmol), and CuI (57 mg. 0.3 mmol) in DMSO (2 ml) was bubbled with N$_2$ for 5 mins, and the sealed tube was then heated in a microwave reactor at 120° C. for 20 min, and then at 100° C. for 3 h. The mixture was concentrated, and residue was purified by HPLC to afford Cpd. No. 146 (21 mg, 0.05 mmol) in 50% yield. LC-MS: [M+H]+=445.12.

Synthesis of N-((5-fluoro-2,3-dihydrobenzofuran-4-yl)methyl)-1-(methylsulfonyl)-8-(tetrahydro-2H-pyran-4-yl)imidazo[1,5-c]pyrimidin-5-amine (Cpd. No. 169)

To a solution of compound Cpd. No. 146 (10 mg) in MeOH (1 ml) was added Pd/C (2 mg, 20% wt). The reaction mixture was degassed with H$_2$ and stirred under H$_2$ atmosphere at room temperature for 6 h. The mixture was then filtered through celite, and washed with MeOH. Concentration under reduced pressure followed by purification by HPLC to afford Cpd. No. 169 (10 mg) in quantitative yield. LC-MS: [M+H]+=447.14.

Example 17

Synthesis of (S)-4-cyclopropyl-12-(((5-fluoro-2,3-dihydrobenzofuran-4-yl)methyl)amino)-4,5,5a,6,8,9-hexahydro-3H-7-oxa-2,4,9a,11,12a-pentaazabenzo[4,5]cycloocta[1,2,3-cd]inden-3-one (Cpd. No. 147)

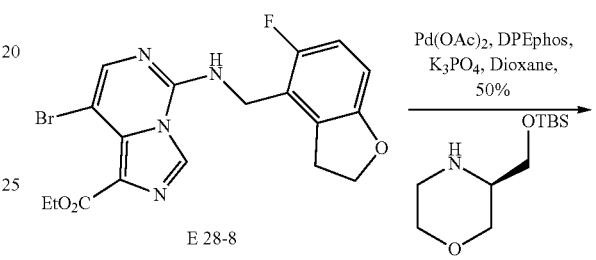

E 28-8

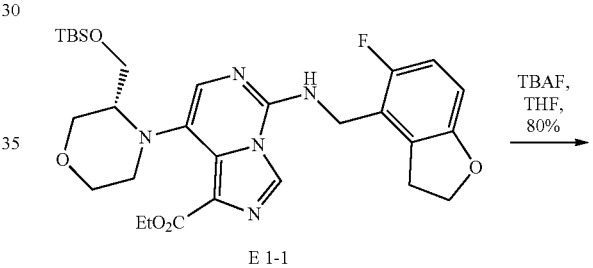

E 1-1

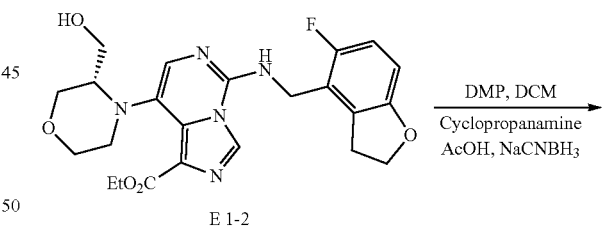

E 1-2

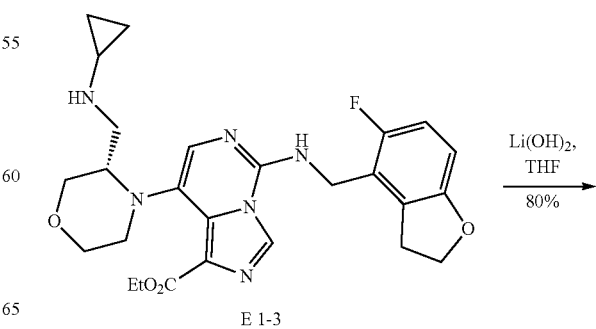

E 1-3

-continued

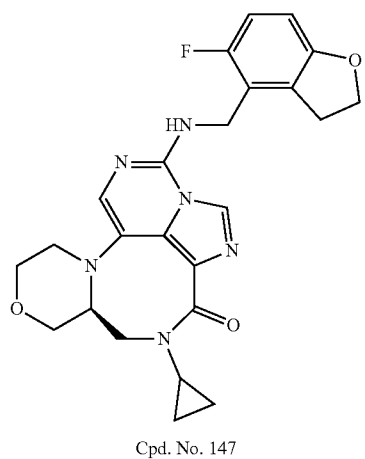

Cpd. No. 147

General Procedure for Palladium Catalyzed Amination Reaction:

An oven-dried 40 ml vial was charged with the E 28-8 (1.0 mmol), Pd(OAc)$_2$ (5 mol %), DPEphos (10 mol %), K$_3$PO$_4$ (2.5 mmol), and the requisite amine (1.5 mmol). An upside down septum was placed over the vial and a needle was inserted (as a vent) while the resulting mixture was purged with argon for several minutes through a second needle. Dioxane (4 ml) was introduced through the septum. The resulting suspension was purged with argon for 3 min. Vial was then quickly capped, then heated to 85° C. for overnight. The mixture was absorbed onto silica gel and purified by flash chromatography (0-10% MeOH in DCM) gives the desired compound E 1-1 (293 mg) in 50% yield. LC-MS: [M+H]+=586.27.

TBAF (1M in THF, 1 ml, 1.0 mmol) was added dropwise to a solution of the E 1-1 (293 mg, 0.5 mmol) in THF (2 ml) at room temperature. The reaction mixture was stirred for 2 hours, after which time it was concentrated in vacuo. Purification by flash chromatography (0-10% MeOH in DCM) gives the desired compound E 99-2 (188 mg, 0.4 mmol) in 80% yield. LC-MS: [M+H]+=472.19.

Compound (E 1-2) was dissolved in dry DCM (~0.2 M), then to this solution 1.5 eq. of DMP was added and the reaction mixture is allowed to stirring for 1 h, monitored via TLC. Upon completion quenched with saturated NH$_4$Cl solution, then extracted with DCM and washed with water and brine. The organic layers were collected and combined, washed with brine, dried over anhydrous Na$_2$SO$_4$, and concentrated in vacuo. Purification was performed on silica gel normal phase column chromatography with increasing amounts of ethyl acetate in hexanes to afford the desired aldehyde.

To the obtained aldehyde was added methanol (~0.2 M), followed by 2.2 eq. of cyclopropanamine, 2 eq. of Na(CN)BH$_3$ and 2 eq. of acetic acid under ice bath. Then remove the ice bath and reaction mixture is allowed to stir for 3 h, monitored via TLC. Upon completion, the reaction mixture was concentrated, and residue was purified by HPLC to afford compound E 1-3 (100 mg, 0.2 mmol) in 50% yield over two steps. LC-MS: [M+H]+=511.23.

A mixture of compound E 1-3 (1 eq.) and LiOH (10 eq.) in THF (10 ml/mmol) and water (5 ml/mmol) was heated at 70° C. for overnight. The mixture was concentrated, and residue was then purified by prep-HPLC to afford Cpd. No. 147 in 80% yield.

Example 18

Synthesis of (5-(((5-fluoro-2,3-dihydrobenzofuran-4-yl)methyl)amino)-8-phenylimidazo[1,5-c]pyrimidin-1-yl)(imino)(methyl)-16-sulfanone (Cpd. No. 178); (5-(((5-fluoro-2,3-dihydrobenzofuran-4-yl)methyl)amino)-8-phenylimidazo[1,5-c]pyrimidin-1-yl)(methyl)(methylimino)-16-sulfanone (Cpd. No. 182); 1-(5-(((5-fluoro-2,3-dihydrobenzofuran-4-yl)methyl)amino)-8-phenylimidazo[1,5-c]pyrimidin-1-yl)-3,4,5,6-tetrahydro-1,2-thiazine 1-oxide (Cpd. No. 186)

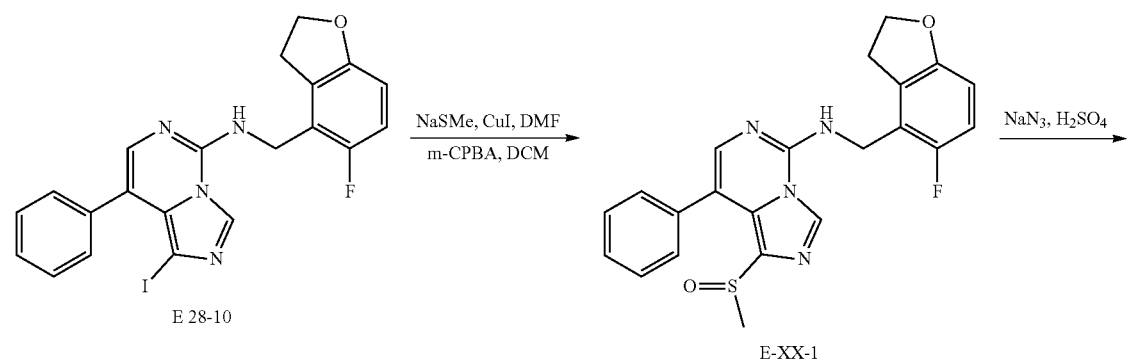

-continued
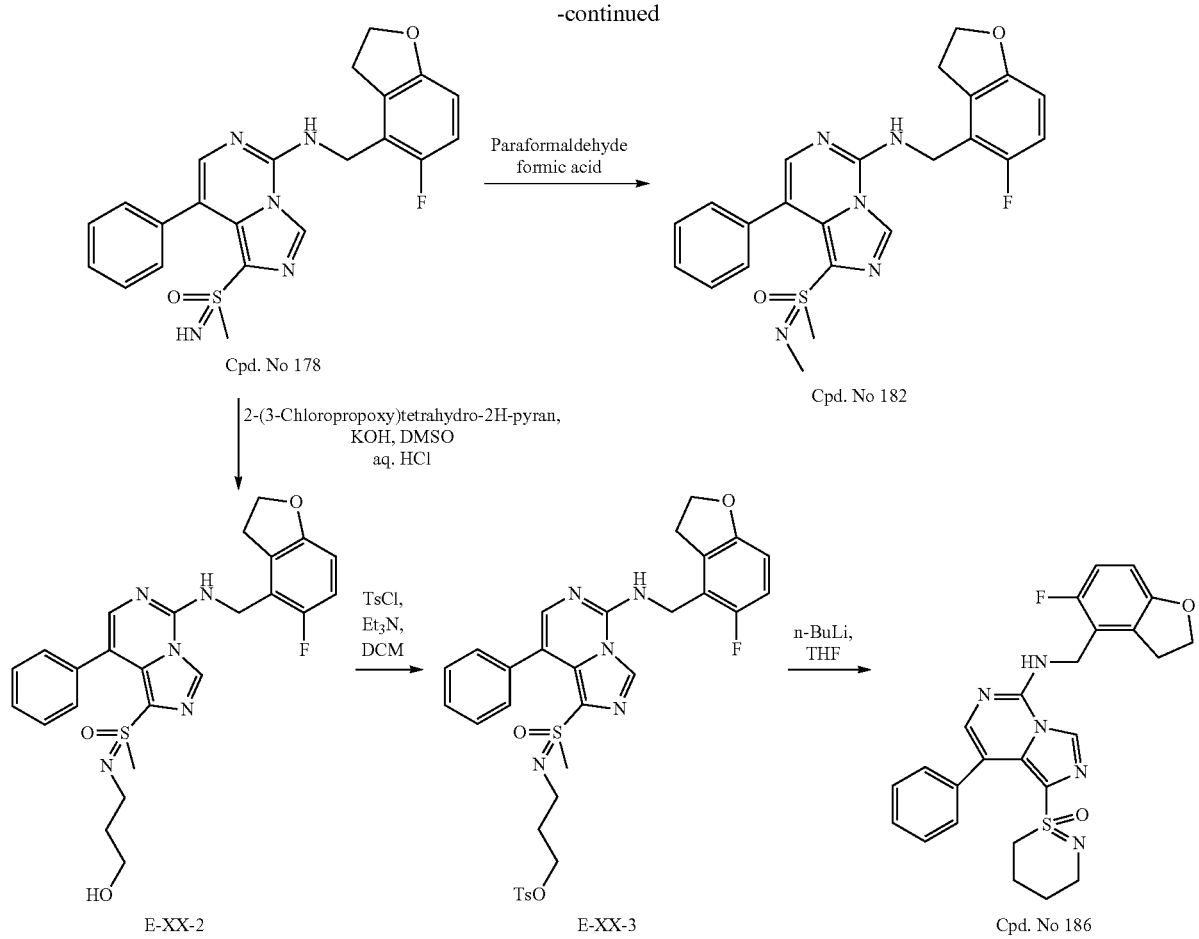
Example 19
Synthesis of 6-Fluorochroman-5-yl)methanamine (A.2)
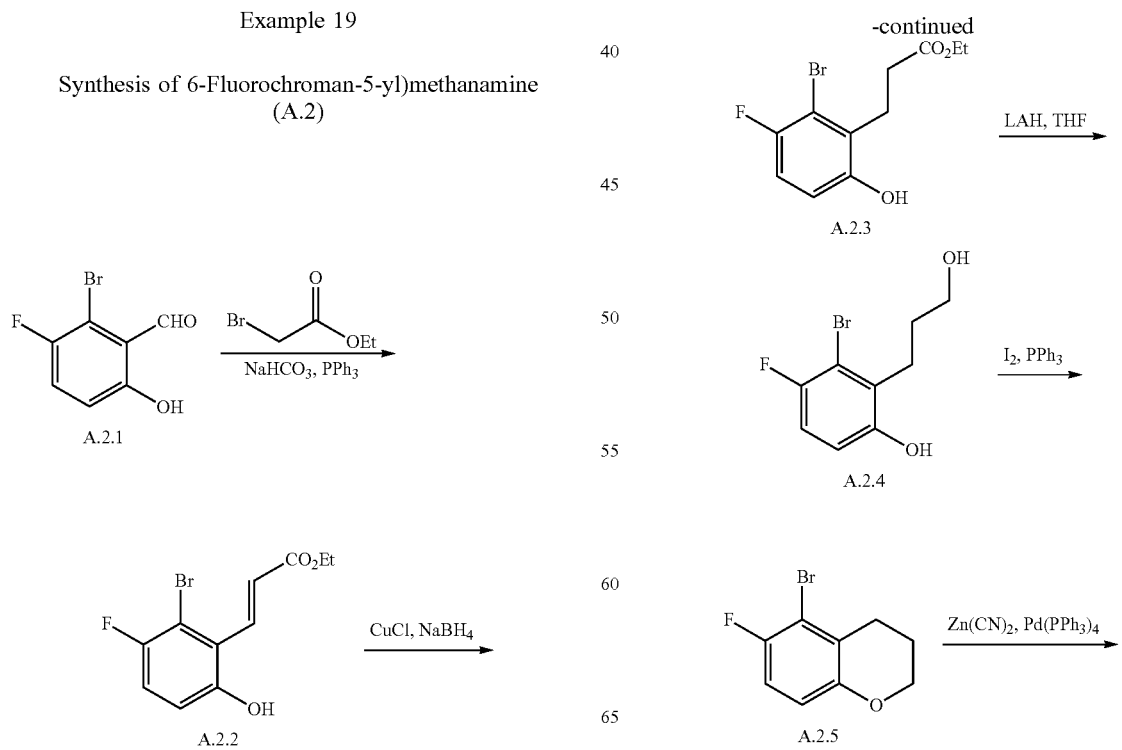

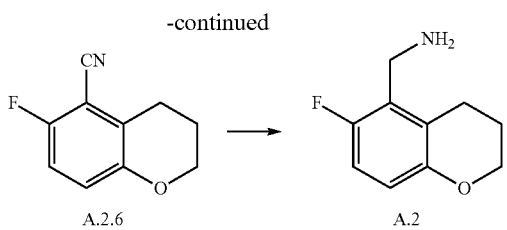

To a round bottomed flask was added 2-bromo-3-fluoro-6-hydroxybenzaldehyde (1 eq.), ethyl bromoacetate (1.5 eq.), saturated aqueous $NaHCO_3$ (2 ml/mmol), and $PPh_3$ (1.4 eq.) in (1 ml/mmol) EtOAc. The reaction mixture was stirred vigorously at room temperature overnight. After consumption of the starting materials, the reaction was diluted with water and extracted with EtOAc (×3). The organic phases were combined, washed with brine, dried over $MgSO_4$, and concentrated under vacuum. The residue was purified on silica gel (0-10% EtOAc/Hexane) to give A.2.2 in 80% yield. LC-MS: [M+H]+=288.97

A mixture of A.2.2 (1 eq.), CuCl (1.1 eq.) in 20 ml MeOH was cooled to 0° C. under argon atmosphere. $NaBH_4$ (2 eq.) was added in portions. After consumption of the starting materials, the reaction was diluted with water and extracted with EtOAc (×3). The organic phases were combined, washed with brine, dried over $MgSO_4$, concentrated under vacuum, and purified by flash chromatography to give A.2.3 in 70% yield as a white solid. LC-MS: [M+H]+=290.97

To a solution of A.2.3 (1 eq.) in THF (4 ml) was added LAH (1 eq.) at 0° C. under argon atmosphere. The reaction mixture was stirred at room temperature for 2 h, then quenched with water and diluted with EtOAc. The reaction mixture was then filtered and purified by flash chromatography to give A.2.4 in 65% yield. LC-MS: [M+H]+=248.98.

Iodine (1.30 eq.) was added to a solution of triphenylphosphine (1.30 eq.) and imidazole (1.35 eq.) in 25 ml dichloromethane at 0° C. The reaction mixture was stirred for 15 min before adding compound A.2.4 in dichloromethane. The yellow precipitate disappeared during a slightly exothermic reaction and imidazole hydrochloride fell out as a white flocculent precipitate. The mixture was stirred at room temperature for at least 1 hr, and 3 ml of methanol was added. Stirring was continued for 30 min. The solution was diluted with dichloromethane and washed with water a brine. The organic phase was dried over $MgSO_4$ and evaporated on a rotary evaporator. The crude material was used in the next step without further purification.

To a solution of 3-bromo-4-fluoro-2-(3-iodopropyl)phenol (1 eq.) in acetone was added $K_2CO_3$ (2 eq.). The mixture was stirred at 50° C. for 12 h. The reaction mixture was filtered and concentrated in vacuo. The reaction mixture was then purified by flash chromatography to give A.2.5 in 65% yield overall yield. LC-MS: [M+H]+=230.97.

To a solution of A.2.5 (1 eq.) and $Zn(CN)_2$ (2 eq.) in DMF (2 ml/mmol) was added $Pd(PPh_3)_4$ (0.1 eq.). The reaction mixture was degassed with $N_2$ and stirred under $N_2$ atmosphere for 24 h at 100° C. After cooling to room temperature, the reaction was diluted with water and extracted with ethyl acetate (2×100 ml). The combined organic phase was washed with brine and dried over anhydrous $Na_2SO_4$. The residue was purified on silica gel (0-20% EtOAc/Hexane) to separate give A.2.6 in 60% yield. LC-MS: [M+H]+=178.05.

A solution of A.2.6 (1 eq.) in THF was treated with LAH (2 eq., 1M solution of LAH in THF) at 0° C. The temperature was increased to 50° C. and the reaction mixture was stirred overnight. After cooling to room temperature, the reaction was slowly quenched with satd. $Na_2SO_4$ at 0° C. It was the filtered and washed several times with ethyl acetate. Purification by flash chromatography (0-10% MeOH in DCM containing 1% trimethylamine) gives the desired compound A.2 in 70% yield. LC-MS: [M+H]+=182.09.

Example 20

Synthesis of 5-Fluoro-2,3-dihydrobenzofuran-4-yl)methan-d2-amine (A.3)

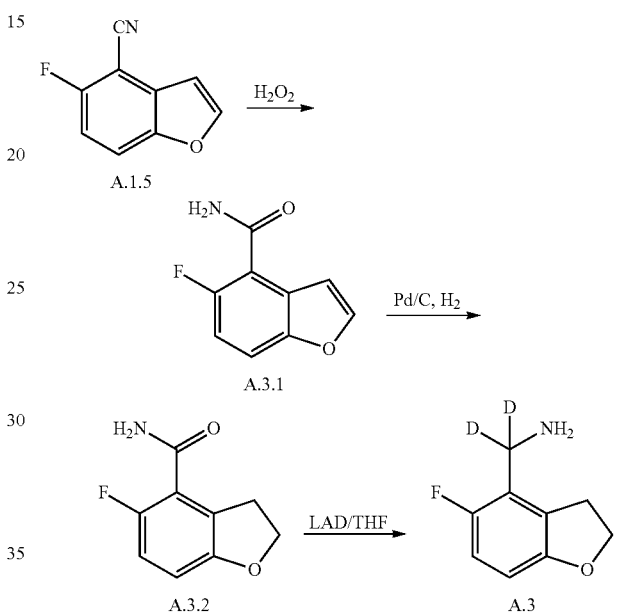

To a solution of 5-fluorobenzofuran-4-carbonitrile (2.00 gm, 12.4 mmol, 1.0 eq.) in DMSO (20 ml) was added $H_2O_2$ (7.04 gm, 62.1 mmol, 6 ml) and $K_2CO_3$ (1.72 gm, 12.4 mmol, 1.0 eq.) at 0° C. The reaction mixture was stirred at room temperature for 1 h, poured into ice-water (5.0 ml). and stirred for 10 min. The reaction mixture was filtered and concentrated under vacuum to give 5-fluorobenzofuran-4-carboxamide (A.3.1, 1.80 gm, 10.1 mmol, 80%) yield as a white solid. LC-MS: [M+H]+=180.03.

To a solution of compound A.3.1 (1 gm, 5.05 mmol) in MeOH (50 ml) was added Pd/C (100 mg, 10% wt). The reaction mixture was degassed with $H_2$ and stirred under $H_2$ atmosphere for 6 h at 40° C. The mixture was then filtered through celite and washed with MeOH. Concentration under reduced pressure followed by purification by flash chromatography (0-10% MeOH in DCM containing 1% trimethylamine) fave the desired compound intermediate A.3.2 (859 mg, 4.71 mmol) in 85% yield. LC-MS: [M+H]+=182.05.

Compound A.3.2 (2.3 gm, 12.63 mmol) in 15 ml of THF was treated with LAD (36 ml 1M solution of LAD in THF) at 0° C. After that temperature was increased to 50° C. and the reaction mixture was stirred overnight. After cooling to room temperature, the reaction was slowly quenched with satd. $Na_2SO_4$ at 0° C. It was then filtered and washed several times with ethyl acetate. Purification by flash chromatography (0-10% MeOH in DCM containing 1% trimethylamine) gave the desired compound A.3 (1.50 gm, 8.84 mmol) in 70% yield. LC-MS: [M+H]+=170.08. $^1$H NMR (400 MHz, CDCl$_3$): 6.82-6.76 (m, 1H), 6.59 (dd, J=8.8, 4.0 Hz, 1H), 4.59 (t, J=8.8 Hz, 2H), 3.27 (t, J=8.8 Hz, 2H).

Example 21

Synthesis of N-((3-Bromo-6-methylpyridin-2-yl)methyl)-2,2,2-trifluoroethan-1-amine (A.4)

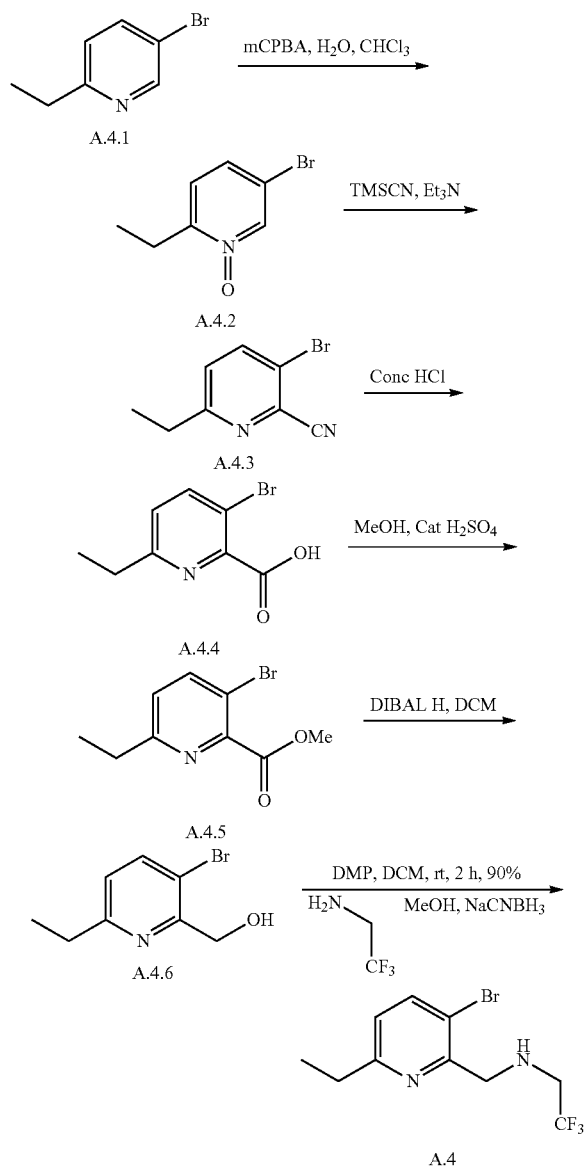

To a solution of 5-bromo-2-ethylpyridine (A.4.1, 554 mg, 3.0 mmol, 1.0 eq.) in CHCl$_3$ (8 ml, 0.38 M) was added 77% mCPBA (5.44 gm, 12.0 mmol, 4.0 eq.), and the reaction mixture was stirred at room temperature overnight. After cooling to room temperature, Ca(OH)$_2$ (1.5 gm, 15.9 mmol, 5.3 eq.) was added, and the resulting precipitate was stirred for 30 minutes. The precipitate was filtered and washed with 3:1 CHCl$_3$/methanol. The filtrate was then concentrated in vacuo, and the residue was purified by column chromatography using 0-100% ethyl acetate in hexane to give the desired N-oxide (A.4.2, 482 mg, 2.4 mmol). LC-MS: [M+H]+=201.97.

To a solution of 5-bromo-2-ethylpyridine 1-oxide (A.4.2, 400 mg, 2.0 mmol) in acetonitrile (10 ml, 0.2 M) was added trimethylsilyl cyanide (TMSCN) (793 mg, 8.0 mmol, 4.0 eq.) and triethylamine (606 mg, 6.0 mmol, 3.0 eq.). The reaction was heated at 100° C. overnight. After cooling to room temperature, the solvent was concentrated under vacuum, and the residue was purified by column chromatography using 0-50% ethyl acetate in hexane to give 3-bromo-6-ethyl picolinonitrile (A.4.3, 293 mg, 1.4 mmol, 70% yield). LC-MS: [M+H]+=210.97.

3-Bromo-6-ethyl picolinonitrile (A.4.3, 1 gm, 4.78 mmol) was dissolved in conc. hydrochloric acid (20 ml) and stirred at 110° C. for 2 days. The reaction mixture was allowed to cool to room temperature and was evaporated to dryness. The crude product was used in the next step without further purification. LC-MS: [M+H]+=229.97.

3-Bromo-6-ethylpicolinic acid (A.4.4, 5.33 gm, 23.3 mmol) was dissolved in MeOH (50 ml) and cooled to 0° C., and 1.0 ml of H$_2$SO$_4$ was added dropwise. The reaction was then stirred at 90° C. for overnight. The mixture was cooled to room temperature and concentrated under vacuum. The residue was dissolved in ethyl acetate (50 ml) and washed with water and satd. aq. NaCl (2×100 ml), dried over anhydrous Na$_2$SO$_4$ and concentrated under vacuum. The residue was purified by silica gel column chromatography and eluted with EtOAc/Hexane (1:5) to yield methyl 3-bromo-6-ethylpicolinate (A.4.5, 5.09 gm, 20.97 mmol) in 90% yield. LC-MS [M+H]+=243.98

To a solution of methyl 3-bromo-6-ethylpicolinate (A.4.5, 522 mg, 2.15 mmol) in DCM (15 ml) at −60° C. was added DIBAL-H (4.6 ml, 4.60 mmol, 1 M in cyclohexane) dropwise. The reaction mixture was maintained at −60° C. to −15° C. for 30 min, then was allowed to warm to room temperature and stirred for another 12 h. The reaction mixture was cooled to 0° C. and quenched with satd. aq. NH$_4$Cl (50 ml). The resulting mixture was extracted with DCM (3×100 ml), washed with brine (50 ml), dried (Na$_2$SO$_4$), filtered, and concentrated. The residue was purified by silica gel column chromatography and eluted with EtOAc/Hexane (1:3) to afford A.4.6 as a colorless liquid (1.36 mmol, 293 mg, 60%). LC-MS [M+H]+=215.99

An aliquot of (3-bromo-6-ethylpyridin-2-yl)methanol (A.4.6) was dissolved in dry DCM (~0.2 M), then to this solution 1.5 eq. of DMP was added, and the reaction mixture was allowed to stir for 1 h. Upon completion (as monitored by TLC), the reaction was quenched with saturated NH$_4$Cl solution, then extracted with DCM and washed with water and brine. The organic layers were collected and combined, washed with brine, dried over anhydrous Na$_2$SO$_4$, and concentrated in vacuo. Purification was performed on silica gel normal phase column chromatography with increasing amounts of ethyl acetate in hexanes to afford the desired aldehyde.

To the aldehyde was added methanol (~0.2 M), followed by 2.2 eq. of 2,2,2-trifluoroethan-1-amine, 2 eq. of Na(CN)BH$_3$ and 2 eq. of acetic acid at 0° C. The ice bath was removed and the reaction mixture was allowed to stir for 3 h. Upon completion (as monitored by TLC), the reaction mixture was concentrated, and residue was purified by HPLC to afford A.4 in 70% yield. LC-MS: [M+H]+=297.01.

Example 22

Synthesis of (5-Bromo-2-(difluoromethyl)pyridine-4-yl)methanol (A.6)

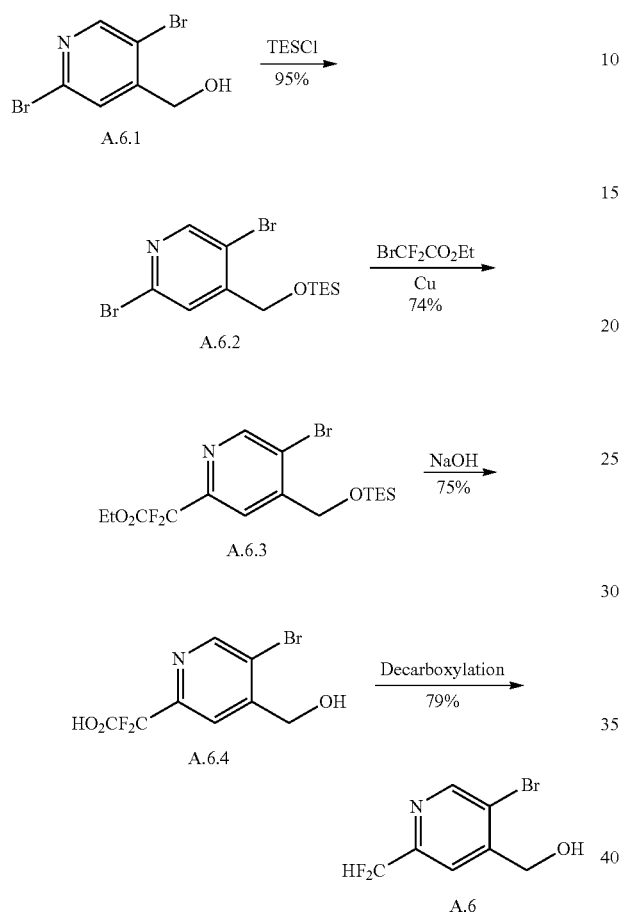

In a 100 mL flask with a stir bar, copper powder (380 mg, 5.94 mmol, 2.25 eq.) and (2,5-dibromopyridin-4-yl) triethylsilylmethanol (A.6.2, 1.006 g, 2.64 mmol, 1.0 eq.) were added. The flask was evacuated and backfilled with $N_2$ atmosphere. Anhydrous DMSO (6 ml) and ethyl bromodifluoroacetate (589 mg, 2.90 mmol, 1.1 eq.) were added. Stirring was started and the mixture was heated to oil bath 70° C. After 2 hours, an aliquot of the reaction mixture was diluted into 1.27 M $KH_2PO_4$ aq. solution and EtOAc was added. After ultrasonification the top organic layer was separated. $KH_2PO_4$ (1.27 M, 40 ml) was added slowly keeping internal temperature below 10° C. The mixture was stirred at 0° C. for 0.5 h before filtering through Celite. The cake was washed with EtOAc (40 ml). The bi-phasic filtrate layers were separated. The organic layer was washed with water and brine, then was concentrated and purified by flash chromatography to give compound A.6.3 (825 mg, 74% yield).

To a solution of A.6.3 (825 mg, 1.95 mmol) in methanol (2 ml) cooled to 0° C. was added 6 N NaOH (1 mL, 3.0 eq.) dropwise. The resulting clear solution was stirred at 0° C. After 3 hours, UPLC-MS analysis indicated clean conversion to the desired product. The reaction mixture was acidified with 4 N HCl (1.5 mL) to pH 3 at 0° C. HPLC purification gave A.6.4 (412 mg, 1.46 mmol, 75%) as a pale yellow solid.

In a 50 ml flask with a stir bar, the difluoroacid A.6.4 (412 mg, 1.46 mmol) was added. The flask was evacuated and backfilled with $N_2$ atmosphere. NMP (2 ml) and 85% $H_3PO_4$ (169 mg, 1.46 mmol) were added. The resulting mixture was heated to oil bath 145° C. and stirred. After 2 h, UPLC-MS indicated complete conversion to the desired product. The mixture was cooled to 15° C. and quenched with 1 N NaOH. The mixture was purified by HPLC to yield gave the desired compound A.6 (274 mg, 1.15 mmol, 79%) as a pale yellow solid.

Example 23

Synthesis of 12-(((5-fluoro-2,3-dihydrobenzofuran-4-yl)methyl)amino)-7-(methyl-d3)-4-(2,2,2-trifluoroethyl)-4,5-dihydro-3H-2,4,6,11,12a-pentaazabenzo[4,5]cycloocta[1,2,3-cd]inden-3-one (Cpd. No. E 19)

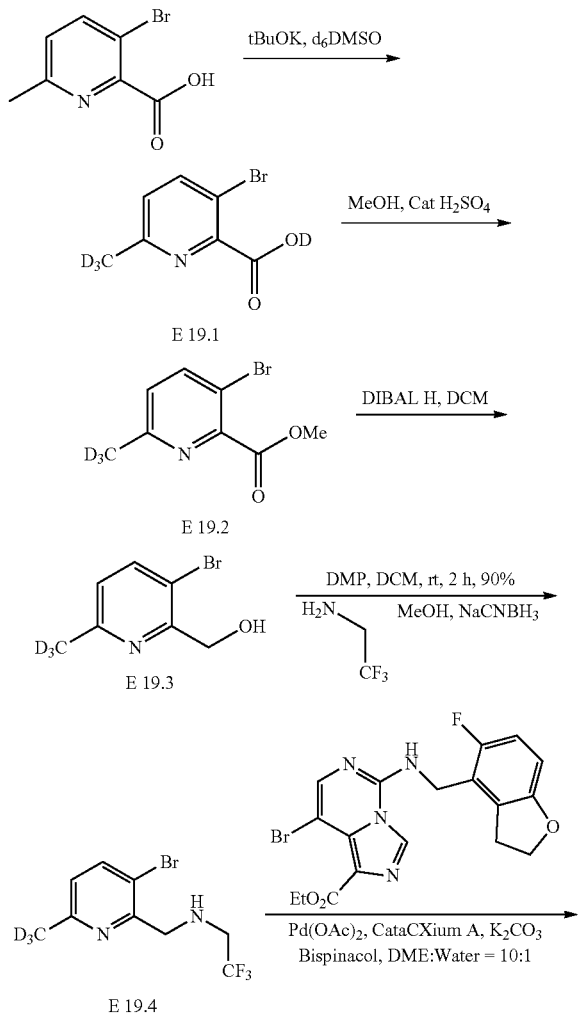

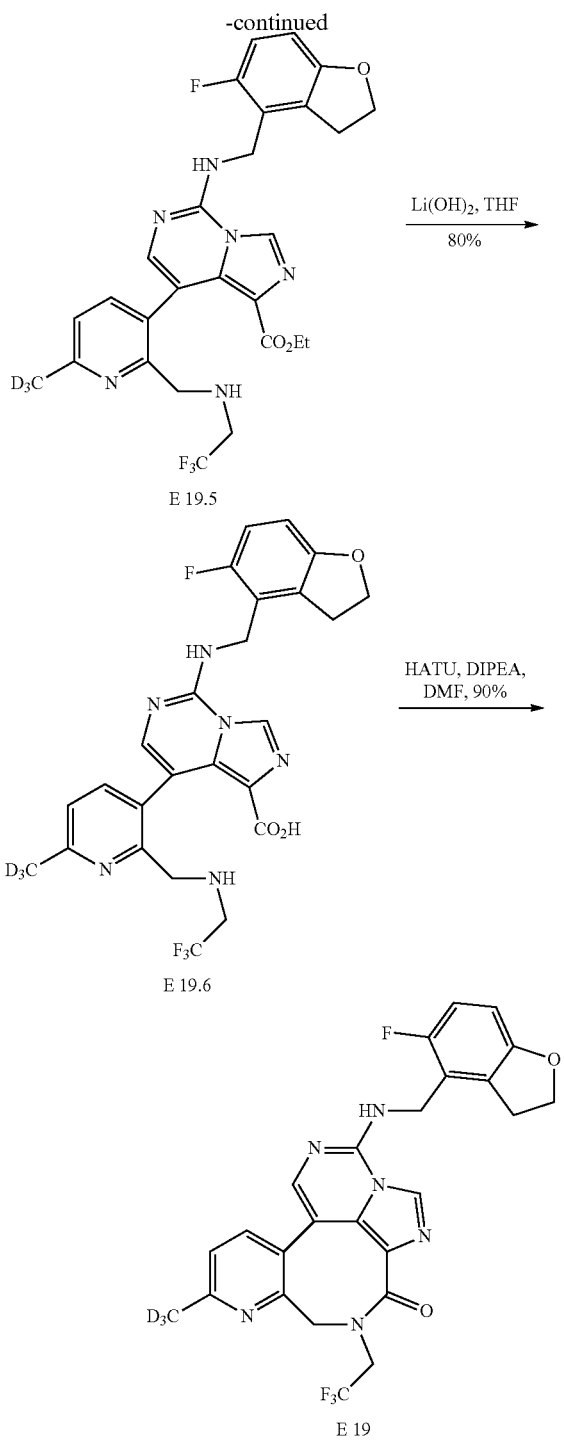

eq.) in MeOH (50 ml). The resulting solution was stirred for 14 h while the temperature was maintained at reflux in an oil bath. The mixture was cooled to room temperature and concentrated under vacuum. The residue was dissolved in ethyl acetate (50 ml) and washed with water and satd. aq. NaCl (2×100 ml), dried over anhydrous $Na_2SO_4$ and concentrated under vacuum. The residue was purified by silica gel column chromatography and eluted with EtOAc/Hexane (1:5) to yield methyl 3-bromo-6-methylpicolinate (E 19.2, 4.7 gm) in 90% yield. LC-MS [M+H]+=232.99.

To a solution of methyl 3-bromo-6-(methyl-d3)picolinate (E 19.2, 520 mg, 2.15 mmol) in DCM (15 ml) at −60° C., DIBAL-H (4.6 ml, 4.60 mmol, 1 M in cyclohexane) was added dropwise. The reaction mixture was maintained at −60° C. to −15° C. for 30 min, allowed to rise to room temperature, and stirred for another 12 h. The reaction mixture was cooled to 0° C. again, and was quenched with satd. aq. $NH_4Cl$ (50 ml). The resulting mixture was extracted with DCM (3×100 ml), washed with brine (50 ml), dried ($Na_2SO_4$), filtered, and concentrated. The residue was purified by silica gel column chromatography and eluted with EtOAc/Hexane (1:3) to afford E 19.3 as a colorless liquid (1.36 mmol, 273 mg, 60%). LC-MS [M+H]+=204.99.

An aliquot of (3-bromo-6-(methyl-d3)pyridin-2-yl) methanol (E 19.3) was dissolved in dry DCM (~0.2 M). To this solution, 1.5 eq. of DMP was added, and the reaction mixture was allowed to stir for 1 h (monitored by TLC). Upon completion, the reaction was quenched with saturated $NH_4Cl$ solution, extracted with DCM, and washed with water and brine. The organic layers were collected and combined, washed with brine, dried over anhydrous $Na_2SO_4$, and concentrated in vacuo. Purification was performed on silica gel normal phase column chromatography with increasing amounts of ethyl acetate in hexanes to afford the desired aldehyde.

To the aldehyde was added methanol (~0.2 M), followed by 2.2 eq. of c trifluoroethan-1-amine, 2 eq. of $Na(CN)BH_3$, and 2 eq. of acetic acid at 0° C. The ice bath was removed and reaction mixture was allowed to stir for 3 h. Upon completion, the reaction mixture was concentrated and residue was purified by HPLC to afford E 19.4 in 70% yield. LC-MS: [M+H]+=286.01.

Palladium (II) acetate (0.1 eq.) and cataCXium A (0.2 eq.) were mixed together in DME (0.5 ml, degassed), and resulting solution was added via pipette to a mixture of ethyl 8-bromo-5-(((5-fluoro-2,3-dihydrobenzofuran-4-yl)methyl)amino) imidazo[1,5-c]pyrimidine-1-carboxylate (1 eq.), the secondary amine E 19.4 (2 eq.), bis-pinacolatediboron (2.0 eq.) and $K_2CO_3$ (4.0 eq.) in DME/$H_2O$ (10:1, 10 ml, degassed) at 70° C. The reaction mixture was the stirred for 12 h. The reaction mixture was concentrated and extracted with ethyl acetate (2×50 ml), washed with water and brine, and dried over $Na_2SO_4$. The mixture was concentrated and residue was purified by HPLC to afford E19.5 in 50% yield. LC-MS: [M+H]+=561.21.

A mixture of compound E 19.5 (1 eq.) and LiOH (10 eq.) in THF (10 ml/mmol) and water (5 ml/mmol) was heated at 70° C. overnight. The mixture was concentrated, and residue was then purified by prep-HPLC to afford E 19.6 in 80% yield. LC-MS: [M+H]+=534.18.

To a mixture of compound E 19.6 (1 eq.) and HATU (2 eq.) in DMF (5 ml/mmol) was added DIPEA (5 eq.). The reaction mixture was allowed to stir overnight, and concentrated. The residue was purified by prep-HPLC to afford Cpd. No. E 19 in 90% yields. LC-MS: [M+H]+=516.17. $^1$H NMR (400 MHz, DMSO-d$^6$) δ 8.85 (s, 1H), 8.71 (t, J=5.1 Hz, 1H), 7.93 (d, J=8.0 Hz, 1H), 7.54 (s, 1H), 7.44 (d, J=8.1

To a flame-dried flask was added 3-bromo-6-methylpicolinic acid (1 gm, 4.67 mmol), followed by potassium tert-butoxide (1.0 gm, 9.34 mmol) and DMSO-d6 (12 mL), and the mixture was stirred at room temperature under argon for 12 h. The reaction mixture was diluted with cold water (10 mL) and extracted with ethyl acetate (20 mL). The ethyl acetate layer was washed with brine (20 mL×2), dried over anhydrous sodium sulfate, and concentrated to yield crude product (E 19.1) in 90% yield. LC-MS: [M+H]+=215.95.

$H_2SO_4$ (1.0 eq.) was added to a solution of 3-bromo-6-(methyl-d3)picolinic acid-d (E 19.1, 5.0 gm, 23.3 mmol, 1.0

Hz, 1H), 6.96 (dd, J=10.3, 8.6 Hz, 1H), 6.71 (dd, J=8.7, 3.9 Hz, 1H), 5.46 (d, J=15.0 Hz, 1H), 4.75 (d, J=4.5 Hz, 2H), 4.71-4.61 (m, 1H), 4.56 (t, J=8.8 Hz, 2H), 4.19 (d, J=15.0 Hz, 1H), 4.08 (dq, J=15.2, 9.0 Hz, 1H), 3.34 (t, J=8.7 Hz, 2H), 2.57 (s, 3H).
Example 24
Synthesis of 8-(6-cyclopropylpyridin-3-yl)-5-(((5-fluoro-2,3-dihydrobenzofuran-4-yl)methyl)amino)-1-(methylsulfonyl)imidazo[1,5-a]pyridine-6-carbonitrile (Cpd. No. E 26)
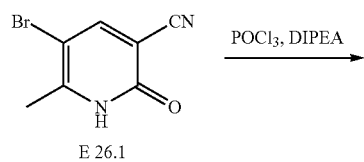
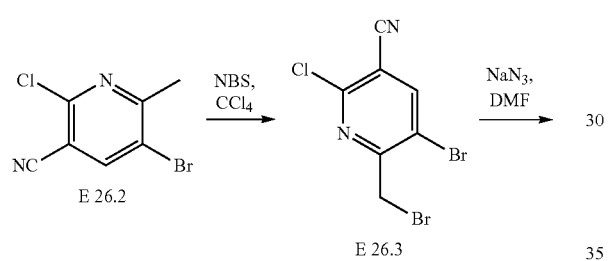
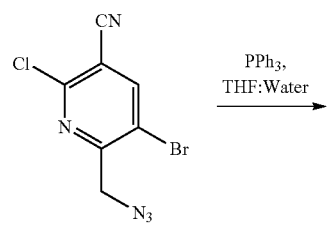
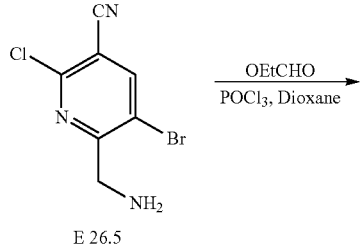
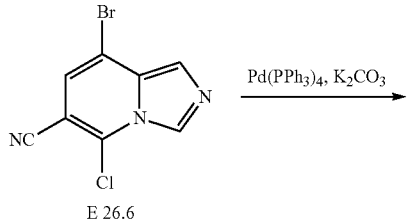
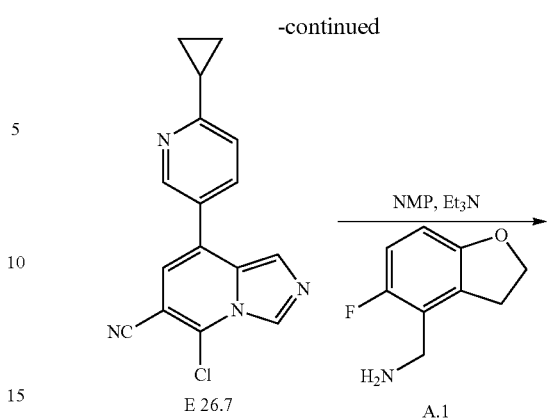
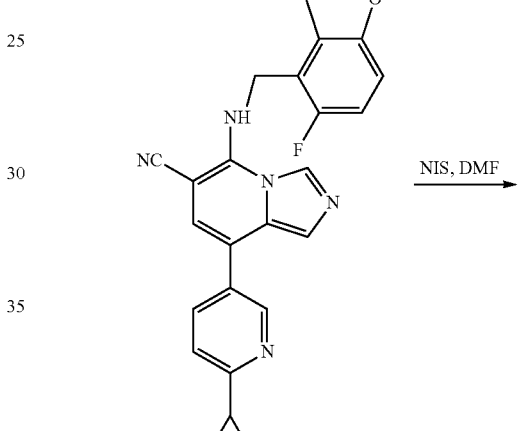
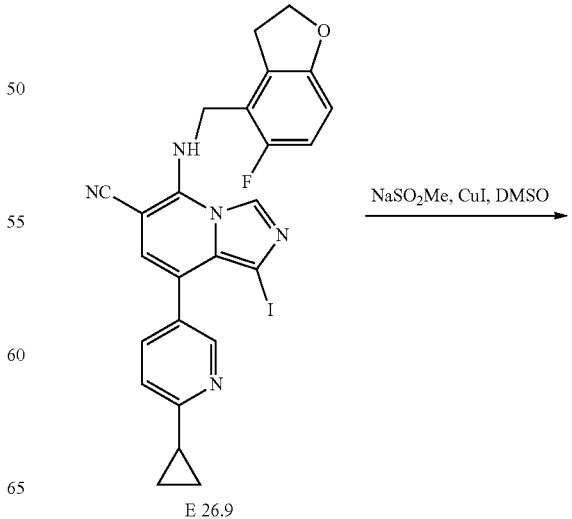

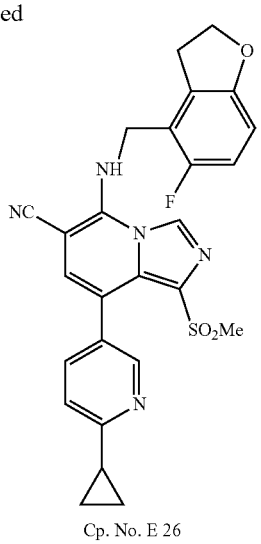

Cp. No. E 26

A mixture of 5-bromo-6-methyl-2-oxo-1,2-dihydropyridine-3-carbonitrile (E 26.1, 120 mg, 0.55 mmol) and DIPEA (145 mg, 1.14 mmol) in POCl₃ (2.0 ml) was refluxed for 3 h. The resulting brown mixture was evaporated in vacuo, and 10 ml of EtOAc and 5 ml aq. NaHCO₃ solution were added. The mixture was extracted with EtOAc (20 ml×3), dried (Na₂SO₄), filtered and concentrated. The residue was purified by flash chromatography (silica gel, eluted with PE/EA=1/3~1/5) to afford E 26.2 (70 mg, 54% yield) as a white solid. LC-MS: [M+H]+=230.1.

To a solution of 5-bromo-2-chloro-6-methylnicotinonitrile (4.46 gm, 19.4 mmol) and NBS (3.79 mg, 21.3 mmol) in CCl₄ (80 ml) was added BPO (469 mg, 1.94 mmol) at room temperature. The resulting mixture was degassed and stirred at 80° C. for 4 h under nitrogen. The reaction mixture was filtered, washed with brine, dried (Na₂SO₄), filtered, and concentrated. The crude product was purified by column chromatography on silica gel (eluted with 10% EtOAc/petroleum ether) to give 5-bromo-6-(bromomethyl)-2-chloronicotinonitrile (E 26.3) as yellow oil (4.1 gm, 74%). LC-MS: [M+H]+=308.83.

To a solution of 5-bromo-6-(bromomethyl)-2-chloronicotinonitrile (4.46 gm, 14.5 mmol) in DMF (50 ml) was added NaN₃ (1.89 gm, 29 mmol). The mixture was stirred room temperature for 2 h, poured into water, and extracted with EtOAc (30 ml×3). The combined organic layers were washed with brine, dried (Na₂SO₄), filtered, and concentrated to give 6-(azidomethyl)-5-bromo-2-chloronicotinonitrile as yellow oil (3.4 gm, yield: 87%), which was used directly to next step. LC-MS: [M+H]+=271.92.

To a solution of 6-(azidomethyl)-5-bromo-2-chloronicotinonitrile (3.4 gm, 12.6 mmol) in THF (50 ml) and H₂O (5 ml) was added PPh₃ (4.93 gm, 18.9 mmol). The resulting mixture was heated at 50° C. for 1 h, and concentrated. The residue was dissolved in 50 ml of aq. HCl and washed with DCM (20 ml×2). The aqueous layer was basified by addition of aq. NaOH to pH~8 and extracted with EtOAc (30 ml×3). The organic layers were dried (Na₂SO₄), filtered, and concentrated to give the desired product 6-(aminomethyl)-5-bromo-2-chloronicotinonitrile as yellow oil (2.28 gm, 74%). LC-MS: [M+H]+=245.93.

To a solution of 6-(aminomethyl)-5-bromo-2-chloronicotinonitrile (2.25 gm, 9.3 mmol) in ethyl formate (40 ml) was added NaHCO₃(391 mg, 4.6 mmol). The mixture was stirred at room temperature for 24 h and filtered. The filtrate was concentrated to give desired compound as brown oil (2.1 gm, 90%), which was used directly to next step. LC-MS: [M+H]+=273.93.

To a solution of the crude compound in dioxane (30 ml) was added POCl₃ (2.59 gm, 16.8 mmol). The mixture was refluxed for 3 h. The reaction mixture was quenched with aq. NaHCO₃ and extracted with EtOAc (30×3). The organic layers were washed with brine, dried (Na₂SO₄), filtered, and concentrated. The crude was purified by column chromatography on silica gel (10% EtOAc/petroleum) to give the desired compound (E.26.6) as light yellow solid (1.6 gm, 83%). LC-MS: [M+H]+=255.91.

A mixture of 8-bromo-5-chloroimidazo[1,5-a]pyridine-6-carbonitrile (60 mg, 0.24 mmol), (6-cyclopropylpyridin-3-yl)boronic acid (50 mg, 0.31 mmol), Pd(dppf)Cl₂ (12 mg, 0.015 mmol) and Na₂CO₃ (81 mg, 0.77 mmol) in H₂O (0.5 ml) and dioxane (1.5 ml) was heated at 110° C. for 1 h under N₂. The reaction mixture was filtered and concentrated. The crude product was purified by prep-HPLC to give 5-chloro-8-(6-cyclopropylpyridin-3-yl)imidazo[1,5-a]pyridine-6-carbonitrile (E 26.7, 74 mg, yield: 90%). LC-MS: [M+H]+=295.06.

To a solution of 5-chloro-8-(6-cyclopropylpyridin-3-yl) imidazo[1,5-a]pyridine-6-carbonitrile (38 mg, 0.13 mmol) and (5-fluoro-2,3-dihydrobenzofuran-4-yl)methanamine (65 mg, 0.39 mmol) in NMP (0.5 ml) was added triethylamine (39 mg, 0.39 mmol) at room temperature The resulting solution was heated at 130° C. by microwave for 1 h. The reaction mixture was concentrated and purified by column chromatography on silica gel (eluted with PE:EA=1:1) to give a yellow solid (E 26.8, 66%). LC-MS (m/z): 426.16 [M+H]+.

To a solution of N-((5-fluoro-2,3-dihydrobenzofuran-4-yl)methyl)-8-phenylimidazo[1,5-c]pyrimidin-5-amine (500 mg, 1.38 mmol) in DMF (10 ml) at 0° C. was added NIS (278 mg, 1.24 mmol). The mixture was stirred at room temperature for 15 min. The reaction mixture was extracted with DCM (4×50 ml), washed with brine (30 ml), dried (Na₂SO₄), and filtered. The filtrate was concentrated, and the residue was purified by column chromatography (silica gel, eluted with 20-50% EtOAc/Hexane) to afford the title compound (E 26.9) as a yellow solid (610 mg, 1.26 mmol, 70%). LC-MS: [M+H]+=552.06.

A mixture of compound E 26.9 (50 mg, 0.09 mmol), MeSO₂Na (30 mg. 0.3 mmol), and CuI (57 mg, 0.3 mmol) in DMSO (2 ml) was bubbled with N₂ for 5 mins, and the sealed tube was then heated in a microwave reactor at 120° C. for 20 min, and then at 100° C. for 3 h. The mixture was concentrated, and residue was purified by HPLC to afford Cpd. No. E 26 (25 mg, 0.05 mmol) in 50% yield. LC-MS: [M+H]+=504.14.

Example 25

Synthesis of N-((5-fluoro-2,3-dihydrobenzofuran-4-yl)methyl)-5-methyl-8-(trifluoromethyl)-6H-2,3,5a,9,12,13a-hexaazabenzo[4,5]cyclopenta[7,8]cycloocta[1,2,3-cd]inden-13-amine (Cpd. No. E 10)

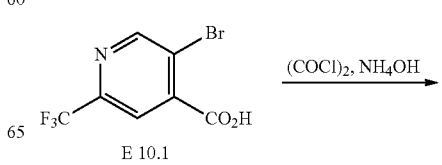

E 10.1

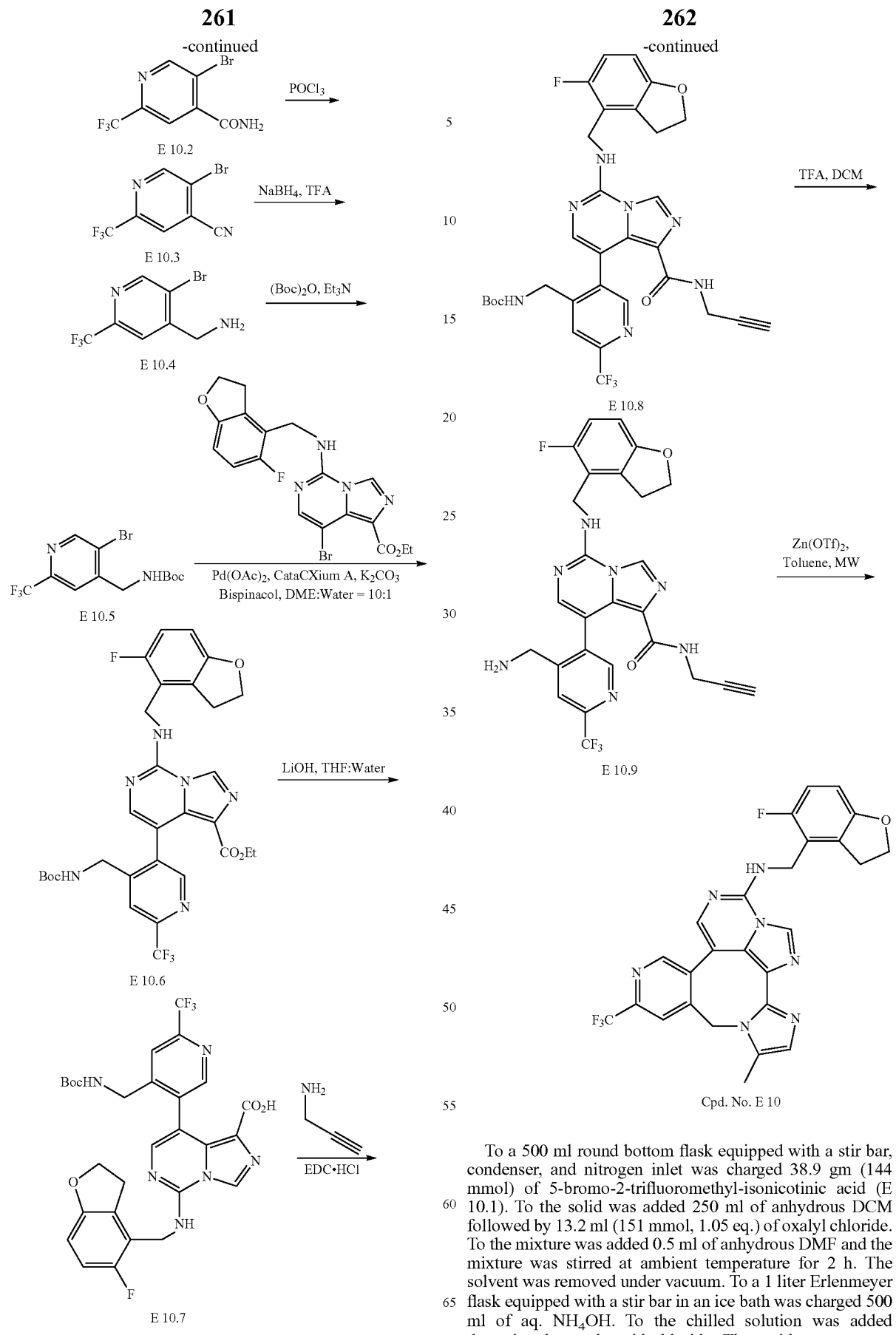

To a 500 ml round bottom flask equipped with a stir bar, condenser, and nitrogen inlet was charged 38.9 gm (144 mmol) of 5-bromo-2-trifluoromethyl-isonicotinic acid (E 10.1). To the solid was added 250 ml of anhydrous DCM followed by 13.2 ml (151 mmol, 1.05 eq.) of oxalyl chloride. To the mixture was added 0.5 ml of anhydrous DMF and the mixture was stirred at ambient temperature for 2 h. The solvent was removed under vacuum. To a 1 liter Erlenmeyer flask equipped with a stir bar in an ice bath was charged 500 ml of aq. NH$_4$OH. To the chilled solution was added dropwise the crude acid chloride. The residue was transferred with a small amount of acetonitrile. The mixture was stirred for 20 minutes following the addition. The resulting precipitate was collected by filtration and washed with water. The filter cake was dried in vacuo at 45° C. affording 5-bromo-2-trifluoromethyl-isonicotinamide (E 10.2, 118 mmol, 31.52 gm, 82% yield) as an off-white solid. LC-MS [M+H]+=269.95.

To a 100 mL round bottom equipped with a stir bar, condenser, and nitrogen inlet was charged 5.2 gm (19.3 mmol) of 5-bromo-2-trifluoromethylisonicotinamide (E 10.2). The solid was diluted with 12 ml of $POCl_3$. The mixture was heated at 70° C. for 3 h. The mixture was cooled to room temperature and poured onto ice. The mixture was neutralized with the careful addition of 50% sodium hydroxide. The resulting off-white solid was collected by filtration, washed with water and dried in vacuo at 50° C. for 18 h. This afforded 4.5 gm of 5-bromo-2-trifluoromethyl-isonicotinonitrile (E 10.3, 4.53 gm, 18.1 mmol) as an off-white solid in a 94% yield. LC-MS [M+H]+=250.95. $^1$H NMR (CDCl$_3$): δ, 9.03 (s, 1H), 7.91 (s, 1H).

NaBH$_4$ (0.66 g, 14.81 mmol) was charged to a 100 ml flask followed by anhydrous THF 20 ml. The mixture was cooled in an ice-water bath. TFA (1.5 ml) was added to THF (4 ml) at that temperature for 0.5 h. The ice-water bath was removed and the resulting mixture was stirred at room temperature for 2 h. 5-bromo-2-(trifluoromethyl)isonicotinonitrile (E 10.3, 2 gm, 8.0 mmol) was dissolved in THF (10 ml). The TFA/NaBH$_4$ mixture was again cooled in an ice-water bath and the nitrile solution was added over 0.5 h. The mixture was allowed to reach ambient temperature while stirring for 16 h. LC analysis of an aliquot revealed completion of the reaction. The mixture was cooled in an ice bath and 10 ml methanol was added slowly. Volatiles were removed under vacuum and ethyl acetate (50 ml) was added. This mixture was washed with water (10 ml). The aqueous layer was washed with ethyl acetate (10 ml) and the combined organic layers were washed with brine (10 ml), dried over Na$_2$SO$_4$, filtered, and concentrated. The residue was purified by purified by reverse phase combi flash (eluted with 1-20% acetonitrile/H$_2$O) to afford the title compound (E 10.4, 1.6 gm, 80%) as a colorless liquid. LC-MS [M+H]+ =254.96.

Compound (E 10.4, 512 mg, 2 mmol) is stirred at room temperature for 3 h with (Boc)$_2$O (0.51 gm, 2.4 mmol, 1.2 eq.) and Et$_3$N (2 eq., 4 mmol, 380 mg) in 20 ml DCM. The residue was purified by a column chromatography using 0-50% EtOAc/Hexane to give desired compound (E 10.5, 560 mg) 80% overall yield. LC-MS [M+H]+=355.16.

Palladium (II) acetate (0.1 eq.) and cataCXium A (0.2 eq.) were mixed together in DME (0.5 ml, degassed) and resulting solution was added via pipette to a mixture of ethyl 8-bromo-5-(((5-fluoro-2,3-dihydrobenzofuran-4-yl)methyl) amino) imidazo[1,5-c]pyrimidine-1-carboxylate (1 eq.), the secondary amine E 10.5 (2 eq.), bis-pinacolatediboron (2.0 eq.) and K$_2$CO$_3$ (4.0 eq.) in DME/H$_2$O (10:1, 10 ml, degassed) at 70° C. The reaction mixture was stirred for 12 h. The reaction mixture was concentrated and extracted with ethyl acetate (2×50 ml), washed with water and brine, and then dried over Na$_2$SO$_4$. The mixture was concentrated, and residue was purified by HPLC to afford E 10.6 in 50% yield. LC-MS: [M+H]+=631.22

A mixture of compound E 10.6 (1 eq.) and LiOH (10 eq.) in THF (10 ml/mmol) and water (5 ml/mmol) was heated at 70° C. for overnight. The mixture was concentrated, and residue was then purified by prep-HPLC to afford E 10.7 in 80% yield. LC-MS: [M+H]+=603.19.

In a 250 ml round bottom flask, a stirred solution of E 10.7 (3.29 gm, 5.47 mmol) and prop-2-yn-1-amine (0.601 gm, 10.94 mmol) in DMF (15 mL) was treated sequentially with EDCI·HCl (2.28 gm, 11.94 mmol), HOBt (1.61 gm, 11.93 mmol) and Et$_3$N (2.03 ml, 14.92 mmol) at room temperature under nitrogen atmosphere. The reaction mixture was stirred at room temperature for 12 h under nitrogen atmosphere. Upon completion of reaction (TLC), the reaction mixture was diluted with ice cold water. The mixture was concentrated, and residue was then purified by prep-HPLC to afford E 10.8 in 80% yield. LC-MS: [M+H]+=640.22

Compound E 10.8 was treated with 25% TFA/DCM at room temperature for 1 h, and the volatiles were removed in vacuo. The crude product was diluted with ethyl acetate, washed with satd. aq. Na$_2$CO$_3$, and brine. The organic layer was dried over Na$_2$SO$_4$ and concentrated under vacuum to provide the compound E 10.9, which was used as crude for the next step. LC-MS: [M+H]+=540.22.

In a 20 ml microwave vial, a solution of compound E 10.9 (0.22 g, 0.42 mmol) and (2-methoxyphenyl)methanamine (0.086 g, 0.63 mmol) in toluene (5 mL) was treated with Zn(OTf)$_2$ (0.009 g, 0.021 mmol) at room temperature under nitrogen atmosphere. The reaction mixture was subjected to microwave irradiation at 140° C. for 1 h. Upon completion of reaction (TLC), the reaction mixture was diluted with water and extracted with EtOAc (30 mL). The organic extract was washed with saturated NaHCO$_3$ and brine, and dried over anhydrous Na$_2$SO$_4$. The solution was concentrated under reduced pressure, and residue obtained was purified by prep-HPLC to afford Cpd. No. E 10 in 40% yields. LC-MS: [M+H]+=522.15.

Example 26

Synthesis of 12-(((5-fluoro-2,3-dihydrobenzofuran-4-yl)methyl)amino)-7-(tetrahydro-2H-pyran-4-yl)-4-(2,2,2-trifluoroethyl)-4,5-dihydro-3H-2,4,6,11,12a-pentaazabenzo[4,5]cycloocta[1,2,3-cd]inden-3-one (Cpd. No. E 45)

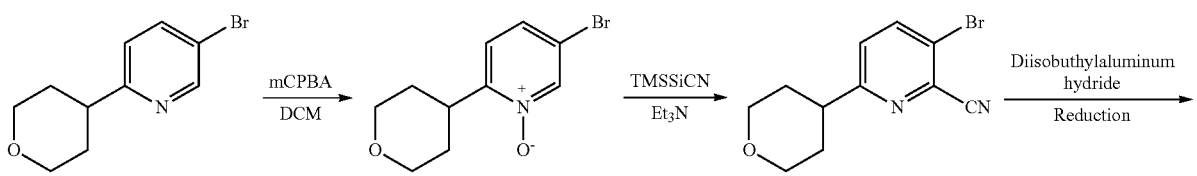

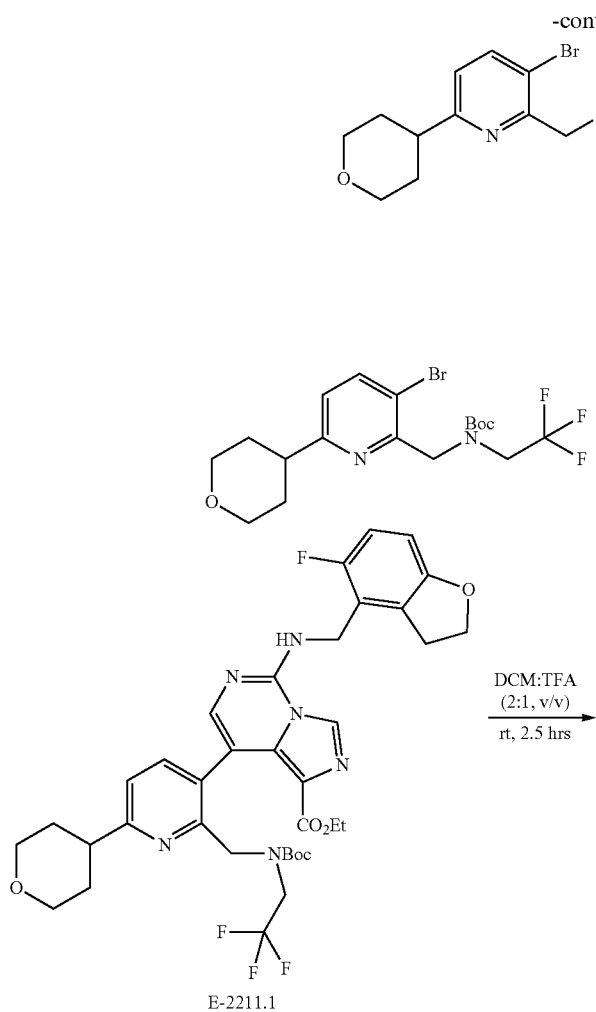

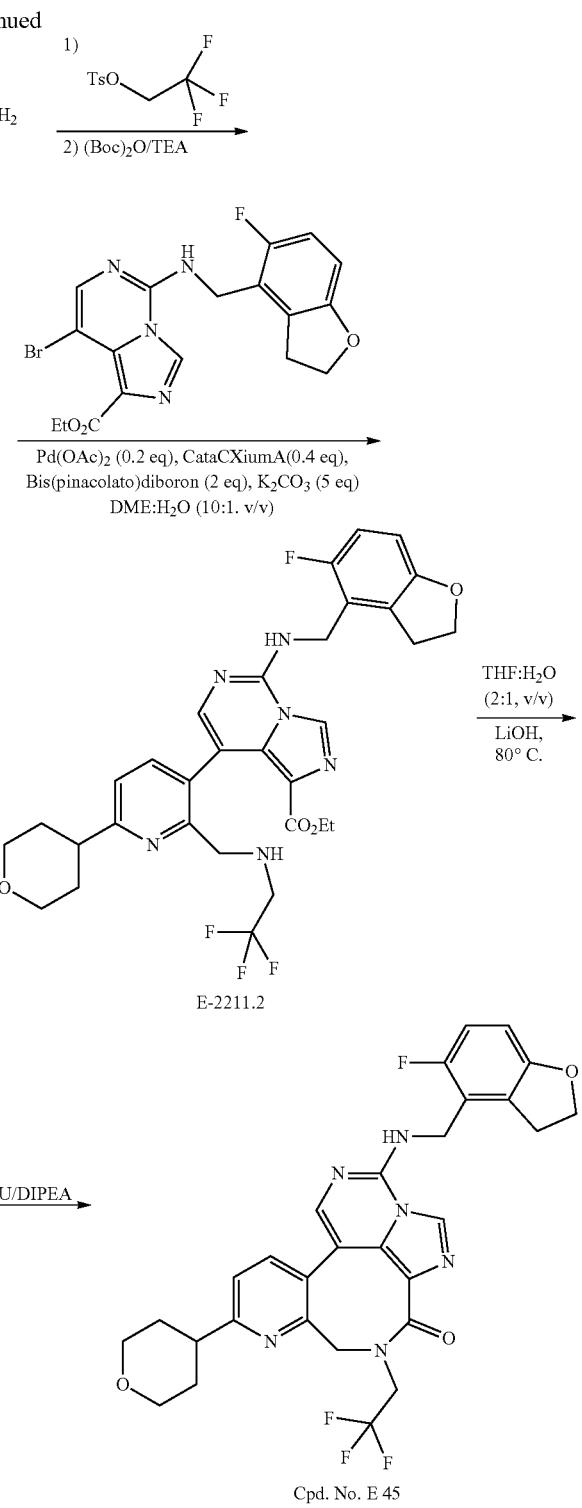

To a solution of 5-bromo-2-(tetrahydro-2H-pyran-4-yl)pyridine (5.00 g, 20.65 mmol) in DCM (100 ml) was added 1.5 eq of mCPBA (5.35 g, 30.97 mmol) slowly. After 4 h the reaction mixture was quenched with 2.0 eq of Ca(OH)$_2$ (3.90 g, 41.3 mmol), and the resulting precipitate was stirred for 30 minutes. The precipitate was filtered and washed with 3:1 DCM/methanol. The filtrate was concentrated in vacuo to give 5-bromo-2-(tetrahydro-2H-pyran-4-yl)pyridine 1-oxide as a crude solid, which was used for the subsequent reaction without further purification.

To the solution of crude 5-bromo-2-(tetrahydro-2H-pyran-4-yl)pyridine 1-oxide (4.00 g, 15.63 mmol) obtained from the previous step in acetonitrile (78 ml, 0.2 M) was added 6.0 eq of trimethylsilyl cyanide (TMSCN) (9.48 g, 94.00 mmol) and 4.5 eq of triethylamine (5.26 g, 70.34 mmol). The reaction was heated at 100° C. overnight. After cooling to room temperature, the solvent was concentrated in vacuo, and the residue was purified by HPLC (Acetonitrile/H$_2$O, started from 25% ACN, obtained compound at 42% ACN in H$_2$O) to give 3-bromo-6-(tetrahydro-2H-pyran-4-yl)picolinonitrile (1.60 g, 5.97 mmol, 29% in yield for 2 steps). LC-MS [M+H]+=266.97/268.96. $^1$H NMR (400 MHz, DMSO-d$_6$) δ 8.30 (d, J=8.4 Hz, 1H), 7.64 (d, J=8.4 Hz, 1H), 3.96-3.93 (m, 2H), 3.46-3.40 (m, 2H), 3.05-2.98 (m, 1H), 1.79-1.68 (m, 4H).

3-bromo-6-(tetrahydro-2H-pyran-4-yl)picolinonitrile (1.60 g, 5.97 mmol) was dissolved in 50 ml of dry DCM and cooled to −78° C. While stirring the solution, 2 eq of DIBAL-H solution in toluene (12 ml, 11.94 mmol) was added dropwise. The mixture was stirred 5 hr, quenched by slow addition of saturated aqueous Rochelle's salt (sodium potassium tartrate), warmed to room temperature, diluted with ethyl acetate, and stirred until two easily separable clear layers were formed. HPLC purification gave (3-bromo-6-(tetrahydro-2H-pyran-4-yl)pyridin-2-yl)methanamine (1.12 g, 4.12 mmol, 69%) as a liquid. LC-MS [M+H]+=271.04/273.03. $^1$H NMR (400 MHz, DMSO-d$_6$) δ 8.29 (s, broad, 2H), 8.07 (d, J=8.4 Hz, 1H), 7.29 (d, J=8.4 Hz, 1H), 4.53-4.22 (m, 2H), 3.48-3.42 (m, 2H), 3.00-2.93 (m, 1H), 1.91-1.69 (m, 4H).

To a solution of (3-bromo-6-(tetrahydro-2H-pyran-4-yl)pyridin-2-yl)methanamine (181 mg, 0.67 mmol) in DCM (10 ml) was added 2.0 eq of 2,2,2-trifluoroethyl 4-methylbenzenesulfonate (311 mg, 1.34 mmol) and 2.0 eq of DIPEA (173 mg, 1.34 mmol). After 3 hrs the reaction mixture was quenched with TFA and H$_2$O, followed by HPLC purification gave N-((3-bromo-6-(tetrahydro-2H-pyran-4-yl)pyridin-2-yl)methyl)-2,2,2-trifluoroethan-1-amine. LC-MS: [M+H]+=354.01.

After freeze drying via lyophilization, the compound was stirred at room temperature for 5 h with 2 eq of (Boc)$_2$O (292 mg, 1.34 mmol) and 3 eq of Et$_3$N (2.01 mmol, 203 mg) in 4 ml DCM. Upon completion the residue was purified by combi-flash column chromatography using 0-100% EtOAc/Hexane to give compound tert-butyl ((3-bromo-6-(tetrahydro-2H-pyran-4-yl)pyridin-2-yl)methyl)(2,2,2-trifluoroethyl) carbamate (85 mg, 0.19 mmol, 28% in yield for 2 steps). LC-MS [M+H]+=454.07.

Palladium (II) acetate (0.2 eq.) and cataCXium A (0.4 eq.) were mixed together in DME (0.5 ml, degassed), and resulting solution was added via pipette to a mixture of ethyl 8-bromo-5-(((5-fluoro-2,3-dihydrobenzofuran-4-yl)methyl)amino) imidazo[1,5-c]pyrimidine-1-carboxylate (1 eq.), tert-butyl ((3-bromo-6-(tetrahydro-2H-pyran-4-yl)pyridin-2-yl)methyl)(2,2,2-trifluoroethyl) carbamate (83 mg, 0.18 mmol, 1.2 eq.), bis-pinacolatediboron (2 eq.) and K$_2$CO$_3$ (5 eq.) in DME/H$_2$O (10:1, 5.0 ml, degassed) at 70° C. The reaction mixture was stirred overnight. Then it was concentrated and extracted with ethyl acetate (2×30 ml), washed with water and brine, and dried over anhydrous Na$_2$SO$_4$. The mixture was concentrated followed by preparative HPLC purification afforded E-2211.1. LC-MS: [M+H]+=729.29. Removal of the Boc protecting group of E-2211.1 afforded E-2211.2. LC-MS: [M+H]+=629.21.

A mixture of compound E-2211.2 (1 eq.) and LiOH (10 eq.) in THF (10 ml/mmol) and water (5 ml/mmol) was heated at 80° C. overnight. The mixture was concentrated, and residue was then purified by prep-HPLC to afford E-2211.3 in 50% yield for the 3 steps.

To a mixture of compound E-2211.3 (1 eq.) and HATU (2 eq.) in DMF (5 ml/mmol) was added DIPEA (5 eq.). The reaction mixture was allowed to stir 2 h, and concentrated.

The residue was purified by prep-HPLC to afford Cpd. No. E 45 in quantitative yield. LC-MS: [M+H]+=583.09. $^1$H NMR (400 MHz, DMSO-d$_6$) δ 8.83 (s, 1H), 8.68 (t, J=4.8 Hz, 1H), 7.90 (d, J=8.4 Hz, 1H), 7.54 (s, 1H), 7.43 (d, J=8.4 Hz, 1H), 6.95 (dd, J=9.6, 8.8 Hz, 1H), 6.72 (dd, J=8.8, 4.0 Hz, 1H), 5.47 (d, J=14.8 Hz, 1H), 4.74 (d, J=4.8 Hz, 2H), 4.70-4.63 (m, 1H), 4.55 (t, J=8.8 Hz, 2H), 4.16 (d, J=14.8 Hz, 1H), 4.07-4.03 (m, 4H), 3.45-3.51 (m, 2H), 3.33 (t, J=8.4 Hz, 2H), 2.97-3.05 (m, 1H), 1.75-1.84 (m, 4H).

Example 27

Synthesis of 7-(tert-butyl)-12-(((5-fluoro-2,3-dihydrobenzofuran-4-yl)methyl)amino)-4-(2,2,2-trifluoroethyl)-4,5-dihydro-3H-2,4,8,11,12a-pentaazabenzo[4,5]cycloocta[1,2,3-cd]inden-3-one (Cpd. No. E 46)

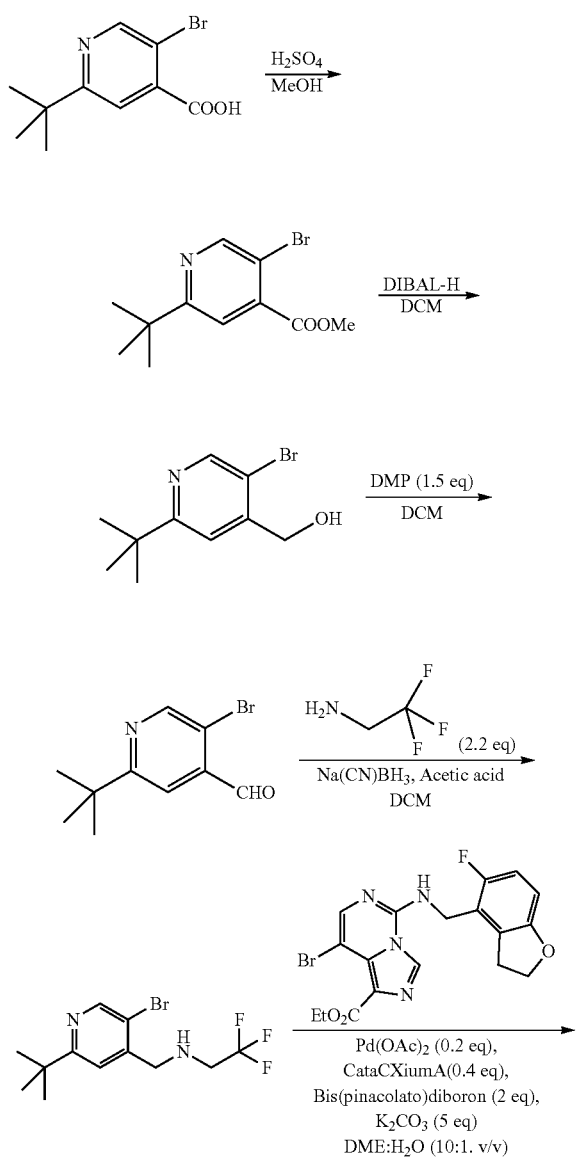

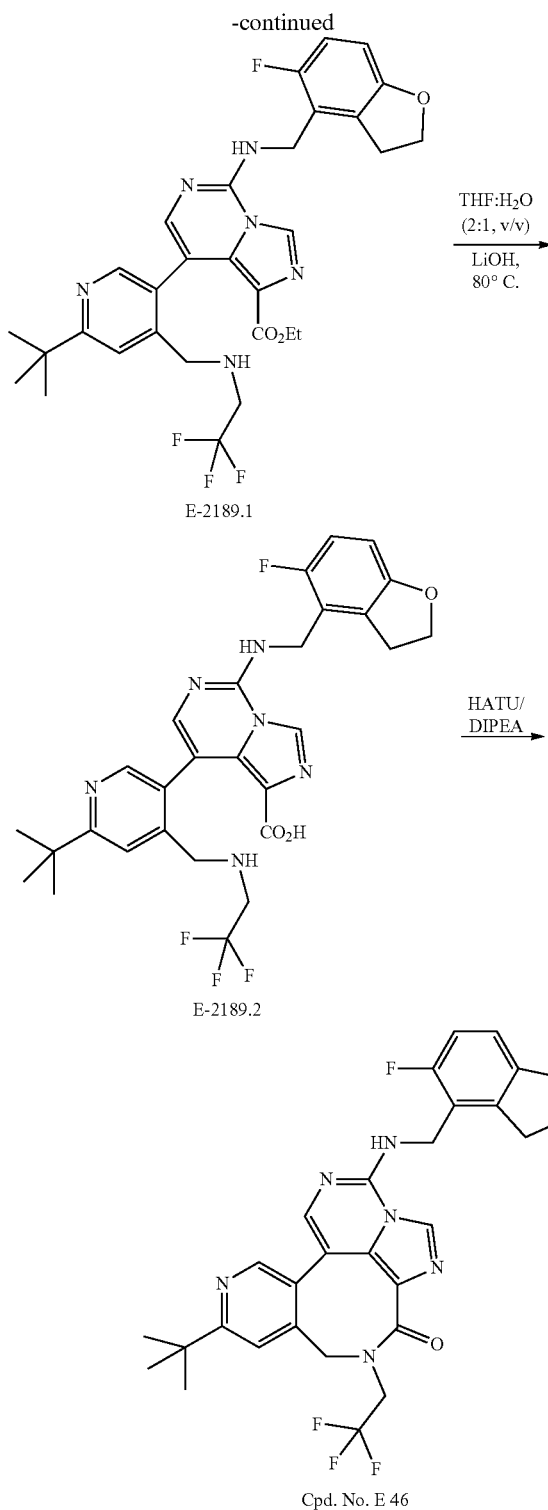

E-2189.1

THF:H₂O
(2:1, v/v)
LiOH,
80° C.

E-2189.2

HATU/
DIPEA

Cpd. No. E 46

H₂SO₄ (0.5 mL, 9.69 mmol, 1.0 eq.) was added to a solution of 5-bromo-2-(tert-butyl)isonicotinic acid (2.5 g, 9.69 mmol, 1.0 eq.) in MeOH (25 ml). The resulting solution was stirred for 14 h at reflux. The mixture was cooled to room temperature and concentrated under vacuum. The residue was dissolved in ethyl acetate (50 ml), washed with water and satd. aq. NaCl (2×50 ml), dried over anhydrous Na₂SO₄, and concentrated under vacuum. The residue was purified by silica gel column chromatography eluted with EtOAc/hexane to yield methyl 5-bromo-2-(tert-butyl)isonicotinate.

To a solution of methyl 5-bromo-2-(tert-butyl)isonicotinate in DCM (50 ml) at −78° C., DIBAL-H (18 ml, 18.90 mmol, 1.05 M in toluene) was added dropwise. The reaction mixture was maintained at −78° C. to −15° C. for 30 min, then was allowed to warm to room temperature and stirred for another 12 h. The reaction mixture was cooled to 0° C. and quenched with satd. aq. NH₄Cl (50 ml). The resulting mixture was extracted with DCM (3×250 ml), washed with brine (150 ml), dried over anhydrous (Na₂SO₄), filtered, and concentrated. The residue was purified by silica gel column chromatography eluted with EtOAc/hexane to afford (5-bromo-2-(tert-butyl)pyridin-4-yl)methanol (1.78 g, 7.28 mmol, 75% for 2 steps). LC-MS [M+H]+=243.98/245.99.

An aliquot of (5-bromo-2-(tert-butyl)pyridin-4-yl)methanol (1.78 g, 7.28 mmol) was dissolved in dry DCM (~0.2 M), then to this solution 1.3 eq. of Dess-Martin periodinane (4.11 g, 9.46 mmol) was added and the reaction mixture is allowed to stir for 1 h, monitored via TLC. Upon completion quenched with saturated NH₄Cl solution, then extracted with DCM. The organic layers were collected and combined, washed with brine, dried over anhydrous Na₂SO₄, and concentrated in vacuo. Purification was performed on silica gel normal phase column chromatography with increasing amounts of ethyl acetate in hexanes to afford the desired 5-bromo-2-(tert-butyl)isonicotinaldehyde.

To 5-bromo-2-(tert-butyl)isonicotinaldehyde was added methanol (~0.2 M), followed by 2.2 eq. of 2,2,2-trifluoroethan-1-amine, 2 eq. of Na(CN)BH₃ and 2 eq. of acetic acid under ice bath. The ice bath was removed and reaction mixture was allowed to stir for 3 h, monitored via TLC. Upon completion, the reaction mixture was concentrated, and residue was purified by HPLC to afford N-((5-bromo-2-(tert-butyl)pyridin-4-yl)methyl)-2,2,2-trifluoroethan-1-amine (800 mg, 2.27 mmol, 31% for 2 steps). LC-MS: [M+H]+=324.89/326.86.

Palladium (II) acetate (0.1 eq.) and cataCXium A (0.2 eq.) were mixed together in DME (0.5 ml, degassed) and the resulting solution was added via pipette to a mixture of ethyl 8-bromo-5-(((5-fluoro-2,3-dihydrobenzofuran-4-yl)methyl)amino) imidazo[1,5-c]pyrimidine-1-carboxylate (1 eq.), N-((5-bromo-2-(tert-butyl)pyridin-4-yl)methyl)-2,2,2-trifluoroethan-1-amine (2 eq.), bis-pinacolatediboron (2 eq.) and K₂CO₃ (5 eq.) in DME/H₂O (10:1, 22 ml, degassed) at 70° C. The reaction mixture was stirred overnight. The reaction mixture was concentrated and extracted with ethyl acetate (2×50 ml), washed with water and brine, and dried over Na₂SO₄. The mixture was concentrated, and residue was purified by HPLC to afford E-2189.1 in ~15% yield. LC-MS: [M+H]+=601.20.

A mixture of compound E-2189.1 (1 eq.) and LiOH (10 eq.) in THF (10 ml/mmol) and water (5 ml/mmol) was heated at 80° C. for overnight. The mixture was concentrated, and residue was purified by prep-HPLC to afford E-2189.2 and Cpd. No. E 46 in ~5:1 ratio. LC-MS: [M+H]+=573.15.

To a mixture of compound E-2189.2 (1 eq.) and HATU (2 eq.) in DMF (5 ml/mmol) was added DIPEA (5 eq.). The reaction mixture was allowed to stir 2 h. The reaction mixture was concentrated, and the residue was purified by prep-HPLC to give Cpd. No. E 46 in a combined yield of ~90%. LC-MS: [M+H]+=555.10. ¹H NMR (400 MHz, DMSO-d₆) δ 8.85 (s, 1H), 8.72 (t, 1H), 8.65 (d, J=2.4, 1H), 7.91 (d, J=7.8 Hz, 1H), 7.58 (d, J=1.6 Hz, 1H), 6.96 (t, J=8.8 Hz, 1H), 6.71 (dd, J=8.8, 4.0 Hz, 1H), 5.34 (d, J=14.8 Hz, 1H), 4.75 (d, J=4.0 Hz, 2H), 4.56 (t, J=8.8 Hz, 2H), 4.29 (d, J=14.8 Hz, 1H), 4.06-4.12 (m, 1H), 3.34 (t, J=8.8 Hz, 2H), 1.40 (s, 9H).

Example 28

Synthesis of 4-(2,2-difluoroethyl)-12-(((5-fluoro-2,3-dihydrobenzofuran-4-yl)methyl)amino)-7-isopropyl-4,5-dihydro-3H-2,4,6,11,12a-pentaazabenzo[4,5]cycloocta[1,2,3-cd]inden-3-one (Cpd. No. E 47)

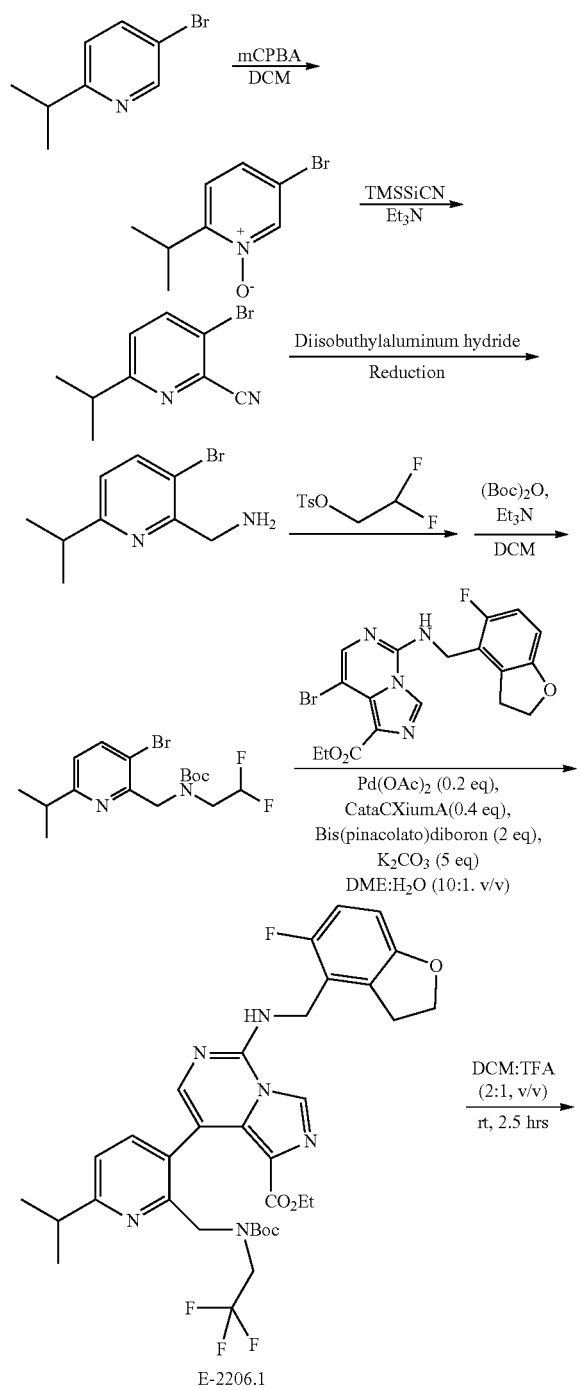

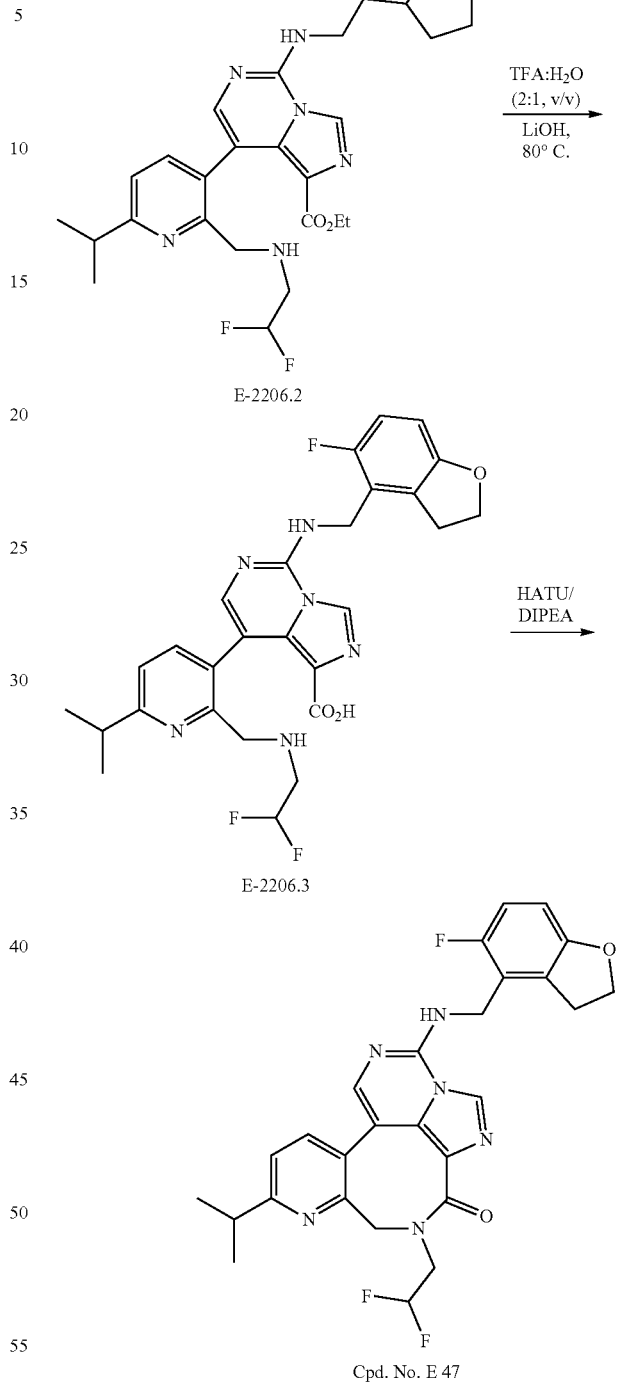

To a solution of 5-bromo-2-isopropylpyridine (1.00 g, 5.00 mmol) in DCM (20 ml) was added 1.5 eq of mCPBA. After 4 h the reaction mixture was quenched with 2.0 eq of $Ca(OH)_2$, and the resulting precipitate was stirred for 30 minutes. The precipitate was filtered and washed with 3:1 DCM/methanol. The filtrate was concentrated in vacuo to give 5-bromo-2-isopropylpyridine 1-oxide as a crude solid, which was used for the subsequent reaction without further purification.

To the solution of crude 5-bromo-2-isopropylpyridine 1-oxide obtained from the previous step in acetonitrile (20 ml, 0.2 M) was added 6.0 eq of trimethylsilyl cyanide (TMSCN) and 4.5 eq of triethylamine. The reaction was heated at 100° C. overnight. After cooling to room temperature, the solvent was concentrated in vacuo, and the residue was purified by pre-HPLC to give 3-bromo-6-isopropylpicolinonitrile (443 mg, 1.97 mmol, 39% in yield for 2 steps). LC-MS [M+H]+=225.01/227.03.

3-bromo-6-isopropylpicolinonitrile (443 mg, 1.97 mmol) was dissolved in 10 ml of dry DCM and cooled to −78° C. While stirring the solution, 2 eq of DIBAL-H solution in toluene was added dropwise. The mixture was stirred 5 h, then quenched by slow addition of saturated aqueous Rochelle's salt (sodium potassium tartrate). The reaction mixture was allowed to warm, diluted with ethyl acetate, and stirred until two easily separable clear layers formed. HPLC purification gave (3-bromo-6-isopropylpyridin-2-yl)methanamine as a liquid. LC-MS [M+H]+=229.01/230.97. $^1$H NMR (400 MHz, DMSO-$d_6$) δ 8.34 (s, broad, 2H), 8.04 (d, J=8.4 Hz, 1H), 7.28 (d, J=8.4 Hz, 1H), 4.24-4.23 (m, 2H), 3.33-3.02 (m, 1H), 1.26 (d, J=6.8 Hz, 6H).

To a solution of (3-bromo-6-isopropylpyridin-2-yl)methanamine (107 mg, 0.47 mmol) in DCM (10 ml) was added 2.0 eq of 2,2-difluoroethyl 4-methylbenzenesulfonate (200 mg, 0.94 mmol) and 2.0 eq of DIPEA. After 3 h the reaction mixture was quenched with TFA and H$_2$O. HPLC purification gave N-((3-bromo-6-isopropylpyridin-2-yl)methyl)-2, 2-difluoroethan-1-amine. LC-MS [M+H]+=293.04/285.09.

After freeze drying via lyophilization, the N-((3-bromo-6-isopropylpyridin-2-yl)methyl)-2,2-difluoroethan-1-amine (103 mg, 0.35 mmol) was stirred at room temperature for 5 h with 2 eq of (Boc)$_2$O (153 mg, 0.70 mmol) and 3 eq of Et$_3$N (203 mg, 1.05 mmol) in 3 ml dry DCM. Upon completion the residue was purified by combi-flush column chromatography using 0-100% EtOAc/Hexane to give tert-butyl ((3-bromo-6-isopropylpyridin-2-yl)methyl)(2,2-difluoroethyl)carbamate (52 mg, 0.13 mmol, 28% in yield for 2 steps).

Palladium (II) acetate (0.2 eq.) and cataCXium A (0.4 eq.) were mixed together in DME (0.5 ml, degassed), and the resulting solution was added via pipette to a mixture of ethyl 8-bromo-5-(((5-fluoro-2,3-dihydrobenzofuran-4-yl)methyl) amino) imidazo[1,5-c]pyrimidine-1-carboxylate (1 eq.), tert-butyl ((3-bromo-6-isopropylpyridin-2-yl)methyl)(2,2-difluoroethyl)carbamate (52 mg, 0.13 mmol, 1.2 eq.), bis-pinacolatediboron (2.0 eq.) and K$_2$CO$_3$ (5.0 eq.) in DME/H$_2$O (10:1, 4.0 ml, degassed) at 70° C. The reaction mixture was stirred overnight. Then it was concentrated and extracted with ethyl acetate (2×30 ml), washed with water and brine, and dried over Na$_2$SO$_4$. The mixture was concentrated and purified by HPLC to afford E-2206.1. LC-MS: [M+H]+=669.33. The Boc protecting group of E-2206.1 was removed to afford E-2206.2. LC-MS: [M+H]+=569.17.

A mixture of E-2206.2 (1 eq.) and LiOH (10 eq.) in THF (10 ml/mmol) and water (5 ml/mmol) was heated at 80° C. overnight. The mixture was concentrated, and residue was then purified by prep-HPLC to afford E-2206.3. LC-MS: [M+H]+=541.10.

To a mixture of E-2206.3 (1 eq.) and HATU (2 eq.) in DMF (3 ml/mmol) was added DIPEA (5 eq.). The reaction mixture was allowed to stir 2 h, and concentrated. The residue was purified by prep-HPLC to afford Cpd. No. E 47 in quantitative yield. LC-MS: [M+H]+=523.15. $^1$H NMR (400 MHz, DMSO-$d_6$) δ 8.80 (s, 1H), 8.63 (t, 1H), 7.85 (d, J=8.0 Hz, 1H), 7.49 (s, 1H), 7.37 (d, J=8.0 Hz, 1H), 6.94 (dd, J=9.6, 8.8 Hz, 1H), 6.70 (dd, J=8.8, 4.0 Hz, 1H), 6.29 (t, J=57.2 Hz, 1H), 5.40 (d, J=8.4 Hz, 1H), 4.72 (d, J=3.6 Hz, 2H), 4.54 (t, J=8.8 Hz, 2H), 4.14 (d, J=14.8 Hz, 1H), 4.09-4.03 (m, 1H), 3.75-3.33 (m, 1H), 3.33 (t, J=8.8 Hz, 2H), 3.10-3.03 (m, 2H), 1.29-1.22 (m, 6H).

Example 29

Synthesis of 7-(1,4-dioxan-2-yl)-12-(((5-fluoro-2,3-dihydrobenzofuran-4-yl)methyl)amino)-4-(2,2,2-trifluoroethyl)-4,5-dihydro-3H-2,4,6,11,12a-pentaazabenzo[4,5]cycloocta[1,2,3-cd]inden-3-one (Cpd. No. E 48)

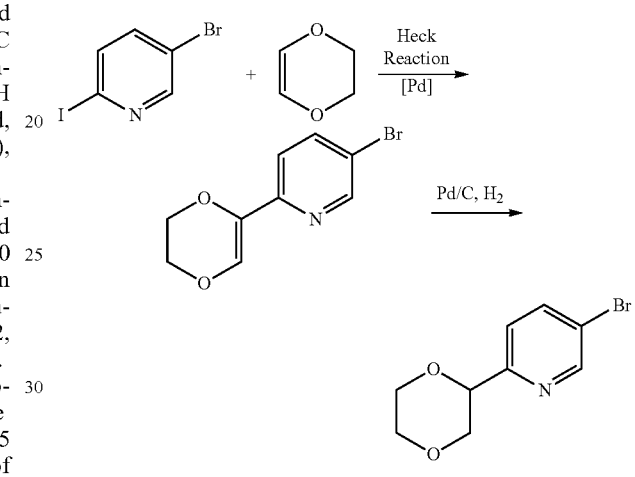

Cpd. No. E 48 can be prepared using the methodology described in the EXAMPLEs above starting from 5-bromo-2-(1,4-dioxan-2-yl)pyridine.

Example 30

Synthesis of 7-((1,4-dioxan-2-yl)methyl)-12-(((5-fluoro-2,3-dihydrobenzofuran-4-yl)methyl)amino)-4-(2,2,2-trifluoroethyl)-4,5-dihydro-3H-2,4,6,11,12a-pentaazabenzo[4,5]cycloocta[1,2,3-cd]inden-3-one (Cpd. No. E 49)

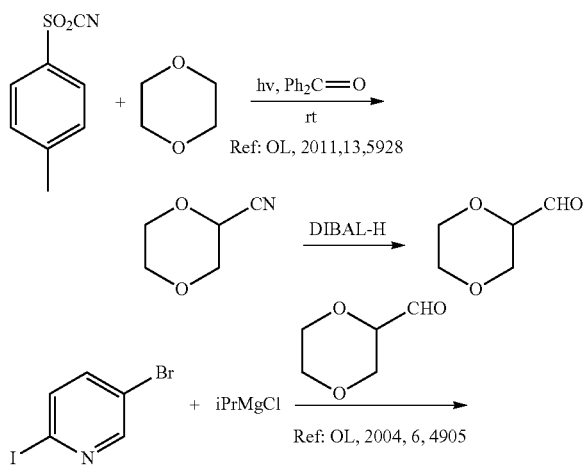

-continued

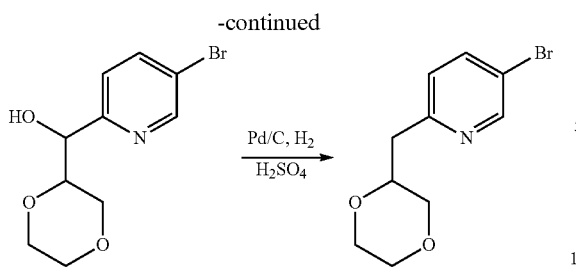

Cpd. No. E 49 can be prepared using the methodology described in the EXAMPLEs above starting from 2-((1,4-dioxan-2-yl)methyl)-5-bromopyridine.

Example 31

Compound Characterization

The compounds of Table 2 were prepared using methodology described in EXAMPLES 1-17, see, e.g., "Synthetic method" column, and known in the art. All compounds were characterized by mass spectroscopy and/or $^1$H NMR as the TFA salt.

TABLE 2

| Cpd. No. | $^1$H NMR (400 MHz)/LC-MS data | Synthetic method |
|---|---|---|
| 1 | LC-MS: [M + H]+ = 376.14 | Example 5 |
| 2 | LC-MS: [M + H]+ = 404.14 | Example 5 |
| 3 | $^1$H NMR (400 MHz, DMSO-d$_6$) δ 9.50 (s, 1H), 8.67 (s, 1H), 8.53 (t, J = 5.1 Hz, 1H), 7.99 (s, 1H), 7.88-7.80 (m, 1H), 7.19 (dd, J = 6.1, 1.6 Hz, 2H), 7.02 (ddd, J = 8.3, 6.1, 2.4 Hz, 1H), 6.96 (dd, J = 10.3, 8.7 Hz, 1H), 6.71 (dd, J = 8.6, 3.9 Hz, 1H), 4.73 (d, J = 4.8 Hz, 2H), 4.56 (t, J = 8.7 Hz, 2H), 3.31 (d, J = 8.5 Hz, 2H).<br>LC-MS: [M + H]+ = 402.12 | Example 3 |
| 4 | $^1$H NMR (400 MHz, DMSO-d$_6$) δ 9.26 (s, 1H), 8.66 (s, 1H), 8.66 (t, J = 5.1 Hz, 1H), 8.32 (dd, J = 8.1, 1.7 Hz, 1H), 8.19 (dd, J = 4.5, 1.6 Hz, 1H), 8.06 (s, 1H), 7.09 (dd, J = 8.0, 4.6 Hz, 1H), 6.96 (dd, J = 10.4, 8.7 Hz, 1H), 6.71 (dd, J = 8.6, 3.9 Hz, 1H), 4.73 (d, J = 4.9 Hz, 2H), 4.56 (t, J = 8.7 Hz, 2H), 3.31 (d, J = 8.5 Hz, 2H).<br>LC-MS: [M + H]+ = 403.12 | Example 3 |
| 5 | $^1$H NMR (400 MHz, DMSO-d$_6$) δ 9.77 (s, 1H), 8.76 (t, J = 5.1 Hz, 1H), 8.70 (s, 1H), 8.15-8.01 (m, 2H), 7.75 (d, J = 2.0 Hz, 1H), 7.47 (dd, J = 8.5, 2.0 Hz, 1H), 6.96 (dd, J = 10.3, 8.7 Hz, 1H), 6.71 (dd, J = 8.6, 3.9 Hz, 1H), 4.74 (d, J = 5.0 Hz, 2H), 4.56 (t, J = 8.7 Hz, 2H), 3.36 (t, J = 8.7 Hz, 2H), 3.21 (s, 3H).<br>LC-MS: [M + H]+ = 480.11 | Example 3 |
| 6 | $^1$H NMR (400 MHz, DMSO-d$_6$) δ 8.87 (s, 1H), 8.73 (t, J = 5.1 Hz, 1H), 7.68 (s, 1H), 7.60-7.51 (m, 2H), 7.48 (qd, J = 7.5, 1.7 Hz, 1H), 6.97 (dd, J = 10.3, 8.7 Hz, 1H), 6.72 (dd, J = 8.7, 3.9 Hz, 1H), 5.78 (d, J = 12.4 Hz, 1H), 5.04 (d, J = 12.5 Hz, 1H), 4.76 (d, J = 4.8 Hz, 2H), 4.57 (t, J = 8.7 Hz, 2H), 3.36 (t, J = 8.8 Hz, 2H).<br>LC-MS: [M + H]+ = 417.13 | Example 1 |
| 7 | $^1$H NMR (400 MHz, DMSO-d$_6$) δ 8.87 (s, 1H), 8.74 (t, J = 5.1 Hz, 1H), 7.66 (s, 1H), 7.62 (dd, J = 8.7, 5.6 Hz, 1H), 7.48 (dd, J = 9.2, 2.8 Hz, 1H), 7.38 (td, J = 8.6, 2.8 Hz, 1H), 7.02-6.91 (m, 1H), 6.72 (dd, J = 8.6, 3.9 Hz, 1H), 5.76 (d, J = 12.5 Hz, 1H), 5.03 (d, J = 12.5 Hz, 1H), 4.76 (d, J = 4.8 Hz, 2H), 4.57 (t, J = 8.8 Hz, 2H), 3.35 (t, J = 8.7 Hz, 2H).<br>LC-MS: [M + H]+ = 435.12 | Example 1 |
| 8 | $^1$H NMR (400 MHz, DMSO-d$_6$) δ 8.88 (d, J = 9.5 Hz, 2H), 7.98 (d, J = 1.8 Hz, 1H), 7.92-7.84 (m, 1H), 7.79 (d, J = 14.4 Hz, 2H), 6.97 (t, J = 9.5 Hz, 1H), 6.72 (dd, J = 8.7, 3.9 Hz, 1H), 5.87 (d, J = 12.5 Hz, 1H), 5.20 (d, J = 12.7 Hz, 1H), 4.78 (d, J = 4.8 Hz, 2H), 4.57 (t, J = 8.7 Hz, 2H), 3.36 (t, J = 8.8 Hz, 2H).<br>LC-MS: [M + H]+ = 485.12 | Example 1 |
| 9 | LC-MS: [M + H]+ = 417.12 | Example 1 |
| 10 | LC-MS: [M + H]+ = 416.10 | Example 1 |
| 11 | $^1$H NMR (400 MHz, DMSO-d$_6$) δ 8.89 (s, 1H), 8.81 (t, J = 5.1 Hz, 1H), 7.75 (s, 1H), 7.57 (td, J = 8.1, 6.0 Hz, 1H), 7.42 (dd, J = 8.0, 1.1 Hz, 1H), 7.35 (ddd, J = 9.4, 8.2, 1.1 Hz, 1H), 6.97 (dd, J = 10.3, 8.7 Hz, 1H), 6.72 (dd, J = 8.7, 3.9 Hz, 1H), 5.67 (dd, J = 12.9, 2.6 Hz, 1H), 5.29 (d, J = 13.1 Hz, 1H), 4.86-4.66 (m, 2H), 4.57 (t, J = 8.8 Hz, 2H), 3.36 (t, J = 8.7 Hz, 2H).<br>LC-MS: [M + H]+ = 435.12 | Example 1 |

TABLE 2-continued

| Cpd. No. | ¹H NMR (400 MHz)/LC-MS data | Synthetic method |
|---|---|---|
| 13 | ¹H NMR (400 MHz, DMSO-d₆) δ 8.98 (d, J = 2.7 Hz, 2H), 8.92 (s, 1H), 8.16 (s, 1H), 7.92 (s, 1H), 6.97 (dd, J = 10.3, 8.7 Hz, 1H), 6.72 (dd, J = 8.6, 3.9 Hz, 1H), 5.91 (brs, 1H), 5.22 (brs, 1H), 4.79 (d, J = 4.8 Hz, 2H), 4.57 (t, J = 8.7 Hz, 2H), 3.36 (t, J = 8.7 Hz, 2H). LC-MS: [M + H]+ = 486.11 | Example 1 |
| 14 | ¹H NMR (400 MHz, DMSO-d₆) δ 9.00 (d, J = 5.1 Hz, 1H), 8.92 (s, 1H), 8.32 (d, J = 8.1 Hz, 1H), 8.05 (d, J = 8.3 Hz, 1H), 7.83 (s, 1H), 6.97 (dd, J = 10.3, 8.7 Hz, 1H), 6.72 (dd, J = 8.7, 3.9 Hz, 1H), 6.12-5.96 (m, 1H), 5.06 (d, J = 12.6 Hz, 1H), 4.78 (d, J = 4.9 Hz, 2H), 4.57 (t, J = 8.8 Hz, 2H), 3.36 (t, J = 8.7 Hz, 2H). LC-MS: [M + H]+ = 486.11 | Example 1 |
| 15 | ¹H NMR (400 MHz, DMSO-d₆) δ 8.79 (s, 1H), 8.53 (t, J = 5.1 Hz, 1H), 8.24 (t, J = 7.4 Hz, 1H), 7.53-7.35 (m, 4H), 7.33-7.24 (m, 1H), 7.03-6.90 (m, 1H), 6.72 (dd, J = 8.7, 3.9 Hz, 1H), 4.83-4.70 (m, 3H), 4.57 (t, J = 8.8 Hz, 2H), 4.03 (dd, J = 14.2, 5.7 Hz, 1H), 3.35 (t, J = 8.7 Hz, 2H). LC-MS: [M + H]+ = 416.14 | Example 2 |
| 17 | ¹H NMR (400 MHz, DMSO-d₆) δ 8.79 (s, 1H), 8.57 (t, J = 5.1 Hz, 1H), 8.22 (d, J = 7.6 Hz, 1H), 7.50 (dd, J = 8.6, 5.7 Hz, 1H), 7.41 (s, 1H), 7.24 (td, J = 8.6, 2.7 Hz, 1H), 7.11 (dd, J = 9.2, 2.8 Hz, 1H), 6.96 (dd, J = 10.3, 8.7 Hz, 1H), 6.71 (dd, J = 8.7, 3.8 Hz, 1H), 4.77-4.33 (m, 3H), 4.56 (t, J = 8.7 Hz, 2H), 3.97 (dd, J = 14.6, 5.4 Hz, 1H), 3.35 (t, J = 8.7 Hz, 2H). LC-MS: [M + H]+ = 434.14 | Example 2 |
| 18 | ¹H NMR (400 MHz, DMSO-d₆) δ 8.90 (s, 1H), 8.85 (t, J = 5.1 Hz, 1H), 7.96 (d, J = 8.0 Hz, 1H), 7.71 (s, 1H), 7.46 (d, J = 8.1 Hz, 1H), 6.96 (t, J = 9.5 Hz, 1H), 6.72 (dd, J = 8.7, 3.8 Hz, 1H), 5.91 (d, J = 12.2 Hz, 1H), 4.95 (d, J = 12.1 Hz, 1H), 4.76 (d, J = 4.2 Hz, 2H), 4.56 (t, J = 8.7 Hz, 2H), 3.35 (t, J = 8.8 Hz, 2H), 2.57 (s, 3H). LC-MS: [M + H]+ = 432.14 | Example 1 |
| 19 | ¹H NMR (400 MHz, DMSO-d₆) δ 8.82 (s, 1H), 8.69 (t, J = 5.1 Hz, 1H), 8.24 (dd, J = 8.8, 5.7 Hz, 1H), 7.74 (d, J = 8.3 Hz, 2H), 7.71-7.59 (m, 1H), 7.52 (s, 1H), 6.96 (t, J = 9.5 Hz, 1H), 6.72 (dd, J = 8.6, 3.8 Hz, 1H), 4.86 (dd, J = 14.6, 8.8 Hz, 1H), 4.76 (d, J = 4.5 Hz, 2H), 4.56 (t, J = 8.7 Hz, 2H), 4.11 (dd, J = 14.7, 5.5 Hz, 1H), 3.35 (t, J = 8.8 Hz, 2H). LC-MS: [M + H]+ = 484.13 | Example 2 |
| 20 | ¹H NMR (400 MHz, DMSO-d₆) δ 8.84 (s, 1H), 8.64 (s, 1H), 8.49 (t, J = 7.2 Hz, 1H), 7.49 (s, 1H), 7.46-7.38 (m, 1H), 7.35-7.18 (m, 2H), 6.95 (t, J = 9.4 Hz, 1H), 6.71 (dd, J = 8.7, 3.8 Hz, 1H), 4.74 (s, 2H), 4.58 (dt, J = 17.7, 7.8 Hz, 3H), 4.31 (dd, J = 15.1, 5.8 Hz, 1H), 3.34 (t, J = 8.8 Hz, 2H). LC-MS: [M + H]+ = 434.14 | Example 2 |
| 21 | ¹H NMR (400 MHz, DMSO-d₆) δ 8.84 (s, 1H), 8.64 (d, J = 5.8 Hz, 1H), 8.40 (dd, J = 8.4, 6.0 Hz, 1H), 7.93 (d, J = 8.0 Hz, 1H), 7.49-7.39 (m, 2H), 6.96 (dd, J = 10.3, 8.7 Hz, 1H), 6.71 (dd, J = 8.6, 3.9 Hz, 1H), 4.95 (dd, J = 14.4, 8.5 Hz, 1H), 4.75 (d, J = 4.3 Hz, 2H), 4.56 (t, J = 8.8 Hz, 2H), 4.05 (dd, J = 14.4, 5.9 Hz, 1H), 3.34 (t, J = 8.7 Hz, 2H), 2.56 (s, 3H). LC-MS: [M + H]+ = 431.15 | Example 2 |
| 22 | ¹H NMR (400 MHz, DMSO-d₆) δ 8.83 (s, 2H), 8.76 (t, J = 5.2 Hz, 1H), 8.23 (dd, J = 8.8, 5.7 Hz, 1H), 7.77 (s, 1H), 7.65 (s, 1H), 6.96 (t, J = 9.5 Hz, 1H), 6.72 (dd, J = 8.7, 3.8 Hz, 1H), 4.93 (dd, J = 14.5, 8.8 Hz, 1H), 4.77 (d, J = 4.8 Hz, 2H), 4.57 (t, J = 8.7 Hz, 2H), 4.17 (dd, J = 14.6, 5.6 Hz, 1H), 3.35 (t, J = 8.7 Hz, 2H). LC-MS: [M + H]+ = 485.13 | Example 2 |
| 23 | ¹H NMR (400 MHz, DMSO-d₆) δ 8.79 (s, 1H), 8.59 (t, J = 5.1 Hz, 1H), 8.21 (dd, J = 8.9, 5.6 Hz, 1H), 7.49 (s, 1H), 7.35-7.27 (m, 2H), 7.26-7.18 (m, 1H), 6.96 (dd, J = 10.3, 8.6 Hz, 1H), 6.71 (dd, J = 8.7, 3.9 Hz, 1H), 4.75 (q, J = 5.0 Hz, 3H), 4.56 (t, J = 8.8 Hz, 2H), 3.97 (dd, J = 14.7, 5.5 Hz, 1H), 3.35 (t, J = 8.7 Hz, 2H). LC-MS: [M + H]+ = 434.14 | Example 2 |
| 24 | ¹H NMR (400 MHz, DMSO-d₆) δ 8.90 (s, 1H), 8.85 (s, 1H), 7.88 (d, J = 1.7 Hz, 1H), 7.86-7.74 (m, 3H), | Example 1 |

TABLE 2-continued

| Cpd. No. | ¹H NMR (400 MHz)/LC-MS data | Synthetic method |
|---|---|---|
| | 6.96 (dd, J = 10.3, 8.7 Hz, 1H), 6.72 (dd, J = 8.6, 3.9 Hz, 1H), 5.86 (d, J = 12.5 Hz, 1H), 5.15 (d, J = 12.4 Hz, 1H), 4.77 (d, J = 3.8 Hz, 2H), 4.57 (t, J = 8.8 Hz, 2H), 3.37 (dt, J = 9.0, 5.1 Hz, 2H).<br>LC-MS: [M + H]+ = 485.12 | |
| 25 | ¹H NMR (400 MHz, DMSO-d₆) δ 8.84 (s, 1H), 8.77 (t, J = 5.1 Hz, 1H), 8.57-8.45 (m, 1H), 8.18 (d, J = 8.1 Hz, 1H), 7.94 (d, J = 8.1 Hz, 1H), 7.55 (s, 1H), 6.96 (dd, J = 10.3, 8.7 Hz, 1H), 6.72 (dd, J = 8.6, 3.9 Hz, 1H), 5.07 (dd, J = 14.4, 8.3 Hz, 1H), 4.77 (d, J = 4.8 Hz, 2H), 4.57 (t, J = 8.8 Hz, 2H), 4.10 (dd, J = 14.4, 6.0 Hz, 1H), 3.35 (t, J = 8.7 Hz, 2H).<br>LC-MS: [M + H]+ = 485.12 | Example 2 |
| 26 | ¹H NMR (400 MHz, DMSO-d₆) δ 8.81 (s, 1H), 8.65 (t, J = 5.1 Hz, 1H), 8.28 (t, J = 7.0 Hz, 1H), 7.76 (dq, J = 3.7, 1.9 Hz, 2H), 7.60-7.43 (m, 2H), 6.96 (dd, J = 10.3, 8.7 Hz, 1H), 6.71 (dd, J = 8.6, 3.9 Hz, 1H), 4.85 (dd, J = 14.5, 8.8 Hz, 1H), 4.75 (d, J = 4.8 Hz, 2H), 4.57 (t, J = 8.8 Hz, 2H), 4.07 (dd, J = 14.6, 5.5 Hz, 1H), 3.36 (dd, J = 9.6, 7.5 Hz, 2H).<br>LC-MS: [M + H]+ = 484.13 | Example 2 |
| 27 | ¹H NMR (400 MHz, DMSO-d₆) δ 9.02 (t, J = 5.5 Hz, 1H), 8.90 (s, 1H), 7.98 (d, J = 2.0 Hz, 1H), 7.86 (dd, J = 8.6, 2.0 Hz, 1H), 7.78 (d, J = 8.2 Hz, 1H), 7.74 (s, 1H), 6.96 (dd, J = 7.5, 1.6 Hz, 1H), 6.92-6.79 (m, 2H), 6.07 (s, 2H), 5.87 (d, J = 12.7 Hz, 1H), 5.20 (d, J = 12.6 Hz, 1H), 4.79 (d, J = 5.3 Hz, 2H).<br>LC-MS: [M + H]+ = 469.10 | Example 1 |
| 28 | ¹H NMR (400 MHz, DMSO-d₆) δ 8.92 (s, 1H), 8.53 (t, J = 4.3 Hz, 1H), 7.98 (s, 1H), 7.94-7.83 (m, 1H), 7.83-7.71 (m, 2H), 7.50-7.33 (m, 1H), 6.96 (d, J = 8.4 Hz, 1H), 6.89 (t, J = 8.9 Hz, 1H), 5.87 (d, J = 12.5 Hz, 1H), 5.20 (d, J = 12.4 Hz, 1H), 4.80 (s, 2H), 3.87 (d, J = 1.0 Hz, 3H).<br>LC-MS: [M + H]+ = 473.11 | Example 1 |
| 29 | ¹H NMR (400 MHz, DMSO-d₆) δ 9.05 (t, J = 5.2 Hz, 1H), 8.92 (s, 1H), 8.27 (d, J = 7.9 Hz, 1H), 8.07 (s, 1H), 7.95 (d, J = 7.8 Hz, 1H), 6.97 (dd, J = 10.3, 8.7 Hz, 1H), 6.72 (dd, J = 8.7, 3.8 Hz, 1H), 5.95 (s, 1H), 5.23 (s, 1H), 4.81 (d, J = 5.0 Hz, 2H), 4.57 (t, J = 8.7 Hz, 2H), 3.36 (dd, J = 9.6, 7.5 Hz, 2H).<br>LC-MS: [M + H]+ = 486.11 | Example 1 |
| 30 | ¹H NMR (400 MHz, DMSO-d₆) δ 9.06-8.94 (m, 2H), 8.92 (s, 1H), 8.40 (dd, J = 2.1, 0.8 Hz, 1H), 7.87 (s, 1H), 6.95 (dd, J = 10.3, 8.6 Hz, 1H), 6.70 (dd, J = 8.6, 3.9 Hz, 1H), 6.05 (d, J = 12.2 Hz, 1H), 5.06 (d, J = 12.0 Hz, 1H), 4.86-4.67 (m, 2H), 4.57 (t, J = 8.7 Hz, 2H), 3.37 (t, J = 8.7 Hz, 2H).<br>LC-MS: [M + H]+ = 486.11 | Example 1 |
| 31 | ¹H NMR (400 MHz, DMSO-d₆) δ 8.88 (s, 1H), 8.79 (t, J = 5.1 Hz, 1H), 7.71 (t, J = 4.3 Hz, 2H), 7.63 (dd, J = 2.6, 1.1 Hz, 1H), 7.52 (ddd, J = 8.7, 2.6, 1.1 Hz, 1H), 6.96 (dd, J = 10.3, 8.6 Hz, 1H), 6.72 (dd, J = 8.7, 3.9 Hz, 1H), 5.80 (d, J = 12.5 Hz, 1H), 5.11 (d, J = 12.5 Hz, 1H), 4.77 (d, J = 4.5 Hz, 2H), 4.57 (t, J = 8.7 Hz, 2H), 3.36 (t, J = 8.8 Hz, 2H).<br>LC-MS: [M + H]+ = 501.11 | Scheme 1 |
| 32 | ¹H NMR (400 MHz, DMSO-d₆) δ 9.08 (t, J = 5.1 Hz, 1H), 8.92 (s, 1H), 8.88 (s, 1H), 8.07 (s, 1H), 8.01 (s, 1H), 7.03-6.90 (m, 1H), 6.72 (dd, J = 8.6, 3.9 Hz, 1H), 5.95 (s, 1H), 5.26 (s, 1H), 4.79 (d, J = 4.9 Hz, 2H), 4.58 (t, J = 8.7 Hz, 2H), 3.37 (t, J = 8.8 Hz, 2H).<br>LC-MS: [M + H]+ = 486.11 | Example 1 |
| 33 | ¹H NMR (400 MHz, CDCl₃) δ 9.35 (s, 1H), 7.89 (d, J = 8.1 Hz, 1H), 7.78 (d, J = 8.1 Hz, 1H), 7.56 (s, 1H), 6.66 (d, J = 9.2 Hz, 1H), 6.59-6.45 (m, 1H), 5.43 (d, J = 14.5 Hz, 1H), 4.81 (d, J = 6.1 Hz, 2H), 4.50 (t, J = 8.4 Hz, 2H), 4.24 (d, J = 14.4 Hz, 1H), 3.33 (t, J = 8.4 Hz, 2H), 3.16 (s, 3H).<br>LC-MS: [M + H]+ = 499.14 | Example 4 |
| 34 | ¹H NMR (400 MHz, methanol-d₄) δ 8.84 (s, 1H), 8.74 (s, 1H), 7.96 (s, 1H), 7.69 (s, 1H), 6.87 (t, J = 9.5 Hz, 1H), 6.66 (dd, J = 8.8, 3.7 Hz, 1H), 5.54 (d, J = 14.8 Hz, 1H), 4.81 (d, J = 6.1 Hz, 2H), 4.61 (t, J = 8.8 Hz, 2H), 4.28 (d, J = 14.8 Hz, 1H), 3.43 (t, J = 8.8 Hz, 2H), 3.16 (s, 3H).<br>LC-MS: [M + H]+ = 499.14 | Example 4 |

TABLE 2-continued

| Cpd. No. | ¹H NMR (400 MHz)/LC-MS data | Synthetic method |
|---|---|---|
| 35 | ¹H NMR (400 MHz, methanol-d₄) δ 8.78 (s, 1H), 8.14 (d, J = 8.1 Hz, 1H), 7.88 (d, J = 8.1 Hz, 1H), 7.65 (s, 1H), 6.87 (t, J = 9.4 Hz, 1H), 6.66 (d, J = 8.6 Hz, 1H), 5.54 (d, J = 16.3 Hz, 1H), 4.81 (d, J = 6.1 Hz, 2H), 4.61-4.53 (m, 3H), 4.01 (s, 1H), 3.74 (dq, J = 48.4, 11.0, 10.5 Hz, 5H), 3.60-3.45 (m, 2H), 3.42 (t, J = 9.1 Hz, 2H), 3.33-3.30 (m, 1H).<br>LC-MS: [M + H]+ = 485.17 | Example 4 |
| 37 | ¹H NMR (400 MHz, methanol-d₄) δ 8.82 (t, J = 4.7 Hz, 2H), 7.95 (d, J = 4.3 Hz, 1H), 7.69 (s, 1H), 6.86 (t, J = 9.5 Hz, 1H), 6.71-6.58 (m, 1H), 5.47 (dd, J = 15.0, 9.3 Hz, 1H), 4.81 (d, J = 6.1 Hz, 2H), 4.68-4.49 (m, 3H), 4.09-3.76 (m, 4H), 3.76-3.47 (m, 4H), 3.41 (q, J = 8.6 Hz, 3H).<br>LC-MS: [M + H]+ = 585.17 | Example 4 |
| 38 | ¹H NMR (400 MHz, methanol-d₄) δ 8.85 (s, 1H), 8.75 (s, 1H), 8.00 (s, 1H), 7.69 (s, 1H), 6.87 (t, J = 9.5 Hz, 1H), 6.66 (d, J = 8.9 Hz, 1H), 5.46 (d, J = 14.9 Hz, 1H), 4.81 (d, J = 6.1 Hz, 2H), 4.61 (t, J = 8.7 Hz, 2H), 4.32 (d, J = 15.0 Hz, 1H), 3.92 (dd, J = 13.7, 8.9 Hz, 1H), 3.58 (t, J = 11.7 Hz, 2H), 3.43 (t, J = 8.7 Hz, 2H), 3.11 (dd, J = 13.7, 5.7 Hz, 1H), 2.99 (dd, J = 29.9, 11.6 Hz, 2H), 2.90 (s, 3H), 2.23 (s, 1H), 2.07 (d, J = 14.4 Hz, 1H), 1.98 (d, J = 14.6 Hz, 1H), 1.64 (d, J = 14.1 Hz, 2H).<br>LC-MS: [M + H]+ = 596.23 | Example 4 |
| 39 | ¹H NMR (400 MHz, DMSO-d₆) δ 8.87 (t, J = 4.8 Hz, 1H), 8.83 (s, 1H), 8.16 (d, J = 7.8 Hz, 1H), 7.86 (d, J = 7.8 Hz, 1H), 7.82 (s, 1H), 6.95 (dd, J = 10.3, 8.6 Hz, 1H), 6.70 (dd, J = 8.7, 3.9 Hz, 1H), 5.39 (d, J = 15.0 Hz, 1H), 4.77 (d, J = 4.9 Hz, 2H), 4.55 (t, J = 8.8 Hz, 2H), 4.20 (d, J = 15.0 Hz, 1H), 3.33 (td, J = 8.5, 4.5 Hz, 2H), 2.98 (s, 3H).<br>LC-MS: [M + H]+ = 499.14 | Example 4 |
| 40 | ¹H NMR (400 MHz, DMSO-d₆) δ 8.89 (s, 1H), 8.85 (s, 1H), 8.17 (d, J = 7.8 Hz, 1H), 7.86-7.79 (m, 2H), 6.94 (dd, J = 10.3, 8.7 Hz, 1H), 6.70 (dd, J = 8.6, 3.9 Hz, 1H), 5.34 (dd, J = 15.2, 6.4 Hz, 1H), 4.84-4.69 (m, 2H), 4.54 (t, J = 8.7 Hz, 2H), 4.35 (dd, J = 15.2, 10.1 Hz, 1H), 3.96-3.83 (m, 1H), 3.81-3.41 (m, 6H), 3.39-3.21 (m, 3H), 3.11-2.90 (m, 1H).<br>LC-MS: [M + H]+ = 585.17 | Example 4 |
| 41 | ¹H NMR (400 MHz, DMSO-d₆) δ 8.80 (s, 1H), 8.76 (t, J = 5.1 Hz, 1H), 8.20 (d, J = 8.1 Hz, 1H), 7.95 (d, J = 8.1 Hz, 1H), 7.57 (s, 1H), 7.01-6.92 (m, 1H), 6.72 (dd, J = 8.7, 3.9 Hz, 1H), 5.38 (d, J = 14.8 Hz, 1H), 4.77 (d, J = 4.9 Hz, 2H), 4.56 (t, J = 8.8 Hz, 2H), 4.24 (d, J = 14.7 Hz, 1H), 3.42 (t, J = 8.7 Hz, 2H), 2.63 (tt, J = 7.4, 4.2 Hz, 1H), 0.99 (ddd, J = 10.9, 7.0, 5.1 Hz, 1H), 0.92 (ddt, J = 9.4, 7.1, 3.5 Hz, 1H), 0.81-0.74 (m, 1H), 0.72-0.64 (m, 1H).<br>LC-MS: [M + H]+ = 525.15 | Example 4 |
| 42 | ¹H NMR (400 MHz, methanol-d₄) δ 8.76 (s, 1H), 8.17 (d, J = 8.1 Hz, 1H), 7.90 (d, J = 8.1 Hz, 1H), 7.67 (s, 1H), 6.86 (t, J = 9.5 Hz, 1H), 6.65 (dd, J = 8.5, 3.6 Hz, 1H), 5.57 (d, J = 14.7 Hz, 1H), 4.81 (d, J = 6.1 Hz, 2H), 4.59 (t, J = 8.7 Hz, 2H), 4.35 (d, J = 14.7 Hz, 1H), 3.81 (dd, J = 13.5, 8.5 Hz, 1H), 3.57 (d, J = 12.5 Hz, 2H), 3.52-3.37 (m, 3H), 2.97 (dd, J = 24.7, 12.5 Hz, 2H), 2.88 (s, 3H), 2.28 (brs, 1H), 1.98 (t, J = 13.7 Hz, 2H), 1.65 (t, J = 13.5 Hz, 2H).<br>LC-MS: [M + H]+ = 596.23 | Example 4 |
| 43 | ¹H NMR (400 MHz, methanol-d₄) δ 8.82 (s, 1H), 8.76 (s, 1H), 7.99 (s, 1H), 7.67 (s, 1H), 6.89-6.79 (m, 1H), 6.63 (dd, J = 8.7, 3.8 Hz, 1H), 5.46 (d, J = 15.0 Hz, 1H), 4.86 (s, 2H), 4.82 (d, J = 14.9 Hz, 1H), 4.58 (td, J = 8.7, 1.2 Hz, 2H), 3.95 (d, J = 14.4 Hz, 1H), 3.49 (d, J = 14.5 Hz, 1H), 3.41 (t, J = 8.7 Hz, 2H), 0.91 (t, J = 2.4 Hz, 1H), 0.86-0.72 (m, 3H).<br>LC-MS: [M + H]+ = 555.16 | Example 4 |
| 44 | ¹H NMR (400 MHz, methanol-d₄) δ 8.75 (s, 1H), 8.15 (d, J = 8.1 Hz, 1H), 7.88 (d, J = 8.1 Hz, 1H), 7.66 (s, 1H), 6.87 (t, J = 9.5 Hz, 1H), 6.66 (dd, J = 8.8, 3.8 Hz, 1H), 5.54 (d, J = 14.8 Hz, 1H), 4.86 (s, 2H), 4.82 (d, J = 14.9 Hz, 1H), 4.60 (t, J = 8.7 Hz, 2H), 4.15 (d, J = 14.1 Hz, 1H), 3.58 (d, J = 14.1 Hz, 1H), 3.42 (t, J = | Example 4 |

TABLE 2-continued

| Cpd. No. | ¹H NMR (400 MHz)/LC-MS data | Synthetic method |
|---|---|---|
| | 8.7 Hz, 2H), 0.92 (s, 1H), 0.80 (dd, J = 17.3, 9.1 Hz, 3H). LC-MS: [M + H]+ = 555.16 | |
| 45 | ¹H NMR (400 MHz, methanol-$d_4$) δ 8.83 (s, 1H), 8.77 (brs, 1H), 8.02 (s, 1H), 7.70 (s, 1H), 6.95-6.80 (m, 1H), 6.66 (dd, J = 8.7, 3.9 Hz, 1H), 5.45 (d, J = 14.8 Hz, 1H), 4.60 (t, J = 8.8 Hz, 2H), 4.39 (d, J = 15.0 Hz, 1H), 3.96 (s, 2H), 3.85 (s, 1H), 3.56-3.35 (m, 4H), 3.42 (m, 2H), 3.15-3.10 (m, 1H), 2.32-2.22 (m, 1H), 1.57 (dd, J = 24.7, 12.9 Hz, 2H), 1.49-1.26 (m, 2H). LC-MS: [M + H]+ = 583.20 | Example 4 |
| 46 | ¹H NMR (400 MHz, methanol-$d_4$) δ 8.74 (s, 1H), 8.15 (d, J = 8.1 Hz, 1H), 7.89 (d, J = 8.1 Hz, 1H), 7.65 (s, 1H), 6.86 (t, J = 9.5 Hz, 1H), 6.66 (d, J = 8.6 Hz, 1H), 5.56 (d, J = 14.7 Hz, 1H), 4.60 (t, J = 8.7 Hz, 2H), 4.37 (d, J = 14.9 Hz, 1H), 3.94 (d, J = 11.1 Hz, 2H), 3.69 (d, J = 13.7 Hz, 1H), 3.56-3.35 (m, 4H), 3.42 (t, J = 8.7 Hz, 2H), 3.34-3.30 (m, 1H), 2.32-2.22 (m, 1H), 1.57 (dd, J = 24.7, 12.9 Hz, 2H), 1.49-1.26 (m, 2H). LC-MS: [M + H]+ = 583.20 | Example 4 |
| 47 | ¹H NMR (400 MHz, methanol-$d_4$) δ 8.74 (s, 1H), 8.15 (d, J = 8.1 Hz, 1H), 7.88 (d, J = 8.1 Hz, 1H), 7.63 (s, 1H), 6.87 (dd, J = 10.3, 8.7 Hz, 1H), 6.66 (dd, J = 8.7, 3.9 Hz, 1H), 5.52 (d, J = 14.6 Hz, 1H), 4.85 (s, 2H), 4.67-4.46 (m, 2H), 4.35 (d, J = 14.6 Hz, 1H), 3.91 (dd, J = 13.4, 6.9 Hz, 1H), 3.57 (dd, J = 13.4, 7.4 Hz, 1H), 3.42 (t, J = 8.7 Hz, 2H), 2.44-2.21 (m, 1H), 2.11 (ddt, J = 11.9, 7.6, 4.0 Hz, 2H), 1.98 (q, J = 11.4 Hz, 2H), 1.32 (s, 3H). LC-MS: [M + H]+ = 583.20 | Example 4 |
| 48 | ¹H NMR (400 MHz, methanol-$d_4$) δ 8.83 (s, 1H), 8.75 (s, 1H), 8.05 (s, 1H), 7.69 (s, 1H), 6.93-6.81 (m, 1H), 6.66 (dd, J = 8.7, 3.9 Hz, 1H), 5.42 (d, J = 14.9 Hz, 1H), 4.84 (d, J = 1.0 Hz, 2H), 4.65-4.52 (m, 2H), 4.08 (d, J = 14.2 Hz, 1H), 3.42 (t, J = 8.7 Hz, 2H), 3.08 (d, J = 14.2 Hz, 1H), 2.68 (s, 1H), 1.42-1.18 (m, 6H). LC-MS: [M + H]+ = 557.18 | Example 4 |
| 49 | ¹H NMR (400 MHz, methanol-$d_4$) δ 8.83 (s, 1H), 8.76 (q, J = 1.5 Hz, 1H), 7.94 (s, 1H), 7.66 (s, 1H), 6.86 (t, J = 9.7 Hz, 1H), 6.65 (d, J = 8.5 Hz, 1H), 5.41 (d, J = 14.9 Hz, 1H), 4.84 (d, J = 1.0 Hz, 2H), 4.59 (t, J = 8.8 Hz, 2H), 4.34 (d, J = 14.9 Hz, 1H), 4.00 (dd, J = 13.6, 7.3 Hz, 1H), 3.41 (t, J = 8.7 Hz, 2H), 3.26 (dd, J = 13.6, 6.8 Hz, 1H), 2.31 (q, J = 8.1 Hz, 1H), 2.14 (ddt, J = 17.7, 12.2, 5.1 Hz, 2H), 2.05-1.87 (m, 2H), 1.33 (s, 3H). LC-MS: [M + H]+ = 583.20 | Example 4 |
| 50 | ¹H NMR (400 MHz, methanol-$d_4$) δ 8.77 (s, 1H), 8.13 (d, J = 8.0 Hz, 1H), 7.67-7.51 (m, 2H), 6.85 (dd, J = 10.3, 8.7 Hz, 1H), 6.64 (dd, J = 8.7, 3.8 Hz, 1H), 5.49 (d, J = 15.1 Hz, 1H), 4.82 (s, 2H), 4.65-4.50 (m, 2H), 4.35 (d, J = 15.1 Hz, 1H), 3.98 (dd, J = 13.6, 7.6 Hz, 1H), 3.49 (dd, J = 13.5, 6.4 Hz, 1H), 3.40 (t, J = 8.7 Hz, 2H), 2.72 (s, 3H), 2.33 (q, J = 8.1 Hz, 1H), 2.22-2.04 (m, 2H), 1.99 (td, J = 10.2, 3.8 Hz, 2H), 1.33 (s, 3H). LC-MS: [M + H]+ = 529.22 | Example 4 |
| 51 | ¹H NMR (400 MHz, methanol-$d_4$) δ 8.81 (s, 1H), 8.17 (d, J = 8.1 Hz, 1H), 7.88 (d, J = 8.2 Hz, 1H), 7.66 (s, 1H), 6.94-6.82 (m, 1H), 6.66 (dd, J = 8.7, 3.9 Hz, 1H), 5.56-5.45 (m, 1H), 4.88 (s, 2H), 4.65-4.50 (m, 2H), 4.45-4.41 (m, 1H), 4.12-3.93 (m, 2H), 3.55-3.39 (m, 4H), 3.39-3.36 (m, 2H), 2.58-2.50 (m, 1H), 2.30-2.25 (m, 1H), 1.65-1.60 (m, 1H), 1.38-1.34 (m, 1H). LC-MS: [M + H]+ = 569.18 | Example 4 |
| 52 | ¹H NMR (400 MHz, methanol-$d_4$) δ 8.76 (s, 1H), 8.15 (d, J = 8.1 Hz, 1H), 7.89 (d, J = 8.1 Hz, 1H), 7.65 (s, 1H), 6.85 (t, J = 9.4 Hz, 1H), 6.64 (dd, J = 8.6, 3.8 Hz, 1H), 5.54 (dd, J = 14.8, 6.6 Hz, 1H), 4.85 (s, 2H), 4.59 (t, J = 8.8 Hz, 2H), 4.39 (t, J = 14.0 Hz, 1H), 4.00-3.84 (m, 2H), 3.79-3.75 (m, 2H), 3.64-3.48 (m, 1H), 3.41 (t, J = 8.7 Hz, 2H), 3.24 (q, J = 7.3 Hz, 2H), 2.88 (m, 1H), 2.11-1.92 (m, 2H), 1.84-1.61 (m, 1H). LC-MS: [M + H]+ = 569.18 | Example 4 |

TABLE 2-continued

| Cpd. No. | $^1$H NMR (400 MHz)/LC-MS data | Synthetic method |
|---|---|---|
| 53 | $^1$H NMR (400 MHz, DMSO-d$_6$) δ 8.74 (s, 1H), 8.45 (t, J = 7.2 Hz, 1H), 8.37 (t, J = 5.2 Hz, 1H), 7.64 (s, 1H), 7.44 (s, 1H), 6.93 (dd, J = 10.4, 8.7 Hz, 1H), 6.69 (dd, J = 8.6, 3.9 Hz, 1H), 4.78-4.60 (m, 3H), 4.54 (t, J = 8.7 Hz, 2H), 4.18 (dd, J = 16.0, 5.7 Hz, 1H), 3.88 (s, 3H), 3.30 (t, J = 8.7 Hz, 2H).<br>LC-MS: [M + H]+ = 420.15 | Example 2 |
| 54 | $^1$H NMR (400 MHz, d$_4$-MeOD) δ 8.62 (s, 1H), 7.49-7.52 (m, 2H), 6.85 (t, J = 9.6 Hz, 1H), 6.63 (m, 1H), 4.80 (s, 2H), 4.57 (t, J = 8.4 Hz, 2H), 4.44 (s, 2H), 3.90 (s, 3H), 3.37 (t, J = 8.4 Hz, 2H).<br>LC-MS: [M + H]+ = 421.15 | Example 1 |
| 55 | $^1$H NMR (400 MHz, DMSO-d$_6$) δ 8.80 (s, 1H), 8.21 (d, J = 8.1 Hz, 1H), 7.96 (d, J = 8.0 Hz, 1H), 7.59 (s, 1H), 6.97 (t, J = 9.4 Hz, 1H), 6.72 (dd, J = 8.8, 3.7 Hz, 1H), 5.44 (s, 1H), 4.76 (s, 2H), 4.57 (t, J = 8.7 Hz, 2H), 4.41 (brs, 1H), 3.73 (brs, 1H), 3.38 (t, J = 8.7 Hz, 2H), 3.10 (brs, 1H), 1.28-1.16 (m, 2H), 0.49 (d, J = 39.7 Hz, 2H), 0.24 (s, 1H).<br>LC-MS: [M + H]+ = 539.17 | Example 4 |
| 56 | $^1$H NMR (400 MHz, DMSO-d$_6$) δ 8.73 (s, 1H), 8.33 (s, 1H), 7.33 (s, 1H), 6.96 (t, J = 9.5 Hz, 1H), 6.71 (dd, J = 8.7, 3.8 Hz, 1H), 4.94 (d, J = 16.2 Hz, 1H), 4.72 (s, 2H), 4.55 (t, J = 8.7 Hz, 2H), 4.34 (d, J = 16.2 Hz, 1H), 3.92 (s, 3H), 3.32 (td, J = 8.9, 2.9 Hz, 2H), 2.5-2.45 (m, 1H), 2.28 (s, 3H), 1.04 (d, J = 7.0 Hz, 1H), 0.82 (dd, J = 9.9, 6.3 Hz, 2H), 0.72 (dd, J = 8.3, 4.4 Hz, 1H).<br>LC-MS: [M + H]+ = 474.20 | Example 4 |
| 57 | $^1$H NMR (400 MHz, methanol-d$_4$) δ 8.76 (s, 1H), 8.15 (d, J = 8.1 Hz, 1H), 7.88 (d, J = 8.2 Hz, 1H), 7.65 (s, 1H), 6.94-6.82 (m, 1H), 6.66 (dd, J = 8.7, 3.8 Hz, 1H), 5.54 (d, J = 14.7 Hz, 1H), 4.87 (s, 2H), 4.64-4.57 (m, 2H), 4.52 (d, J = 14.7 Hz, 1H), 4.00-3.89 (m, 1H), 3.75-3.68 (m, 3H), 3.43 (d, J = 8.7 Hz, 2H), 3.40 (s, 3H).<br>LC-MS: [M + H]+ = 543.16 | Example 4 |
| 58 | $^1$H NMR (400 MHz, DMSO-d$_6$) δ 8.84 (s, 1H), 8.80 (t, J = 5.1 Hz, 1H), 8.20 (d, J = 8.1 Hz, 1H), 7.96 (d, J = 8.1 Hz, 1H), 7.58 (s, 1H), 6.96 (t, J = 9.5 Hz, 1H), 6.72 (dd, J = 8.9, 3.8 Hz, 1H), 5.38 (d, J = 14.6 Hz, 1H), 4.77 (d, J = 4.8 Hz, 2H), 4.68 (d, J = 14.6 Hz, 1H), 4.56 (t, J = 8.7 Hz, 2H), 3.79 (d, J = 13.5 Hz, 1H), 3.34 (t, J = 8.7 Hz, 2H), 3.27 (d, J = 13.5 Hz, 1H), 1.18 (s, 3H), 1.13 (s, 3H).<br>LC-MS: [M + H]+ = 557.18 | Example 4 |
| 59 | $^1$H NMR (400 MHz, DMSO-d$_6$) δ 8.85 (brs, 2H), 8.22 (d, J = 8.1 Hz, 1H), 7.94 (d, J = 8.1 Hz, 1H), 7.56 (s, 1H), 6.95 (t, J = 9.5 Hz, 1H), 6.71 (dd, J = 8.8, 3.8 Hz, 1H), 5.37 (d, J = 15.0 Hz, 1H), 4.76 (d, J = 3.7 Hz, 2H), 4.53 (dt, J = 20.8, 7.8 Hz, 3H), 4.37 (d, J = 15.0 Hz, 1H), 3.34 (t, J = 8.7 Hz, 2H), 1.27 (d, J = 6.7 Hz, 3H), 1.07 (d, J = 6.5 Hz, 3H).<br>LC-MS: [M + H]+ = 527.17 | Example 4 |
| 60 | $^1$H NMR (400 MHz, DMSO-d$_6$) δ 8.79 (s, 1H), 8.66 (t, J = 5.1 Hz, 1H), 7.98 (d, J = 1.8 Hz, 1H), 7.81-7.67 (m, 2H), 7.47 (s, 1H), 6.96 (dd, J = 10.3, 8.6 Hz, 1H), 6.71 (dd, J = 8.6, 3.9 Hz, 1H), 5.26 (d, J = 15.1 Hz, 1H), 4.76 (d, J = 4.9 Hz, 2H), 4.56 (t, J = 8.8 Hz, 2H), 4.38 (d, J = 15.1 Hz, 1H), 4.03 (s, 1H), 3.88 (s, 2H), 3.35-3.30 (m, 3H), 2.47-2.21 (m, 3H), 1.59 (d, J = 11.9 Hz, 1H), 0.95 (d, J = 12.2 Hz, 1H).<br>LC-MS: [M + H]+ = 568.54 | Example 4 |
| 61 | LC-MS: [M + H]+ = 530.47 | Example 4 |
| 62 | $^1$H NMR (400 MHz, DMSO-d$_6$) δ 8.84 (s, 1H), 8.70 (t, J = 5.1 Hz, 1H), 7.85-7.69 (m, 3H), 7.52 (s, 1H), 6.96 (dd, J = 10.3, 8.6 Hz, 1H), 6.72 (dd, J = 8.7, 3.9 Hz, 1H), 5.33 (d, J = 15.1 Hz, 1H), 4.77 (d, J = 4.8 Hz, 2H), 4.56 (t, J = 8.7 Hz, 2H), 4.36 (d, J = 15.1 Hz, 1H), 4.10 (dd, J = 33.2, 14.7 Hz, 1H), 3.34 (t, J = 8.7 Hz, 2H), 3.21 (dd, J = 14.7, 12.3 Hz, 1H), 1.39 (dd, J = 40.0, 21.9 Hz, 6H).<br>LC-MS: [M + H]+ = 558.52 | Example 4 |
| 63 | $^1$H NMR (400 MHz, DMSO-d$_6$) δ 8.85 (s, 1H), 8.72 (t, J = 5.1 Hz, 1H), 7.96 (d, J = 1.9 Hz, 1H), 7.80 (dd, J = 8.3, 1.9 Hz, 1H), 7.73 (d, J = 8.2 Hz, 1H), 7.53 (s, 1H), 6.96 (dd, J = 10.3, 8.7 Hz, 1H), 6.71 (dd, J = 8.7, | Example 4 |

TABLE 2-continued

| Cpd. No. | ¹H NMR (400 MHz)/LC-MS data | Synthetic method |
|---|---|---|
| | 3.9 Hz, 1H), 5.36 (d, J = 15.2 Hz, 1H), 4.77 (d, J = 4.0 Hz, 2H), 4.56 (t, J = 8.7 Hz, 2H), 4.33 (dd, J = 15.3, 3.0 Hz, 2H), 3.53 (td, J = 14.2, 9.4 Hz, 1H), 3.34 (t, J = 8.7 Hz, 2H), 1.66 (t, J = 19.3 Hz, 3H). LC-MS: [M + H]+ = 562.48 | |
| 64 | LC-MS: [M + H]+ = 474.48 | Example 4 |
| 65 | ¹H NMR (400 MHz, DMSO-d₆) δ 8.84 (s, 1H), 8.56 (d, J = 6.1 Hz, 1H), 7.53 (ddd, J = 19.8, 9.1, 4.3 Hz, 2H), 7.38 (s, 1H), 7.27 (td, J = 8.5, 2.8 Hz, 1H), 6.95 (dd, J = 10.3, 8.7 Hz, 1H), 6.71 (dd, J = 8.6, 3.9 Hz, 1H), 5.15 (d, J = 15.0 Hz, 2H), 4.77-4.71 (m, 2H), 4.55 (t, J = 8.7 Hz, 2H), 4.25 (d, J = 15.0 Hz, 1H), 4.03 (ddt, J = 12.2, 7.9, 3.9 Hz, 1H), 3.90 (td, J = 12.2, 4.3 Hz, 2H), 3.39-3.28 (m, 4H), 2.30 (qd, J = 12.0, 4.4 Hz, 1H), 1.61 (d, J = 12.3 Hz, 1H), 1.11 (d, J = 12.4 Hz, 1H). LC-MS: [M + H]+ = 518.53 | Example 4 |
| 66 | ¹H NMR (400 MHz, DMSO-d₆) δ 8.81 (s, 1H), 8.67 (d, J = 6.4 Hz, 1H), 7.99 (d, J = 1.9 Hz, 1H), 7.77 (dd, J = 8.3, 1.9 Hz, 1H), 7.70 (d, J = 8.2 Hz, 1H), 7.48 (s, 1H), 6.95 (dd, J = 10.2, 8.7 Hz, 1H), 6.70 (dd, J = 8.6, 3.8 Hz, 1H), 5.23 (d, J = 14.8 Hz, 1H), 4.74 (d, J = 4.7 Hz, 2H), 4.55 (t, J = 8.8 Hz, 2H), 4.24 (d, J = 15.0 Hz, 1H), 3.85 (d, J = 11.4 Hz, 2H), 3.66 (dd, J = 12.9, 8.1 Hz, 1H), 3.33 (t, J = 8.7 Hz, 2H), 3.28-3.15 (m, 2H), 2.96 (s, 1H), 2.07 (s, 1H), 1.56-1.08 (m, 4H). LC-MS: [M + H]+ = 582.20 | Example 4 |
| 67 | ¹H NMR (400 MHz, DMSO-d₆) δ 8.78 (s, 1H), 8.67 (t, J = 5.1 Hz, 1H), 7.82-7.67 (m, 3H), 7.53 (s, 1H), 6.95 (dd, J = 10.3, 8.7 Hz, 1H), 6.70 (dd, J = 8.6, 3.9 Hz, 1H), 5.21 (d, J = 15.0 Hz, 1H), 4.75 (d, J = 4.5 Hz, 2H), 4.55 (t, J = 8.8 Hz, 2H), 4.21 (d, J = 15.0 Hz, 1H), 3.33 (d, J = 17.5 Hz, 2H), 2.31-2.20 (m, 1H), 1.02 (tq, J = 6.8, 4.2, 3.4 Hz, 1H), 0.90-0.69 (m, 3H). LC-MS: [M + H]+ = 524.49 | Example 4 |
| 68 | ¹H NMR (400 MHz, DMSO-d₆) δ 8.84 (s, 1H), 8.76-8.62 (m, 1H), 7.89 (dd, J = 8.1, 1.9 Hz, 1H), 7.78 (dd, J = 8.4, 2.1 Hz, 1H), 7.76-7.63 (m, 1H), 7.50 (s, 1H), 6.95 (dd, J = 10.3, 8.7 Hz, 1H), 6.70 (dd, J = 8.7, 3.9 Hz, 1H), 5.27 (d, J = 15.0 Hz, 1H), 4.75 (d, J = 4.3 Hz, 2H), 4.55 (t, J = 8.8 Hz, 2H), 4.32 (dd, J = 15.1, 9.3 Hz, 1H), 3.91-3.38 (m, 7H), 3.38-3.25 (m, 3H), 3.09 (ddd, J = 53.1, 13.6, 5.9 Hz, 1H). LC-MS: [M + H]+ = 584.54 | Example 4 |
| 69 | ¹H NMR (400 MHz, DMSO-d₆) δ 8.83 (s, 1H), 8.43 (t, J = 4.4 Hz, 1H), 8.21 (d, J = 8.1 Hz, 1H), 7.96 (d, J = 8.1 Hz, 1H), 7.58 (s, 1H), 7.40 (td, J = 8.4, 6.9 Hz, 1H), 6.96 (d, J = 8.4 Hz, 1H), 6.88 (ddd, J = 9.3, 8.4, 0.9 Hz, 1H), 5.38 (d, J = 14.7 Hz, 1H), 4.77 (d, J = 4.2 Hz, 2H), 4.24 (d, J = 14.7 Hz, 1H), 3.86 (s, 3H), 2.62 (tt, J = 7.5, 4.2 Hz, 1H), 1.04-0.87 (m, 2H), 0.77 (tt, J = 9.4, 6.1 Hz, 1H), 0.72-0.62 (m, 1H). LC-MS: [M + H]+ = 513.46 | Example 4 |
| 70 | ¹H NMR (400 MHz, DMSO-d₆) δ 9.07 (s, 2H), 8.88 (s, 1H), 8.68 (s, 1H), 8.54 (t, J = 4.4 Hz, 1H), 8.16 (s, 1H), 7.54 (s, 1H), 7.42 (td, J = 8.4, 6.8 Hz, 1H), 6.97 (d, J = 8.4 Hz, 1H), 6.90 (t, J = 8.9 Hz, 1H), 4.86-4.68 (m, 2H), 3.87 (s, 3H), 2.62 (tt, J = 7.5, 4.2 Hz, 1H), 0.82-0.48 (m, 4H). LC-MS: [M + H]+ = 513.46 | Example 4 |
| 71 | ¹H NMR (400 MHz, DMSO-d₆) δ 8.85 (s, 1H), 8.44 (s, 1H), 8.22 (d, J = 8.1 Hz, 1H), 7.95 (d, J = 8.2 Hz, 1H), 7.56 (s, 1H), 7.40 (td, J = 8.4, 6.9 Hz, 1H), 6.96 (d, J = 8.4 Hz, 1H), 6.88 (t, J = 8.9 Hz, 1H), 5.38 (d, J = 15.1 Hz, 1H), 4.83-4.71 (m, 2H), 4.49 (p, J = 6.9 Hz, 2H), 4.36 (d, J = 15.1 Hz, 1H), 3.35 (q, J = 8.5 Hz, 2H), 1.26 (d, J = 6.9 Hz, 3H), 1.06 (d, J = 6.7 Hz, 3H). LC-MS: [M + H]+ = 515.48 | Example 4 |
| 72 | LC-MS: [M + H]+ = 531.45 | Example 4 |
| 73 | ¹H NMR (400 MHz, DMSO-d₆) δ 9.02-8.67 (m, 2H), 8.11 (d, J = 7.3 Hz, 1H), 7.62 (d, J = 7.4 Hz, 1H), 6.96 (q, J = 9.1 Hz, 1H), 6.72 (dq, J = 8.4, 3.7 Hz, 1H), 5.26 (dd, J = 15.2, 7.2 Hz, 2H), 4.78 (d, J = 6.4 Hz, 2H), 4.56 (q, J = 8.5 Hz, 2H), 4.39 (dd, J = 15.4, 7.0 Hz, 1H), 4.27 (q, J = 7.3 Hz, 1H), 3.35 (q, J = 8.5 | Example 4 |

TABLE 2-continued

| Cpd. No. | $^1$H NMR (400 MHz)/LC-MS data | Synthetic method |
|---|---|---|
| | Hz, 2H), 1.41-1.23 (m, 3H), 1.23-1.06 (m, 3H).<br>LC-MS: [M + H]+ = 527.49 | |
| 74 | LC-MS: [M + H]+ = 581.22 | Example 4 |
| 75 | $^1$H NMR (400 MHz, DMSO-d$_6$) δ 9.45 (s, 1H), 8.78 (s, 1H), 8.60 (t, J = 5.0 Hz, 1H), 7.57 (dd, J = 8.7, 5.7 Hz, 1H), 7.45 (dd, J = 9.3, 2.8 Hz, 1H), 7.38 (s, 1H), 7.29 (td, J = 8.6, 2.8 Hz, 1H), 6.95 (dd, J = 10.3, 8.7 Hz, 1H), 6.70 (dd, J = 8.6, 3.8 Hz, 1H), 5.19 (d, J = 15.2 Hz, 1H), 4.73 (d, J = 5.0 Hz, 2H), 4.55 (t, J = 8.7 Hz, 2H), 4.19 (d, J = 15.2 Hz, 1H), 4.05-3.88 (m, 1H), 3.33 (d, J = 8.8 Hz, 4H), 3.04 (m, 4H), 2.81-2.64 (m, 4H), 1.91 (d, J = 13.4 Hz, 1H), 1.35-1.15 (m, 3H).<br>LC-MS: [M + H]+ = 530.22 | Example 4 |
| 76 | $^1$H NMR (400 MHz, DMSO-d$_6$) δ 8.82 (d, J = 2.3 Hz, 1H), 8.59 (t, J = 5.2 Hz, 1H), 7.54 (td, J = 8.9, 4.2 Hz, 2H), 7.42 (d, J = 1.3 Hz, 1H), 7.31 (td, J = 8.5, 2.7 Hz, 1H), 7.03-6.89 (m, 1H), 6.71 (dd, J = 8.7, 3.8 Hz, 1H), 5.24 (d, J = 15.2 Hz, 1H), 4.74 (d, J = 4.7 Hz, 2H), 4.56 (t, J = 8.7 Hz, 2H), 4.35 (q, J = 15.5 Hz, 2H), 4.18 (d, J = 15.2 Hz, 1H), 3.33 (t, J = 8.7 Hz, 2H), 1.67 (t, J = 19.2 Hz, 3H).<br>LC-MS: [M + H]+ = 512.48 | Example 4 |
| 77 | $^1$H NMR (400 MHz, DMSO-d$_6$) δ 8.85 (d, J = 10.4 Hz, 2H), 8.23 (d, J = 8.1 Hz, 1H), 8.00 (d, J = 8.2 Hz, 1H), 7.63 (s, 1H), 7.01-6.92 (m, 1H), 6.72 (dd, J = 8.7, 3.9 Hz, 1H), 5.54 (d, J = 14.9 Hz, 1H), 4.77 (d, J = 4.9 Hz, 2H), 4.56 (t, J = 8.8 Hz, 2H), 4.30 (dd, J = 13.9, 7.1 Hz, 3H), 3.35 (q, J = 8.5 Hz, 2H), 1.66 (t, J = 19.4 Hz, 3H).<br>LC-MS: [M + H]+ = 563.48 | Example 4 |
| 78 | $^1$H NMR (400 MHz, DMSO-d$_6$) δ 8.82 (s, 1H), 8.57 (d, J = 5.6 Hz, 1H), 7.55 (dd, J = 8.7, 5.7 Hz, 1H), 7.45-7.33 (m, 2H), 7.30 (td, J = 8.5, 2.7 Hz, 1H), 6.95 (dd, J = 10.3, 8.6 Hz, 1H), 6.70 (dd, J = 8.7, 3.8 Hz, 1H), 5.21 (d, J = 15.0 Hz, 1H), 4.82-4.67 (m, 2H), 4.55 (t, J = 8.7 Hz, 2H), 4.24 (d, J = 15.0 Hz, 1H), 4.08 (dd, J = 33.6, 15.1 Hz, 1H), 3.33 (t, J = 8.9 Hz, 3H), 1.44 (d, J = 21.5 Hz, 3H), 1.31 (d, J = 22.2 Hz, 3H).<br>LC-MS: [M + H]+ = 508.52 | Example 4 |
| 79 | $^1$H NMR (400 MHz, DMSO-d$_6$) δ 8.78 (s, 1H), 8.56 (t, J = 5.1 Hz, 1H), 7.52 (ddd, J = 12.1, 9.0, 4.2 Hz, 2H), 7.39 (s, 1H), 7.28 (td, J = 8.6, 2.8 Hz, 1H), 6.95 (dd, J = 10.3, 8.7 Hz, 1H), 6.70 (dd, J = 8.6, 3.8 Hz, 1H), 5.19 (d, J = 15.0 Hz, 1H), 4.71 (dd, J = 15.6, 4.8 Hz, 2H), 4.65-4.46 (m, 3H), 4.18 (d, J = 15.0 Hz, 1H), 4.12-3.93 (m, 1H), 3.47 (td, J = 15.0, 7.5 Hz, 2H), 3.33 (t, J = 8.7 Hz, 2H).<br>LC-MS: [M + H]+ = 480.46 | Example 4 |
| 80 | $^1$H NMR (400 MHz, DMSO-d$_6$) δ 8.80 (s, 1H), 8.58 (t, J = 4.8 Hz, 1H), 7.60 (d, J = 9.2 Hz, 1H), 7.41(d, J = 2.8 Hz, 1H), 7.41 (s, 1H), 7.26-7.31 (m, 1H), 6.95 (t, J = 9.6 Hz, 1H), 6.70 (dd, J = 8.6, 3.9 Hz, 1H), 6.26 (t, J = 56.4 Hz, 1H), 5.24 (d, J = 14.9 Hz, 1H), 4.73 (d, J = 4.9 Hz, 2H), 4.55 (t, J = 8.9 Hz, 2H), 4.19 (d, J = 15.2 Hz, 1H), 4.04-4.14 (m, 1H), 3.58-3.69 (m, 2H), 3.31-3.35 (m, 2H).<br>LC-MS: [M + H]+ = 548.46 | Example 4 |
| 81 | $^1$H NMR (400 MHz, DMSO-d$_6$) δ 8.83 (s, 1H), 8.72 (t, J = 4.8 Hz, 1H), 8.07 (d, J = 1.2 Hz, 1H), 7.79-7.70 (m, 2H), 7.52 (s, 1H), 6.95 (dd, J = 10.3, 8.6 Hz, 1H), 6.71 (dd, J = 8.6, 3.9 Hz, 1H), 6.24 (t, J = 56.4 Hz, 1H), 5.34 (d, J = 15.2 Hz, 1H), 4.75 (d, J = 4.8 Hz, 2H), 4.56 (t, J = 8.9 Hz, 2H), 4.34 (d, J = 15.1 Hz, 1H), 4.03-4.14 (m, 1H), 3.60-3.71 (m, 2H), 3.31-3.36 (m, 2H).<br>LC-MS: [M + H]+ = 548.46 | Example 4 |
| 82 | $^1$H NMR (400 MHz, DMSO-d$_6$) δ 8.87 (d, J = 2.0 Hz, 2H), 8.83 (s, 1H), 8.18 (s, 1H), 7.67 (s, 1H), 6.96 (dd, J = 10.3, 8.7 Hz, 1H), 6.71 (dd, J = 8.7, 3.9 Hz, 1H), 5.48-5.28 (m, 1H), 4.77 (d, J = 4.2 Hz, 2H), 4.56 (t, J = 8.8 Hz, 2H), 4.41-4.20 (m, 2H), 3.62 (td, J = 14.3, 10.0 Hz, 1H), 3.34 (t, J = 8.7 Hz, 2H), 1.66 (t, J = 19.3 Hz, 3H).<br>LC-MS: [M + H]+ = 563.15 | Example 4 |

TABLE 2-continued

| Cpd. No. | ¹H NMR (400 MHz)/LC-MS data | Synthetic method |
|---|---|---|
| 83 | ¹H NMR (400 MHz, DMSO-d$_6$) δ 8.84 (s, 1H), 8.74 (t, J = 5.1 Hz, 1H), 8.17 (d, J = 1.9 Hz, 1H), 7.80 (dd, J = 8.5, 1.9 Hz, 1H), 7.72 (d, J = 8.2 Hz, 1H), 7.54 (s, 1H), 6.96 (dd, J = 10.3, 8.7 Hz, 1H), 6.72 (dd, J = 8.6, 3.9 Hz, 1H), 5.38 (d, J = 15.3 Hz, 1H), 4.76 (d, J = 5.0 Hz, 2H), 4.67-4.58 (m, 1H), 4.56 (t, J = 8.8 Hz, 2H), 4.35 (d, J = 15.3 Hz, 1H), 4.17-4.03 (m, 1H), 3.34 (t, J = 8.8 Hz, 2H).<br>LC-MS: [M + H]+ = 566.13 | Example 4 |
| 84 | ¹H NMR (400 MHz, DMSO-d$_6$) δ 8.85 (dd, J = 14.5, 5.1 Hz, 3H), 8.36 (s, 1H), 7.69 (s, 1H), 7.02-6.92 (m, 1H), 6.72 (dd, J = 8.6, 3.9 Hz, 1H), 5.43 (d, J = 15.1 Hz, 1H), 4.77 (d, J = 5.0 Hz, 2H), 4.69-4.51 (m, 3H), 4.38 (d, J = 15.1 Hz, 1H), 4.21-4.11 (m, 1H), 3.34 (t, J = 8.8 Hz, 2H).<br>LC-MS: [M + H]+ = 567.13 | Example 4 |
| 85 | ¹H NMR (400 MHz, DMSO-d$_6$) δ 8.87 (s, 1H), 8.81 (d, J = 7.0 Hz, 2H), 8.02 (s, 1H), 7.66 (s, 1H), 6.96 (t, J = 9.5 Hz, 1H), 6.72 (dd, J = 8.6, 3.8 Hz, 1H), 5.34 (d, J = 15.2 Hz, 1H), 4.77 (d, J = 4.8 Hz, 2H), 4.56 (t, J = 8.8 Hz, 2H), 4.36 (d, J = 15.1 Hz, 1H), 4.21 (td, J = 8.3, 3.7 Hz, 1H), 3.34 (t, J = 8.8 Hz, 2H), 3.19-3.02 (m, 2H), 2.92 (d, J = 19.6 Hz, 2H).<br>LC-MS: [M + H]+ = 575.15 | Example 4 |
| 86 | ¹H NMR (400 MHz, DMSO-d$_6$) δ 8.77 (s, 1H), 8.64 (t, J = 5.1 Hz, 1H), 7.42 (s, 1H), 6.95 (dd, J = 10.3, 8.7 Hz, 1H), 6.70 (dd, J = 8.6, 3.9 Hz, 1H), 5.03 (d, J = 15.4 Hz, 1H), 4.72 (d, J = 4.9 Hz, 2H), 4.55 (t, J = 8.8 Hz, 2H), 4.19 (d, J = 15.4 Hz, 1H), 3.30 (t, J = 8.7 Hz, 2H), 2.78 (tt, J = 7.6, 4.1 Hz, 1H), 2.66 (s, 3H), 1.02 (ddt, J = 9.2, 6.8, 4.3 Hz, 1H), 0.89 (dtd, J = 9.6, 7.0, 5.3 Hz, 1H), 0.77 (dtd, J = 9.6, 7.0, 5.1 Hz, 1H), 0.64 (ddt, J = 9.2, 6.9, 4.8 Hz, 1H).<br>LC-MS: [M + H]+ = 477.14 | Example 4 |
| 87 | ¹H NMR (400 MHz, DMSO-d$_6$) δ 8.76 (s, 1H), 8.58 (t, J = 5.1 Hz, 1H), 7.51 (d, J = 5.1 Hz, 1H), 7.46 (s, 1H), 7.16 (d, J = 5.1 Hz, 1H), 6.95 (dd, J = 10.3, 8.6 Hz, 1H), 6.71 (dd, J = 8.7, 3.9 Hz, 1H), 5.01 (d, J = 15.2 Hz, 1H), 4.72 (d, J = 4.9 Hz, 2H), 4.55 (t, J = 8.7 Hz, 2H), 4.10 (d, J = 15.2 Hz, 1H), 3.32 (t, J = 8.7 Hz, 2H), 2.50 (m, 1H), 1.04-0.92 (m, 1H), 0.88-0.65 (m, 3H).<br>LC-MS: [M + H]+ = 462.13 | Example 4 |
| 88 | ¹H NMR (400 MHz, DMSO-d$_6$) δ 8.75 (s, 1H), 8.50 (t, J = 5.1 Hz, 1H), 7.63-7.50 (m, 2H), 7.32 (d, J = 5.3 Hz, 1H), 6.95 (dd, J = 10.3, 8.7 Hz, 1H), 6.70 (dd, J = 8.6, 3.9 Hz, 1H), 5.31 (d, J = 16.1 Hz, 1H), 4.80-4.65 (m, 2H), 4.55 (t, J = 8.7 Hz, 2H), 4.17 (d, J = 16.1 Hz, 1H), 3.32 (t, J = 8.7 Hz, 2H), 2.72-2.59 (m, 1H), 1.04-0.93 (m, 1H), 0.77 (dddd, J = 16.2, 10.0, 7.6, 4.4 Hz, 3H).<br>LC-MS: [M + H]+ = 462.13 | Example 4 |
| 89 | ¹H NMR (400 MHz, DMSO-d$_6$) δ 8.86-8.80 (m, 2H), 8.27 (s, 1H), 7.66 (s, 1H), 6.96 (t, J = 8.8 Hz, 1H), 6.71 (dd, J = 8.6, 3.8 Hz, 1H), 6.24 (t, J = 56.4 Hz, 1H), 5.40 (d, J = 14.8 Hz, 1H), 4.76 (d, J = 4.0 Hz, 1H), 4.56 (d, J = 8.8 Hz, 1H), 4.37 (d, J = 14.8 Hz, 1H), 4.13-4.03 (m, 1H), 3.77-3.68 (m, 2H), 3.36-3.32 (m, 2H).<br>LC-MS: [M + H]+ = 549.13 | Example 4 |
| 90 | ¹H NMR (400 MHz, DMSO-d$_6$) δ 8.86 (s, 1H), 8.85-8.74 (m, 2H), 8.15 (s, 1H), 7.63 (s, 1H), 6.96 (dd, J = 10.3, 8.7 Hz, 1H), 6.72 (dd, J = 8.7, 3.9 Hz, 1H), 5.25 (d, J = 14.8 Hz, 1H), 4.77 (d, J = 4.8 Hz, 2H), 4.56 (t, J = 8.8 Hz, 2H), 4.32 (d, J = 14.8 Hz, 1H), 3.78 (dq, J = 13.8, 6.9 Hz, 1H), 3.34 (t, J = 8.9 Hz, 2H), 3.12 (dq, J = 13.6, 6.7 Hz, 1H), 1.10 (t, J = 7.0 Hz, 3H).<br>LC-MS: [M + H]+ = 513.15 | Example 4 |
| 91 | ¹H NMR (400 MHz, DMSO-d$_6$) δ 8.89 (t, J = 5.1 Hz, 1H), 8.82 (s, 1H), 7.68 (s, 1H), 6.95 (dd, J = 10.3, 8.7 Hz, 1H), 6.71 (dd, J = 8.7, 3.9 Hz, 1H), 5.22 (d, J = 15.6 Hz, 1H), 4.74 (d, J = 4.8 Hz, 2H), 4.55 (t, J = 8.7 Hz, 2H), 4.35 (d, J = 15.6 Hz, 1H), 3.32 (t, J = 8.7 Hz, 2H), 2.76 (tt, J = 7.4, 4.1 Hz, 1H), 1.03-0.73 (m, 3H), 0.71-0.60 (m, 1H).<br>LC-MS: [M + H]+ = 531.11 | Example 4 |

TABLE 2-continued

| Cpd. No. | ¹H NMR (400 MHz)/LC-MS data | Synthetic method |
|---|---|---|
| 92 | LC-MS: [M + H]+ = 488.15 | Example 4 |
| 93 | ¹H NMR (400 MHz, DMSO-d$_6$) δ 8.81 (s, 1H), 8.68 (t, J = 5.0 Hz, 1H), 7.97 (d, J = 1.9 Hz, 1H), 7.85-7.66 (m, 2H), 7.47 (d, J = 3.8 Hz, 1H), 6.95 (dd, J = 10.3, 8.7 Hz, 1H), 6.71 (dd, J = 8.6, 3.9 Hz, 1H), 5.30 (d, J = 15.0 Hz, 1H), 4.75 (d, J = 4.5 Hz, 2H), 4.55 (t, J = 8.8 Hz, 2H), 4.39 (d, J = 15.0 Hz, 1H), 4.07-3.88 (m, 3H), 3.33 (t, J = 8.7 Hz, 2H), 2.42-2.19 (m, 2H), 1.59 (dt, J = 13.0, 7.7 Hz, 1H), 1.12 (d, J = 6.2 Hz, 3H), 1.08 (dd, J = 15.7, 6.1 Hz, 1H), 1.02 (d, J = 6.3 Hz, 3H), 0.84 (dt, J = 12.2, 5.7 Hz, 1H).<br>LC-MS: [M + H]+ = 596.22 | Example 4 |
| 94 | ¹H NMR (400 MHz, DMSO-d$_6$) δ 9.04 (t, J = 4.8 Hz, 1H), 8.88 (s, 1H), 8.61 (dd, J = 3.6, 1.4 Hz, 1H), 8.25 (dd, J = 8.0, 1.6 Hz, 1H), 8.14 (s, 1H), 7.53 (dd, J = 8.0, 4.4 Hz, 1H), 6.96 (t, J = 8.8 Hz, 1H), 6.71 (dd, J = 8.8, 4.0 Hz, 1H), 5.05 (d, J = 14.0 Hz, 1H), 4.79 (t, J = 6.4 Hz, 2H), 4.53-4.58 (m, 3H), 3.34 (t, J = 8.8 Hz, 2H).<br>LC-MS: [M + H]+ = 438.09 | Example 6 |
| 95 | ¹H NMR (400 MHz, DMSO-d$_6$) δ 8.98 (t, J = 4.8 Hz, 1H), 8.86 (s, 1H), 8.15 (d, J = 8.4 Hz, 1H), 8.10 (s, 1H), 7.40 (d, J = 8.4 Hz, 1H), 6.96 (t, J = 8.8 Hz, 1H), 6.71 (dd, J = 8.4, 4.0 Hz, 1H), 5.01 (d, J = 14.0 Hz, 1H), 4.78 (d, J = 5.6 Hz, 2H), 4.57-4.53 (m, 3H), 3.33 (t, J = 8.8 Hz, 2H), 2.55 (s, 3H).<br>LC-MS: [M + H]+ = 452.11 | Example 6 |
| 96 | LC-MS: [M + H]+ = 469.10 | Example 6 |
| 97 | LC-MS: [M + H]+ = 466.12 | Example 6 |
| 98 | LC-MS: [M + H]+ = 597.21 | Example 4 |
| 99 | ¹H NMR (400 MHz, CDCl$_3$) δ 8.60 (s, 1H), 7.55-7.35 (m, 6H), 6.77 (dd, J = 10.1, 8.7 Hz, 1H), 6.61 (dd, J = 8.7, 3.9 Hz, 1H), 4.82 (s, 2H), 4.61 (t, J = 8.7 Hz, 2H), 3.40 (t, J = 8.7 Hz, 2H), 2.86 (s, 3H).<br>LC-MS: [M + H]+ = 439.12. | Example 14 |
| 100 | ¹H NMR (400 MHz, CDCl$_3$) δ 8.12 (s, 1H), 8.03 (d, J = 8.4 Hz, 2H), 7.68 (d, J = 8.4 Hz, 2H), 7.49 (s, 1H), 6.95-6.83 (m, 1H), 6.72 (dd, J = 8.7, 4.0 Hz, 1H), 5.68 (s, 1H), 4.88 (d, J = 4.9 Hz, 2H), 4.66 (t, J = 8.7 Hz, 2H), 3.45 (t, J = 8.7 Hz, 2H), 3.16 (s, 3H), 3.14 (s, 3H).<br>LC-MS: [M + H]+ = 517.09 | Example 14 |
| 101 | ¹H NMR (400 MHz, methanol-d$_4$) δ 8.78 (d, J = 1.5 Hz, 1H), 8.73 (dd, J = 5.9, 1.8 Hz, 1H), 8.44 (dt, J = 7.9, 1.5 Hz, 1H), 7.95 (dd, J = 7.8, 6.0 Hz, 1H), 7.59 (d, J = 0.9 Hz, 1H), 6.88 (td, J = 9.5, 9.1, 1.9 Hz, 1H), 6.67 (dd, J = 8.6, 4.0 Hz, 1H), 4.88 (d, J = 4.9 Hz, 2H), 4.60 (td, J = 8.7, 1.5 Hz, 2H), 3.43 (t, J = 8.7 Hz, 2H), 3.11-3.00 (m, 3H), 2.63 (s, 3H).<br>LC-MS: [M + H]+ = 454.12. | Example 14 |
| 102 | ¹H NMR (400 MHz, CDCl$_3$) δ 8.74 (d, J = 2.1 Hz, 1H), 8.39 (s, 1H), 8.05-7.91 (m, 1H), 7.78 (dd, J = 8.1, 0.7 Hz, 1H), 7.49 (s, 1H), 6.89-6.72 (m, 1H), 6.65 (dd, J = 8.7, 3.9 Hz, 1H), 6.46 (s, 1H), 4.85 (s, 2H), 4.63 (t, J = 8.7 Hz, 2H), 3.41 (t, J = 8.7 Hz, 2H), 3.08 (s, 3H).<br>LC-MS: [M + H]+ = 508.09. | Example 14 |
| 103 | ¹H NMR (400 MHz, methanol-d$_4$) δ 8.87-8.80 (m, 1H), 8.76 (d, J = 0.9 Hz, 1H), 8.51 (dd, J = 8.3, 2.1 Hz, 1H), 7.95 (d, J = 8.3 Hz, 1H), 7.62 (d, J = 0.8 Hz, 1H), 6.91-6.82 (m, 1H), 6.66 (dt, J = 9.0, 3.4 Hz, 1H), 4.85 (s, 2H), 4.60 (td, J = 8.7, 1.4 Hz, 2H), 3.41 (t, J = 8.7 Hz, 2H), 3.18 (s, 3H), 2.86 (s, 3H).<br>LC-MS: [M + H]+ = 454.12 | Example 14 |
| 104 | ¹H NMR (400 MHz, methanol-d$_4$) δ 8.68 (s, 1H), 7.52-7.31 (m, 3H), 7.18-7.04 (m, 2H), 6.92-6.81 (m, 1H), 6.66 (dd, J = 8.6, 3.8 Hz, 1H), 4.84 (d, J = 1.0 Hz, 2H), 4.59 (t, J = 8.7 Hz, 2H), 3.39 (t, J = 8.7 Hz, 2H), 3.00 (s, 3H).<br>LC-MS: [M + H]+ = 457.10 | Example 14 |
| 105 | ¹H NMR (400 MHz, methanol-d$_4$) δ 8.79 (dd, J = 2.0, 1.0 Hz, 1H), 8.75 (s, 1H), 8.23-8.01 (m, 2H), 7.57 (s, 1H), 6.93-6.80 (m, 1H), 6.67 (dd, J = 8.6, 3.9 Hz, 1H), 4.84 (d, J = 1.0 Hz, 2H), 4.60 (t, J = 8.7 Hz, 2H), 3.41 (t, J = 8.8 Hz, 2H), 3.28 (s, 3H), 3.14 (s, 3H).<br>LC-MS: [M + H]+ = 518.08 | Example 14 |

TABLE 2-continued

| Cpd. No. | $^1$H NMR (400 MHz)/LC-MS data | Synthetic method |
|---|---|---|
| 106 | $^1$H NMR (400 MHz, methanol-d$_4$) δ 8.63 (s, 1H), 7.76 (s, 1H), 7.59 (s, 1H), 7.44 (s, 1H), 6.85 (t, J = 9.6 Hz, 1H), 6.64 (dd, J = 8.4, 3.6 Hz, 1H), 4.81 (s, 2H), 4.57 (t, J = 8.4 Hz, 2H), 3.94 (s, 3H), 3.36 (t, J = 8.8 Hz, 2H), 3.00 (s, 3H), 2.66 (s, 2H). LC-MS: [M + H]+ = 443.12 | Example 14 |
| 107 | $^1$H NMR (400 MHz, methanol-d$_4$) δ 8.74 (s, 1H), 8.73-8.67 (m, 1H), 8.06 (d, J = 2.2 Hz, 1H), 7.77 (d, J = 8.0 Hz, 1H), 7.54 (s, 1H), 6.96-6.77 (m, 2H), 6.73-6.61 (m, 1H), 4.86 (d, J = 1.1 Hz, 2H), 4.60 (t, J = 8.7 Hz, 2H), 3.41 (t, J = 8.7 Hz, 2H), 3.11 (s, 3H). LC-MS: [M + H]+ = 490.10 | Example 14 |
| 108 | $^1$H NMR (400 MHz, methanol-d$_4$) δ 8.54 (s, 1H), 8.05 (d, J = 8.0 Hz, 1H), 7.53 (d, J = 8.0 Hz, 1H), 7.33 (s, 1H), 6.65 (t, J = 9.2 Hz, 1H), 6.44 (dd, J = 8.6, 3.6 Hz, 1H), 4.63 (t, J = 6.4 Hz, 2H), 4.37 (t, J = 8.8 Hz, 1H), 3.20 (t, J = 8.8 Hz, 2H), 2.85 (s, 3H), 2.60 (s, 3H), 2.36 (s, 3H). LC-MS: [M + H]+ = 468.14 | Example 14 |
| 109 | LC-MS: [M + H]+ = 522.11 | Example 14 |
| 110 | $^1$H NMR (400 MHz, DMSO-d$_6$) δ 8.92 (s, 1H), 8.73 (s, 1H), 7.80 (d, J = 1.9 Hz, 1H), 7.73 (dd, J = 7.9, 2.0 Hz, 1H), 7.45 (d, J = 7.9 Hz, 1H), 7.36 (s, 1H), 6.96 (dd, J = 10.3, 8.6 Hz, 1H), 6.72 (dd, J = 8.6, 3.9 Hz, 1H), 4.75 (q, J = 14.4 Hz, 2H), 4.56 (t, J = 8.7 Hz, 2H), 3.41-3.29 (m, 2H), 3.23 (s, 3H), 2.99 (s, 3H), 2.20 (s, 3H). LC-MS: [M + H]+ = 531.10. | Example 14 |
| 111 | $^1$H NMR (400 MHz, DMSO-d$_6$) δ 8.94 (d, J = 2.0 Hz, 1H), 8.91 (s, 1H), 8.65 (s, 1H), 8.15 (d, J = 8.4 Hz, 1H), 7.60-7.49 (m, 2H), 7.03-6.91 (m, 1H), 6.72 (dt, J = 8.4, 2.9 Hz, 1H), 4.76 (d, J = 4.2 Hz, 2H), 4.56 (td, J = 8.8, 2.0 Hz, 2H), 3.33 (t, J = 8.7 Hz, 2H), 3.13 (s, 3H), 2.36-2.25 (m, 1H), 1.26 (d, J = 8.1 Hz, 2H), 1.18-1.03 (m, 2H). LC-MS: [M + H]+ = 480.14 | Example 14 |
| 112 | $^1$H NMR (400 MHz, CDCl$_3$) δ 8.32 (s, 1H), 8.03 (d, J = 7.9 Hz, 2H), 7.61 (d, J = 8.0 Hz, 2H), 7.40 (s, 1H), 6.87 (t, J = 9.4 Hz, 1H), 6.70 (dd, J = 8.6, 3.9 Hz, 1H), 4.87 (s, 2H), 4.65 (t, J = 8.7 Hz, 2H), 3.44 (t, J = 8.7 Hz, 2H), 3.14 (s, 3H). LC-MS: [M + H]+ = 507.10 | Example 14 |
| 113 | $^1$H NMR (400 MHz, CDCl$_3$) δ 7.72 (d, J = 7.8 Hz, 2H), 7.52 (d, J = 7.9 Hz, 2H), 7.40 (s, 1H), 6.89 (t, J = 9.5 Hz, 1H), 6.71 (dd, J = 8.6, 3.8 Hz, 1H), 4.86 (s, 2H), 4.66 (t, J = 8.6 Hz, 2H), 3.45 (t, J = 8.7 Hz, 2H). LC-MS: [M + H]+ = 497.11 | Example 14 |
| 114 | $^1$H NMR (400 MHz, DMSO) δ 8.86 (s, 1H), 8.66 (s, 1H), 7.41-7.38 (m, 2H), 7.31 (s, 1H), 7.24 (t, J = 8.8 Hz, 2H), 6.94 (t, J = 9.6 Hz, 1H), 6.71 (dd, J = 8.4, 3.6 Hz, 1H), 4.72 (d, J = 4.0 Hz, 1H), 4.54 (t, J = 8.8 Hz, 2H), 3.32 (t, J = 8.4 Hz, 2H). LC-MS: [M + H]+ = 447.11 | Example 14 |
| 115 | $^1$H NMR (400 MHz, DMSO) δ 8.92-8.91 (m, 2H), 8.28 (d, J = 8.0 Hz, 1H), 7.79 (d, J = 8.0 Hz, 1H), 7.42 (s, 1H), 6.95 (t, J = 9.6 Hz, 1H), 6.71 (dd, J = 8.4, 3.6 Hz, 1H), 4.80-4.68 (m, 2H), 4.55 (t, J = 8.4 Hz, 2H), 3.35-3.31 (m, 2H), 2.76 (s, 3H), 2.48 (s, 3H). LC-MS: [M + H]+ = 458.15 | Example 14 |
| 116 | $^1$H NMR (400 MHz, DMSO) δ 8.90 (s, 1H), 8.84 (t, J = 4.8 Hz, 1H), 8.78 (d, J = 1.2 Hz, 1H), 8.11 (dd, J = 8.0, 1.2 Hz, 1H), 7.99 (d, J = 8.0 Hz, 1H), 7.49 (s, 1H), 6.95 (t, J = 9.6 Hz, 1H), 6.70 (dd, J = 8.4, 3.6 Hz, 1H), 4.75 (d, J = 4.4 Hz, 2H), 4.55 (t, J = 8.8 Hz, 2H), 3.33 (t, J = 8.4 Hz, 2H). LC-MS: [M + H]+ = 498.10 | Example 14 |
| 117 | $^1$H NMR (400 MHz, methanol-d$_4$) δ 8.76 (t, J = 1.5 Hz, 2H), 8.14 (dd, J = 8.0, 2.2 Hz, 1H), 7.78 (d, J = 8.1 Hz, 1H), 7.43 (s, 1H), 6.97-6.77 (m, 2H), 6.69-6.59 (m, 1H), 4.85 (d, J = 1.1 Hz, 2H), 4.59 (t, J = 8.7 Hz, 2H), 3.40 (t, J = 8.7 Hz, 2H), 1.58 (d, J = 13.7 Hz, 6H). LC-MS: [M + H]+ = 488.13 | Example 14 |
| 118 | $^1$H NMR (400 MHz, methanol-d$_4$) δ 8.72 (d, J = 1.1 Hz, 1H), 7.65-7.53 (m, 2H), 7.36 (s, 1H), 7.22 (t, J = 8.8 Hz, 2H), 6.93-6.81 (m, 1H), 6.66 (dd, J = 8.7, 3.9 Hz, 1H), 4.83 (d, J = 1.0 Hz, 2H), 4.59 (t, J = 8.7 | Example 14 |

TABLE 2-continued

| Cpd. No. | ¹H NMR (400 MHz)/LC-MS data | Synthetic method |
|---|---|---|
| | Hz, 2H), 3.38 (t, J = 8.7 Hz, 2H), 1.46 (s, 3H), 1.42 (s, 3H).<br>LC-MS: [M + H]+ = 455.13 | |
| 119 | ¹H NMR (400 MHz, methanol-d₄) δ 8.82 (d, J = 2.1 Hz, 1H), 8.77 (d, J = 1.2 Hz, 1H), 8.17 (ddd, J = 8.1, 2.2, 0.7 Hz, 1H), 7.88 (dd, J = 8.1, 0.8 Hz, 1H), 7.45 (s, 1H), 6.92-6.81 (m, 1H), 6.66 (dd, J = 8.6, 3.9 Hz, 1H), 4.85 (d, J = 1.1 Hz, 2H), 4.59 (t, J = 8.7 Hz, 2H), 3.40 (t, J = 8.6 Hz, 2H), 1.62 (s, 3H), 1.58 (s, 3H).<br>LC-MS: [M + H]+ = 506.12 | Example 14 |
| 120 | ¹H NMR (400 MHz, CDCl₃) δ 8.81 (s, 1H), 8.60 (s, 1H), 8.04 (d, J = 7.9 Hz, 1H), 7.83 (d, J = 8.0 Hz, 1H), 7.43 (s, 1H), 7.29 (d, J = 1.4 Hz, 1H), 6.87 (t, J = 9.4 Hz, 1H), 6.71 (dd, J = 8.6, 3.8 Hz, 1H), 4.88 (s, 2H), 4.66 (t, J = 8.4 Hz, 2H), 3.45 (t, J = 8.7 Hz, 2H), 1.98 (ddq, J = 27.6, 14.5, 7.6 Hz, 4H), 1.01 (dt, J = 18.4, 7.6 Hz, 6H).<br>LC-MS: [M + H]+ = 534.06 | Example 14 |
| 121 | ¹H NMR (400 MHz, CDCl₃) δ 8.32 (s, 1H), 7.72 (d, J = 7.9 Hz, 2H), 7.63 (d, J = 7.9 Hz, 2H), 7.37 (s, 1H), 6.87 (t, J = 9.5 Hz, 1H), 6.69 (dd, J = 8.7, 3.9 Hz, 1H), 4.85 (s, 2H), 4.64 (t, J = 8.7 Hz, 2H), 3.45 (t, J = 8.7 Hz, 2H), 1.91 (s, 2H), 1.64 (td, J = 14.2, 7.4 Hz, 2H), 0.96 (dt, J = 17.0, 7.6 Hz, 6H).<br>LC-MS: [M + H]+ = 533.06 | Example 14 |
| 122 | ¹H NMR (400 MHz, CDCl₃) δ 8.30 (s, 1H), 8.07-7.94 (m, 2H), 7.68-7.58 (m, 2H), 7.39 (d, J = 1.5 Hz, 1H), 6.89 (t, J = 9.5 Hz, 1H), 6.76-6.62 (m, 1H), 4.87 (s, 2H), 4.66 (t, J = 8.6 Hz, 2H), 3.47 (t, J = 8.7 Hz, 2H), 3.15 (d, J = 1.5 Hz, 3H), 2.06 (dq, J = 13.8, 7.4 Hz, 2H), 1.89 (dq, J = 14.4, 7.3 Hz, 2H), 1.00 (dt, J = 18.8, 7.6 Hz, 6H).<br>LC-MS: [M + H]+ = 543.15 | Example 14 |
| 123 | ¹H NMR (400 MHz, DMSO) δ 8.96 (s, 1H), 8.29 (d, J = 8.0 Hz, 1H), 7.75 (d, J = 8.0 Hz, 1H), 7.35 (s, 1H), 6.94 (t, J = 8.8 Hz, 1H), 6.70 (dd, J = 8.4, 3.6 Hz, 1H), 4.80-4.68 (m, 2H), 4.55 (t, J = 8.8 Hz, 2H), 3.34 (t, J = 8.0 Hz, 2H), 2.71 (s, 3H), 2.48 (s, 3H), 1.63 (d, J = 14.0 Hz, 3H), 1.31 (d, J = 14.0 Hz, 3H).<br>LC-MS: [M + H]+ = 466.17 | Example 14 |
| 124 | ¹H NMR (400 MHz, DMSO) δ 8.95 (s, 1H), 8.76 (s, 1H), 8.23 (d, J = 8.0 Hz, 1H), 7.72 (d, J = 8.0 Hz, 1H), 7.32 (s, 1H), 6.96 (t, J = 8.8 Hz, 1H), 6.72 (dd, J = 8.4, 3.6 Hz, 1H), 4.74-4.70 (m, 2H), 4.57 (t, J = 8.4 Hz, 2H), 3.36 (t, J = 8.0 Hz, 2H), 2.74 (s, 2H), 2.069-1.983 (m, 1H), 1.845-1.759 (m, 1H), 1.52-1.49 (m, 2H), 0.97-0.89 (m, 3H), 0.67-0.59 (m, 3H).<br>LC-MS: [M + H]+ = 483.16 | Example 14 |
| 125 | ¹H NMR (400 MHz, DMSO) δ 8.87 (s, 1H), 8.53 (s, 1H), 7.53-7.51 (m, 2H), 6.94 (t, J = 8.8 Hz, 1H), 6.70 (dd, J = 8.4, 3.6 Hz, 1H), 4.71 (d, J = 4.8 Hz, 2H), 4.55 (t, J = 8.8 Hz, 2H), 3.33 (t, J = 8.4 Hz, 2H), 1.77-1.68 (m, 2H), 1.44-1.33 (m, 2H), 0.83-0.75 (m, 6H).<br>LC-MS: [M + H]+ = 493.20 | Example 14 |
| 126 | ¹H NMR (400 MHz, CDCl₃) δ 10.13 (s, 1H), 7.66 (s, 1H), 7.61 (d, J = 1.0 Hz, 1H), 7.57-7.51 (m, 4H), 7.51-7.45 (m, 1H), 7.37 (dd, J = 1.8, 0.8 Hz, 1H), 6.41 (dd, J = 3.2, 0.8 Hz, 1H), 6.34 (dd, J = 3.2, 1.8 Hz, 1H), 4.89 (s, 2H).<br>LC-MS: [M + H]+ = 291.11 | Example 13 |
| 127 | ¹H NMR (400 MHz, CDCl₃) δ 8.81 (s, 1H), 7.49 (d, J = 1.0 Hz, 1H), 7.41 (d, J = 6.7 Hz, 3H), 7.34 (dq, J = 3.3, 1.7 Hz, 3H), 6.35 (d, J = 3.2 Hz, 1H), 6.30 (dt, J = 3.1, 1.4 Hz, 1H), 4.87 (s, 2H), 3.87 (q, J = 7.1 Hz, 2H), 0.88 (t, J = 7.1 Hz, 3H).<br>LC-MS: [M + H]+ = 363.017 | Example 13 |
| 128 | ¹H NMR (400 MHz, CDCl₃) δ 9.22 (s, 1H), 7.55-7.43 (m, 3H), 7.38-7.30 (m, 3H), 6.40 (s, 1H), 6.36 (s, 1H), 6.31 (brs, 1H), 4.86 (s, 2H), 2.54 (s, 3H).<br>LC-MS: [M + H]+ = 348.13. | Example 15 |
| 129 | ¹H NMR (400 MHz, methanol-d₄) δ 8.71 (s, 1H), 7.46-7.33 (m, 7H), 7.33-7.26 (m, 1H), 7.03 (dd, J = 8.3, 1.1 Hz, 1H), 6.94 (td, J = 7.5, 1.1 Hz, 1H), 4.84 (s, 2H), 3.91 (s, 3H), 3.80 (q, J = 7.2 Hz, 2H), 0.86 (t, J = 7.1 Hz, 3H).<br>LC-MS: [M + H]+ = 403.16 | Example 15 |

TABLE 2-continued

| Cpd. No. | $^1$H NMR (400 MHz)/LC-MS data | Synthetic method |
|---|---|---|
| 130 | $^1$H NMR (400 MHz, methanol-$d_4$) δ 8.70 (s, 1H), 7.48-7.31 (m, 7H), 6.90 (dt, J = 8.4, 0.9 Hz, 1H), 6.80 (ddd, J = 9.3, 8.4, 0.9 Hz, 1H), 4.88 (s, 2H), 3.91 (s, 3H), 3.79 (q, J = 7.1 Hz, 2H), 0.86 (t, J = 7.1 Hz, 3H). LC-MS: [M + H]+ = 421.16 | Example 15 |
| 131 | $^1$H NMR (400 MHz, methanol-$d_4$) δ 8.66 (s, 1H), 7.52-7.23 (m, 6H), 7.11 (td, J = 9.2, 5.1 Hz, 1H), 6.96 (td, J = 9.2, 2.0 Hz, 1H), 4.92 (s, 2H), 3.88 (s, 3H), 3.79 (q, J = 7.1 Hz, 2H), 0.86 (t, J = 7.1 Hz, 3H). LC-MS: [M + H]+ = 439.15 | Example 15 |
| 132 | $^1$H NMR (400 MHz, methanol-$d_4$) δ 8.70 (s, 1H), 7.50-7.29 (m, 6H), 7.15-6.98 (m, 2H), 6.91-6.77 (m, 1H), 4.86 (s, 2H), 3.85-3.77 (m, 2H), 3.76 (s, 3H), 0.86 (t, J = 7.1 Hz, 3H). LC-MS: [M + H]+ = 421.15 | Example 15 |
| 133 | $^1$H NMR (400 MHz, methanol-$d_4$) δ 8.73 (s, 1H), 7.52-7.31 (m, 6H), 7.21-7.05 (m, 2H), 4.99 (d, J = 1.7 Hz, 2H), 3.90 (s, 3H), 3.79 (q, J = 7.1 Hz, 2H), 0.85 (t, J = 7.1 Hz, 3H). LC-MS: [M + H]+ = 455.12 | Example 15 |
| 134 | $^1$H NMR (400 MHz, methanol-$d_4$) δ 8.70 (s, 1H), 7.47-7.31 (m, 6H), 6.95 (ddt, J = 7.7, 1.4, 0.7 Hz, 1H), 6.88-6.75 (m, 2H), 5.99 (s, 2H), 4.84 (s, 2H), 3.80 (q, J = 7.1 Hz, 2H), 0.86 (t, J = 7.1 Hz, 3H). LC-MS: [M + H]+ = 417.14 | Example 15 |
| 135 | $^1$H NMR (400 MHz, methanol-$d_4$) δ 8.70 (s, 1H), 7.50-7.25 (m, 6H), 6.91-6.83 (m, 1H), 6.67 (dd, J = 8.6, 3.9 Hz, 1H), 4.84 (d, J = 1.1 Hz, 2H), 4.59 (t, J = 8.7 Hz, 2H), 3.80 (q, J = 7.2 Hz, 2H), 3.44-3.35 (m, 2H), 0.86 (t, J = 7.1 Hz, 3H). LC-MS: [M + H]+ = 433.15 | Example 15 |
| 136 | $^1$H NMR (400 MHz, methanol-$d_4$) δ 8.80 (s, 1H), 7.50-7.30 (m, 7H), 7.23 (s, 1H), 7.07 (d, J = 8.2 Hz, 1H), 7.04-6.91 (m, 1H), 4.89 (s, 2H), 3.91 (s, 3H), 2.52 (s, 3H). LC-MS: [M + H]+ = 388.16 | Example 15 |
| 137 | $^1$H NMR (400 MHz, methanol-$d_4$) δ 8.80 (s, 1H), 7.42 (m, 6H), 7.30 (s, 1H), 6.94 (d, J = 8.4 Hz, 1H), 6.84 (ddd, J = 9.4, 8.4, 0.9 Hz, 1H), 4.89 (s, 2H), 3.92 (s, 3H), 2.51 (s, 3H). LC-MS: [M + H]+ = 406.16 | Example 15 |
| 138 | $^1$H NMR (400 MHz, methanol-$d_4$) δ 8.70 (s, 1H), 7.50-7.36 (m, 5H), 7.34 (s, 1H), 7.14 (dt, J = 9.5, 4.7 Hz, 1H), 7.06-6.88 (m, 1H), 4.93 (s, 2H), 3.89 (d, J = 1.0 Hz, 3H), 2.50 (s, 3H). LC-MS: [M + H]+ = 424.15 | Example 15 |
| 139 | $^1$H NMR (400 MHz, methanol-$d_4$) δ 8.75 (s, 1H), 7.55-7.35 (m, 5H), 7.30 (s, 1H), 7.16-7.02 (m, 2H), 6.91 (dd, J = 8.6, 4.2 Hz, 1H), 4.93 (s, 2H), 3.78 (d, J = 1.4 Hz, 3H), 2.51 (s, 3H). LC-MS: [M + H]+ = 406.16 | Example 15 |
| 140 | $^1$H NMR (400 MHz, methanol-$d_4$) δ 8.66 (s, 1H), 7.51-7.31 (m, 6H), 7.23-7.02 (m, 2H), 4.99 (d, J = 1.8 Hz, 2H), 3.91 (s, 3H), 2.50 (s, 3H). LC-MS: [M + H]+ = 440.12 | Example 15 |
| 141 | $^1$H NMR (400 MHz, methanol-$d_4$) δ 9.02 (s, 1H), 7.55-7.35 (m, 5H), 7.21 (s, 1H), 7.00 (d, J = 7.5 Hz, 1H), 6.97-6.83 (m, 2H), 6.03 (s, 2H), 4.90 (s, 2H), 2.52 (s, 3H). LC-MS: [M + H]+ = 402.14 | Example 15 |
| 142 | $^1$H NMR (400 MHz, methanol-$d_4$) δ 8.64 (s, 1H), 7.50-7.29 (m, 6H), 6.92-6.81 (m, 1H), 6.67 (dd, J = 8.7, 3.9 Hz, 1H), 4.83 (d, J = 1.2 Hz, 2H), 4.59 (t, J = 8.7 Hz, 2H), 3.38 (t, J = 8.7 Hz, 2H), 2.51 (s, 3H). LC-MS: [M + H]+ = 418.16 | Example 15 |
| 143 | $^1$H NMR (400 MHz, DMSO-$d_6$) δ 8.85 (s, 1H), 8.61 (s, 1H), 7.44-7.31 (m, 6H), 6.94 (t, J = 8.8 Hz, 1H), 6.71 (dd, J = 8.4, 4.0 Hz, 1H), 4.73 (d, 2H), 4.54 (t, J = 8.8 Hz, 2H), 3.31 (t, J = 8.8 Hz, 2H). LC-MS: [M + H]+ = 429.12 | Example 14 |
| 144 | $^1$H NMR (400 MHz, DMSO-$d_6$) δ 8.85 (s, 1H), 8.52 (s, 1H), 7.58-7.56 (m, 2H), 7.42-7.41 (m, 2H), 7.29 (s, 1H), 6.94 (t, J = 9.2 Hz, 1H), 6.70 (dd, J = 8.4, 4.0 Hz, 1H), 4.73 (d, J = 4.0 Hz, 2H), 4.54 (t, J = 8.8 Hz, 2H), 3.31 (t, J = 8.8 Hz, 2H), 1.21 (s, 1H), 1.18 (s, 1H). LC-MS: [M + H]+ = 437.14 | Example 14 |

TABLE 2-continued

| Cpd. No. | $^1$H NMR (400 MHz)/LC-MS data | Synthetic method |
|---|---|---|
| E 1 | $^1$H NMR (400 MHz, DMSO-d$^6$) δ 8.85 (s, 1H), 8.62 (t, J = 4.9 Hz, 1H), 7.87 (d, J = 8.0 Hz, 1H), 7.44 (s, 1H), 7.36 (d, J = 8.0 Hz, 1H), 6.96 (dd, J = 10.3, 8.6 Hz, 1H), 6.71 (dd, J = 8.6, 3.9 Hz, 1H), 5.23 (d, J = 14.9 Hz, 1H), 4.74 (d, J = 4.5 Hz, 2H), 4.55 (t, J = 8.8 Hz, 2H), 4.46 (p, J = 6.9 Hz, 1H), 4.24 (d, J = 14.9 Hz, 1H), 3.33 (t, J = 8.7 Hz, 2H), 2.53 (s, 3H), 1.27 (d, J = 6.8 Hz, 3H), 1.13 (d, J = 6.7 Hz, 3H). LC-MS: [M + H]+ = 473.20 | |
| E 2 | $^1$H NMR (400 MHz, DMSO-d$^6$) δ 8.79 (d, J = 14.9 Hz, 3H), 7.80 (s, 1H), 7.52 (s, 1H), 6.95 (dd, J = 10.3, 8.7 Hz, 1H), 6.70 (dd, J = 8.6, 3.9 Hz, 1H), 5.22 (d, J = 14.9 Hz, 1H), 4.75 (d, J = 4.7 Hz, 2H), 4.55 (t, J = 8.8 Hz, 2H), 4.27 (d, J = 14.9 Hz, 1H), 4.19 (p, J = 6.8 Hz, 1H), 3.32 (t, J = 8.7 Hz, 2H), 2.64 (s, 3H), 1.24 (dd, J = 35.6, 6.8 Hz, 6H). LC-MS: [M + H]+ = 473.20 | |
| E 3 | $^1$H NMR (400 MHz, DMSO-d$^6$) δ 8.85 (s, 1H), 8.71 (t, J = 5.1 Hz, 1H), 7.93 (d, J = 8.0 Hz, 1H), 7.54 (s, 1H), 7.44 (d, J = 8.1 Hz, 1H), 6.96 (dd, J = 10.3, 8.6 Hz, 1H), 6.71 (dd, J = 8.7, 3.9 Hz, 1H), 5.46 (d, J = 15.0 Hz, 1H), 4.75 (d, J = 4.5 Hz, 2H), 4.71-4.61 (m, 1H), 4.56 (t, J = 8.8 Hz, 2H), 4.19 (d, J = 15.0 Hz, 1H), 4.08 (dq, J = 15.2, 9.0 Hz, 1H), 3.34 (t, J = 8.7 Hz, 2H), 2.57 (s, 3H). LC-MS: [M + H]+ = 513.15 | |
| E 4 | $^1$H NMR (400 MHz, DMSO-d$^6$) δ 8.79 (s, 1H), 8.71 (t, J = 5.1 Hz, 1H), 8.04 (d, J = 1.8 Hz, 1H), 7.88 (dd, J = 8.1, 1.8 Hz, 1H), 7.71 (d, J = 8.1 Hz, 1H), 7.46 (s, 1H), 6.96 (dd, J = 10.3, 8.7 Hz, 1H), 6.71 (dd, J = 8.6, 3.9 Hz, 1H), 5.19 (d, J = 15.1 Hz, 1H), 4.80-4.69 (m, 2H), 4.55 (t, J = 8.8 Hz, 2H), 4.23 (d, J = 15.3 Hz, 1H), 4.17 (q, J = 6.8 Hz, 1H), 3.33 (t, J = 8.7 Hz, 2H), 1.29 (d, J = 6.7 Hz, 3H), 1.17 (d, J = 6.8 Hz, 3H). LC-MS: [M + H]+ = 483.19 | |
| E 5 | $^1$H NMR (400 MHz, DMSO-d$^6$) δ 8.86 (s, 1H), 8.84-8.70 (m, 2H), 7.86 (s, 1H), 7.62 (s, 1H), 6.96 (dd, J = 10.3, 8.6 Hz, 1H), 6.71 (dd, J = 8.6, 3.9 Hz, 1H), 5.22 (d, J = 15.0 Hz, 1H), 4.77 (d, J = 4.9 Hz, 2H), 4.56 (t, J = 8.8 Hz, 2H), 4.40 (d, J = 15.1 Hz, 1H), 4.35-4.17 (m, 1H), 3.33 (t, J = 8.7 Hz, 2H), 2.62-2.54 (m, 1H), 2.34-2.27 (m, 1H), 2.27-2.09 (m, 2H), 1.70 (ddt, J = 25.8, 10.6, 7.5 Hz, 2H). LC-MS: [M + H]+ = 539.17 | |
| E 6 | $^1$H NMR (400 MHz, DMSO-d$^6$) δ 8.86 (d, J = 4.0 Hz, 1H), 8.74 (d, J = 6.5 Hz, 1H), 8.03 (d, J = 8.2 Hz, 1H), 7.58-7.42 (m, 2H), 6.94 (dd, J = 10.2, 8.7 Hz, 1H), 6.70 (dd, J = 8.6, 3.8 Hz, 1H), 6.47-6.09 (m, 1H), 5.46 (d, J = 15.1 Hz, 1H), 4.74 (d, J = 3.5 Hz, 2H), 4.55 (t, J = 8.7 Hz, 2H), 4.26 (dt, J = 15.3, 5.5 Hz, 1H), 4.12 (dddd, J = 23.0, 13.9, 10.0, 3.2 Hz, 1H), 3.80 (qd, J = 12.9, 4.7 Hz, 1H), 3.33 (t, J = 8.7 Hz, 2H), 2.59 (t, J = 2.9 Hz, 3H). LC-MS: [M + H]+ = 495.47 | |
| E 7 | $^1$H NMR (400 MHz, DMSO-d$^6$) δ 8.87 (d, J = 4.6 Hz, 1H), 8.70 (d, J = 5.9 Hz, 1H), 7.99 (d, J = 7.9 Hz, 1H), 7.63-7.43 (m, 2H), 6.96 (t, J = 9.4 Hz, 1H), 6.71 (dd, J = 8.5, 3.9 Hz, 1H), 5.42 (d, J = 15.1 Hz, 1H), 4.76 (d, J = 4.1 Hz, 2H), 4.56 (t, J = 8.7 Hz, 2H), 4.36-4.17 (m, 2H), 3.80 (td, J = 14.1, 7.1 Hz, 1H), 3.34 (t, J = 8.6 Hz, 2H), 2.59 (s, 3H), 1.66 (dd, J = 21.1, 17.6 Hz, 3H). LC-MS: [M + H]+ = 509.18 | |
| E 8 | $^1$H NMR (400 MHz, DMSO-d$^6$) δ 8.84 (d, J = 3.6 Hz, 2H), 8.22 (d, J = 8.1 Hz, 1H), 7.98 (d, J = 8.1 Hz, 1H), 7.62 (s, 1H), 6.95 (dd, J = 10.3, 8.7 Hz, 1H), 6.71 (dd, J = 8.6, 3.8 Hz, 1H), 6.54 (brs, 1H), 5.56 (d, J = 14.9 Hz, 1H), 4.76 (d, J = 5.0 Hz, 2H), 4.55 (t, J = 8.8 Hz, 2H), 4.28 (d, J = 14.9 Hz, 1H), 4.10 (dt, J = 22.2, 11.0 Hz, 1H), 3.65 (qd, J = 13.1, 5.2 Hz, 1H), 3.34 (t, J = 8.6 Hz, 2H). LC-MS: [M + H]+ = 549.13 | |
| E 9 | $^1$H NMR (400 MHz, DMSO-d$^6$) δ 8.83 (d, J = 10.8 Hz, 2H), 8.73 (s, 1H), 7.86 (s, 1H), 7.57 (s, 1H), 6.95 (dd, J = 10.3, 8.7 Hz, 1H), 6.70 (dd, J = 8.6, 3.9 Hz, 1H), 6.47-6.09 (m, 1H), 5.36 (d, J = 14.9 Hz, 1H), 4.75 (d, J = 4.2 Hz, 2H), 4.55 (t, J = 8.8 Hz, 2H), 4.25 | |

TABLE 2-continued

| Cpd. No. | $^1$H NMR (400 MHz)/LC-MS data | Synthetic method |
|---|---|---|
| | (d, J = 14.9 Hz, 1H), 4.10 (dddd, J = 22.8, 13.5, 9.2, 3.3 Hz, 1H), 3.68-3.45 (m, 1H), 3.33 (t, J = 8.7 Hz, 2H), 2.63 (s, 3H).<br>LC-MS: [M + H]+ = 495.16 | |
| E 10 | $^1$H NMR (400 MHz, DMSO-d$^6$) δ 9.08 (s, 1H), 9.01 (s, 1H), 8.85 (s, 1H), 8.06 (s, 1H), 7.80 (s, 1H), 7.47 (d, J = 1.3 Hz, 1H), 6.98 (dd, J = 10.3, 8.7 Hz, 1H), 6.74 (dd, J = 8.6, 3.9 Hz, 1H), 5.79 (d, J = 14.7 Hz, 1H), 5.57 (d, J = 14.8 Hz, 1H), 4.88-4.72 (m, 2H), 4.59 (t, J = 8.9 Hz, 3H), 3.34 (t, J = 8.6 Hz, 2H), 2.56-2.53 (m, 3H).<br>LC-MS: [M + H]+ = 522.16 | |
| E 11 | $^1$H NMR (400 MHz, DMSO-d$^6$) δ 8.79 (d, J = 8.1 Hz, 2H), 8.70 (t, J = 5.1 Hz, 1H), 7.86 (s, 1H), 7.56 (s, 1H), 7.08 (d, J = 55.0 Hz, 1H), 6.99-6.85 (m, 1H), 6.70 (dd, J = 8.7, 3.9 Hz, 1H), 5.20 (d, J = 14.9 Hz, 1H), 4.75 (d, J = 4.7 Hz, 2H), 4.55 (t, J = 8.8 Hz, 2H), 4.36 (d, J = 15.0 Hz, 1H), 4.25 (q, J = 6.8 Hz, 1H), 3.33 (t, J = 8.7 Hz, 2H), 1.27 (d, J = 6.7 Hz, 3H), 1.17 (d, J = 6.8 Hz, 3H).<br>LC-MS: [M + H]+ = 509.18 | |
| E 12 | $^1$H NMR (400 MHz, DMSO-d$^6$) δ 8.83 (s, 1H), 8.66 (brs, 1H), 7.88 (d, J = 8.0 Hz, 1H), 7.54 (s, 1H), 7.40 (d, J = 8.1 Hz, 1H), 6.96 (dd, J = 10.3, 8.7 Hz, 1H), 6.71 (dd, J = 8.6, 3.8 Hz, 1H), 5.46 (d, J = 14.9 Hz, 1H), 4.75 (d, J = 4.9 Hz, 2H), 4.67 (dd, J = 15.2, 9.5 Hz, 1H), 4.56 (t, J = 8.8 Hz, 2H), 4.17 (d, J = 14.9 Hz, 1H), 4.14-3.99 (m, 1H), 3.34 (t, J = 8.6 Hz, 2H), 2.82 (q, J = 7.6 Hz, 2H), 1.28 (td, J = 7.6, 1.3 Hz, 3H).<br>LC-MS: [M + H]+ = 527.49 | |
| E 13 | $^1$H NMR (400 MHz, DMSO-d$^6$) δ 8.82 (s, 1H), 8.64 (t, J = 5.2 Hz, 1H), 7.87 (d, J = 8.1 Hz, 1H), 7.51 (s, 1H), 7.38 (d, J = 8.1 Hz, 1H), 6.96 (dd, J = 10.3, 8.7 Hz, 1H), 6.71 (dd, J = 8.6, 3.9 Hz, 1H), 5.41 (d, J = 14.7 Hz, 2H), 4.75 (d, J = 4.9 Hz, 2H), 4.56 (t, J = 8.8 Hz, 2H), 4.20-4.14 (m, 2H), 3.80-3.76 (m, 1H), 3.34 (t, J = 8.6 Hz, 2H), 2.82 (q, J = 7.6 Hz, 2H), 1.28 (t, J = 7.6 Hz, 3H).<br>LC-MS: [M + H]+ = 509.50 | |
| E 14 | $^1$H NMR (400 MHz, DMSO-d$^6$) δ 8.83 (s, 1H), 8.65 (t, J = 5.1 Hz, 1H), 7.80 (d, J = 8.1 Hz, 1H), 7.51 (s, 1H), 7.41 (d, J = 8.1 Hz, 1H), 6.95 (dd, J = 10.3, 8.7 Hz, 1H), 6.71 (dd, J = 8.7, 3.9 Hz, 1H), 5.41 (d, J = 14.8 Hz, 1H), 4.75 (d, J = 4.8 Hz, 2H), 4.68 (dd, J = 15.2, 9.6 Hz, 1H), 4.56 (t, J = 8.8 Hz, 2H), 4.08 (d, J = 14.8 Hz, 1H), 3.96 (dt, J = 15.3, 9.2 Hz, 1H), 3.34 (t, J = 8.7 Hz, 2H), 2.28-2.21 (m, 1H), 1.32-1.15 (m, 1H), 1.16-0.99 (m, 3H).<br>LC-MS: [M + H]+ = 539.17 | |
| E 15 | $^1$H NMR (400 MHz, DMSO-d$^6$) δ 8.83 (s, 1H), 8.66 (t, J = 5.1 Hz, 1H), 7.88 (d, J = 8.1 Hz, 1H), 7.54 (s, 1H), 7.41 (d, J = 8.1 Hz, 1H), 6.96 (dd, J = 10.3, 8.7 Hz, 1H), 6.71 (dd, J = 8.7, 3.9 Hz, 1H), 5.47 (d, J = 14.9 Hz, 1H), 4.75 (d, J = 4.9 Hz, 2H), 4.67 (dd, J = 15.0, 9.5 Hz, 1H), 4.56 (t, J = 8.8 Hz, 2H), 4.17 (d, J = 14.8 Hz, 1H), 4.13-3.98 (m, 1H), 3.34 (t, J = 8.7 Hz, 2H), 3.09 (p, J = 6.9 Hz, 1H), 1.29 (dd, J = 6.9, 5.4 Hz, 6H).<br>LC-MS: [M + H]+ = 541.18 | |
| E 16 | $^1$H NMR (400 MHz, DMSO-d$^6$) δ 8.85 (s, 1H), 8.65 (d, J = 5.4 Hz, 1H), 7.91 (d, J = 8.0 Hz, 1H), 7.52 (s, 1H), 7.43 (d, J = 8.1 Hz, 1H), 6.96 (dd, J = 10.3, 8.7 Hz, 1H), 6.71 (dd, J = 8.6, 3.9 Hz, 1H), 5.40 (d, J = 14.8 Hz, 1H), 4.75 (d, J = 4.4 Hz, 2H), 4.56 (t, J = 8.8 Hz, 2H), 4.27-4.12 (m, 3H), 3.34 (t, J = 8.7 Hz, 2H), 2.84 (q, J = 7.6 Hz, 2H), 1.67 (t, J = 19.3 Hz, 3H), 1.29 (t, J = 7.6 Hz, 3H).<br>LC-MS: [M + H]+ = 523.19 | |
| E 17 | $^1$H NMR (400 MHz, DMSO-d$^6$) δ 9.06 (s, 1H), 8.88 (t, J = 5.1 Hz, 1H), 8.60 (dd, J = 4.8, 1.6 Hz, 1H), 7.92 (dd, J = 8.0, 1.6 Hz, 1H), 7.67 (s, 1H), 7.57 (dd, J = 7.9, 4.8 Hz, 1H), 7.45 (d, J = 1.3 Hz, 1H), 6.98 (t, J = 9.5 Hz, 1H), 6.73 (dd, J = 8.6, 3.9 Hz, 1H), 5.82 (d, J = 14.4 Hz, 1H), 5.34 (d, J = 14.3 Hz, 1H), 4.78 | |

TABLE 2-continued

| Cpd. No. | ¹H NMR (400 MHz)/LC-MS data | Synthetic method |
|---|---|---|
| | (t, J = 4.6 Hz, 2H), 4.59 (t, J = 8.8 Hz, 2H), 3.34 (t, J = 8.7 Hz, 2H), 2.60 (s, 3H). LC-MS: [M + H]+ = 454.17 | |
| E 18 | ¹H NMR (400 MHz, DMSO-d⁶) δ 9.04 (s, 1H), 8.85 (s, 1H), 7.78 (d, J = 8.0 Hz, 1H), 7.62 (s, 1H), 7.42 (d, J = 7.8 Hz, 2H), 7.03-6.91 (m, 1H), 6.72 (dd, J = 8.7, 3.9 Hz, 1H), 5.76 (d, J = 14.3 Hz, 1H), 5.27 (d, J = 14.2 Hz, 1H), 4.76 (d, J = 3.9 Hz, 2H), 4.58 (t, J = 8.8 Hz, 2H), 3.34 (t, J = 8.7 Hz, 2H), 2.61 (s, 3H), 2.53 (s, 3H). LC-MS: [M + H]+ = 468.18 | |
| E 19 | ¹H NMR (400 MHz, DMSO-d⁶) δ 8.85 (s, 1H), 8.71 (t, J = 5.1 Hz, 1H), 7.93 (d, J = 8.0 Hz, 1H), 7.54 (s, 1H), 7.44 (d, J = 8.1 Hz, 1H), 6.96 (dd, J = 10.3, 8.6 Hz, 1H), 6.71 (dd, J = 8.7, 3.9 Hz, 1H), 5.46 (d, J = 15.0 Hz, 1H), 4.75 (d, J = 4.5 Hz, 2H), 4.71-4.61 (m, 1H), 4.56 (t, J = 8.8 Hz, 2H), 4.19 (d, J = 15.0 Hz, 1H), 4.08 (dq, J = 15.2, 9.0 Hz, 1H), 3.34 (t, J = 8.7 Hz, 2H), 2.57 (s, 3H). LC-MS: [M + H]+ = 516.15 | |
| E 20 | LC-MS: [M + H]+ = 515.18 | |
| E 21 | LC-MS: [M + H]+ = 518.18 | |
| E 22 | LC-MS: [M + H]+ = 517.18 | |
| E 23 | LC-MS: [M + H]+ = 520.20 | |
| E 24 | LC-MS: [M + H]+ = 571.19 | |
| E 25 | LC-MS: [M + H]+ = 492.14 | |
| E 26 | LC-MS: [M + H]+ = 504.14 | |
| E 27 | LC-MS: [M + H]+ = 478.12 | |
| E 28 | ¹H NMR (400 MHz, DMSO-d⁶) δ 8.74 (s, 1H), 8.44 (t, J = 5.1 Hz, 1H), 7.48 (t, J = 6.7 Hz, 1H), 7.38 (td, J = 7.4, 1.6 Hz, 1H), 7.29 (td, J = 7.4, 1.4 Hz, 1H), 7.22 (td, J = 7.5, 1.4 Hz, 2H), 7.10 (s, 1H), 6.96 (dd, J = 10.3, 8.6 Hz, 1H), 6.72 (dd, J = 8.6, 3.9 Hz, 1H), 4.85-4.62 (m, 2H), 4.56 (t, J = 8.8 Hz, 2H), 3.38-3.20 (m, 4H), 2.82 (dd, J = 8.9, 6.2 Hz, 2H). LC-MS: [M + H]+ = 430.16 | |
| E 29 | LC-MS: [M + H]+ = 445.17 | |
| E 30 | LC-MS: [M + H]+ = 527.17 | |
| E 31 | LC-MS: [M + H]+ = 541.18 | |
| E 32 | LC-MS: [M + H]+ = 508.14 | |
| E 33 | LC-MS: [M + H]+ = 508.14 | |
| E 34 | LC-MS: [M + H]+ = 454.17 | |
| E 35 | LC-MS: [M + H]+ = 523.14 | |
| E 36 | LC-MS: [M + H]+ = 455.15 | |
| E 37 | LC-MS: [M + H]+ = 536.17 | |
| E 38 | LC-MS: [M + H]+ = 482.20 | |
| E 39 | LC-MS: [M + H]+ = 527.17 | |
| E 40 | ¹H NMR (400 MHz, DMSO-d⁶) δ 9.02-8.67 (m, 2H), 8.11 (d, J = 7.3 Hz, 1H), 7.62 (d, J = 7.4 Hz, 1H), 6.96 (q, J = 9.1 Hz, 1H), 6.72 (dq, J = 8.4, 3.7 Hz, 1H), 5.26 (dd, J = 15.2, 7.2 Hz, 2H), 4.78 (d, J = 6.4 Hz, 2H), 4.56 (q, J = 8.5 Hz, 2H), 4.39 (dd, J = 15.4, 7.0 Hz, 1H), 4.27 (q, J = 7.3 Hz, 1H), 3.35 (q, J = 8.5 Hz, 2H), 1.41-1.23 (m, 3H), 1.23-1.06 (m, 3H). LC-MS: [M + H]+ = 527.17 | |
| E 41 | ¹H NMR (400 MHz, DMSO-d⁶) δ 8.86 (s, 1H), 8.68 (t, J = 5.1 Hz, 1H), 7.95 (d, J = 8.0 Hz, 1H), 7.52 (s, 1H), 7.46 (d, J = 8.1 Hz, 1H), 6.95 (dd, J = 10.3, 8.7 Hz, 1H), 6.70 (dd, J = 8.6, 3.9 Hz, 1H), 5.40 (d, J = 14.9 Hz, 1H), 4.75 (d, J = 4.2 Hz, 2H), 4.55 (t, J = 8.7 Hz, 2H), 4.27 (dd, J = 17.6, 13.4 Hz, 2H), 3.78 (td, J = 14.0, 6.8 Hz, 1H), 3.33 (t, J = 8.7 Hz, 2H), 2.57 (s, 3H), 1.65 (t, J = 19.3 Hz, 3H). LC-MS: [M + H]+ = 509.18 | |
| E 42 | ¹H NMR (400 MHz, DMSO-d⁶) δ 8.85 (s, 1H), 8.78 (d, J = 8.3 Hz, 2H), 8.10 (s, 1H), 7.64 (s, 1H), 7.16-6.83 (m, 2H), 6.71 (dd, J = 8.6, 3.9 Hz, 1H), 5.39 (d, J = 15.2 Hz, 1H), 4.76 (d, J = 4.8 Hz, 2H), 4.69-4.48 (m, 3H), 4.35 (d, J = 15.1 Hz, 1H), 4.06 (dt, J = 15.1, 9.1 Hz, 1H), 3.34 (t, J = 8.7 Hz, 2H). LC-MS: [M + H]+ = 549.13 | |
| E 43 | LC-MS: [M + H]+ = 545.16 | |
| E 44 | ¹H NMR (400 MHz, DMSO-d⁶) δ 8.81 (d, J = 25.3 Hz, 3H), 8.02 (s, 1H), 7.63 (s, 1H), 7.19-6.81 (m, 2H), 6.71 (dd, J = 8.6, 3.8 Hz, 1H), 6.44-6.03 (m, 1H), 5.36 (d, J = 15.0 Hz, 1H), 4.76 (d, J = 4.8 Hz, 2H), 4.55 (t, J = 8.8 Hz, 2H), 4.35 (d, J = 14.9 Hz, | |

TABLE 2-continued

| Cpd. No. | $^1$H NMR (400 MHz)/LC-MS data | Synthetic method |
|---|---|---|
| | 1H), 4.06 (dt, J = 15.1, 9.1 Hz, 1H), 3.66 (td, J = 13.0, 10.9, 4.6 Hz, 1H), 3.34 (t, J = 8.8 Hz, 2H). LC-MS: [M + H]+ = 531.14 | |
| E 48 | LC-MS: [M + H]+ = 585.18 | Example 26 |
| E 49 | LC-MS: [M + H]+ = 599.20 | Example 26 |
| E 50 | LC-MS: [M + H]+ = 555.21 | Example 26 |
| E 51 | LC-MS: [M + H]+ = 555.21 | Example 26 |
| E 52 | LC-MS: [M + H]+ = 553.19 | Example 26 |

Example 27

Biological Assays

Representative Compounds of the Disclosure were tested in the EED Alpha screen binding assay and anti-proliferative activities ($IC_{50}$ values) were determined in Karpas 422 and Pfeiffer cell lines for 7 day treatments. "N/A" stands for "not assessed".

Analysis of Cell Proliferation:

The human B cell lymphoma cell KARPAS422 was purchased from the American Type Culture Collection (ATCC), and was cultured using standard cell culture conditions in RPMI-1640 (Invitrogen, cat #11875) supplemented with 10% FBS (Invitrogen, cat #10099-141) in humidified incubator at 370 C, 5% $CO_2$. To assess the effect of PRC2 inhibition on cell growth, cells were seeded in 96-well cell culture plates at a density of 2 000-3 000 cells/well in 200 L of culture medium, and treated with serially diluted compounds for 7 days at 37° C. in an atmosphere of 5% $CO_2$. Cell growth was evaluated by a lactate dehydrogenase-based WST-8 assay (Dojindo Molecular Technologies) using a Tecan Infinite M1000 multimode microplate reader (Tecan, Morrisville, NC). The WST-8 reagent was added to the plate, incubated for 1-4 h, and read at 450 nm. The readings were normalized to the DMSO-treated cells, and the $IC_{50}$ was calculated by non-linear regression analysis using GraphPad Prism 6 software EED-H3K27Me3 peptide competition binding assay by AlphaScreen (α-screen)

To assess the potency in the EED-H3K27Me3 competition binding assay, representative Compounds of the Disclosure were serially diluted 3-fold in DMSO to obtain a total of twelve concentrations. The compounds at each concentration (2.5 µl of each) were transferred into a 384-well Perkin Elmer OptiPlate-384 white plates. 5 µl of solutions containing 20 nM EED (1-441)-His protein in the buffer (25 mM HEPES, pH 8, 0.02% Tween-20, 0.5% BSA) were added to the wells and then incubated with compound for 15 min. 2.5 µl of solutions containing 20 nM biotin-H3K27Me3 (19-33) peptide in the buffer (25 mM HEPES, pH 8, 0.02% Tween-20, 0.5% BSA) were added to the wells and then incubated with compound for 30 min. AlphaScreen detection beads mix was prepared immediately before use by mixing nickel chelate acceptor beads and streptavidin donor beads in a 1:1 ratio (Perkin Elmer, Product No. 6760619C/M/R) into the buffer described above. Then 10 µl of the detection beads mix was added to the plate and incubated in the dark at RT for 1 h. The final concentration of donor and acceptor beads was 10 µg/ml for each. Plates were read on CLARIOStar plate reader (BMG Labtech) using the AlphaScreen setting adapted for optimal signal detection with a 615 nm filter, after sample excitation at 680 nm. The emission signal at 615 nm was used to quantify compound inhibition. AlphaScreen signals were normalized based on the reading coming from the positive (maximum signal control) and negative controls (minimum signal control) to give percentage of activities left. The data were then fit to a dose response equation to get the $IC_{50}$ values.

The results are presented in Tables 2A and 2B.

TABLE 2A

| Cpd. No. | Pfeiffer Cell line (nM) | Karpas Cell line (nM) | Alpha screen (nM) |
|---|---|---|---|
| 1 | >100 | >100 | >10 |
| 2 | >100 | >100 | >10 |
| 3 | 83.95 | N/A | 6.88 |
| 4 | >100 | >100 | >10 |
| 5 | 18.05 | 32.23 | 0.26 |
| 6 | 0.22 | 1.98 | 0.19 |
| 7 | 0.68 | 3.35 | 0.61 |
| 8 | 0.57 | 2.91 | 1.97 |
| 9 | 1.81 | 5.60 | 0.84 |
| 10 | 2.93 | 15.82 | 1.11 |
| 11 | 1.22 | 4.61 | 0.75 |
| 12 | 0.65 | 3.84 | 0.34 |
| 13 | 1.99 | 9.03 | 1.09 |
| 14 | 0.36 | 3.49 | 3.35 |
| 15 | 1.25 | 4.36 | 0.52 |
| 16 | 3.39 | 14.67 | 0.70 |
| 17 | 4.17 | 20.51 | 0.66 |
| 18 | 0.73 | 15.28 | 0.70 |
| 19 | 0.79 | 9.60 | 1.13 |
| 20 | 0.90 | 13.88 | 0.61 |
| 21 | 0.61 | 14.95 | 0.55 |
| 22 | 4.88 | 45.57 | 0.67 |
| 23 | 9.95 | 89.21 | 1.18 |
| 24 | 38.38 | >100 | 4.75 |
| 25 | 0.29 | 16.46 | 3.31 |
| 26 | 32.91 | 41.4 | 9.84 |
| 27 | >100 | >100 | 5.87 |
| 28 | >100 | >100 | 2.58 |
| 29 | N/A | N/A | 20.73 |
| 30 | N/A | N/A | 2.03 |
| 31 | N/A | 3.68 | 0.6041 |
| 32 | 11.6 | 84.41 | 1.84 |
| 33 | 0.22 | 1.11 | 1.06 |
| 34 | 0.35 | 2.64 | 0.67 |
| 35 | 0.12 | 1.23 | 1.16 |
| 36 | 1.04 | 5.66 | 1.44 |
| 37 | 0.25 | 1.79 | 0.94 |
| 38 | 3.22 | 15.71 | 1.25 |
| 39 | 22.67 | >100 | 26.14 |
| 40 | 38.78 | >100 | 10.48 |
| 41 | 1.03 | 1.69 | 0.60 |
| 42 | 4.19 | 4.01 | 0.84 |
| 43 | 1.05 | 5.46 | 1.05 |
| 44 | 1.03 | 2.44 | 1.34 |
| 45 | 0.61 | 6.15 | 3.39 |
| 46 | N/A | 0.57 | 1.07 |
| 47 | N/A | 0.65 | 0.91 |
| 48 | N/A | 0.74 | 1.65 |
| 49 | N/A | 2.78 | 1.81 |
| 50 | N/A | 0.71 | 1.16 |
| 51 | N/A | 2.08 | 0.70 |

TABLE 2A-continued

| Cpd. No. | Pfeiffer Cell line (nM) | Karpas Cell line (nM) | Alpha screen (nM) |
| --- | --- | --- | --- |
| 52 | N/A | 0.54 | 0.70 |
| 53 | N/A | >100 | 3.96 |
| 54 | N/A | >100 | 0.95 |
| 55 | N/A | 8.08 | 2.14 |
| 56 | N/A | 21.01 | 4.49 |
| 57 | N/A | 2.63 | 4.20 |
| 58 | N/A | N/A | 2.74 |
| 59 | N/A | 39.86 | 2.14 |
| 60 | N/A | 1.18 | N/A |
| 61 | N/A | 1.63 | 1.19 |
| 62 | N/A | 4.86 | 1.44 |
| 63 | N/A | 3.69 | 1.89 |
| 64 | N/A | 2.44 | N/A |
| 65 | N/A | 0.69 | N/A |
| 66 | N/A | 0.74 | 3.61 |
| 67 | N/A | 7.78 | 2.87 |
| 68 | N/A | 1.35 | 3.86 |
| 69 | N/A | >100 | 19.83 |
| 70 | N/A | >100 | >100 |
| 71 | N/A | >100 | 8.94 |
| 72 | N/A | 3.86 | 2.69 |
| 73 | N/A | 11.33 | 0.50 |
| 74 | N/A | 46.98 | 1.67 |
| 75 | N/A | 11.06 | 1.72 |
| 76 | N/A | 14.53 | 0.97 |
| 77 | N/A | 22.46 | 1.90 |
| 78 | N/A | 34.46 | 3.23 |
| 79 | N/A | 15.28 | 1.61 |
| 80 | N/A | 2.42 | 1.61 |
| 81 | N/A | 1.43 | 1.70 |
| 82 | 0.074 | 3.51 | 10.49 |
| 83 | 0.304 | 6.32 | 9.95 |
| 84 | 0.048 | 1.48 | 3.07 |
| 85 | 0.13 | 2.71 | 9.82 |
| 86 | 0.021 | 2.29 | 2.56 |
| 87 | 0.018 | 8.67 | 11.15 |
| 88 | 0.035 | 25.68 | 12.32 |
| 89 | N/A | N/A | N/A |
| 90 | 0.044 | 0.078 | N/A |
| 91 | 0.043 | 5.23 | N/A |
| 92 | N/A | N/A | N/A |
| 93 | 0.55 | 3.71 | N/A |
| 94 | 0.20 | 13.9 | 14.00 |
| 95 | 0.023 | 0.89 | 13.12 |
| 96 | 0.056 | 21.19 | 21.88 |
| 97 | 0.058 | 1.847 | N/A |
| 98 | N/A | N/A | N/A |
| 99 | 0.19 | 0.88 | 3.25 |
| 100 | 1.05 | 0.26 | 0.24 |
| 101 | 1.76 | 5.59 | 0.56 |
| 102 | 0.59 | 0.94 | 0.62 |
| 103 | N/A | 1.88 | 0.59 |
| 104 | N/A | 8.1 | 0.59 |
| 105 | N/A | 10.81 | 1.01 |
| 106 | N/A | 10.6 | 0.556 |
| 107 | N/A | 2.84 | 0.215 |
| 108 | N/A | 6.89 | 0.421 |
| 109 | N/A | 10.87 | 0.53 |
| 110 | N/A | 3.93 | 0.47 |
| 111 | N/A | 1.42 | 0.34 |
| 112 | N/A | 20.32 | 0.83 |
| 113 | N/A | >100 | 0.98 |
| 114 | N/A | >100 | 1.48 |
| 115 | N/A | 50.09 | 2.35 |
| 116 | N/A | >100 | 1.98 |
| 117 | N/A | 19.49 | 0.19 |
| 118 | N/A | 28.38 | 0.27 |
| 119 | N/A | 27.93 | 0.20 |
| 120 | N/A | >100 | 1.15 |
| 121 | N/A | >100 | 0.31 |
| 122 | N/A | >100 | 0.31 |
| 123 | N/A | 22.88 | 4.74 |
| 124 | N/A | 72.03 | 8.04 |
| 125 | N/A | 91.65 | 27.64 |
| 126 | N/A | >100 | N/A |
| 127 | N/A | >100 | N/A |
| 128 | N/A | >100 | N/A |
| 129 | N/A | >100 | N/A |
| 130 | N/A | >100 | N/A |
| 131 | N/A | >100 | N/A |
| 132 | N/A | >100 | N/A |
| 133 | N/A | >100 | N/A |
| 134 | N/A | >100 | N/A |
| 135 | N/A | 7.07 | N/A |
| 136 | N/A | >100 | N/A |
| 137 | N/A | >100 | N/A |
| 138 | N/A | >100 | N/A |
| 139 | N/A | >100 | N/A |
| 140 | N/A | >100 | N/A |
| 141 | N/A | >100 | N/A |
| 142 | N/A | >100 | N/A |
| 143 | N/A | >100 | N/A |
| 144 | N/A | >10 | N/A |

TABLE 2B $IC_{50}$ definition: A = < 10 nM; B = >10 nM-<100 nM; and C = > 100 nM

| Cpd. No. | Pfeiffer Cell line (nM) | Karpas Cell line (nM) | Alpha screen (nM) |
| --- | --- | --- | --- |
| E 1 | A | A | A |
| E 2 | A | A | A |
| E 3 | A | A | A |
| E 4 | A | A | A |
| E 5 | A | A | A |
| E 6 | A | A | A |
| E 7 | A | A | A |
| E 8 | A | A | A |
| E 9 | A | A | A |
| E 10 | B | B | A |
| E 11 | A | A | A |
| E 12 | A | A | A |
| E 13 | A | A | A |
| E 14 | A | A | A |
| E 15 | A | A | A |
| E 16 | A | A | A |
| E 17 | B | B | A |
| E 18 | A | B | A |
| E 19 | A | A | A |
| E 20 | A | A | A |
| E 21 | A | A | A |
| E 22 | A | A | A |
| E 23 | A | A | A |
| E 24 | B | B | B |
| E 25 | B | B | A |
| E 26 | A | B | B |
| E 27 | A | B | B |
| E 28 | B | C | B |
| E 29 | B | B | B |
| E 30 | B | B | B |
| E 31 | B | B | B |
| E 32 | A | B | B |
| E 33 | B | B | B |
| E 34 | A | B | B |
| E 35 | B | B | B |
| E 36 | B | B | B |
| E 37 | B | B | B |
| E 38 | B | B | B |
| E 39 | A | B | B |
| E 40 | A | A | A |
| E 45 | A | A | A |
| E 46 | A | A | A |
| E 47 | A | A | A |
| E 48 | A | A | A |
| E 49 | A | A | A |
| E 50 | A | A | A |

TABLE 2B-continued

| | IC$_{50}$ definition: A = < 10 nM; B = >10 nM-<100 nM; and C = > 100 nM | | |
|---|---|---|---|
| Cpd. No. | Pfeiffer Cell line (nM) | Karpas Cell line (nM) | Alpha screen (nM) |
| E 51 | A | A | A |
| E 52 | A | A | A |

Example 28

In Vivo Efficacy

Animal experiments were performed under the guidelines of the University of Michigan Committee for Use and Care of Animals using an approved animal protocol. Xenograft tumors were established by injecting 1×10$^7$ Karpas 422 human B cell lymphoma cells in 50% Matrigel subcutaneously on the dorsal side of severe combined immune deficient (SCID) mice, obtained from Charles River, one tumor per mouse. When tumors reached-100 mm$^3$, mice were randomly assigned to treatment and vehicle control groups. Animals were monitored daily for any signs of toxicity and weighed 2-3 times per week during the treatment period and at least weekly after the treatment ended. Tumor size was measured utilizing electronic calipers 2-3 times per week during the treatment period and at least weekly after the treatment ended. Tumor volume was calculated as V=L× W$^2$/2, where L is the length and W is the width of the tumor. The compound was formulated as a suspension in PEG 200 and administered orally by gavage at specific doses. When applicable, results are presented as mean±SEM. Graphing and statistical analysis was performed using GraphPad Prism 7.00 (GraphPad Software).

Figure 2:
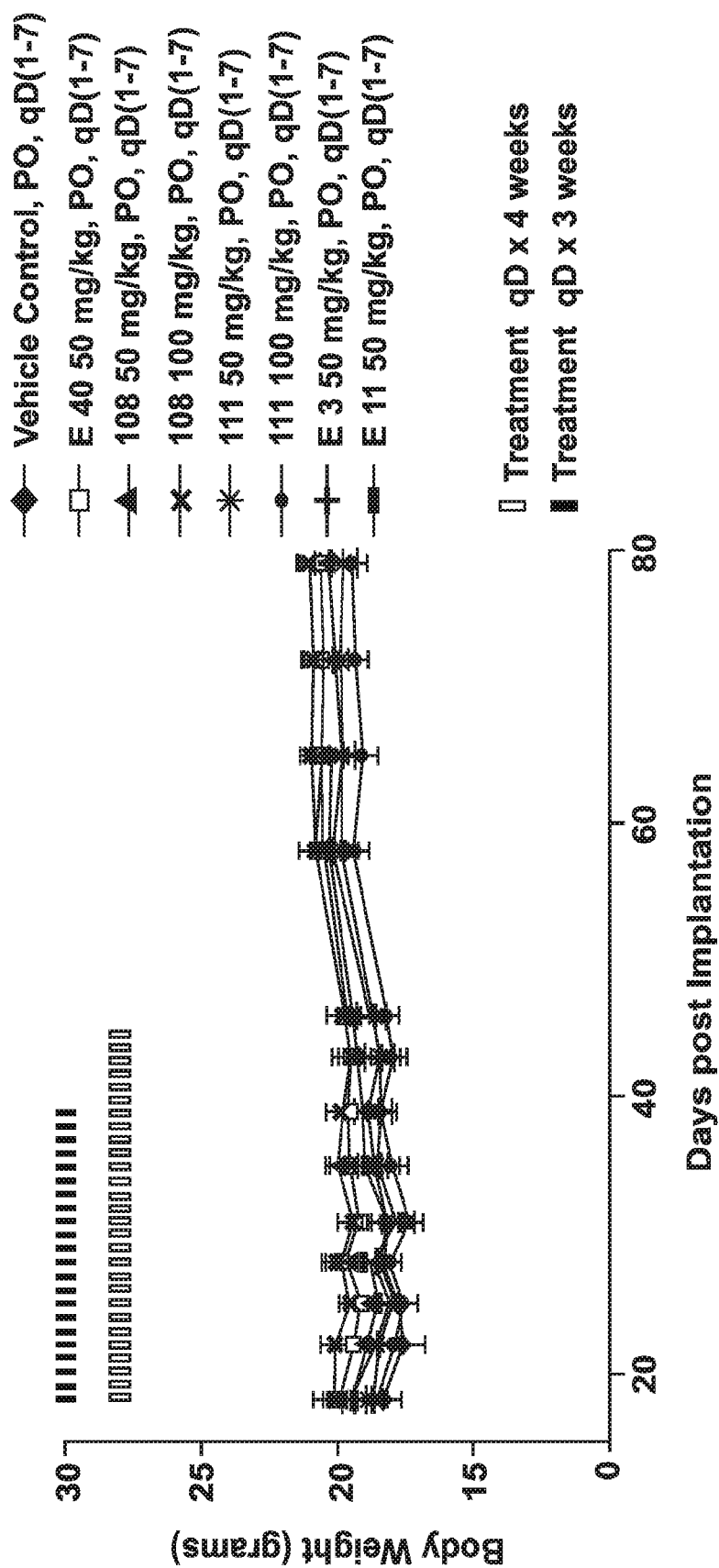
FIG. 2 is a line graph showing the body weight change of tumor-bearing mice treated with representative Compounds of the Disclosure in the KARPAS422 tumor model in mice.

The anti-tumor activity for representative Compounds of the Disclosure are provided in FIG. 1. The body weight of the treated animals is provided in FIG. 2.

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications, and publications cited herein are fully incorporated by reference herein in their entirety.

What is claimed is:

1. A compound of Formula II:

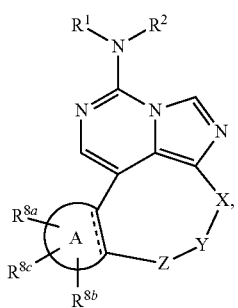

II wherein:

R$^1$ is aralkyl;

R$^2$ is selected from the group consisting of hydrogen and C$_1$-C$_4$ alkyl;

X is selected from the group consisting of —C(R$^{5a}$)(R$^{5b}$)—, —C(=O)—, and —S(=O)$_2$—;

R$^{5a}$ and R$^{5b}$ are independently selected from the group consisting of hydrogen and C$_1$-C$_4$ alkyl;

Y is selected from the group consisting of —C(R$^{6a}$)(R$^{6b}$)—, —S—, —O—, and —N(R$^7$)—; or X and Y taken together form a 5-membered heteroarylenyl;

Z is —C(R$^{6c}$)(R$^{6d}$)$_m$—;

R$^{6a}$ and R$^{6b}$ are independently selected from the group consisting of hydrogen and C$_1$-C$_4$ alkyl;

each R$^{6c}$ and R$^{6d}$ is independently selected from the group consisting of hydrogen and C$_1$-C$_4$ alkyl;

m is 0, 1, or 2;

R$^7$ is selected from the group consisting of hydrogen, C$_1$-C$_6$ alkyl, C$_1$-C$_6$ haloalkyl, optionally substituted C$_3$-C$_8$ cycloalkyl, optionally substituted C$_4$-C$_8$ heterocyclo, hydroxyalkyl, (alkoxy)alkyl, (cycloalkyl)alkyl, and (heterocyclo)alkyl;

R$^{8a}$, R$^{8b}$, and R$^{8c}$ are independently selected from the group consisting of hydrogen, halo, C$_1$-C$_4$ alkyl, C$_1$-C$_4$ haloalkyl, C$_1$-C$_4$ alkoxy, carboxamido, optionally substituted C$_3$-C$_8$ cycloalkyl, optionally substituted 4- to 8-membered heterocyclo, (heterocyclo)C$_1$-C$_4$ alkyl, and alkylsulfonyl;

is a fused phenyl, fused 5-membered heteroaryl, or fused 6-membered heteroaryl;

or a pharmaceutically acceptable salt thereof.

2. The compound of claim 1 of Formula III:

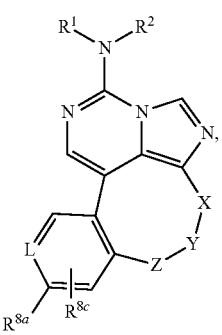

III wherein L is selected from the group consisting of —C(R$^{8b}$)= and —N=, or a pharmaceutically acceptable salt or solvate-thereof.

3. The compound of claim 1 of Formula IV:

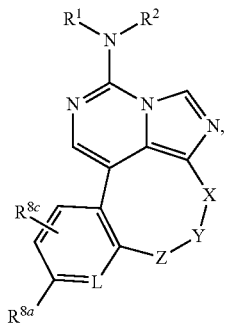

wherein L is selected from the group consisting of —C(R$^{8b}$)= and —N=, or a pharmaceutically acceptable salt thereof.

4. The compound of claim 1, wherein Z is —CH$_2$—, or a pharmaceutically acceptable salt thereof.

5. The compound of claim 1, wherein:
X is selected from the group consisting of —C(R$^{5a}$)(R$^{5b}$)—, —C(=O)—, and —S(=O)$_2$—; and
Y is selected from the group consisting of —C(R$^{6a}$)(R$^{6b}$)—, —S—, —O—, and —N(R$^7$)—, or a pharmaceutically acceptable salt or solvate-thereof.

6. The compound claim 1, wherein X is —C(=O)—, or a pharmaceutically acceptable salt thereof.

7. The compound of claim 1, wherein Y is —N(R$^7$)—, or a pharmaceutically acceptable salt thereof.

8. The compound of claim 1, wherein X and Y taken together form a 5-membered heteroarylenyl, or a pharmaceutically acceptable salt thereof.

9. The compound of claim 1, wherein:
R$^1$ is R$^1$-1:

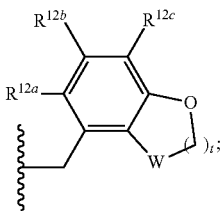

R$^{12a}$, R$^{12b}$, and R$^{12c}$ are each independently selected from the group consisting of hydrogen, halo, C$_1$-C$_4$ alkyl, C$_1$-C$_4$ haloalkyl, and C$_1$-C$_4$ alkoxy;
W is selected from the group consisting of —CH$_2$— and —C(=O)—; and
t is 1 or 2,
or a pharmaceutically acceptable salt or solvate-thereof.

10. The compound of claim 9, wherein:
R$^{12a}$ is fluoro; and
R$^{12b}$ and R$^{12c}$ are independently selected from the group consisting of hydrogen and fluoro,
or a pharmaceutically acceptable salt thereof.

11. The compound of claim 1 selected from the group consisting of

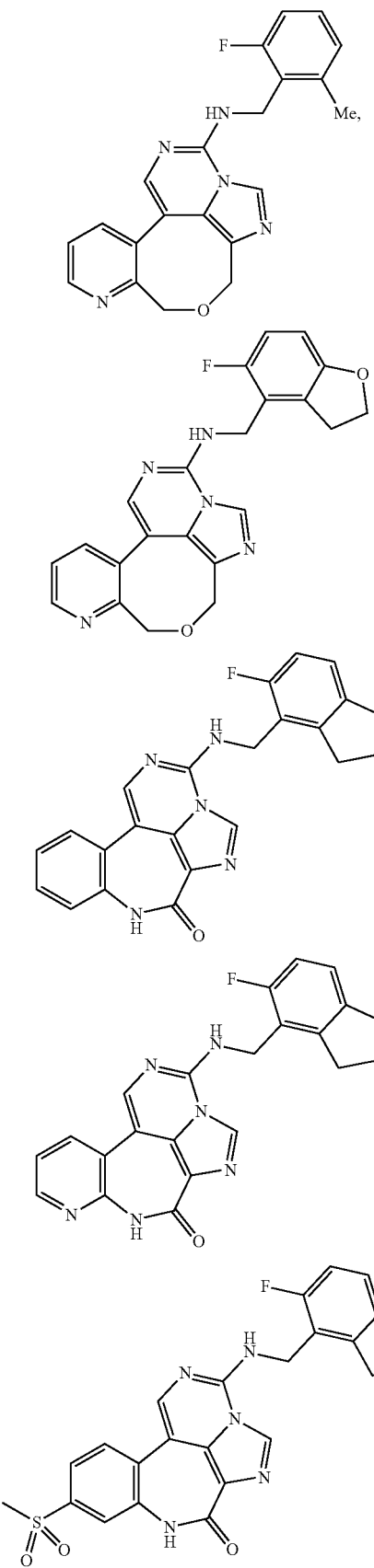

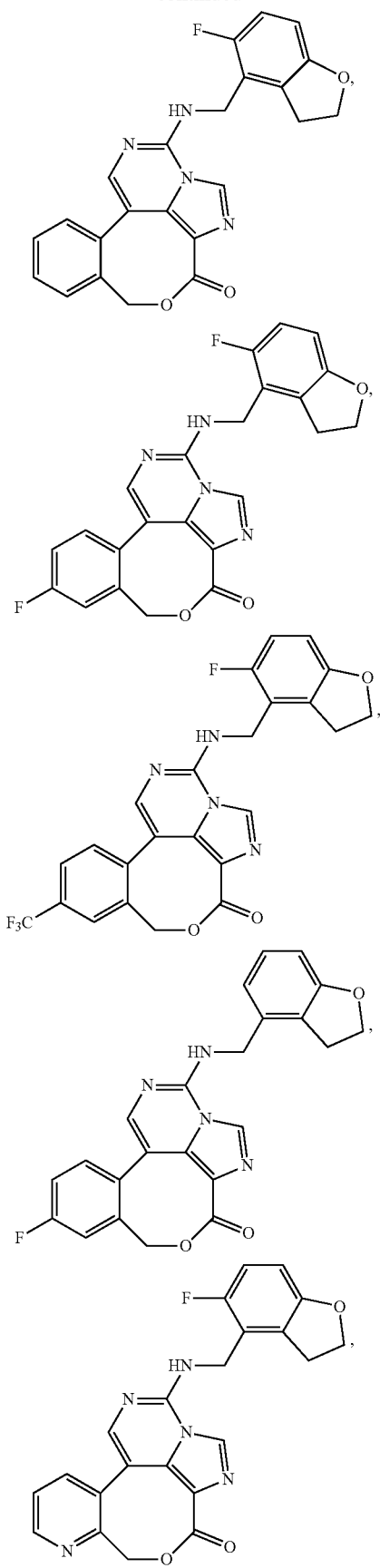
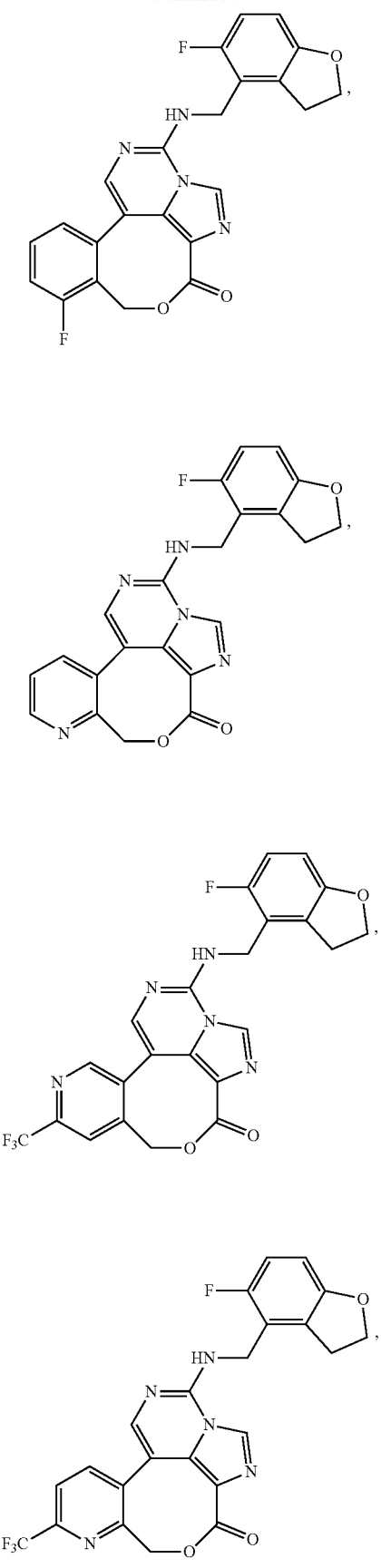

317
-continued
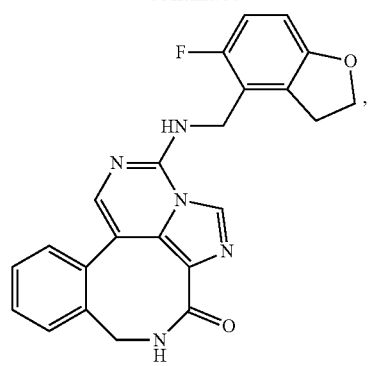
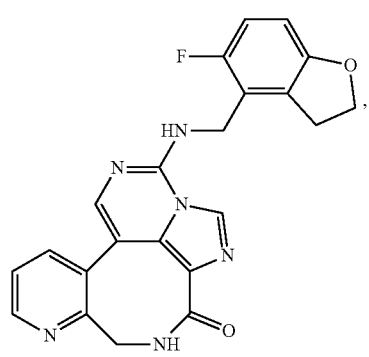
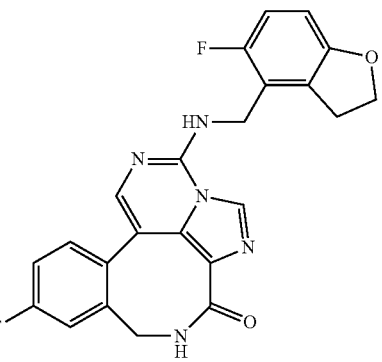
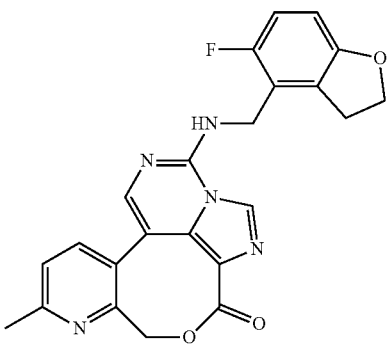
318
-continued
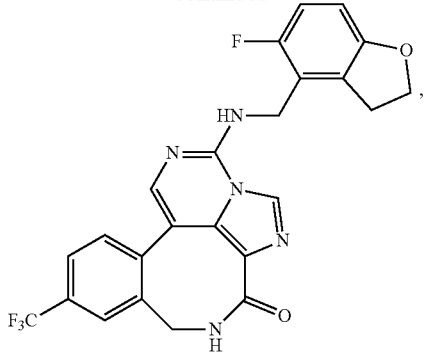
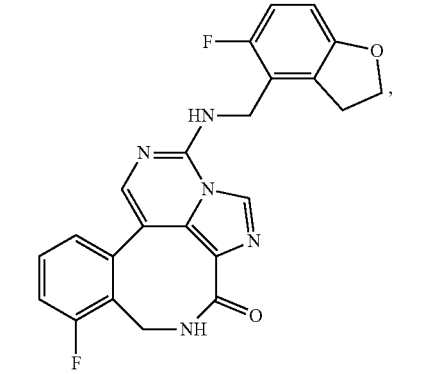
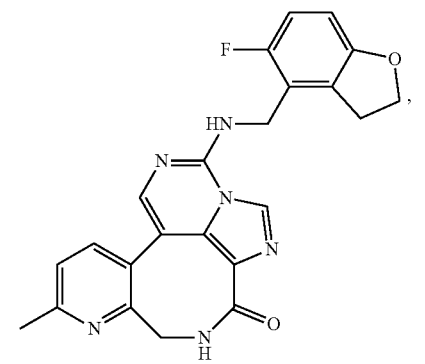
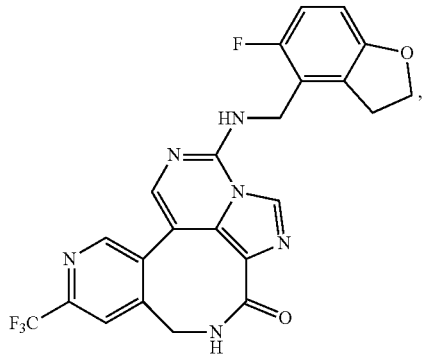

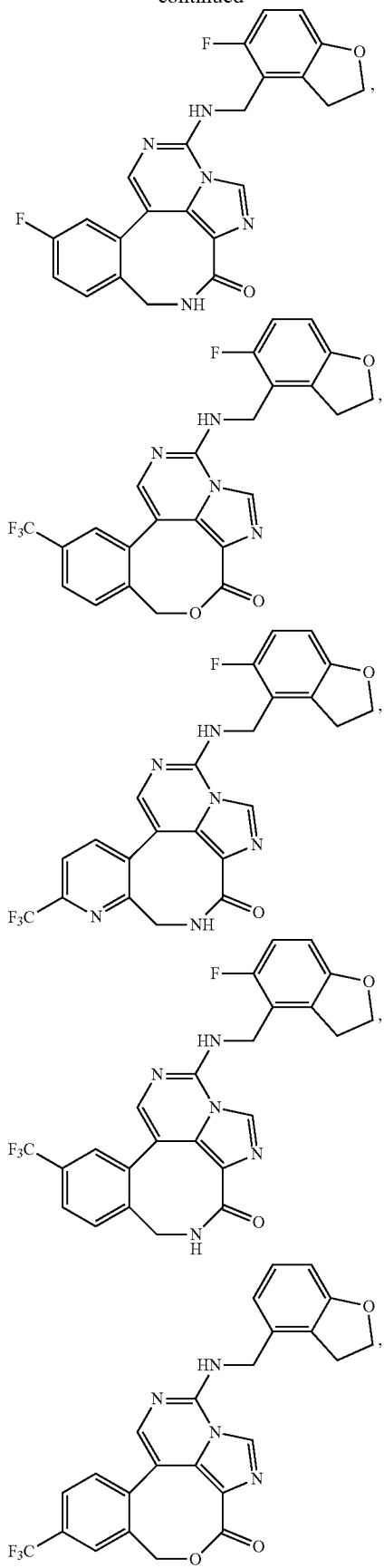
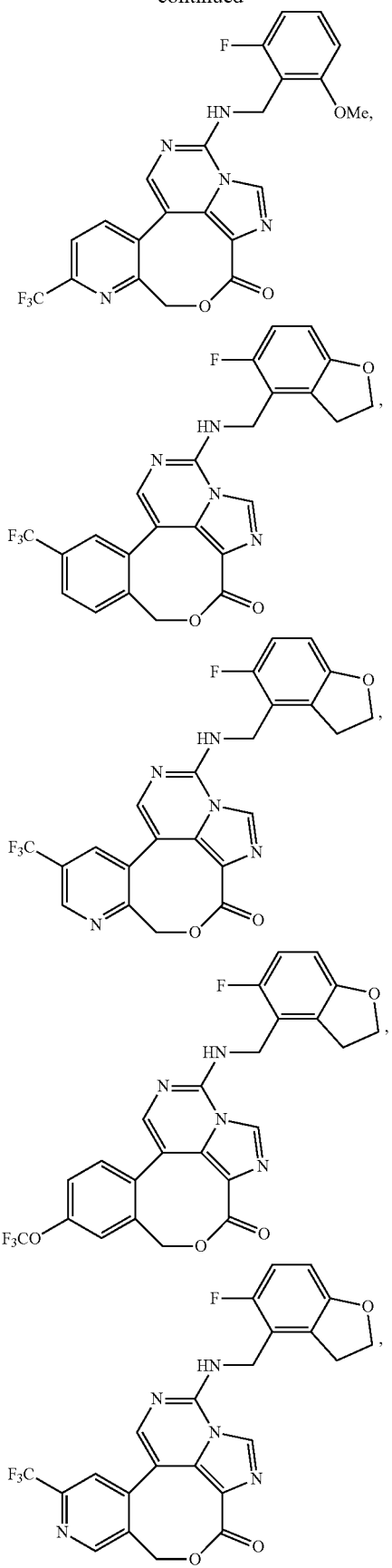

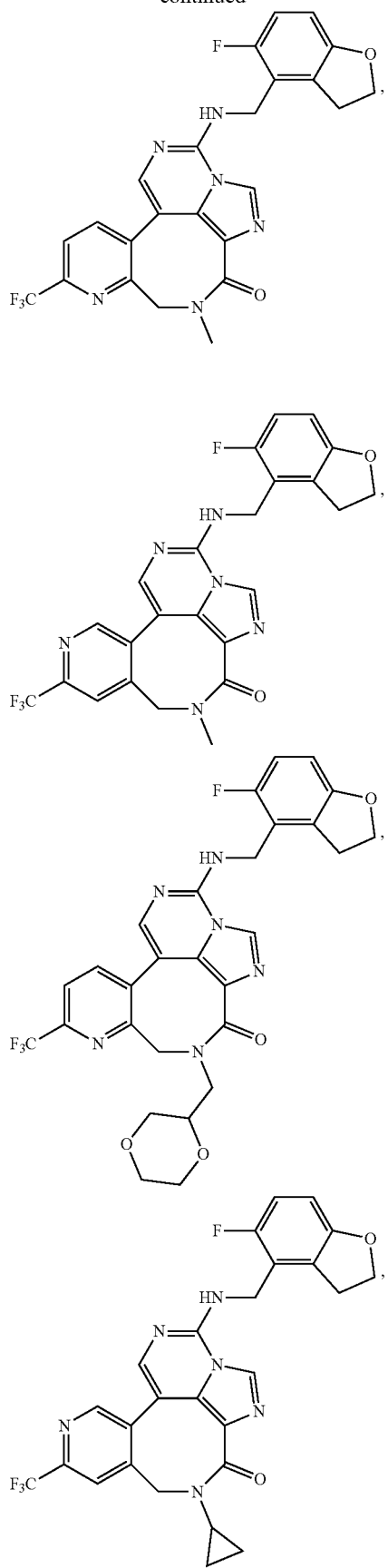
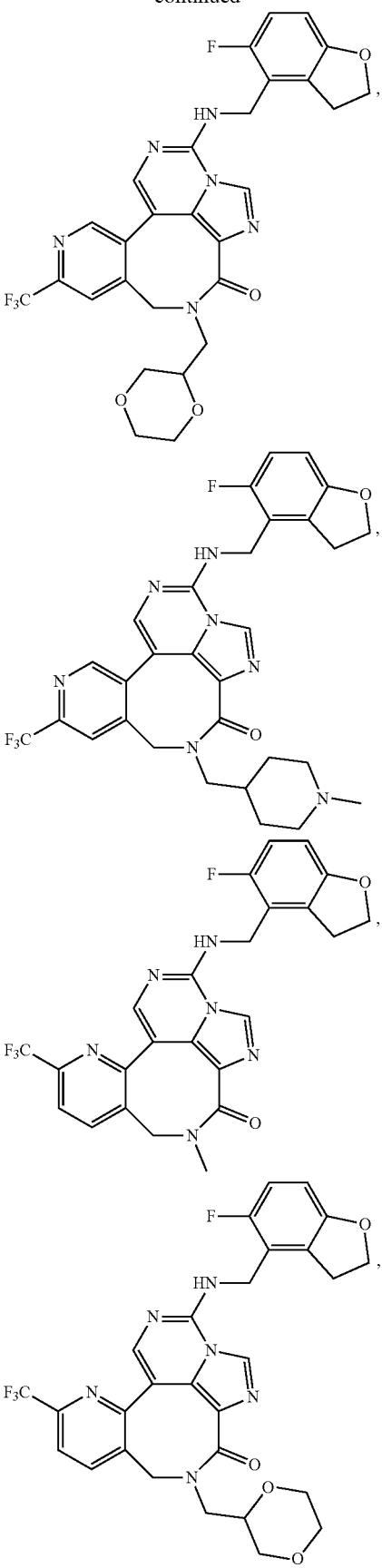

323
-continued
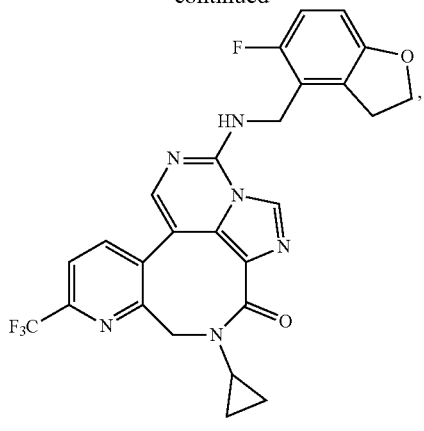
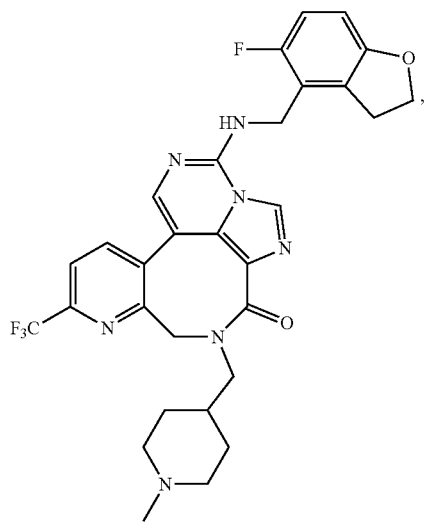
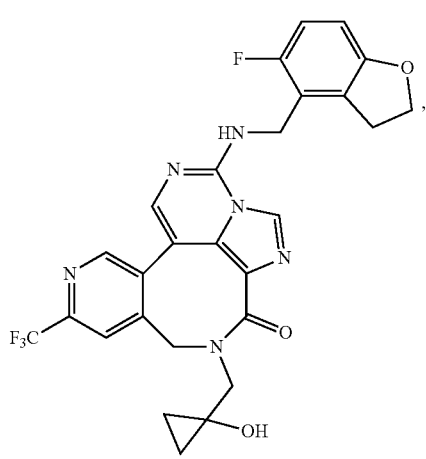
324
-continued
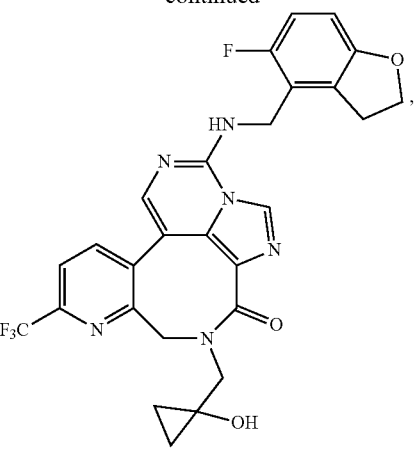
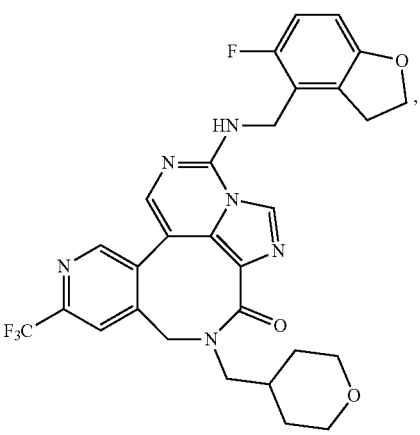
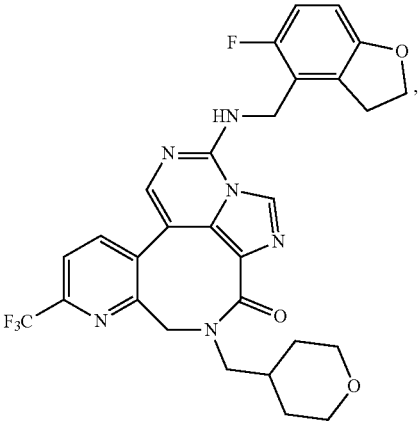
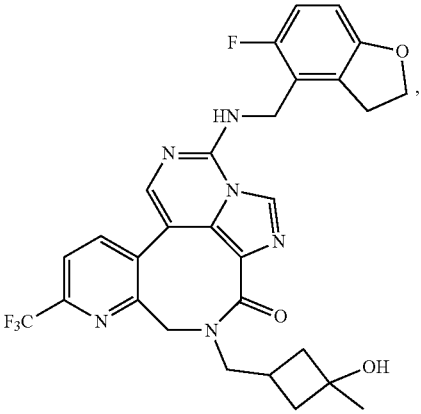

325
-continued
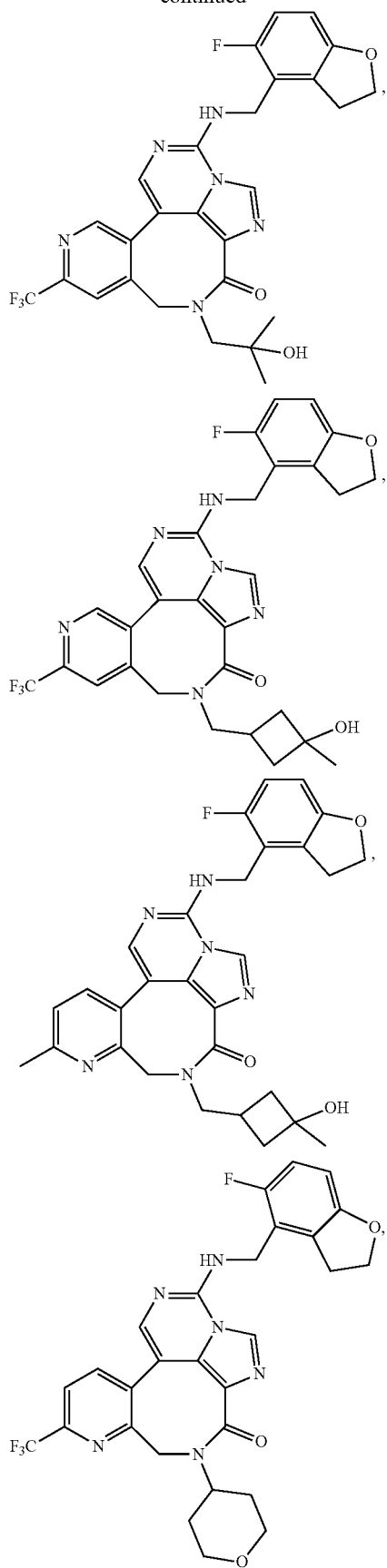
326
-continued
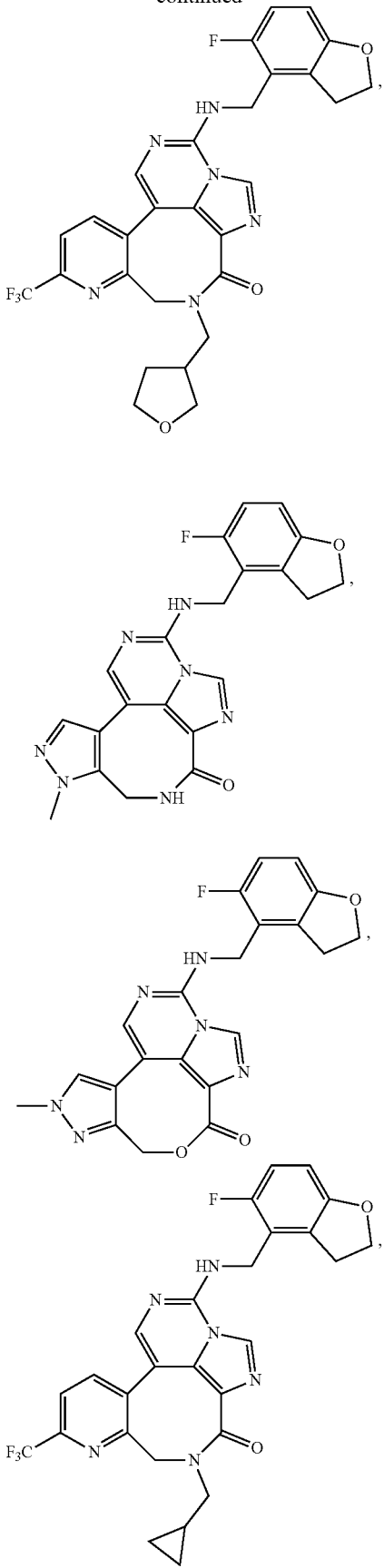

327
-continued
328
-continued
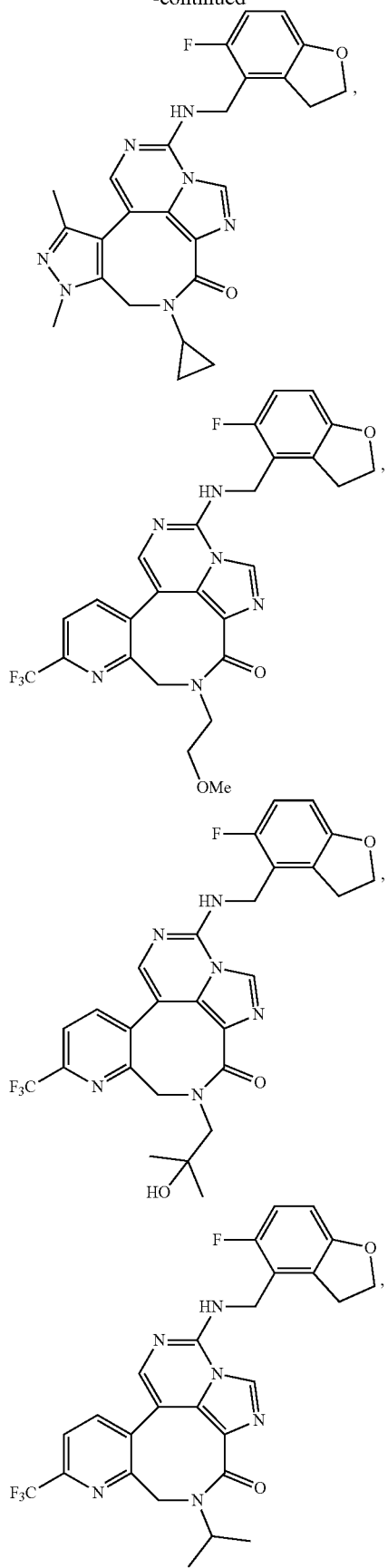
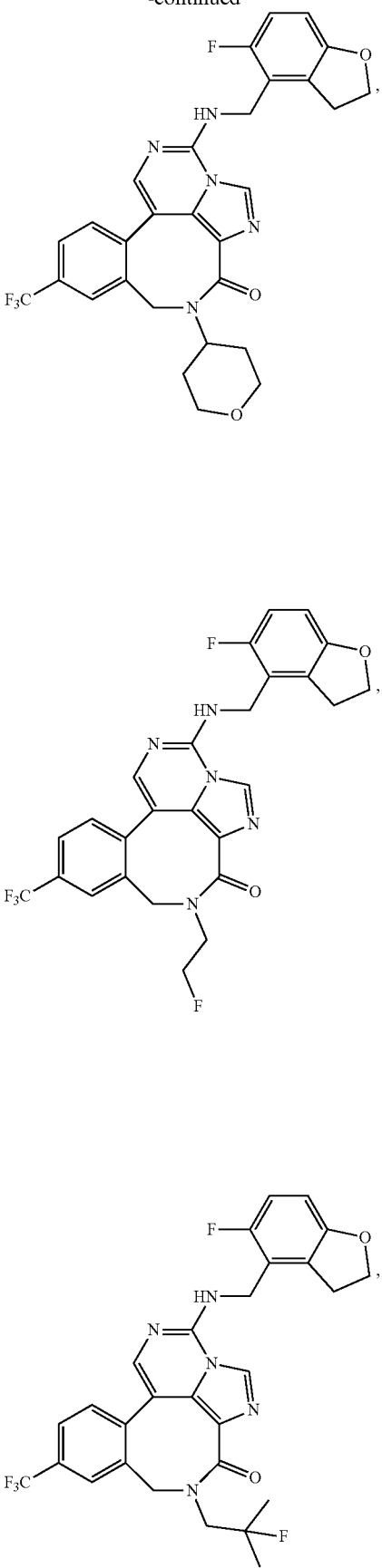

329
-continued
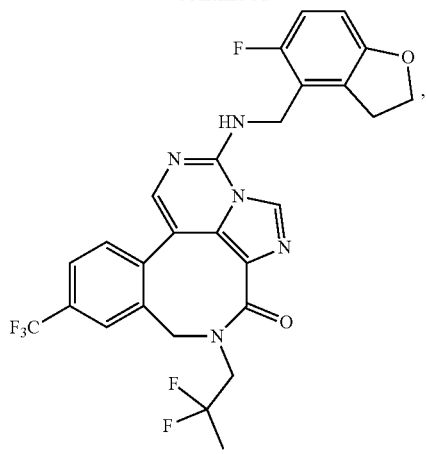
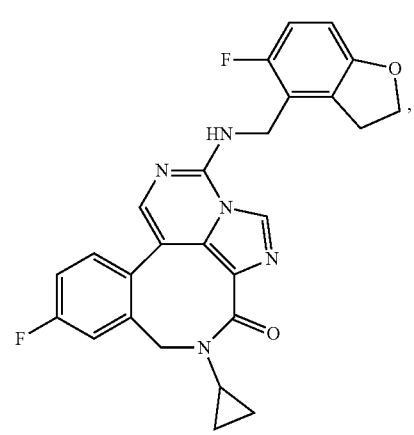
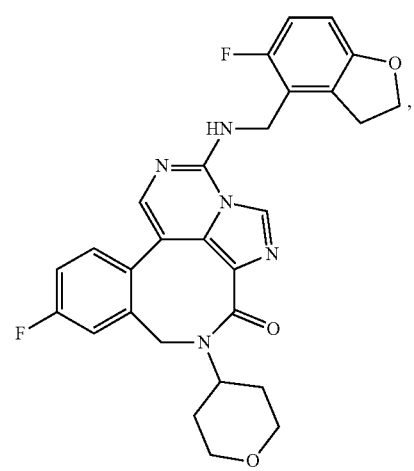
330
-continued
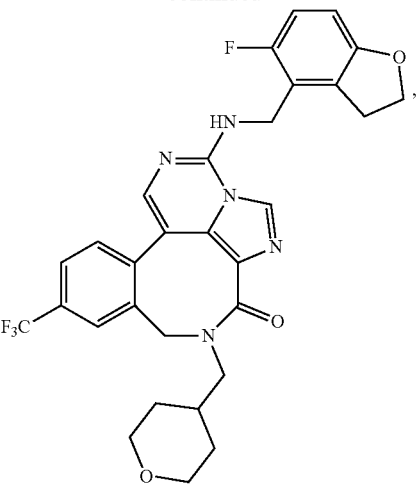
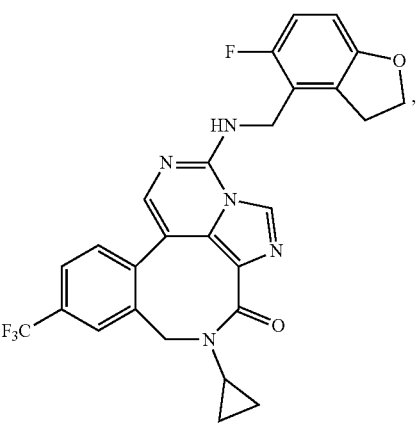
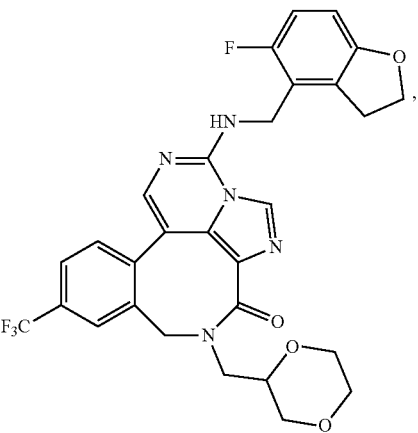

331
-continued
332
-continued
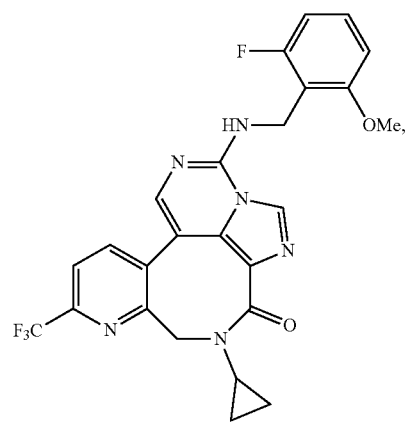
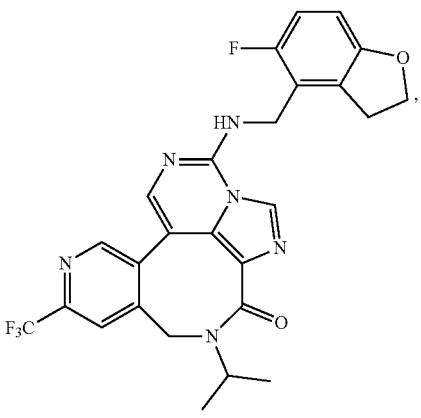

333
-continued
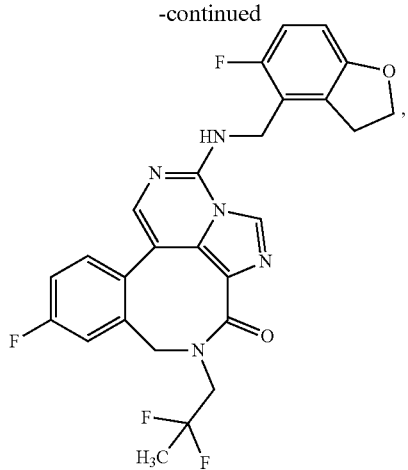
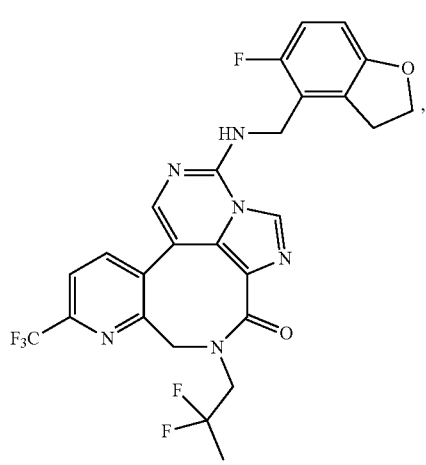
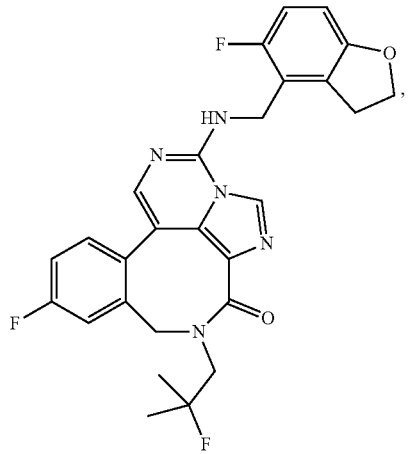
334
-continued
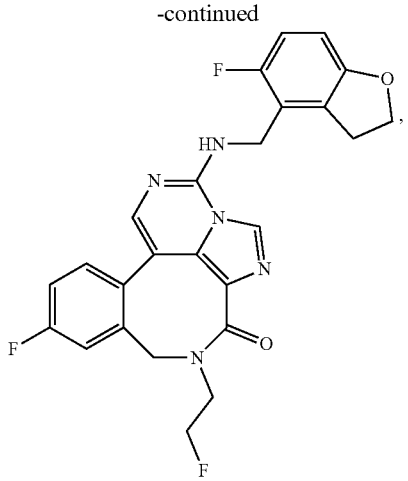
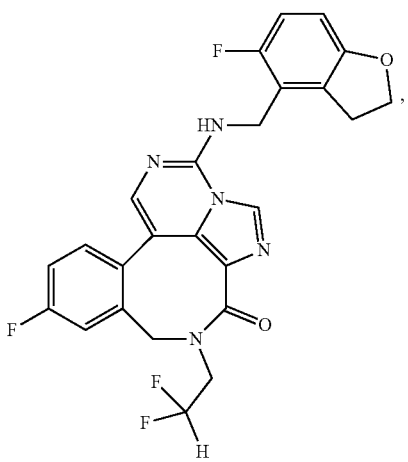
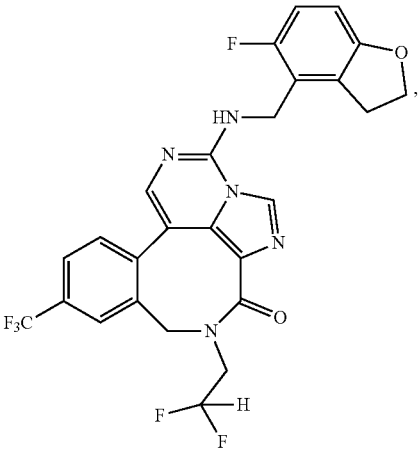

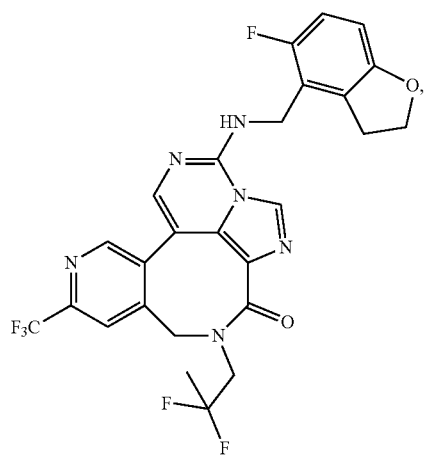
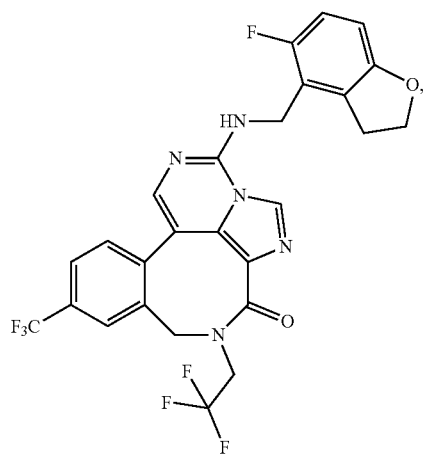
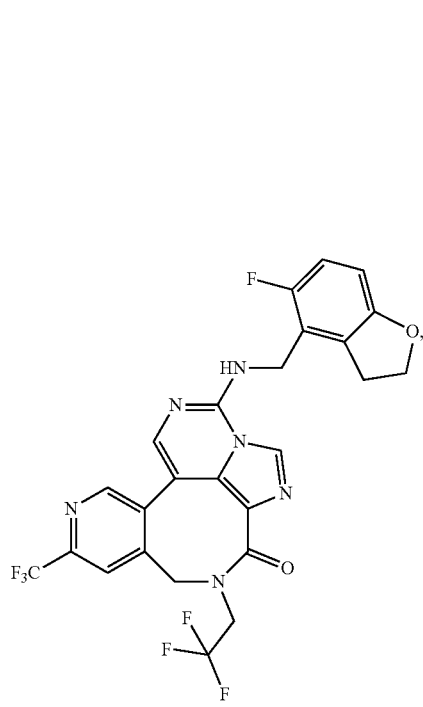
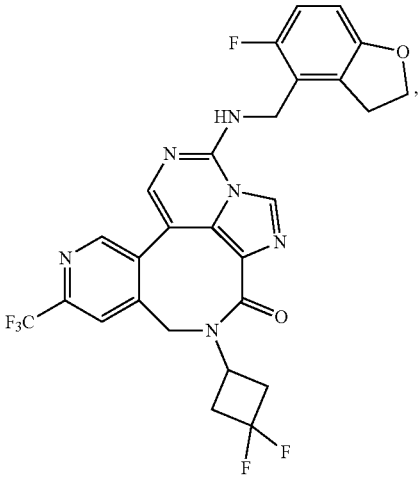
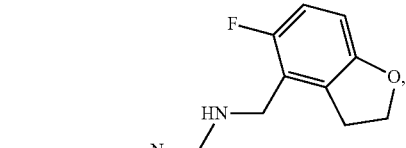
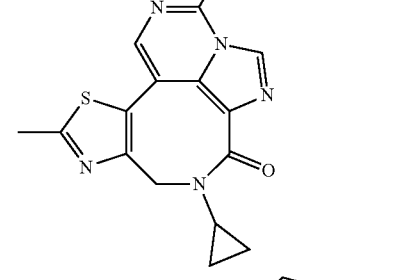
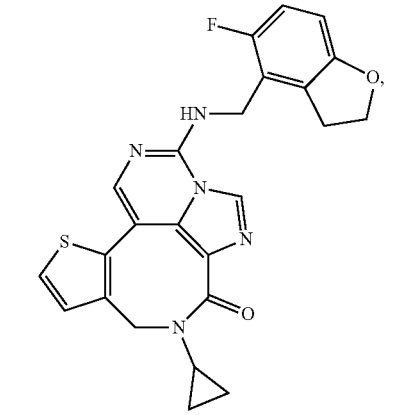
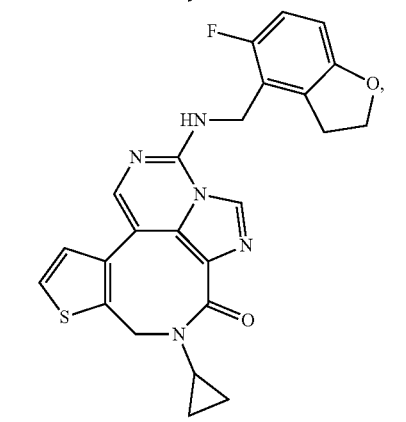

337
-continued
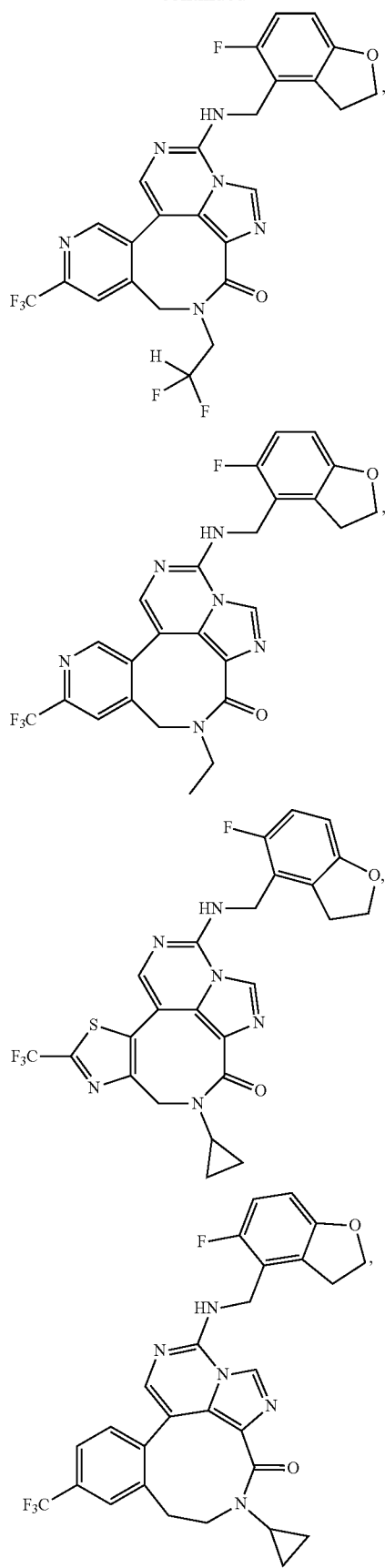
338
-continued
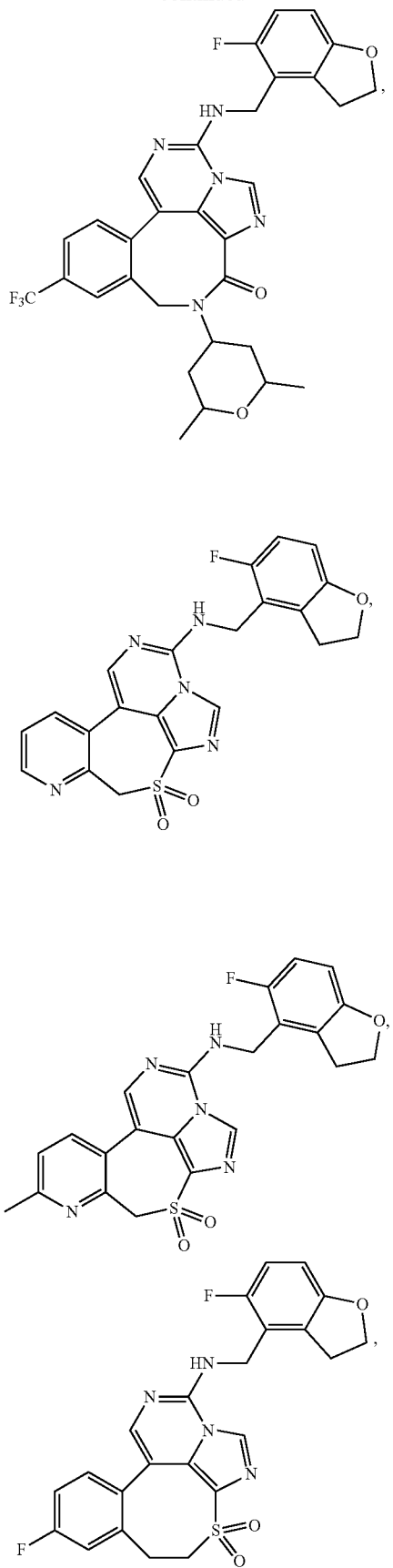

339
-continued
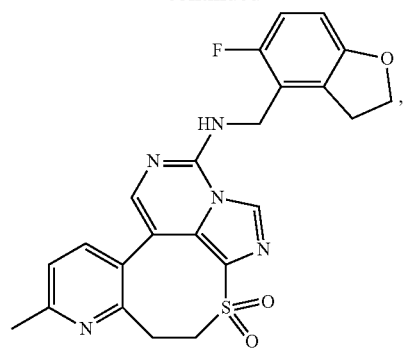
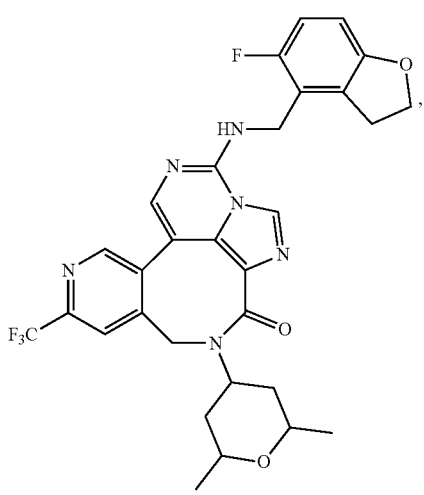
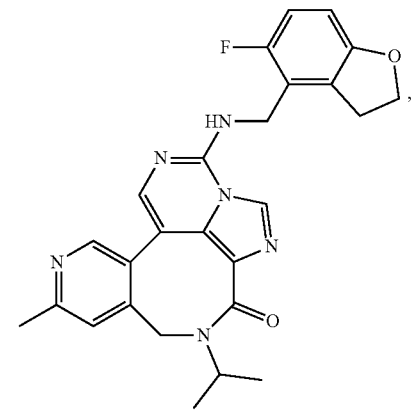
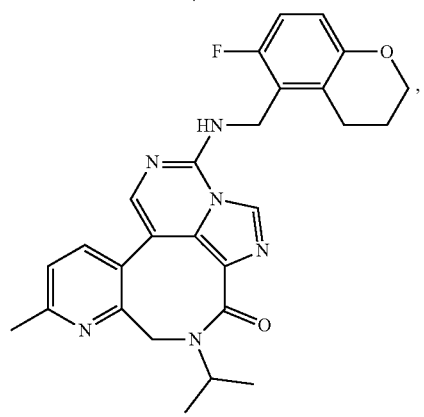
340
-continued
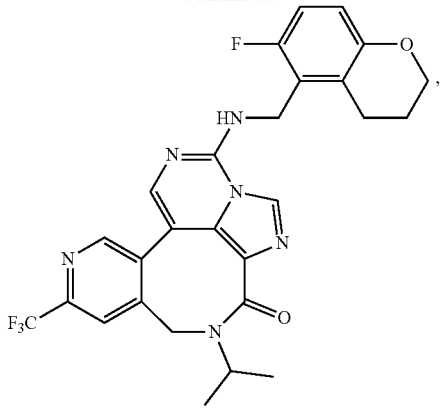
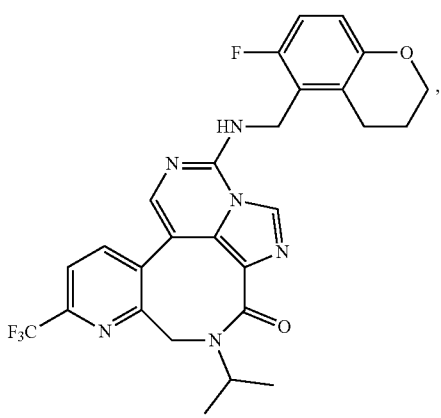
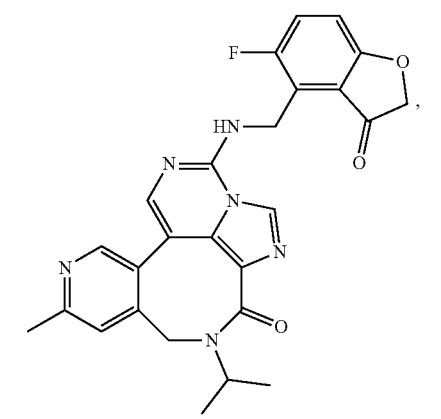
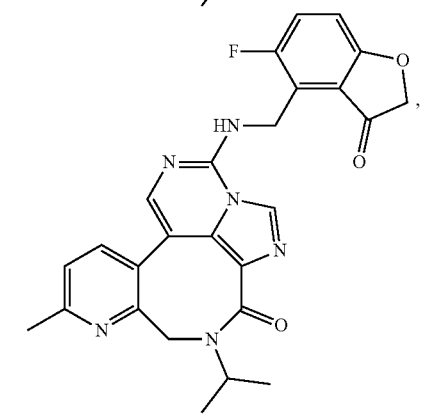

341
-continued
342
-continued
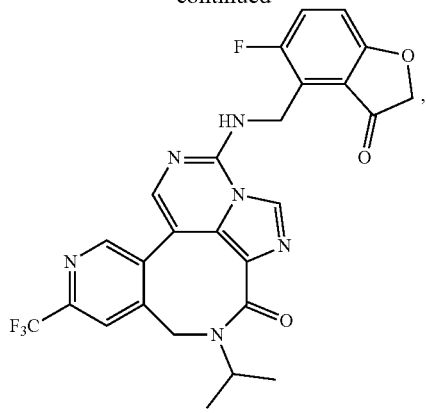
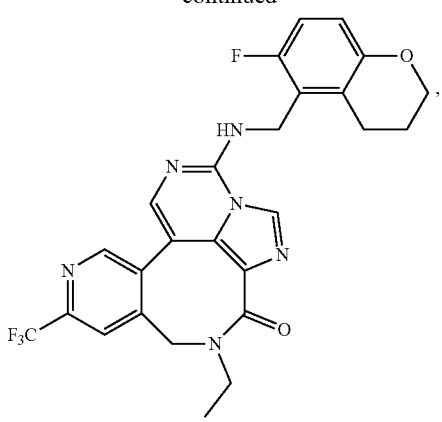

343
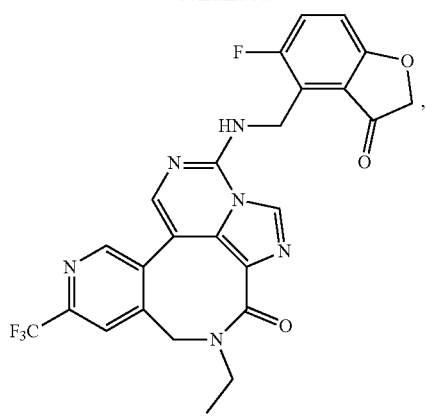
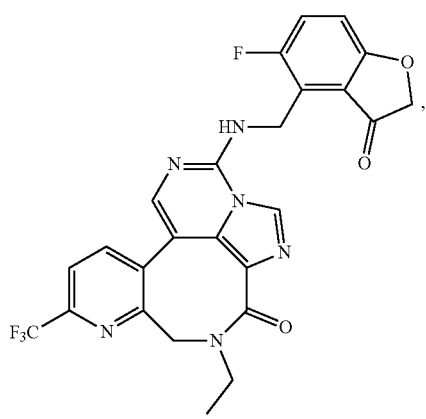
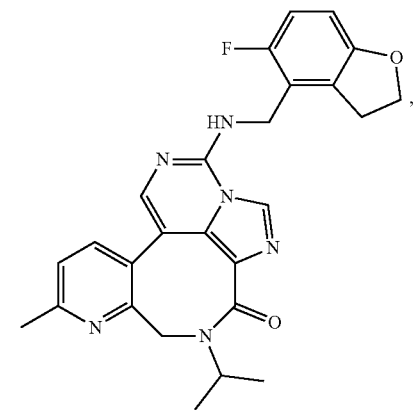
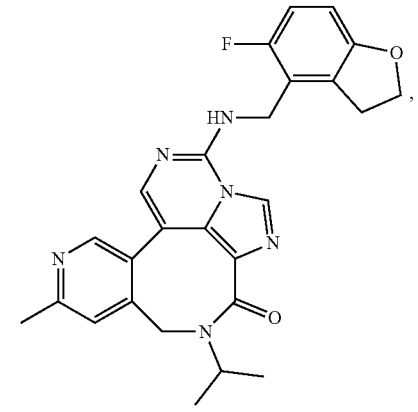
344
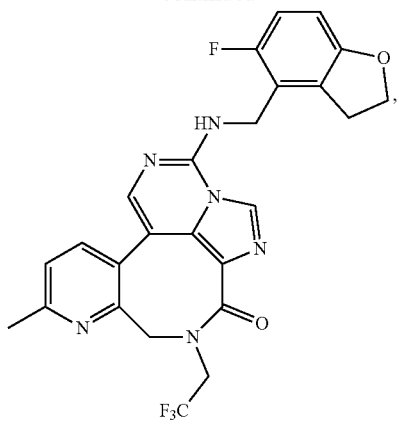
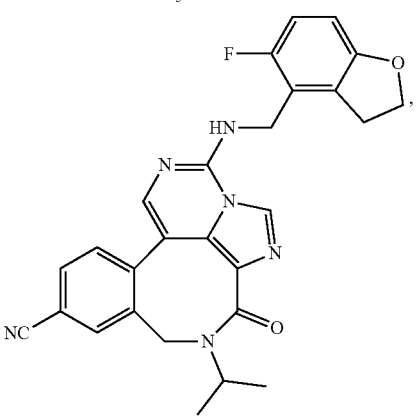
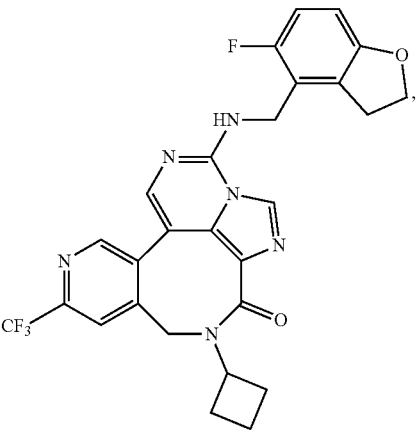
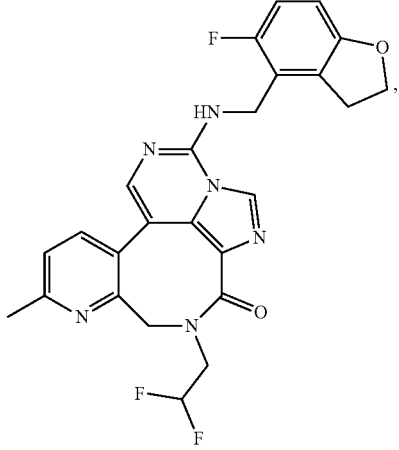

345
-continued
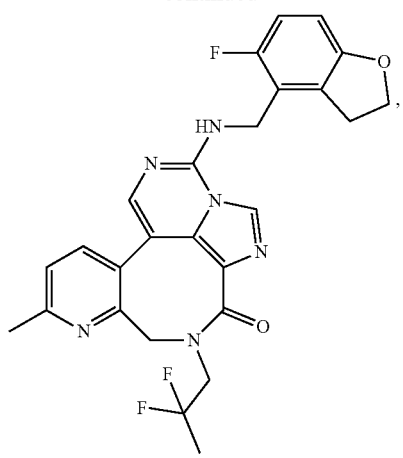
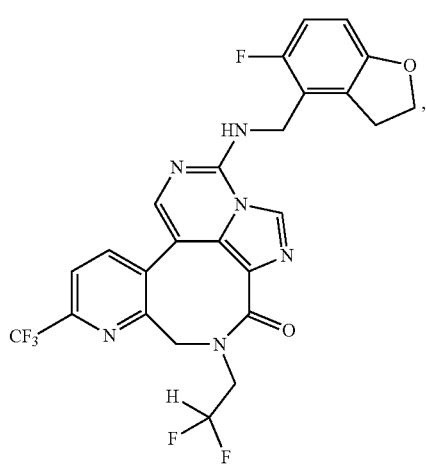
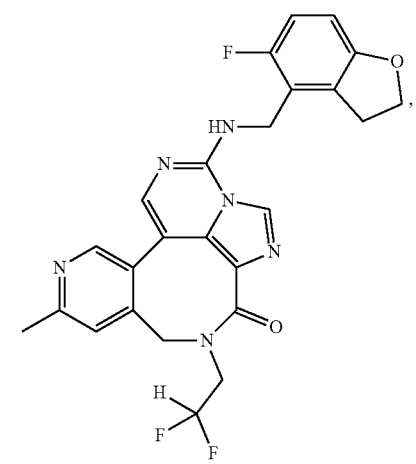
346
-continued
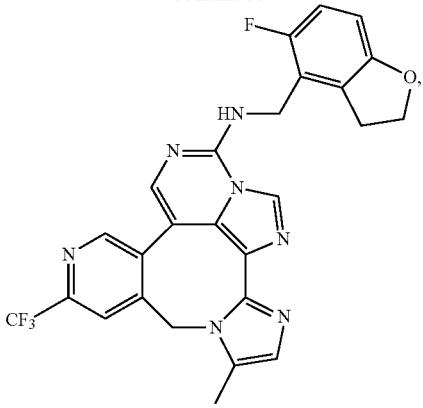
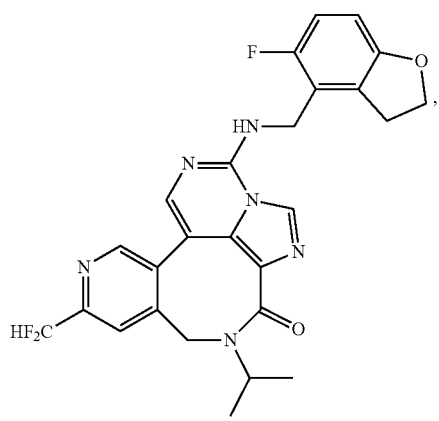
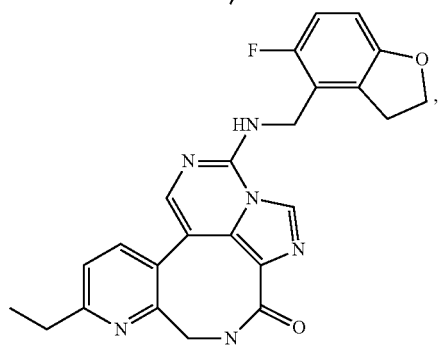
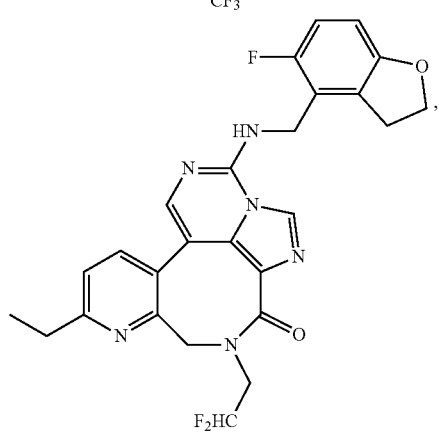

347
-continued
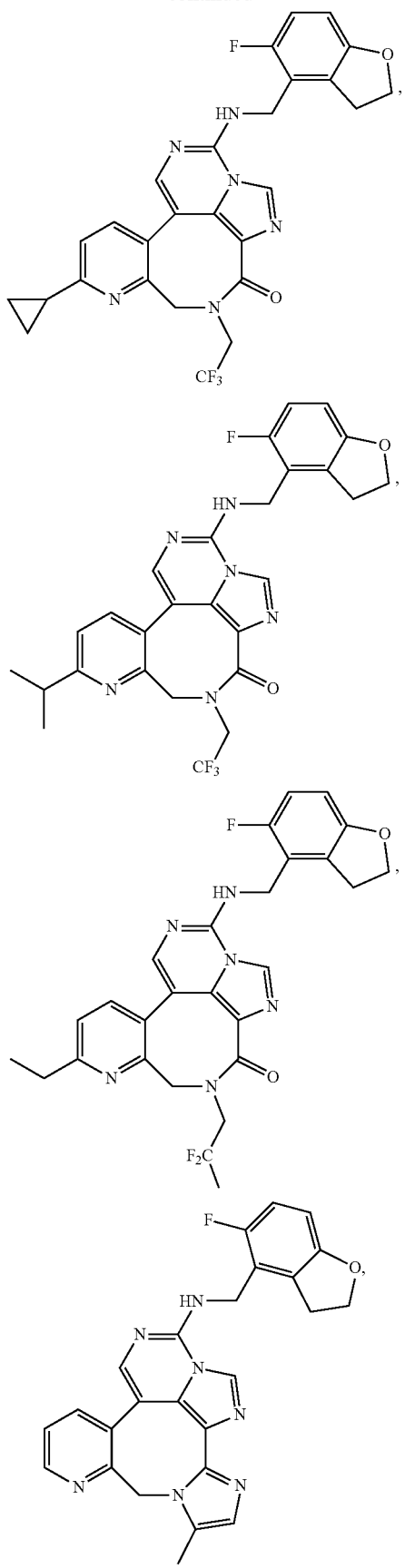
348
-continued
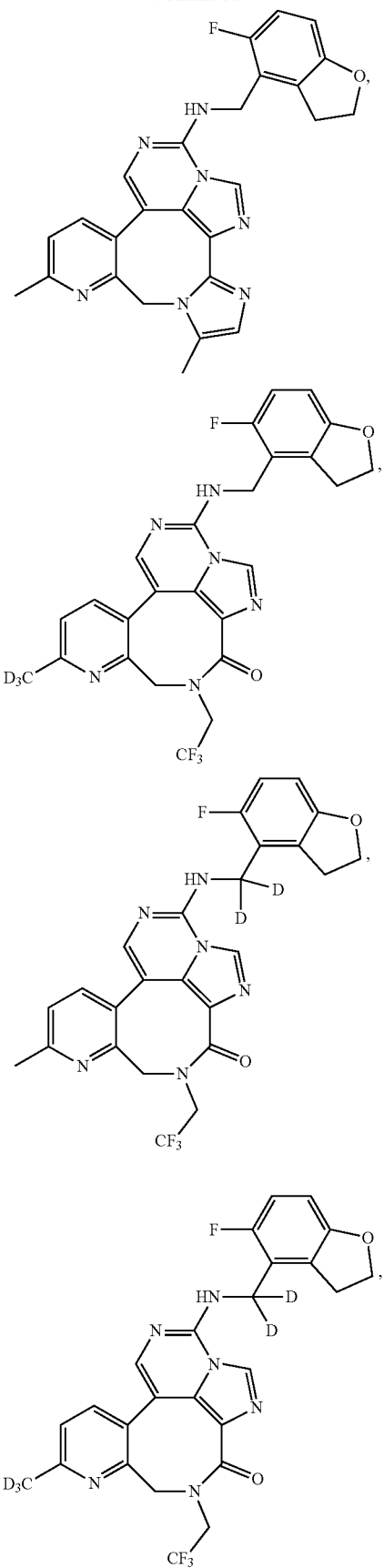

349
-continued
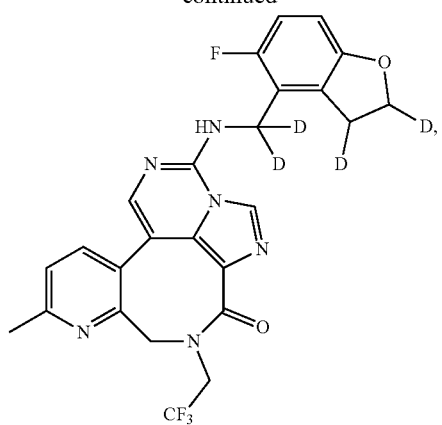
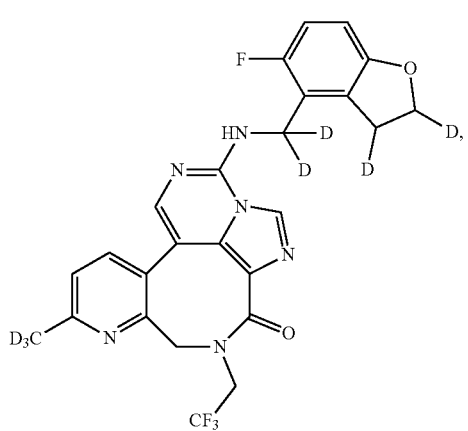
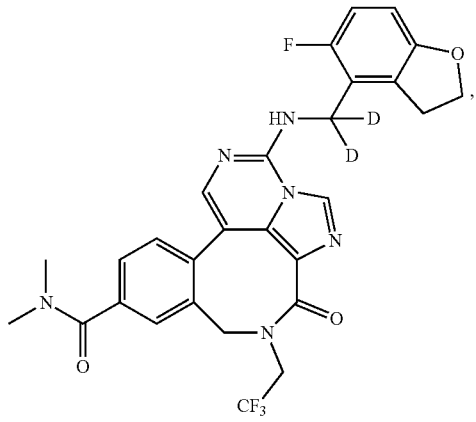
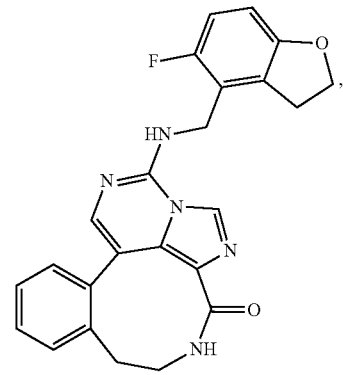
350
-continued
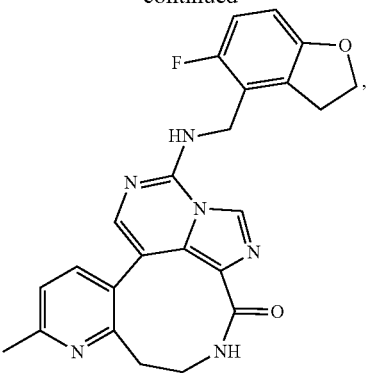
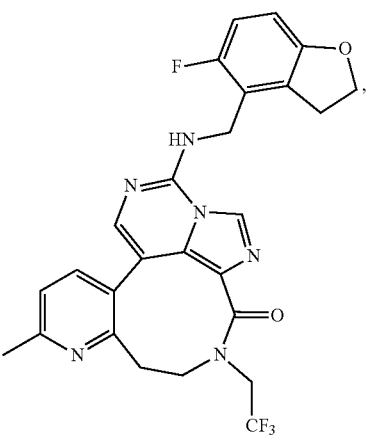
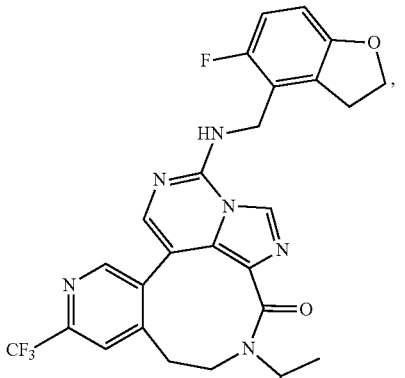
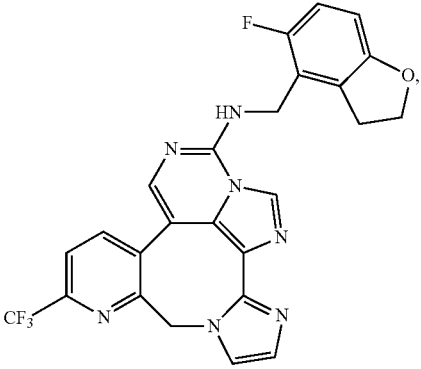

351
-continued
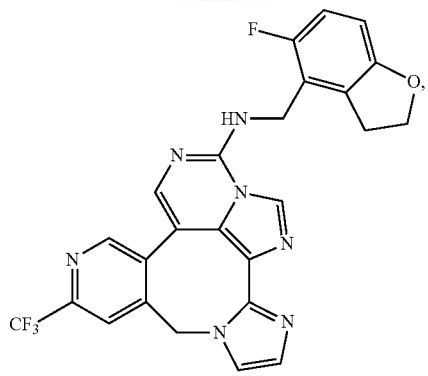
352
-continued
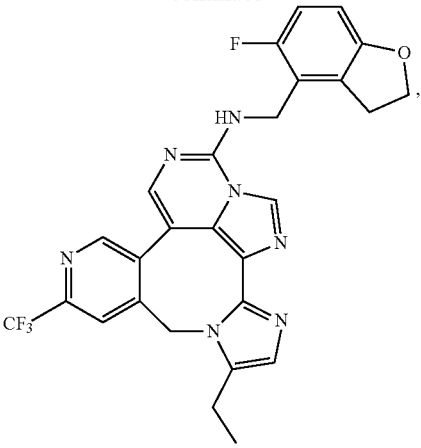
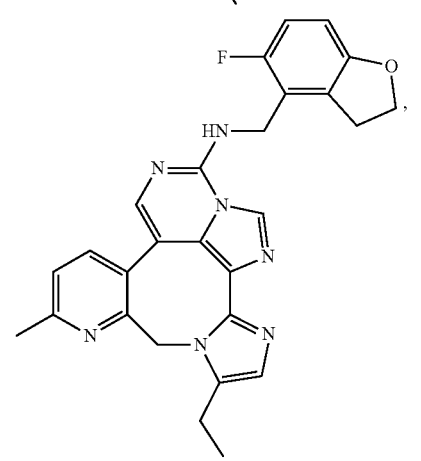
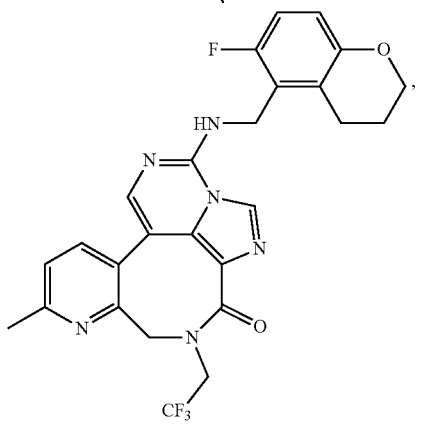
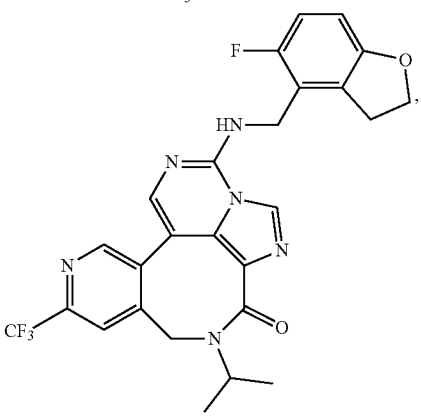

353
-continued
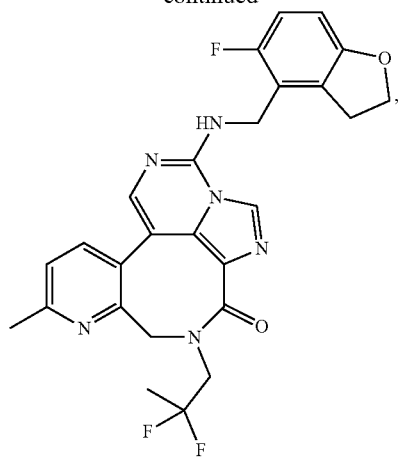
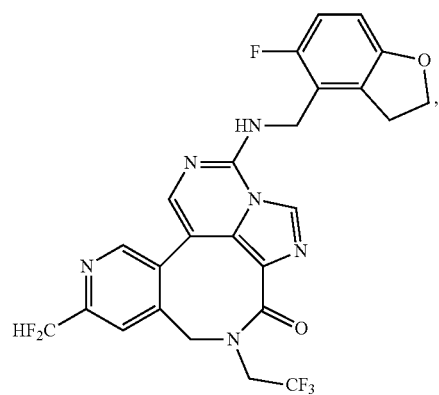
354
-continued
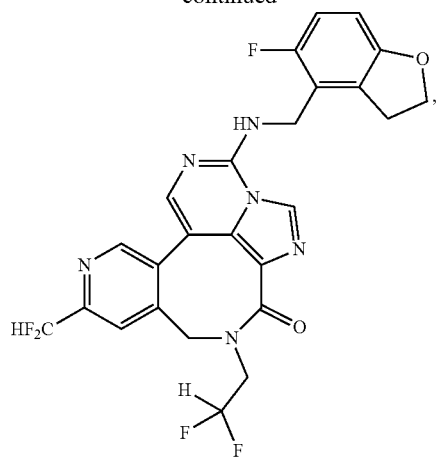
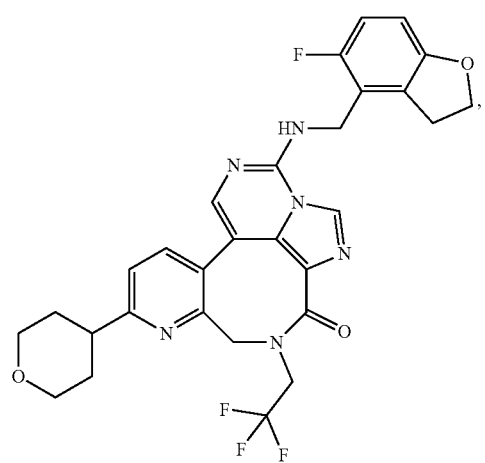
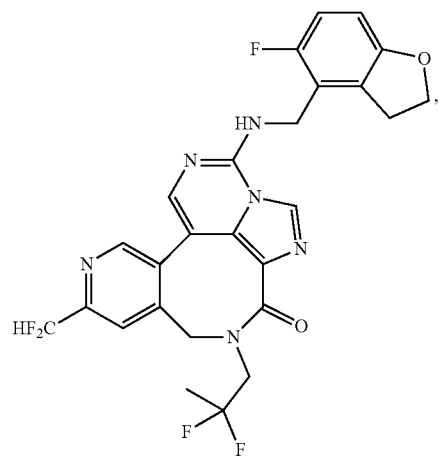
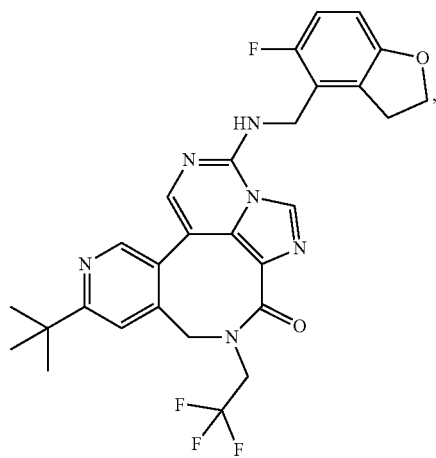

-continued

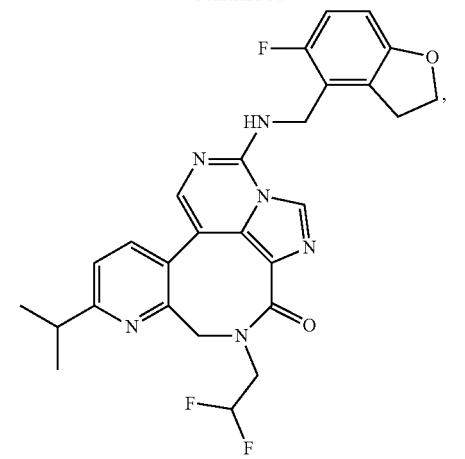

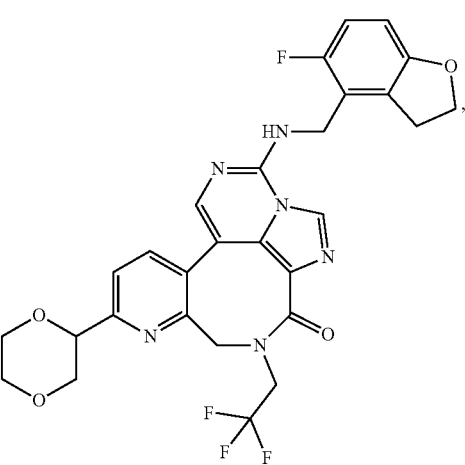

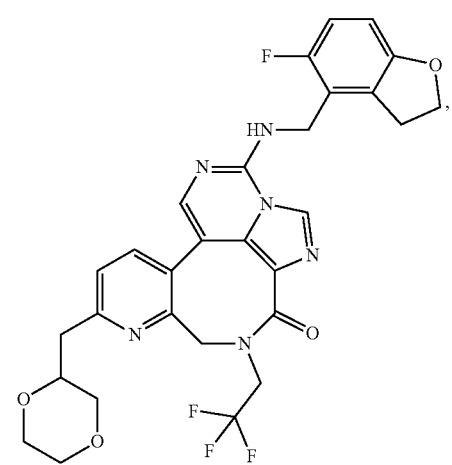

-continued

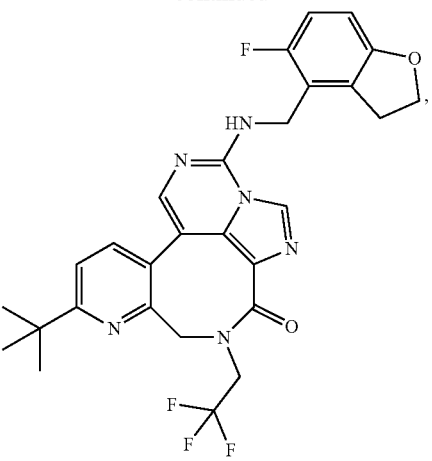

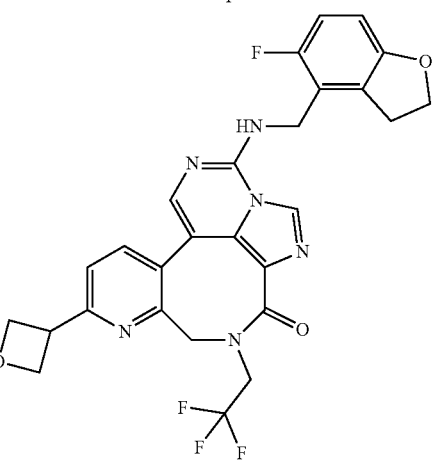

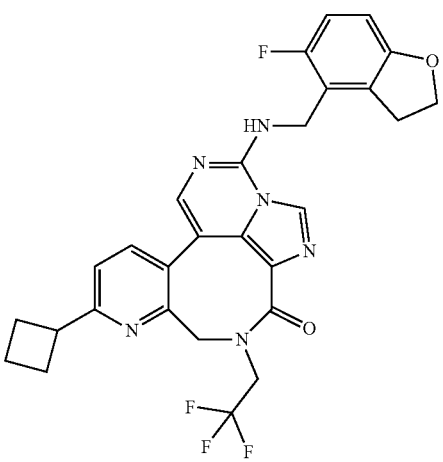

or a pharmaceutically acceptable salt or solvate-thereof.

12. The compound of claim 1 selected from group consisting of:

4-ethyl-12-(((5-fluoro-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one;

12-(((5-fluoro-2,3-dihydrobenzofuran-4-yl)methyl)amino)-4-(2,2,2-trifluoroethyl)-7-(trifluoromethyl)-4,5-dihydro-3H-2,4,8,11,12a-pentaazabenzo[4,5]cycloocta[1,2,3-cd]inden-3-one;

4-cyclopropyl-12-(((5-fluoro-2,3-dihydrobenzofuran-4-yl)methyl)amino)-7-(trifluoromethyl)-4,5-dihydro-3H-2,4,8,11,12a-pentaazabenzo[4,5]cycloocta[1,2,3-cd]inden-3-one;

12-(((5-fluoro-2,3-dihydrobenzofuran-4-yl)methyl) amino)-4-isopropyl-7-(trifluoromethyl)-4,5-dihydro-3H-2,4,8,11,12a-pentaazabenzo[4,5]cycloocta[1,2,3-cd]inden-3-one; and 11-(((5-fluoro-2,3-dihydrobenzofuran-4-yl)methyl) amino)-6-methyl-4H-3-thia-2,5,10,11a-tetraazadibenzo[cd,f]azulene 3,3-dioxide, or a pharmaceutically acceptable salt thereof.

13. A pharmaceutical composition comprising the compound of claim 1, or a pharmaceutically acceptable salt thereof, and a pharmaceutically acceptable carrier.

14. A method of treating cancer wherein the cancer is a lymphoma, in a subject in need thereof, the method comprising administering to the subject a therapeutically effective amount of the compound of claim 1, or a pharmaceutically acceptable salt thereof.

* * * * *